United States Patent
Hoffer et al.

(10) Patent No.: US 12,364,606 B2
(45) Date of Patent: Jul. 22, 2025

(54) FLUOROSCOPIC VISUALIZATION OF HEART VALVE ANATOMY

(71) Applicant: Edwards Lifesciences Innovation (Israel) Ltd., Caesarea (IL)

(72) Inventors: Eran Hoffer, Yahud (IL); Sarit Avivi, Givat Shmuel (IL); Yaron Herman, Givat Ada (IL); Tal Sheps, Givat Shmuel (IL); Ehud Aviv, Costa Mesa, CA (US); Boaz Manash, Givat Ada (IL); Meir Kutzik, Kafir Saba (IL); Or Cohen, Modi'in (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 786 days.

(21) Appl. No.: 17/549,194

(22) Filed: Dec. 13, 2021

(65) Prior Publication Data
US 2022/0233316 A1     Jul. 28, 2022

Related U.S. Application Data

(63) Continuation of application No. PCT/IL2020/050807, filed on Jul. 22, 2020.
(Continued)

(51) Int. Cl.
| A61F 2/24 | (2006.01) |
| A61B 90/00 | (2016.01) |
| A61B 17/064 | (2006.01) |

(52) U.S. Cl.
CPC ............ *A61F 2/2496* (2013.01); *A61B 90/39* (2016.02); *A61F 2/2445* (2013.01);
(Continued)

(58) Field of Classification Search
CPC .... A61F 2/2496; A61F 2/2445; A61F 2/2466; A61F 2250/0098; A61B 90/39; A61B 2090/3966; A61B 2017/0649
See application file for complete search history.

(56) References Cited

U.S. PATENT DOCUMENTS

| 3,604,488 A | 9/1971 | Wishart et al. |
| 3,656,185 A | 4/1972 | Carpentier |

(Continued)

FOREIGN PATENT DOCUMENTS

| EP | 1034753 A1 | 9/2000 |
| EP | 3531975 A1 | 9/2019 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Suba Ganesan
(74) *Attorney, Agent, or Firm* — Edwards Lifesciences

(57) ABSTRACT

A radiopaque frame is transluminally advanced to an atrium of a heart of a subject. The frame is expanded within a valve adjacent the atrium such that part of the frame remains disposed in the atrium. While the frame remains expanded within the valve, progressive portions of an annuloplasty structure are progressively positioned and anchored around the annulus using multiple anchors by, for each of the anchors sequentially (i) while fluoroscopically imaging the frame and a distal end of a delivery tool, and facilitated by mechanical guidance from the frame, positioning the distal end of the delivery tool between the frame and a wall of the atrium; and (ii) driving the anchor into the annulus laterally from the frame. Subsequently, the frame is contracted and withdrawn from the subject while leaving the annuloplasty (Continued)

structure anchored around the annulus. Other embodiments are also described.

21 Claims, 64 Drawing Sheets

Related U.S. Application Data

(60) Provisional application No. 62/988,322, filed on Mar. 11, 2020, provisional application No. 62/877,785, filed on Jul. 23, 2019.

(52) U.S. Cl.
CPC .... *A61F 2/2466* (2013.01); *A61B 2017/0649* (2013.01); *A61B 2090/3966* (2016.02); *A61F 2250/0098* (2013.01)

(56) References Cited

U.S. PATENT DOCUMENTS

| | | | |
|---|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |

(56) References Cited

U.S. PATENT DOCUMENTS

| | | |
|---|---|---|
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |

(56) References Cited

U.S. PATENT DOCUMENTS

| | | |
|---|---|---|
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |

(56) References Cited

U.S. PATENT DOCUMENTS

| | | |
|---|---|---|
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |

(56) References Cited

U.S. PATENT DOCUMENTS

| | | |
|---|---|---|
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |

(56) References Cited

U.S. PATENT DOCUMENTS

| | | |
|---|---|---|
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0066138 A1* | 3/2015 | Alexander ......... A61B 17/0401 623/2.11 |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al."Novel Suture Device for Beating-Heart Mitral Leaflet Approximation", Ann Thorac Surg. 2002, 74:1488-1493.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

AMPLATZER® Cribriform Occluder. A patient guide to Percutaneous, Transcatheter, Atrial Septal Defect Closuer, AGA Medical Corporation, Apr. 2008.

AMPLATZER® Septal Occluder. A patient guide to the Non-Surgical Closuer of the Atrial Septal Defect Using the AMPLATZER Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applica-

(56) References Cited

OTHER PUBLICATIONS tions in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, The Journal of Thoracic Cardiovascular surgery vol. 133 No. 1, Jan. 2007.

Langer et al. RING+STRING, Successful Repair technique for ischemic mitral regurgitation with severe leaflet Tethering, The Department of Thoracic Cardiovascular surgery, Hamburg, Germany, Nov. 2008.

Maisano, "The double-orifice technique as a standardized approach to treat mitral," European Journal of Cardio- thoracic Surgery 17 (2000) 201-205.

O'Reilly S et al., "Heart valve surgery pushes the envelope," Medtech Insight 8(3): 73, 99-108 (2006).

Odell JA et al., "Early Results 04yf a Simplified Method of Mitral Valve Annuloplasty," Circulation 92:150-154 (1995).

Park, Sang C. et al. "A percutaneously adjustable device for banding of the pulmonary trunk." International journal of cardiology 9.4 (1985): 477-484.

Swain CP et al., "An endoscopically deliverable tissue-transfixing device for securing biosensors in the gastrointestinal tract," Gastrointestinal Endoscopy 40(6): 730-734 (1994).

Swenson, O. An experimental implantable urinary sphincter. Invest Urol. Sep. 1976;14(2):100-3.

Swenson, O. and Malinin, T.I., 1978. An improved mechanical device for control of urinary incontinence. Investigative urology, 15(5), pp. 389-391.

Swenson, Orvar. "Internal device for control of urinary incontinence." Journal of pediatric surgery 7.5 (1972): 542-545.

Tajik, Abdul, "Two dimensional real-time ultrasonic imaging of the heart and great vessels", Mayo Clin Proc. vol. 53:271-303, 1978.

\* cited by examiner

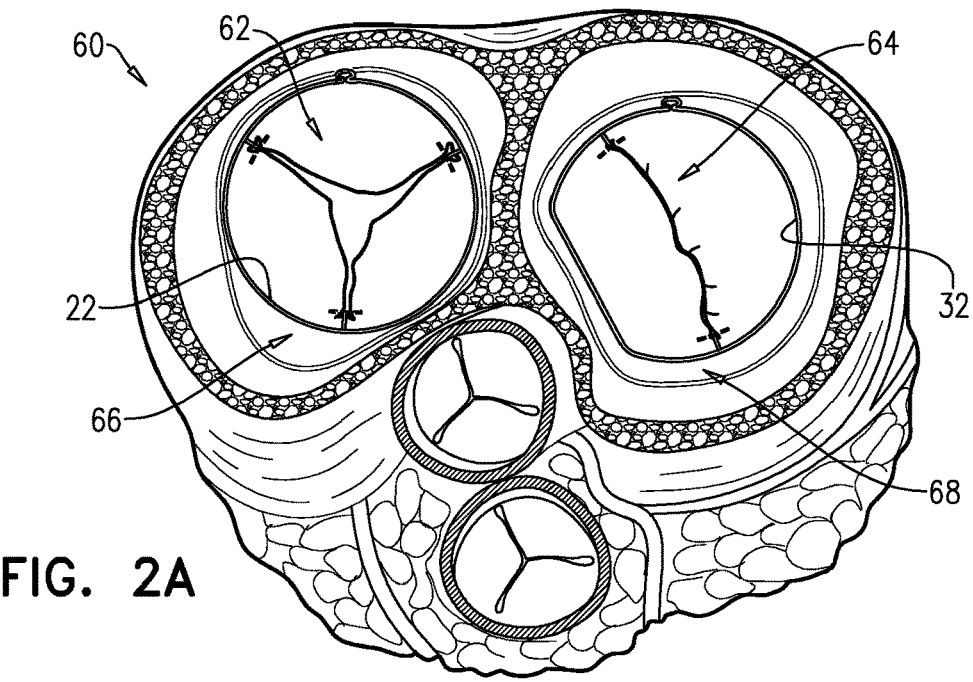
FIG. 2A
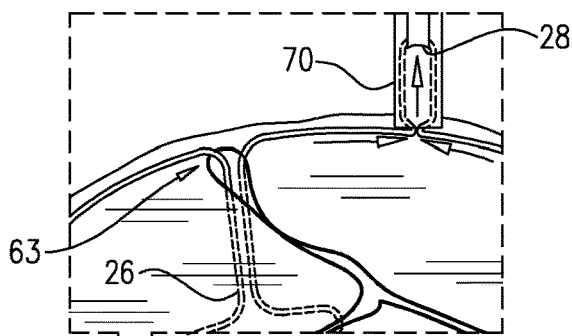
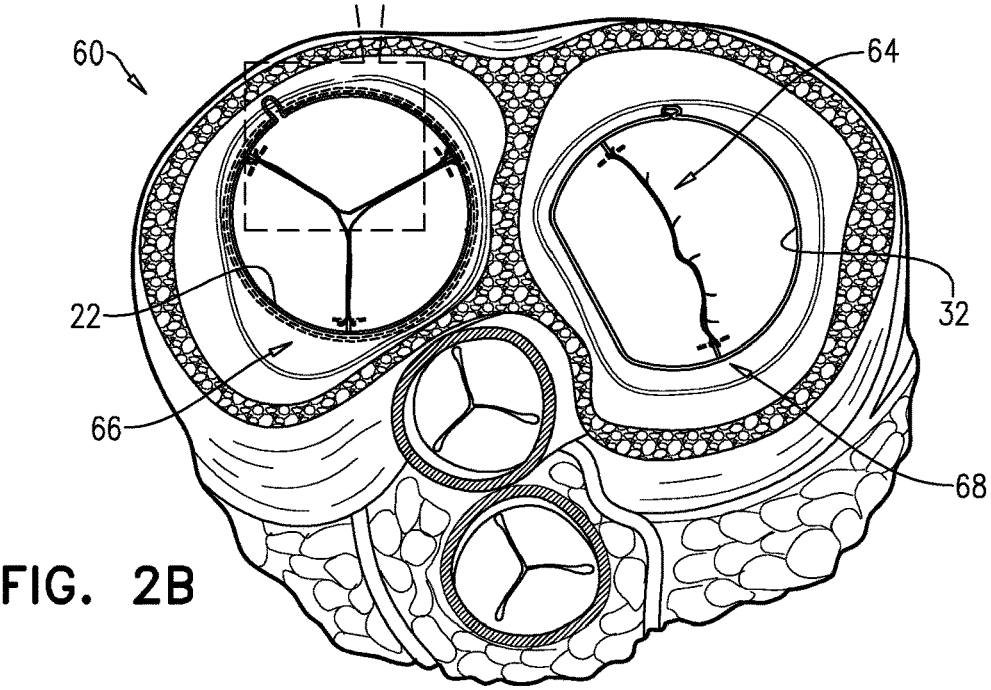
FIG. 2B

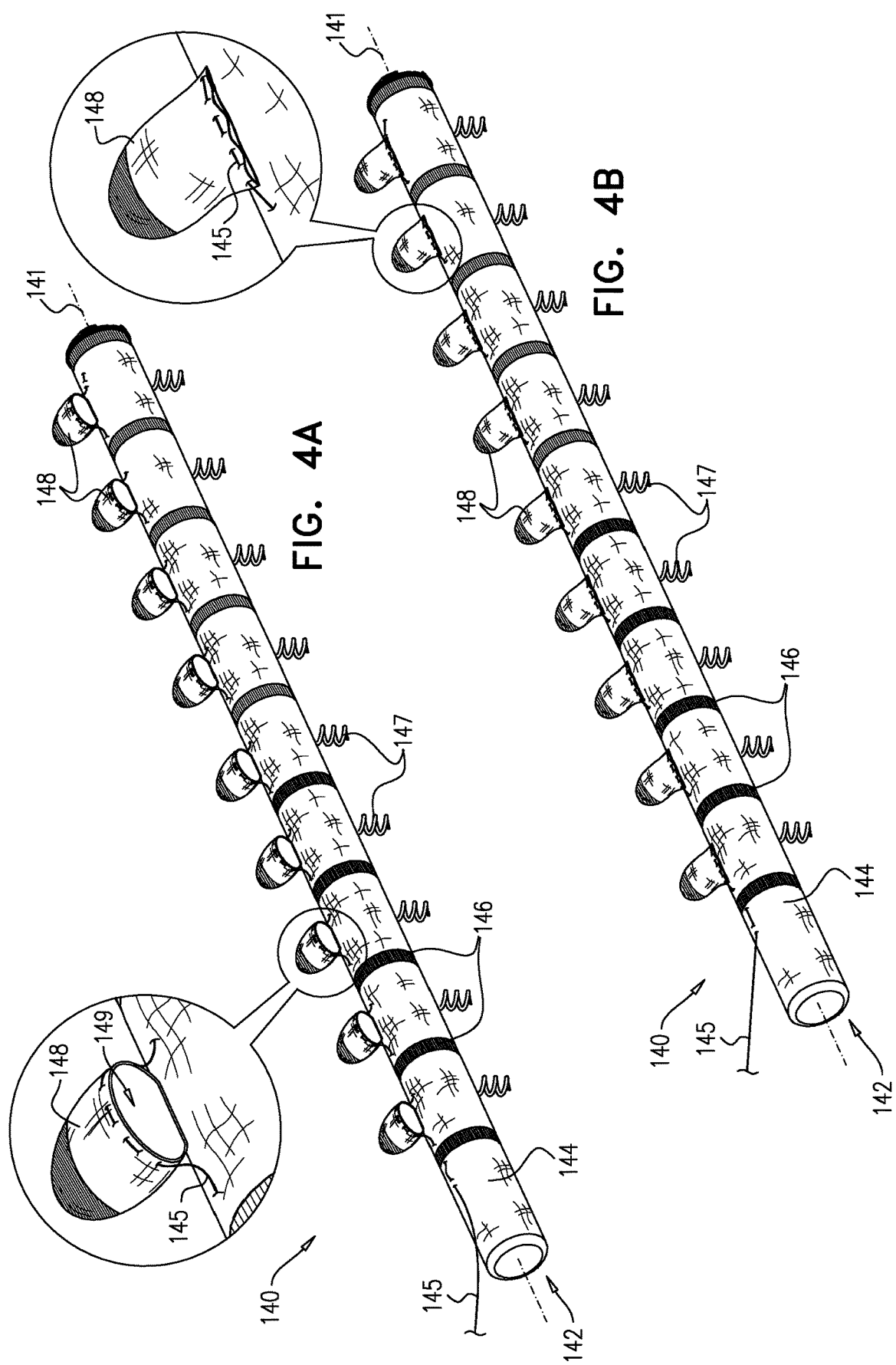

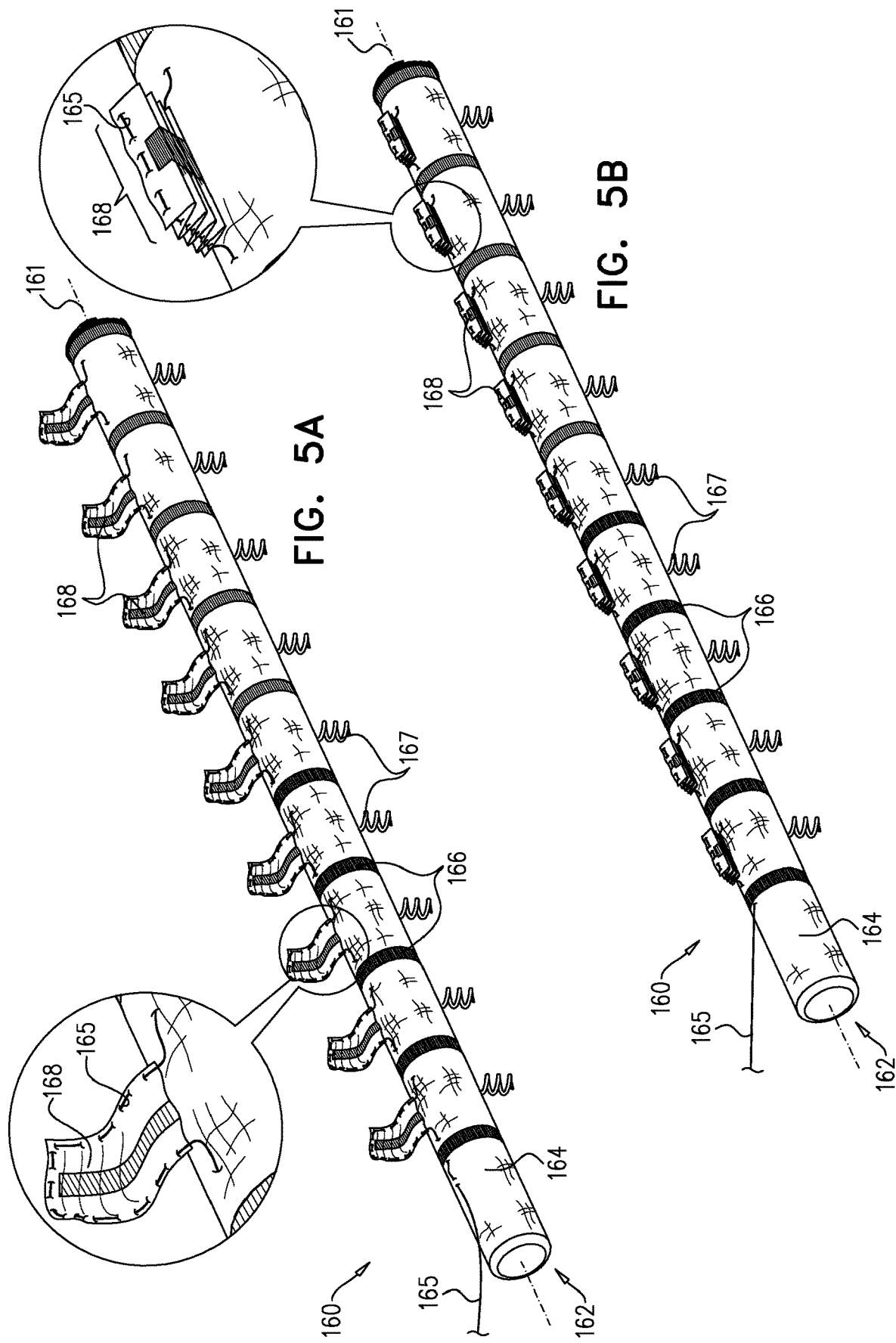

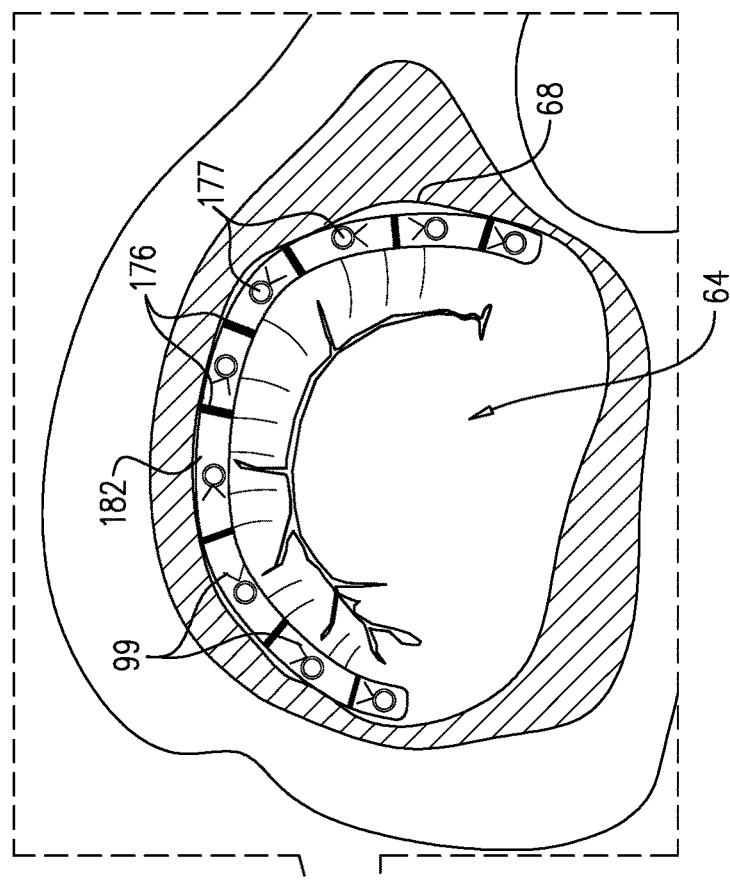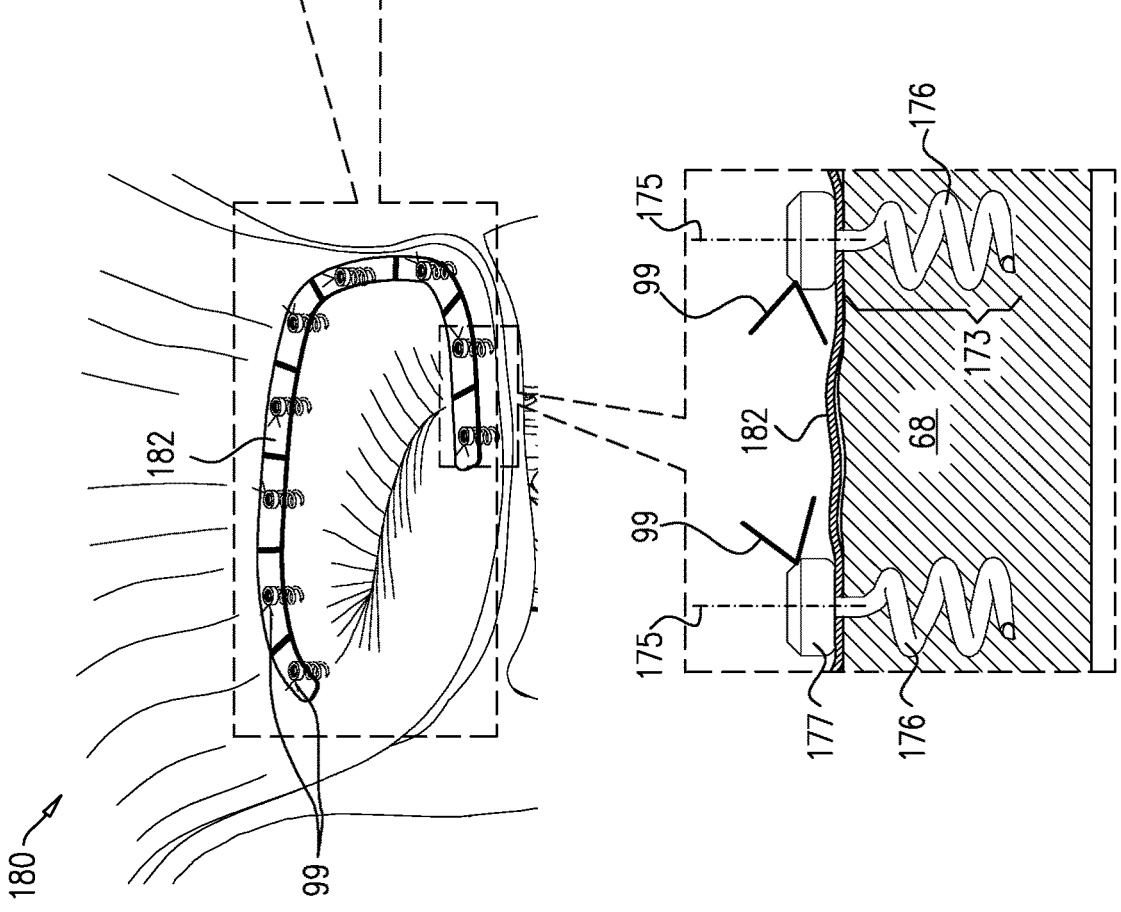
FIG. 6B

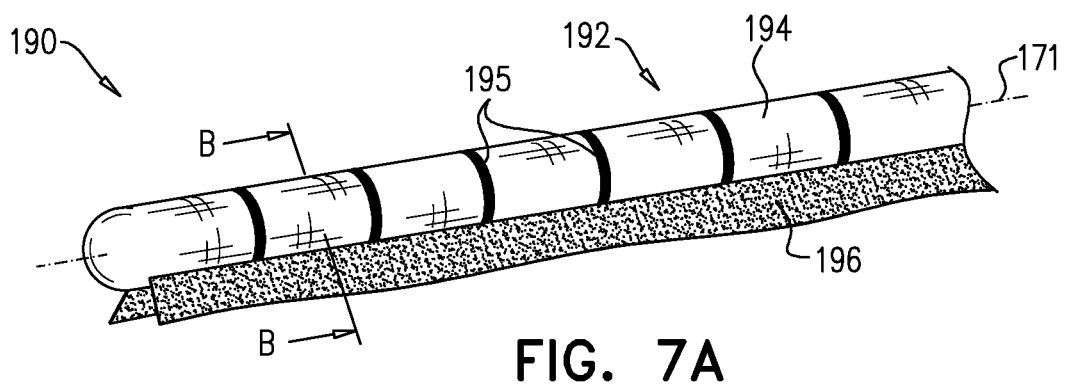
FIG. 7A
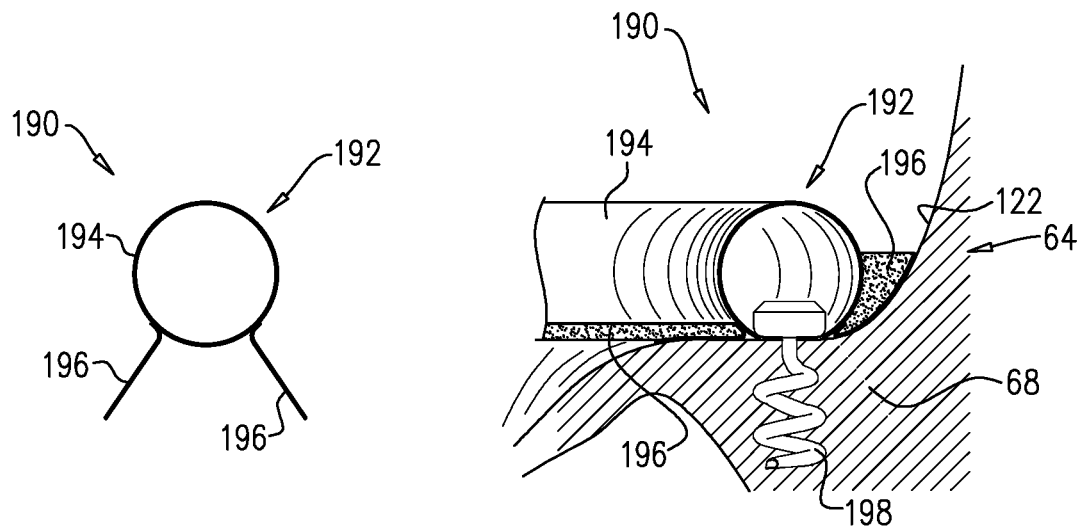
FIG. 7B
FIG. 7C

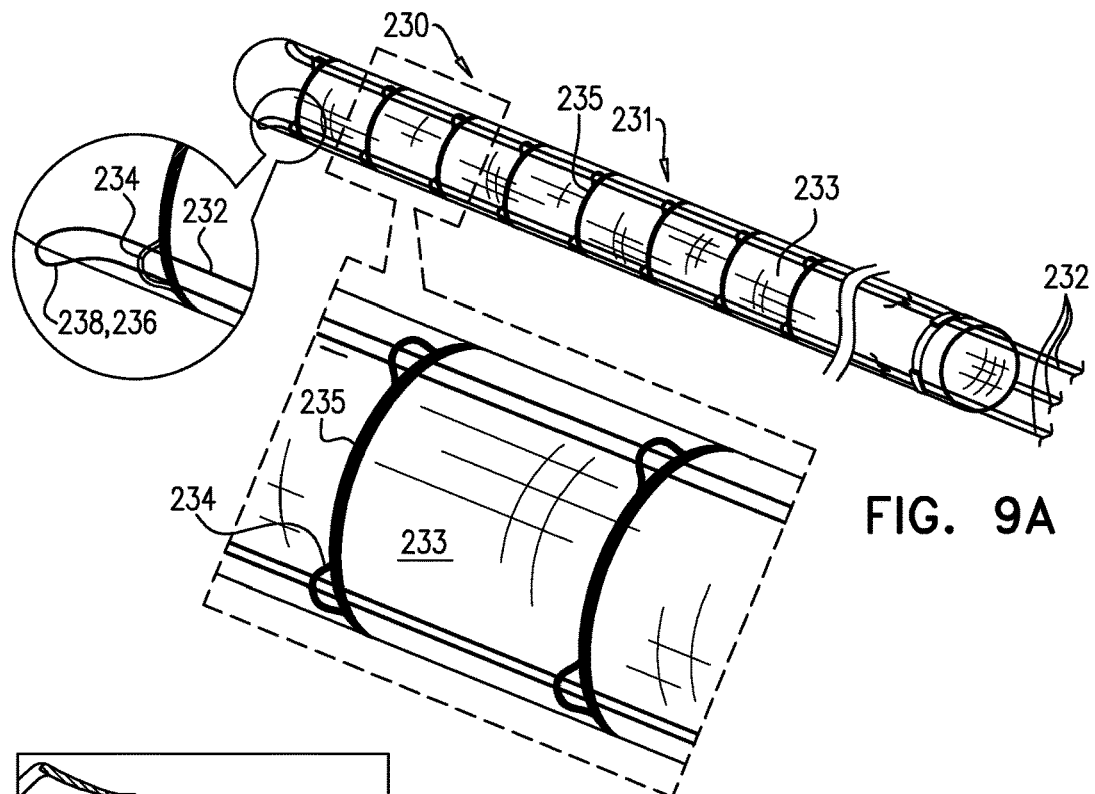
FIG. 9A
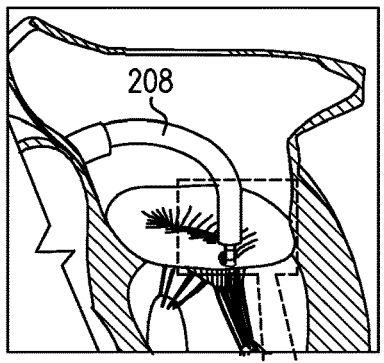
FIG. 9B
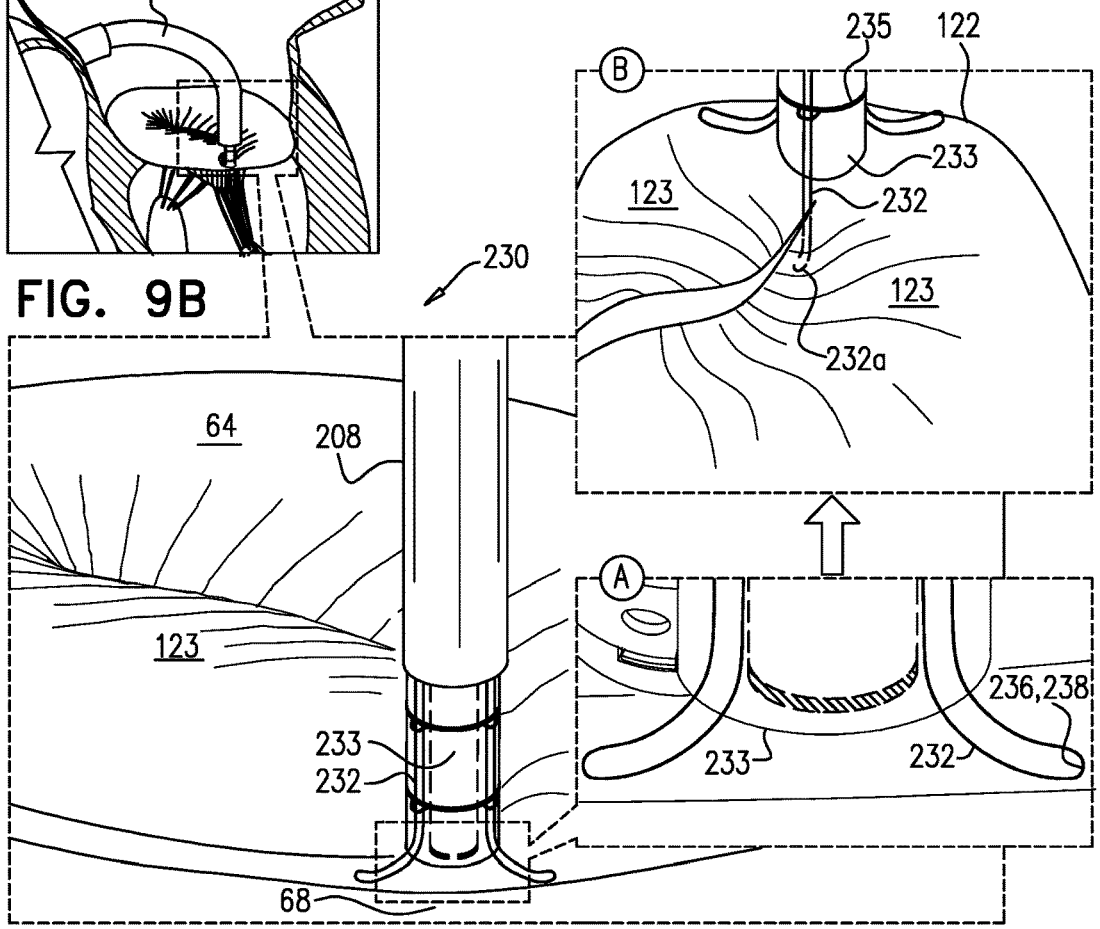

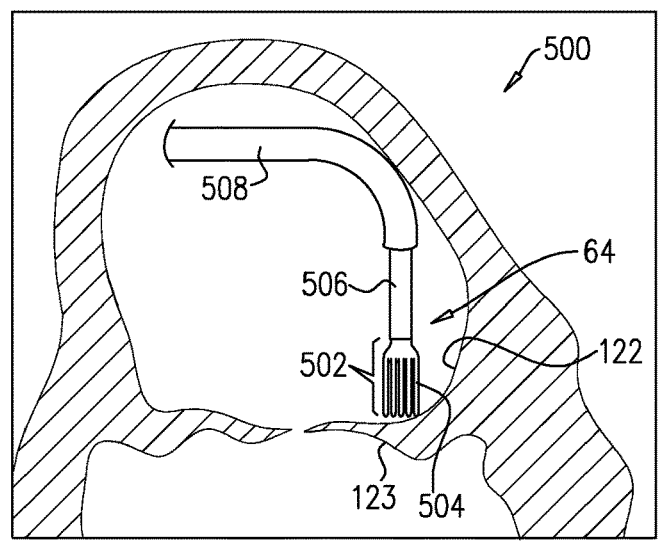
FIG. 33A
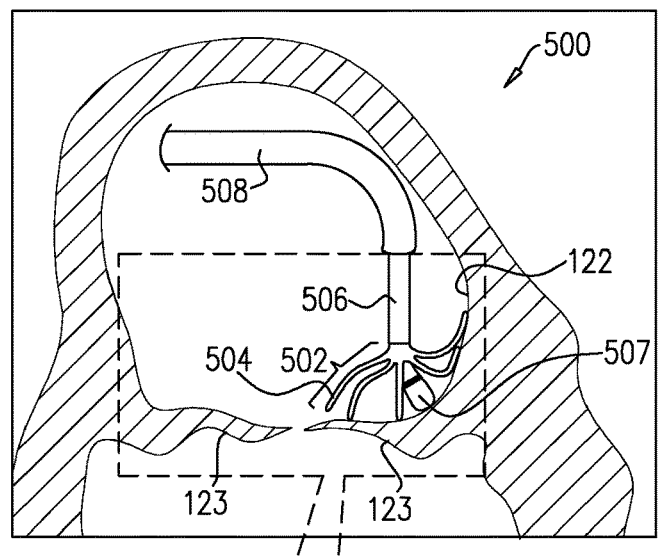
FIG. 33B
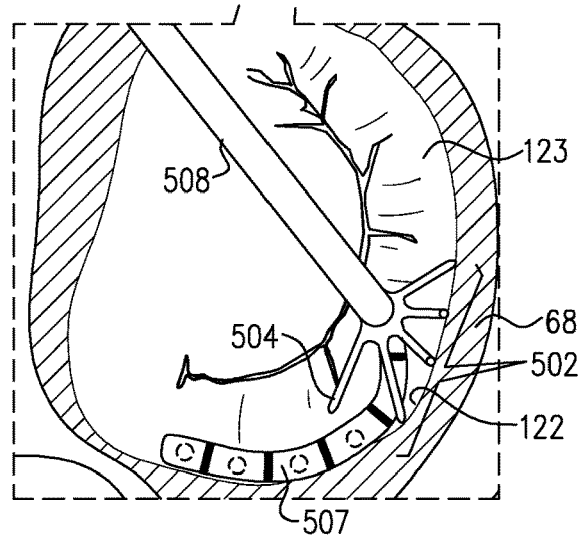

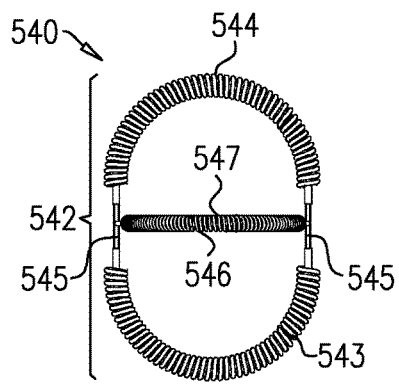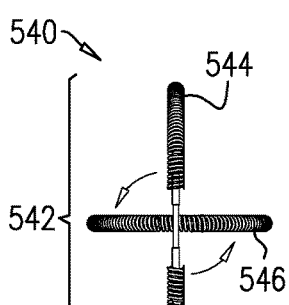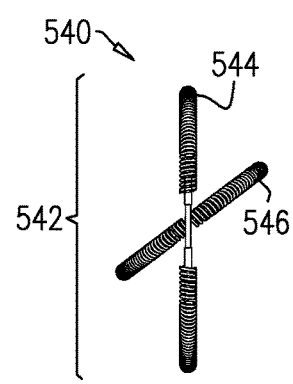
FIG. 37A   FIG. 37B   FIG. 37C
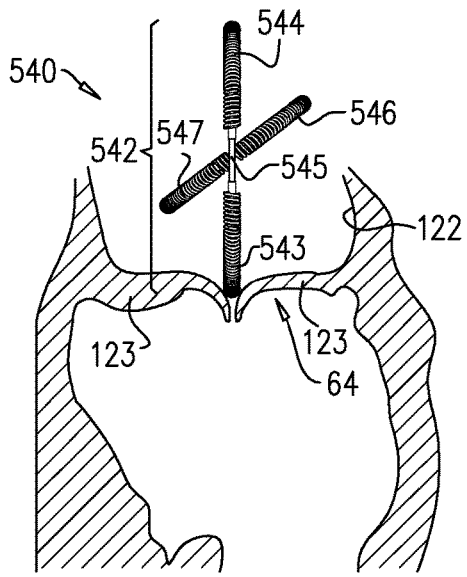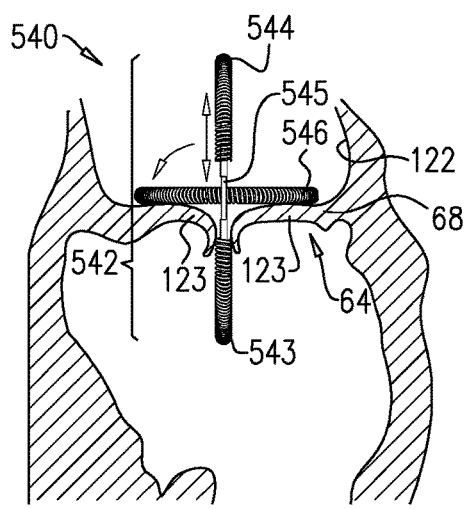
FIG. 37D   FIG. 37E
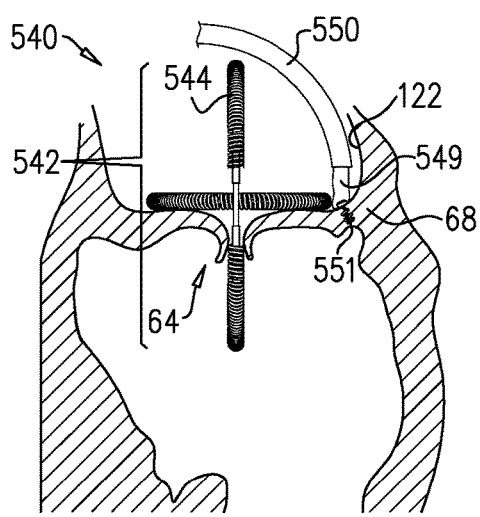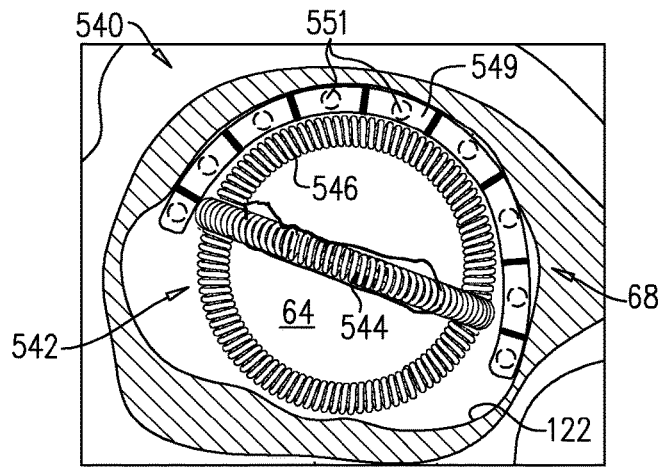
FIG. 37F   FIG. 37G

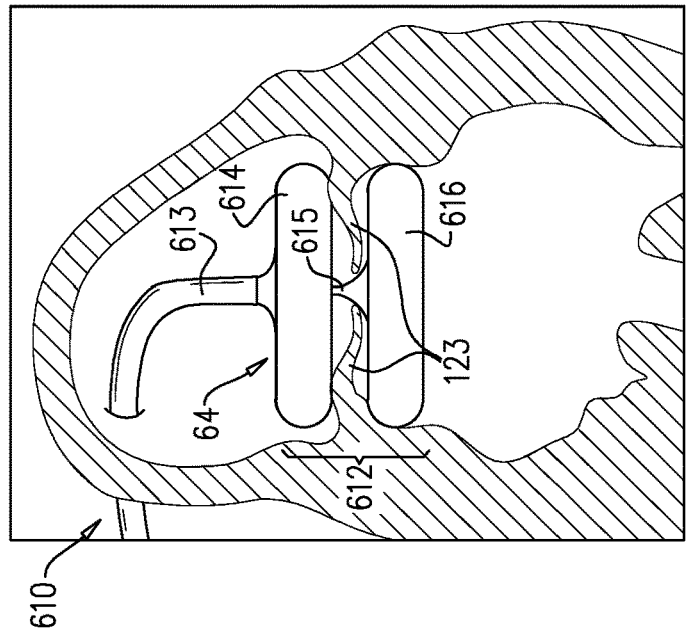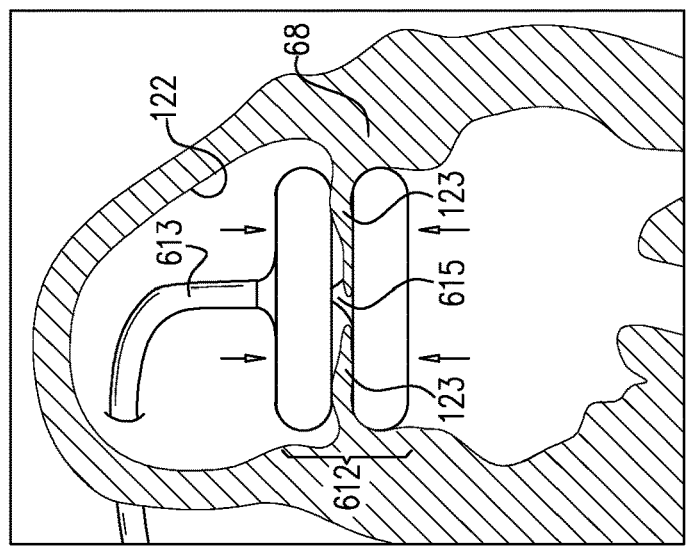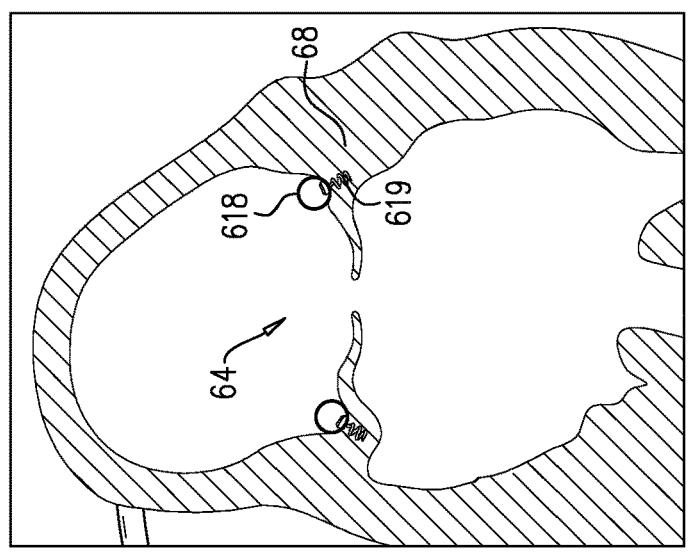
FIG. 43

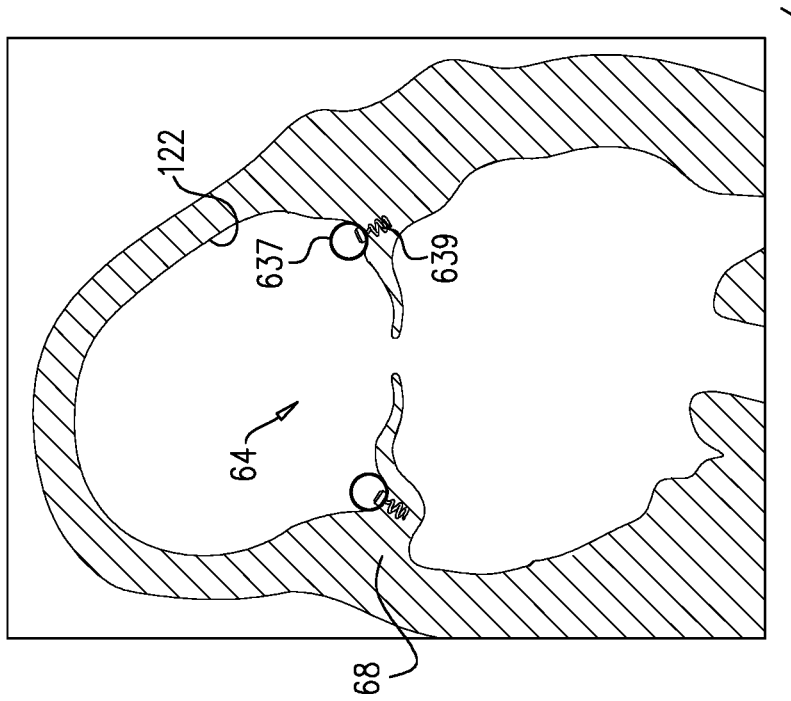
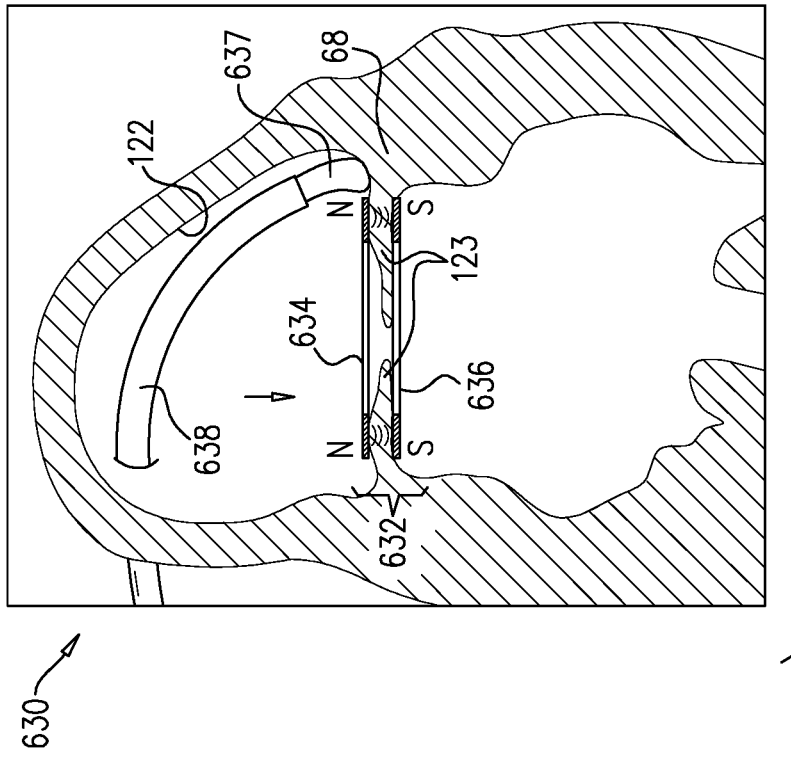
FIG. 45

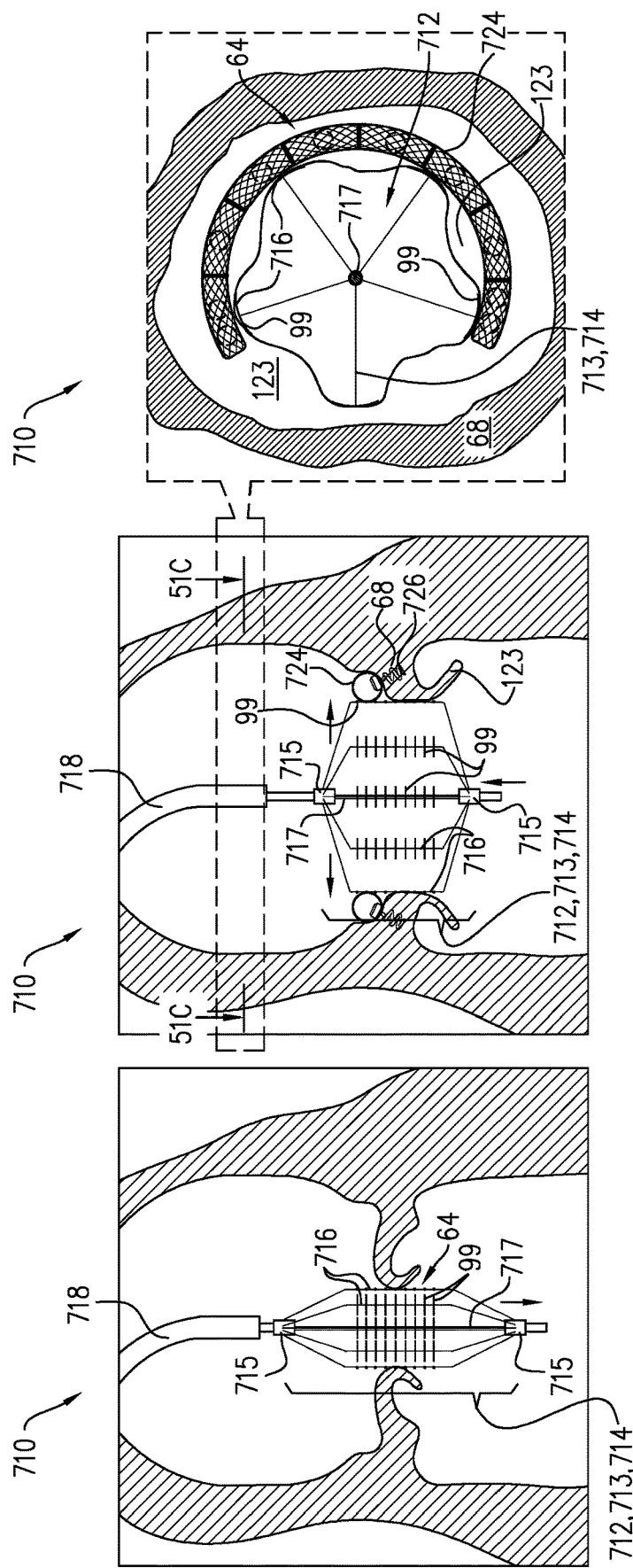

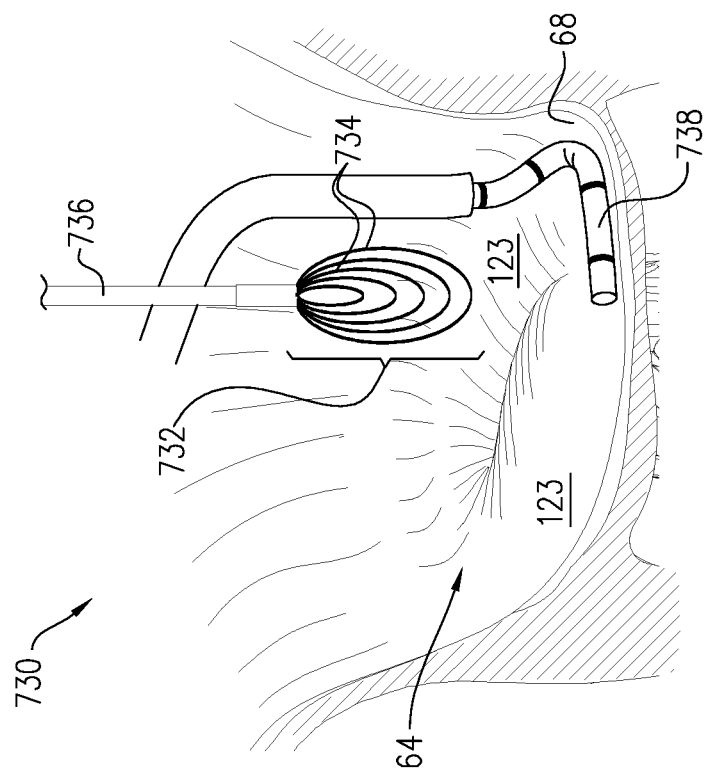
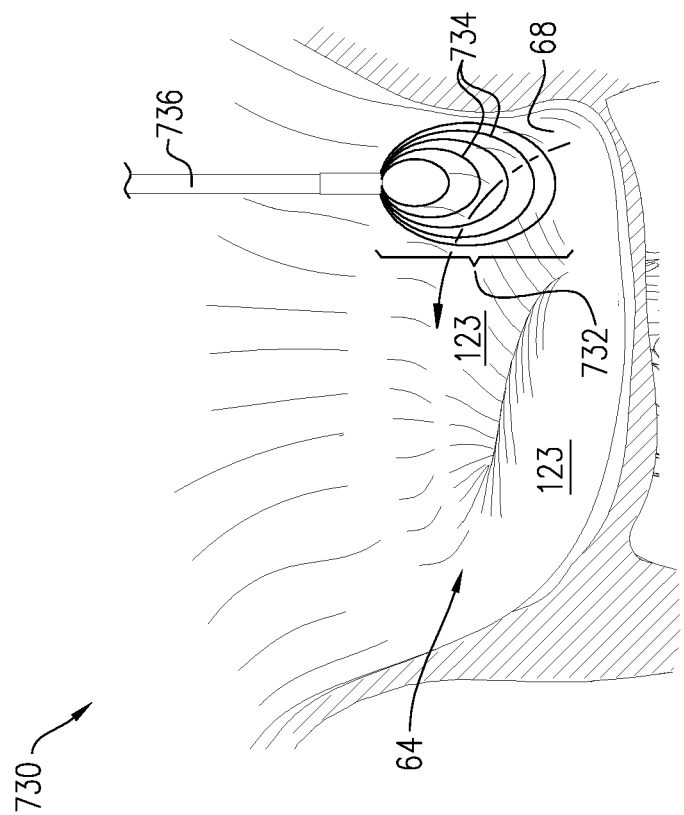
FIG. 52B
FIG. 52A

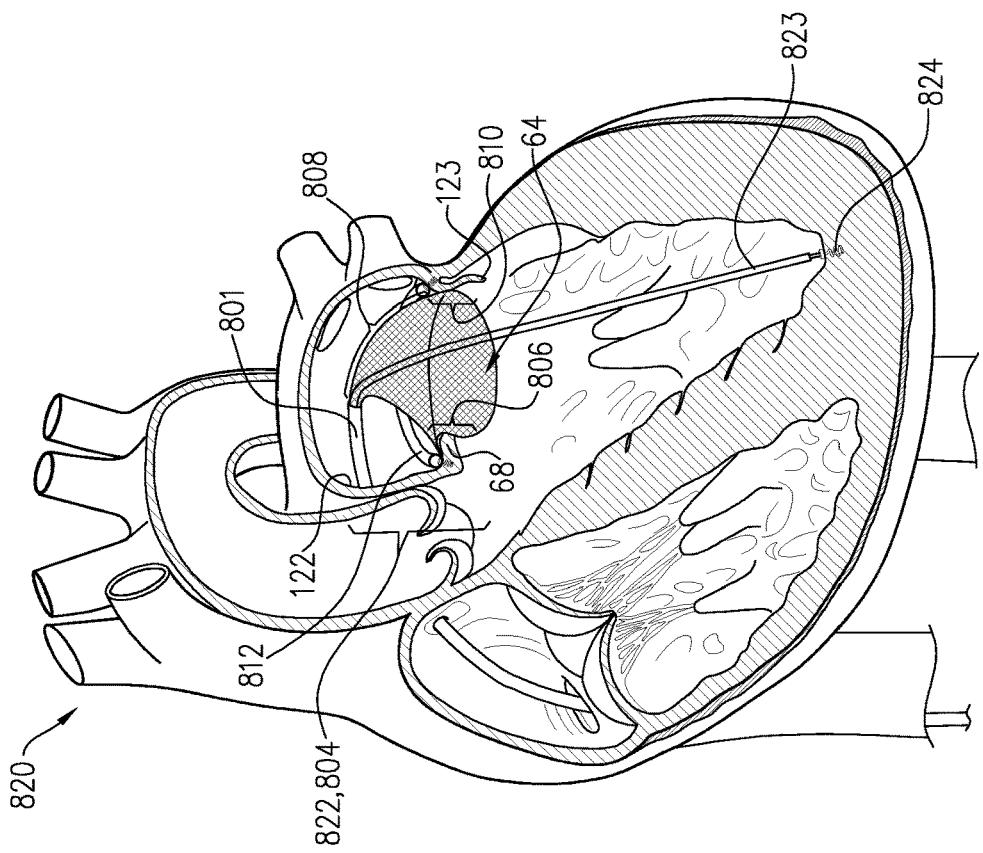
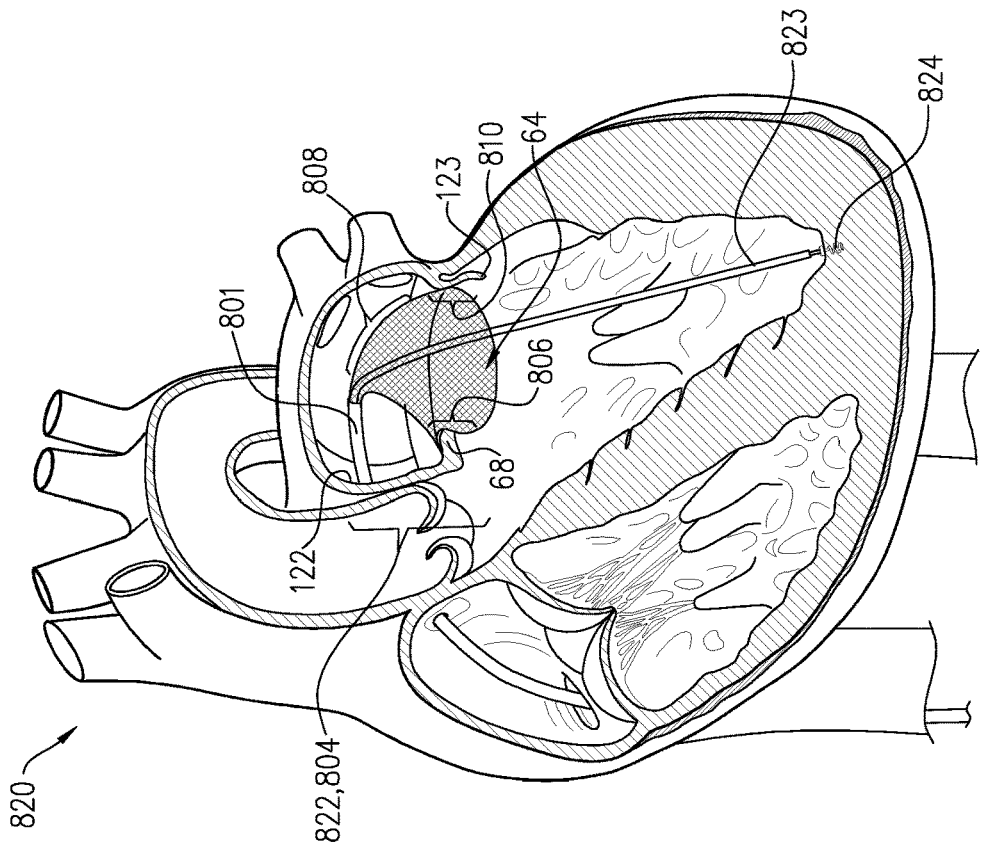

FLUOROSCOPIC VISUALIZATION OF HEART VALVE ANATOMY

CROSS-REFERENCE TO RELATED APPLICATIONS

The present application is the US National Phase of International Patent Application PCT/IL2020/050807 to Sheps et al., filed Jul. 22, 2020, and entitled "Fluoroscopic visualization of heart valve anatomy," which published as WO 2021/014439, and which claims the benefit of:

U.S. Provisional Patent Application No. 62/988,322, filed Mar. 11, 2020 and entitled "Fluoroscopic visualization of heart valve anatomy;" and U.S. Provisional Patent Application No. 62/877,785, filed Jul. 23, 2019 and entitled "Fluoroscopic visualization of heart valve anatomy,"

each of which is incorporated herein by reference in its entirety for all purposes.

BACKGROUND

Implantation of medical devices can be aided by fluoroscopy, for example, in catheter-based procedures involving cardiac valve repair and replacement. Patient exposure to fluoroscopy is ideally kept at a minimum.

SUMMARY OF THE INVENTION

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure can be included in the examples summarized here.

In some applications, systems and methods are provided for aiding implantation of cardiac devices under the guidance of fluoroscopy, using radiopaque devices which act as guides in order to facilitate enhanced imaging of the cardiac space during implantation of the cardiac implant, thereby minimizing patient exposure to fluoroscopy over a given period.

There is therefore provided, in accordance with some applications, a system and/or an apparatus for use with a subject, the system/apparatus including a visualization device or anatomy-marking device (e.g., an annulus-marking device, etc.) including a radiopaque material, and an implant for implantation along the native heart valve annulus of the subject. In some implementations, the visualization device, anatomy-marking device, or annulus-marking device is configured to provide a guide for implantation of the implant along the annulus during implantation, and retrievable following the implantation of the implant.

Throughout this application, the term annulus-marking device is often used for illustration, but the terms anatomy-marking device, heart valve-marking device, and visualization device can be substituted in place of the term "annulus-marking device" and, in any case, the devices can be used to mark or visualize other regions inside a patient's heart and/or other organs.

In some applications, the annulus-marking device and/or the radiopaque material are configured and shaped to define a base frame having a shape such that it tracks a circumference of a native heart valve annulus, and/or one or more struts projecting away from a plane defined by the base frame. The one or more struts can be configured to provide an indicator of one or more commissures of a native heart valve.

In some applications, the annulus-marking device is compressible during delivery toward the native heart valve, and expandable from a compressed state for positioning along the native heart valve annulus.

In an application, the annulus-marking device includes a superelastic material. In an application, the base frame and the one or more struts are fabricated from a single piece.

In an application, the one or more struts are sized so as to provide an indication as to a height of the native heart valve annulus.

In an application, the base frame is circular. In an application, the base frame is substantially D-shaped.

In an application, the base frame includes a wire.

In an application, the base frame includes an adjustment mechanism which expands and contracts a perimeter of the base frame.

In an application, the adjustment mechanism includes a wire that runs at least partially within a lumen of the base frame, and the wire is pullable to adjust the perimeter of the base frame.

In an application, the adjustment mechanism includes a wire that runs at least partially within a lumen of the base frame, and the wire is twistable to adjust the perimeter of the base frame.

In an application, the adjustment mechanism includes a wire that runs at least partially within a lumen of the base frame, and at least a portion of the base frame collapses telescopically in response to pulling of the wire.

In an application, the annulus-marking device includes a plurality of radiopaque filaments coupled at least to the base frame, each one of the plurality of filaments projecting radially away from the base frame and configured to mark the native heart valve annulus and tissue coupled thereto.

In an application, each one of the plurality of radiopaque filaments includes a material that is flexible.

There is further provided, in accordance with some applications, a method, including placing at a native heart valve annulus of a subject an annulus-marking device including a radiopaque material, implanting an implant along the native heart valve annulus of the subject using the annulus-marking device as a guide for implantation of the implant along the annulus under imaging. The method can further include retrieving the annulus-marking device following the implanting.

The annulus-marking device and/or the radiopaque material can be the same as or similar to any annulus-marking device and/or the radiopaque material described herein. In some implementations, the annulus-marking device and/or the radiopaque material are shaped to define a base frame having a shape such that it tracks a circumference of the native heart valve annulus, and/or one or more struts projecting away from a plane defined by the base frame, the one or more struts providing an indicator of one or more commissures of a native heart valve.

The annulus-marking device can be compressible during delivery toward the native heart valve, and expandable from a compressed state for positioning along the native heart valve annulus.

In an application, placing the annulus-marking device includes measuring a height of the annulus using the annulus-marking device.

In an application, the method further includes adjusting a perimeter of the base frame.

In an application, implanting under imaging includes implanting using fluoroscopy.

In an application, retrieving the annulus-marking device following the implanting includes constraining the annulus-marking device within a tool and extracting the annulus-marking device from the subject.

In an application, placing includes placing the annulus-marking device along an annulus of a mitral valve.

In an application, placing includes placing the annulus-marking device along an annulus of a tricuspid valve.

In an application, the annulus-marking device includes a plurality of radiopaque filaments coupled at least to the base frame, each one of the plurality of radiopaque filaments projecting radially away from the base frame, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a system and/or apparatus for use with a subject, the system/apparatus including an implant configured for placement along a native heart valve annulus. The implant including a body portion including flexible material, the body portion having a longitudinal axis that runs along a length of the body portion (e.g., when the implant and/or body portion is straightened), and an annulus-marking device, structure, or assembly including a plurality of radiopaque projections that project away from the longitudinal axis.

The implant can further include a contracting member coupled to the body portion. The contracting member can be coupled to and/or extend along or through the plurality of radiopaque projections in a manner in which during application of tension to the contracting member, the contracting member is configured to change a structural configuration of the plurality of radiopaque projections.

In an application, the contracting member is configured to compress the plurality of radiopaque projections in a radial direction toward the longitudinal axis of the body portion.

In an application, the contracting member is configured to contract the body portion during the application of tension to the contracting member.

In an application, the apparatus further includes an additional contracting member extending along the body portion, the additional contracting member being configured to contract the body portion.

In an application, the body portion includes a plurality of radiopaque markings configured to indicate placement of anchors along the body portion.

In an application, the contracting member extends along a perimeter of each one of the plurality of radiopaque projections.

In an application, the plurality of radiopaque projections are flexible and include a fabric.

In an application, the body portion and the plurality of radiopaque projections are flexible and include a fabric.

In an application, the each one of the plurality of radiopaque projections is shaped so as to define respective flat and planar element.

In an application, each flat and planar element has a longest dimension that is measured a long an axis that is at a nonzero angle with respect to the longitudinal axis of the body portion.

In an application, each one of the plurality of radiopaque projections is shaped so as to define a plurality of tubular elements.

In an application, the contracting member extends along a perimeter of each opening of each of the plurality of tubular elements.

In an application, each one of the plurality of tubular elements tapers away from the longitudinal axis of the body portion.

There is further provided, in accordance with some applications, a method, including placing at a native heart valve annulus of a subject an implant configured for placement along a native heart valve annulus and comprising a body portion and an annulus-marking device; deploying a plurality of tissue anchors through the body portion of the implant and into tissue of the native heart valve annulus under imaging and using the annulus-marking device as guidance; and changing a structural configuration of the implant.

The implant can be the same as or similar to other implants described herein. For example, in some implementations, the implant includes a body portion including flexible material, the body portion having a longitudinal axis that runs along a length of the body portion (e.g., when the implant and/or body portion is straightened), and an annulus-marking device including a plurality of radiopaque projections that project away from the longitudinal axis. The implant can include a contracting member coupled to the body portion. The contracting member can be coupled to and/or extend along or through the plurality of radiopaque projections in a manner in which during application of tension to the contracting member, the contracting member is configured to change a structural configuration of the plurality of radiopaque projections.

In some applications, changing a structural configuration of the implant comprises changing a structural configuration of the plurality of radiopaque projections by applying tension to the contracting member plurality of radiopaque projections by applying tension to the contracting member.

In an application, changing the structural configuration of the plurality of radiopaque projections includes compressing the plurality of radiopaque projections in the radial direction toward the longitudinal axis of the body portion.

In an application, applying the tension to the contracting member includes adjusting a perimeter of the implant by contracting the body portion using the contracting member.

In an application, the implant includes an additional contracting member extending along the body portion, and the method further includes adjusting a perimeter of the implant by contracting the body portion using the additional contracting member.

In an application, placing includes placing the implant along an annulus of a mitral valve.

In an application, placing includes placing the implant along an annulus of a tricuspid valve.

In an application, changing the structural configuration of the plurality of radiopaque projections includes sequentially changing the structural configuration of the plurality of radiopaque projections.

In an application, the body portion includes a plurality of radiopaque markings configured to indicate placement of anchors along the body portion and deploying the plurality of tissue anchors includes deploying each one of the plurality of tissue anchors in accordance with a respective radiopaque marking.

In an application, the contracting member extends along a perimeter of each one of the plurality of radiopaque projections, and changing the structural configuration of the plurality of radiopaque projections includes compressing the plurality of radiopaque projections by drawing each one of the plurality of radiopaque projections toward the longitudinal axis by contracting the contracting member along the perimeter of each one of the plurality of radiopaque projections.

In an application, the plurality of radiopaque projections are flexible and include a fabric.

In an application, the each one of the plurality of radiopaque projections is shaped so as to define a plurality of flat and planar elements and changing the structural configuration of the plurality of radiopaque projections includes drawing each one of the plurality of radiopaque projections toward the longitudinal axis by folding each one of the plurality of flat and planar elements.

In an application, each one of the plurality of radiopaque projections is shaped so as to define a plurality of tubular elements.

In an application, the contracting member extends along a perimeter of each opening of each of the plurality of tubular elements, and changing the structural configuration of the plurality of radiopaque projections includes closing each opening of each of the plurality of tubular elements.

In an application, each one of the plurality of tubular elements tapers away from the longitudinal axis of the body portion.

In an application, the method further includes viewing tissue of the native heart valve annulus and tissue coupled thereto under imaging the plurality of radiopaque projections.

In an application, viewing tissue includes imaging using fluoroscopy.

In an application, viewing the tissue of the native heart valve annulus and tissue coupled thereto includes imaging the plurality of radiopaque projections with respect to the tissue of the native heart valve annulus and the tissue coupled thereto by viewing the plurality of radiopaque projections against the tissue.

In an application, viewing the tissue of the native heart valve annulus includes imaging the plurality of radiopaque projections with respect to the tissue of the native heart valve annulus and the tissue coupled thereto by viewing movement of the plurality of radiopaque projections responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus, including a tissue anchor including a distal tissue-coupling element having a longitudinal axis measured from a distal end to a proximal end of the distal tissue-coupling element, the distal tissue-coupling element configured for anchoring into and/or securing to tissue of a native heart valve annulus; and an annulus-marking device coupled to the tissue anchor. In some implementations, the annulus-marking device includes a radiopaque material and/or is configured to project away from the longitudinal axis of the distal tissue-coupling element.

In an application, the distal tissue-coupling element is hollow, and the annulus-marking device extends through a lumen of the distal tissue-coupling element.

In an application, the tissue anchor includes a proximal head coupled to the proximal end of the distal tissue-coupling element, the annulus-marking device being coupled to the proximal head.

In an application, the apparatus further includes an annuloplasty structure including a tubular body portion, and the proximal head is configured to be disposed within the tubular body portion while the distal tissue-coupling element is configured to be anchored within the tissue of the native heart valve annulus.

In an application, the annulus-marking device is coupled to the distal tissue-coupling element.

In an application, the annulus-marking device is coupled to the distal end of the distal tissue-coupling element.

In an application, the apparatus further includes an annuloplasty structure including a fabric, and the annulus-marking device is configured to pass through the fabric of the annuloplasty structure.

In an application, the annulus-marking device includes one or more radiopaque filaments configured to mark the native heart valve annulus and tissue coupled thereto.

In an application, each one of the one or more radiopaque filaments includes a material that is flexible.

There is further provided, in accordance with some applications, a method, including marking a location of a native heart valve annulus of a subject by implanting in tissue of the native heart valve annulus a tissue anchor including a distal tissue-coupling element having a longitudinal axis measured from a distal end to a proximal end of the distal tissue-coupling element, the distal tissue-coupling element configured for anchoring into tissue of the native heart valve annulus.

An annulus-marking device can be coupled to the tissue anchor, the annulus-marking device including a radiopaque material. The annulus-marking device can be configured to project away from the longitudinal axis of the distal tissue-coupling element.

The method further includes imaging the location, and during the imaging, viewing the annulus-marking device with respect to tissue of the native heart valve annulus.

In an application, imaging tissue includes imaging using fluoroscopy.

In an application, marking the location includes marking the location along an annulus of a mitral valve.

In an application, marking the location includes marking the location along an annulus of a tricuspid valve.

In an application, the method further includes viewing tissue of the native heart valve annulus and tissue coupled thereto under imaging the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus includes imaging the annulus-marking device with respect to the tissue of the native heart valve annulus and the tissue coupled thereto by viewing movement of the annulus-marking device responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

In an application, the tissue anchor includes a proximal head coupled to the proximal end of the distal tissue-coupling element, the annulus-marking device being coupled to the proximal head.

In an application, the method further includes implanting along the native heart valve annulus an annuloplasty structure including a tubular body portion, and implanting the tissue anchor includes positioning the proximal head is within the tubular body portion while implanting the distal tissue-coupling element within the tissue of the native heart valve annulus.

In an application, the annulus-marking device is coupled to the distal tissue-coupling element.

In an application, the annulus-marking device is coupled to the distal end of the distal tissue-coupling element.

In an application, the method further includes implanting along the native heart valve annulus an annuloplasty structure including a fabric, and implanting the tissue anchor includes passing the annulus-marking device through the fabric of the annuloplasty structure.

In an application, the passing the annulus-marking device through the fabric of the annuloplasty structure includes passing the annulus-marking device through the fabric of a portion of the annuloplasty structure before the portion of the annuloplasty structure is positioned along the native heart valve annulus, and the method further includes imaging the native heart valve annulus before the portion of the annuloplasty structure is positioned along the native heart valve annulus.

In an application, the annulus-marking device includes one or more radiopaque filaments configured to mark the native heart valve annulus and tissue coupled thereto.

In an application, each one of the one or more radiopaque filaments includes a material that is flexible.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus for use with a subject, the system/apparatus including an implant configured for placement along a native heart valve annulus. The implant can include a body portion including flexible material, the body portion having a longitudinal axis that runs along a length of the body portion (e.g., when the implant and/or body portion is straightened). The implant can also include an annulus-marking device including one or more planar radiopaque fins that extends along at least a portion of the body portion ad projects away from the longitudinal axis, each one of the one or more planar radiopaque fins has a longest dimension that is measured along the longitudinal axis.

In an application, the body portion includes a plurality of radiopaque markings configured to indicate placement of anchors along the body portion.

In an application, the one or more planar radiopaque fins includes a flexible fabric.

In an application, the one or more planar radiopaque fins includes two or more planar radiopaque fins.

In an application, the apparatus further includes at least one tissue anchor deployable through the body portion of the implant in-between the two or more planar radiopaque fins.

There is further provided, in accordance with some applications, a method, including placing at a native heart valve annulus of a subject an implant configured for placement along a native heart valve annulus, the implant including a body portion including flexible material; and an annulus-marking device. The method further including deploying at least one tissue anchor through the body portion of the implant and into tissue of the native heart valve annulus under imaging and using the annulus-marking device as guidance.

In some implementations, the body portion has a longitudinal axis that runs along a length of the body portion (e.g., when the implant and/or body portion is straightened), and the annulus-marking devices includes one or more planar radiopaque fins that extends along at least a portion of the body portion and projects away from the longitudinal axis. In some implementations, each one of the one or more planar radiopaque fins has a longest dimension that is measured along the longitudinal axis.

In an application, deploying under imaging includes imaging using fluoroscopy.

In an application, placing includes placing the implant along an annulus of a mitral valve.

In an application, placing includes placing the implant along an annulus of a tricuspid valve.

In an application, the body portion includes a plurality of radiopaque markings configured to indicate placement of anchors along the body portion, and deploying the plurality of tissue anchors includes deploying each one of the plurality of tissue anchors in accordance with a respective radiopaque marking.

In an application, the one or more planar radiopaque fins are flexible and include a fabric.

In an application, the one or more planar radiopaque fins includes two or more planar radiopaque fins.

In an application, deploying the at least one tissue anchor through the body portion of the implant includes deploying the at least one tissue anchor through the body portion of the implant in-between the two or more planar radiopaque fins.

In an application, the method further includes viewing tissue of the native heart valve annulus and tissue coupled thereto under imaging the one or more planar radiopaque fins.

In an application, viewing the tissue of the native heart valve annulus and tissue coupled thereto includes imaging the one or more planar radiopaque fins with respect to the tissue of the native heart valve annulus and the tissue coupled thereto by viewing the one or more planar radiopaque fins against the tissue.

In an application, viewing the tissue of the native heart valve annulus includes imaging the one or more planar radiopaque fins with respect to the tissue of the native heart valve annulus and the tissue coupled thereto by viewing movement of the one or more planar radiopaque fins responsively to movement of the tissue.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus for use with a subject, the system/apparatus including an implant configured for placement along a native heart valve annulus of the subject, the implant including a body portion including a flexible material. The system/apparatus also including an annulus-marking device.

The annulus-marking device can be the same as or similar to other annulus-marking devices herein. For example, in some implementations, the annulus-marking device includes a scaffolding including radiopaque material. The scaffolding can be collapsible and expandable and configured, when expanded, to run alongside at least one side of the body portion of the implant. In some implementations, a plurality of radiopaque filaments are coupled to the scaffolding at at least a distal end of the scaffolding, the plurality of filaments being configured to mark the native heart valve annulus and/or tissue coupled thereto.

In an application, the body portion includes a plurality of radiopaque markings configured to indicate placement of anchors along the body portion.

In an application, each one of the plurality of radiopaque filaments includes a material that is flexible.

In an application, the scaffolding includes a plurality of struts collectively arranged in a triangular shape, and the scaffolding is generally planar and runs alongside a lateral wall of the body portion when the scaffolding is expanded.

In an application, the annulus-marking device is coupled to a delivery tool which is configured to deliver the implant to the native heart valve annulus, and the annulus-marking device is retrievable upon removal of the delivery tool from the subject.

In an application, the delivery tool is configured to surround a portion of the body portion of the implant, and the annulus-marking device is configured to surround the body portion of the implant at least in part.

In an application, the delivery tool includes a fin that is coupled to a distal portion of the delivery tool and to a portion of the scaffolding in a manner in which movement of the fin responsively to blood flow rotationally orients the scaffolding with respect to the body portion of the implant.

In an application, the scaffolding is coupled to a ring at a proximal end of the scaffolding, the ring surrounding at least a portion of the body portion of the implant and moveable proximally and distally with respect to the body portion of the implant in a manner in which the scaffolding is moveable to multiple locations along the body portion of the implant.

In an application, the scaffolding is shaped so as to partially surround a given portion of the body portion of the implant, the plurality of radiopaque filaments includes a first subset of radiopaque filaments having a first length and a second subset of filaments having a second length that is greater than the first length, and the first and second subsets are configured to rotationally orient the scaffolding with respect to the implant.

In an application, the scaffolding is semitubular. In an application, the scaffolding is planar and generally triangular. In an application, the scaffolding is frustoconical. However, other shapes are also possible.

In an application, the scaffolding is shaped so as to partially surround a given portion of the body portion of the implant, the plurality of radiopaque filaments includes a first subset of radiopaque filaments having a first rigidity and a second subset of filaments having a second rigidity that is greater than the first rigidity, and the first and second subsets are configured to rotationally orient the scaffolding with respect to the implant.

In an application, the scaffolding is semitubular. In an application, the scaffolding is planar and generally triangular. In an application, the scaffolding is frustoconical. However, other shapes are also possible.

In an application, the scaffolding includes a plurality of struts collectively arranged in a frustoconical shape, and the scaffolding surrounds at least a portion of the body portion of the implant.

In an application, the scaffolding is moveable proximally and distally with respect to the body portion of the implant in a manner in which the scaffolding is moveable to multiple locations along the body portion of the implant.

There is further provided, in accordance with some applications, a method, including placing at a native heart valve annulus of a subject an implant including a body portion including flexible material; and viewing the placing under imaging by imaging an annulus-marking device.

In some applications, the annulus-marking device comprises a scaffolding including radiopaque material, the scaffolding being collapsible and expandable and configured, when expanded, to run alongside at least one side of the body portion of the implant. In some implementations, a plurality of radiopaque filaments are coupled to the scaffolding at at least a distal end of the scaffolding, the plurality of filaments being configured to mark the native heart valve annulus and tissue coupled thereto.

In an application, viewing the placing further includes imaging a plurality of radiopaque markings of the body portion of the implant, and deploying anchors along the body portion in accordance with the imaging the plurality of radiopaque markings of the body portion of the implant.

In an application, each one of the plurality of radiopaque filaments includes a material that is flexible.

In an application, the scaffolding includes a plurality of struts collectively arranged in a triangular shape, the scaffolding is generally planar and runs alongside a lateral wall of the body portion when the scaffolding is expanded, and imaging the annulus-marking device includes imaging the triangular shape of the scaffolding with respect to the tissue and the body portion of the implant.

In an application, placing the implant includes delivering the implant using a delivery tool that is coupled to the annulus-marking device, and the method further includes retrieving the annulus-marking device during removing of the delivery tool from the subject.

In an application, the delivery tool is configured to surround a portion of the body portion of the implant, and the annulus-marking device is configured to surround the body portion of the implant at least in part.

In an application, the delivery tool includes a fin that is coupled to a distal portion of the delivery tool and to a portion of the scaffolding, and the method further includes rotationally orienting the scaffolding with respect to the body portion of the implant responsively to movement of the fin responsively to blood flow.

In an application, the scaffolding is coupled to a ring at a proximal end of the scaffolding, the ring surrounding at least a portion of the body portion of the implant and moveable proximally and distally with respect to the body portion of the implant, and the method further includes facilitating moving of the scaffolding to multiple locations along the body portion of the implant.

In an application, the scaffolding is shaped so as to partially surround a given portion of the body portion of the implant, the plurality of radiopaque filaments includes a first subset of radiopaque filaments having a first length and a second subset of filaments having a second length that is greater than the first length, and the method further includes rotationally orienting the scaffolding with respect to the implant using the first and second subsets.

In an application, the scaffolding is semitubular. In an application, the scaffolding is planar and generally triangular. In an application, the scaffolding is frustoconical. Other shapes are also possible.

In an application, the scaffolding is shaped so as to partially surround a given portion of the body portion of the implant, the plurality of radiopaque filaments includes a first subset of radiopaque filaments having a first rigidity and a second subset of filaments having a second rigidity that is greater than the first rigidity, and the method further includes rotationally orienting the scaffolding with respect to the implant using the first and second subsets.

In an application, the scaffolding is semitubular. In an application, the scaffolding is planar and generally triangular. In an application, the scaffolding is frustoconical. Other shapes are also possible.

In an application, the scaffolding includes a plurality of struts collectively arranged in a frustoconical shape, and the scaffolding surrounds at least a portion of the body portion of the implant.

In an application, the scaffolding is moveable proximally and distally with respect to the body portion of the implant, and the method further includes facilitating moving of the scaffolding to multiple locations along the body portion of the implant.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus for use with a subject, the system/apparatus including an annulus-marking device including a radiopaque material and an implant for implantation along the annulus of the valve of the subject.

The annulus-marking device and/or radiopaque material can be the same as or similar to other annulus-marking devices and/or radiopaque materials described elsewhere herein. For example, in some implementations, the annulus-marking device and/or radiopaque material is shaped to define a tubular stent body having a central longitudinal axis and configured for placement within a native heart valve of the subject; and/or a plurality of extensions coupled to a proximal end of the tubular stent body and projecting away from the longitudinal axis of the stent body, the plurality of extensions configured for placement along a circumference of an annulus of the native heart valve.

The annulus-marking device can be compressible during delivery toward the native heart valve, and expandable from a compressed state for positioning in the native heart valve.

In an application, the annulus-marking device is configured to provide a guide for implantation of the implant along the annulus during implantation and is retrievable following the implantation of the implant.

In an application, the annulus-marking device includes a superelastic material.

In an application, the stent body and the plurality of extensions are fabricated from a single piece.

In an application, the tubular stent body includes two or more prosthetic leaflets.

In an application, the apparatus further includes a plurality of anchors, each anchor of the plurality of anchors being configured to anchor the implant to the annulus of the native valve, and each one of the anchors is configured for implantation between adjacent extensions of the plurality of extensions.

There is further provided, in accordance with some applications, a method, including placing at a native heart valve of a subject an annulus-marking device including a radiopaque material shaped to define: (1) a tubular stent body having a central longitudinal axis and configured for placement within the native heart valve of the subject; and (2) a plurality of extensions coupled to a proximal end of the tubular stent body and projecting away from the longitudinal axis of the stent body, the plurality of extensions configured for placement along a circumference of an annulus of the native heart valve. The method further includes implanting an implant along the annulus using the annulus-marking device as a guide for implantation of the implant along the annulus under imaging. The method can include retrieving the annulus-marking device following the implanting.

In some applications, the annulus-marking device is compressible during delivery toward the native heart valve, and expandable from a compressed state for positioning in the native heart valve.

In an application, implanting under imaging includes implanting using fluoroscopy.

In an application, retrieving the annulus-marking device following the implanting includes constraining the annulus-marking device within a tool and extracting the annulus-marking device from the subject.

In an application, placing includes placing the annulus-marking device within a mitral valve. In an application, placing includes placing the annulus-marking device within a tricuspid valve.

In an application, implanting the implant includes anchoring the implant to the annulus of the native valve by deploying a respective anchor of a plurality of anchors between adjacent extensions of the plurality of extensions.

In an application, retrieving the annulus-marking device following the implanting includes sliding the plurality of extensions from under the implant.

In an application, the method further includes viewing tissue of the native heart valve annulus and tissue coupled thereto using the plurality of extensions.

In an application, viewing the tissue of the native heart valve annulus and tissue coupled thereto includes imaging the annulus-marking device with respect to the tissue of the native heart valve annulus and the tissue coupled thereto by viewing the plurality of extensions against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of extensions responsively to movement of the tissue.

This method can be performed on a living animal or on a simulation, such as on a cadaver, cadaver heart, simulator (e.g. with the body parts, tissue, etc. being simulated), etc.

There is further provided, in accordance with some applications, a method, including placing at a native heart valve annulus of a subject an annulus-marking device including a mapping catheter, using the mapping catheter, generating a map of the native heart valve annulus under imaging, and responsively to generating the map, implanting an implant at the native heart valve annulus under imaging.

In an application, implanting under imaging includes implanting using fluoroscopy.

In an application, the method further includes retrieving the annulus-marking device following the generating of the map, and subsequently, extracting the annulus-marking device from the subject.

In an application, placing includes placing the annulus-marking device along an annulus of a mitral valve. In an application, placing includes placing the annulus-marking device along an annulus of a tricuspid valve.

In an application, the mapping catheter includes radiopaque material, and generating the map includes imaging the mapping catheter under fluoroscopy.

In an application, the mapping catheter includes magnetic subunits, and generating the map includes generating a magnetic field and mapping the valve under magnetic imaging.

In an application, the mapping catheter includes electrodes, and generating the map includes generating the using the electrodes.

In an application, the method further includes retrieving the mapping catheter. In an application, retrieving the mapping catheter includes retrieving the mapping catheter prior to the implanting, and the implanting includes implanting under the guidance of the map generated by the mapping catheter. In an application, retrieving the mapping catheter includes retrieving the mapping catheter subsequently to the implanting.

In an application, the method further includes viewing tissue of the native heart valve annulus and tissue coupled thereto using the mapping catheter.

In an application, viewing the tissue of the native heart valve annulus and tissue coupled thereto includes imaging the annulus-marking device with respect to the tissue of the native heart valve annulus and the tissue coupled thereto by viewing the mapping catheter against the tissue.

In an application, viewing the tissue of the native heart valve annulus and tissue coupled thereto includes imaging the annulus-marking device with respect to the tissue of the native heart valve annulus and the tissue coupled thereto by viewing movement of the mapping catheter responsively to movement of the tissue.

This method can be performed on a living animal or on a simulation, such as on a cadaver, cadaver heart, simulator (e.g. with the body parts, tissue, etc. being simulated), etc.

There is further provided, in accordance with some applications, a method, including placing within at least an atrium of a heart of a subject an annulus-marking device including a radiopaque material shaped to define a plurality of expandable elements which expand radially within the atrium such that the plurality of expandable elements provides an indication as to a location of a native heart valve annulus of a native heart valve of the subject. In some applications, the annulus-marking device is compressible during delivery toward the native heart valve, and expandable from a compressed state for positioning at least within the atrium. The method further includes implanting an implant along the native heart valve annulus of the subject using the annulus-marking device as a guide for implantation of the implant along the annulus under imaging. In some applications, the method includes retrieving the annulus-marking device following the implanting.

In an application, implanting under imaging includes implanting using fluoroscopy. In an application, retrieving the annulus-marking device following the implanting includes constraining the annulus-marking device within a tool and extracting the annulus-marking device from the subject.

In an application, placing includes placing the annulus-marking device in a left atrium. In an application, placing includes placing the annulus-marking device in a right atrium.

In an application, the plurality of expandable elements collectively form the annulus-marking device into a generally spherical shape, and implanting the implant includes positioning the implant between the annulus-marking device and tissue of an atrial wall.

In an application, the plurality of expandable elements include a plurality of woven radiopaque fibers assuming a mesh.

In an application, the plurality of expandable elements include a plurality of curved wires. In an application, implanting the implant includes positioning the implant between the annulus-marking device and tissue of an atrial wall and deploying a tissue anchor at a site along the annulus marked between successive curved wires.

In an application, each one of the plurality of curved wires has a proximal end and a distal end and a middle section between the proximal and distal ends.

In an application, a collective proximal diameter of the proximal ends of the plurality of expandable elements is equal to a collective distal diameter of the distal ends of the plurality of expandable elements, and a collective middle diameter of the plurality of expandable elements is greater than the collective proximal diameter and greater than the collective distal diameter.

In an application, the plurality of expandable elements collectively form the annulus-marking device into a partially-spherical shape, and implanting an implant includes positioning the implant between the annulus-marking device and tissue of an atrial wall and deploying a tissue anchor at a site along the annulus marked between successive expandable elements.

In an application, the plurality of expandable elements include a plurality of struts collectively forming a partially-spherical stent. In an application, the partially-spherical stent includes a plurality of radiopaque filaments coupled at distal end of the partially-spherical stent, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

In an application, the plurality of expandable elements include a plurality of curved wires.

In an application, placing the annulus-marking device including expanding the annulus-marking device in a manner in which a distal end of each one of the plurality of expandable elements is disposed within the atrium.

In an application, placing the annulus-marking device including expanding the annulus-marking device in a manner in which a distal end of each one of the plurality of expandable elements is disposed within a ventricle of the heart.

In an application, the plurality of expandable elements collectively form the annulus-marking device into a partially-bulbous shape, and implanting the implant includes positioning the implant between the annulus-marking device and tissue of an atrial wall and deploying a tissue anchor at a site along the annulus marked between successive expandable elements.

In an application, the method further includes delivering a radiopaque helical stent between the plurality of expandable elements. In an application, delivering the helical stent includes delivering the helical stent between native leaflets of the native heart valve. In an application, delivering the helical stent between native leaflets of the native heart valve includes positioning a distal end of the helical stent in a ventricle of the heart of the subject.

In an application, the plurality of expandable elements include a plurality of curved wires each having proximal and distal ends and a middle section between the proximal and distal ends.

In an application, a collective proximal diameter of the proximal ends of the plurality of expandable elements is smaller than a collective distal diameter of the distal ends of the plurality of expandable elements, and a collective middle diameter of the plurality of expandable elements is greater than the collective proximal diameter and greater than the collective distal diameter.

In an application, placing the annulus-marking device including expanding the annulus-marking device in a manner in which the distal end of each one of the plurality of expandable elements is disposed within the atrium.

In an application, placing the annulus-marking device including expanding the annulus-marking device in a manner in which the distal end of each one of the plurality of expandable elements is disposed within a ventricle of the heart.

In an application, the method further includes viewing tissue of the native heart valve annulus and tissue coupled thereto by viewing the plurality of expandable elements.

In an application, viewing the tissue of the native heart valve annulus and tissue coupled thereto includes imaging the plurality of expandable elements with respect to the tissue of the native heart valve annulus and the tissue coupled thereto by viewing the plurality of expandable elements against the tissue.

In an application, viewing the tissue of the native heart valve annulus and tissue coupled thereto includes imaging the plurality of expandable elements with respect to the tissue of the native heart valve annulus and the tissue coupled thereto by viewing movement of the plurality of expandable elements responsively to movement of the tissue.

In an application, viewing the tissue of the native heart valve annulus and tissue coupled thereto includes imaging the plurality of expandable elements with respect to the tissue of the native heart valve annulus, tissue of at least one leaflet, and tissue of an atrial wall.

In an application, the annulus-marking device includes a plurality of radiopaque filaments coupled at least to a distal end of the annulus-marking device, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus for use with a subject, the system/apparatus including:
an annulus-marking device including a radiopaque material shaped to define:
(1) a tubular stent body having a central longitudinal axis and configured for placement within a native heart valve of the subject; and
(2) a frame coupled to a proximal end of the tubular stent body and projecting away from the longitudinal axis of the stent body, the frame configured for placement along at least a part of a circumference of an annulus of the native heart valve, the annulus-marking device being:
compressible during delivery toward the native heart valve, and
expandable from a compressed state for positioning in the native heart valve; and
an implant for implantation along the annulus of the valve of the subject,
and the annulus-marking device is:
configured to provide a guide for implantation of the implant along the annulus and within a space defined by the frame, and
retrievable following the implantation of the implant.

In an application, the annulus-marking device includes a superelastic material.

In an application, the stent body and the frame are fabricated from a single piece.

In an application, the tubular stent body includes two or more prosthetic leaflets.

There is further provided, in accordance with some applications, a method, including placing at a native heart valve of a subject an annulus-marking device including a radiopaque material shaped to define: (1) a tubular stent body having a central longitudinal axis and configured for placement within the native heart valve of the subject; and (2) a frame coupled to a proximal end of the tubular stent body and projecting away from the longitudinal axis of the stent body, the frame configured for placement along at least a part of a circumference of an annulus of the native heart valve. In some applications, the annulus-marking device is compressible during delivery toward the native heart valve, and expandable from a compressed state for positioning in the native heart valve. The method further includes implanting an implant along the annulus using the annulus-marking device as a guide for implantation of the implant along the annulus and within a space defined by the frame under imaging. Some methods include retrieving the annulus-marking device following the implanting.

In an application, implanting under imaging includes implanting using fluoroscopy.

In an application, retrieving the annulus-marking device following the implanting includes constraining the annulus-marking device within a tool and extracting the annulus-marking device from the subject.

In an application, placing includes placing the annulus-marking device within a mitral valve. In an application, placing includes placing the annulus-marking device within a tricuspid valve.

In an application, retrieving the annulus-marking device following the implanting includes sliding the frame around the implant and proximally away from the annulus.

In an application, the method further includes viewing tissue of the native heart valve annulus and tissue coupled thereto using the frame.

In an application, viewing the tissue of the native heart valve annulus and tissue coupled thereto includes imaging the annulus-marking device with respect to the tissue of the native heart valve annulus and the tissue coupled thereto by viewing the frame against the tissue.

In an application, viewing the tissue of the native heart valve annulus and tissue coupled thereto includes imaging the annulus-marking device with respect to the tissue of the native heart valve annulus and the tissue coupled thereto by viewing movement of frame responsively to movement of the tissue.

This method can be performed on a living animal or on a simulation, such as on a cadaver, cadaver heart, simulator (e.g. with the body parts, tissue, etc. being simulated), etc.

There is further provided, in accordance with some applications, a method, including: placing within at least an atrium of a heart of a subject an annulus-marking device including a radiopaque material shaped to define a plurality of expandable elements which include respective curved sections at distal ends thereof, plurality of expandable elements being configured to expand radially within the atrium such that the plurality of expandable elements provides an indication as to a location of a native heart valve annulus of a native heart valve of the subject. In some applications, the annulus-marking device is compressible during delivery toward the native heart valve, and expandable from a compressed state for positioning at least within the atrium.

The method can further include implanting an implant along the native heart valve annulus of the subject and within a concave section of each one of the plurality of expandable elements using the annulus-marking device as a guide for implantation of the implant along the annulus under imaging. The method can also include retrieving the annulus-marking device following the implanting.

In an application, placing the annulus-marking device includes placing the annulus-marking device while the implant is disposed within the concave sections of the plurality of expandable elements.

In an application, implanting the implant includes placing the implant within the concave sections of the plurality of expandable elements subsequently to the placing of the annulus-marking device.

In an application, implanting under imaging includes implanting using fluoroscopy.

In an application, retrieving the annulus-marking device following the implanting includes constraining the annulus-marking device within a tool and extracting the annulus-marking device from the subject.

In an application, retrieving the annulus-marking device following the implanting includes sliding the curved sections of the plurality of expandable elements from under the implant.

In an application, placing includes placing the annulus-marking device in a left atrium. In an application, placing includes placing the annulus-marking device in a right atrium.

In an application, placing the annulus-marking device including expanding the annulus-marking device in a manner in which a distal end of each one of the plurality of expandable elements is disposed within the atrium.

In an application, the plurality of expandable elements collectively form the annulus-marking device into a partially-pear shape, and implanting an implant includes deploying a tissue anchor at a site along the annulus marked between successive expandable elements.

In an application, the plurality of expandable elements collectively form the annulus-marking device into a partially-bulbous shape, and implanting the implant includes deploying a tissue anchor at a site along the annulus marked between successive expandable elements.

In an application, the plurality of expandable elements include a plurality of curved wires each having proximal and distal ends and a middle section between the proximal and distal ends.

In an application, a collective proximal diameter of the proximal ends of the plurality of expandable elements is smaller than a collective distal diameter of the distal ends of the plurality of expandable elements, and a collective middle diameter of the plurality of expandable elements is greater than the collective proximal diameter and greater than the collective distal diameter.

In an application, the method further includes viewing tissue of the native heart valve annulus and tissue coupled thereto by viewing the plurality of expandable elements.

In an application, viewing the tissue of the native heart valve annulus and tissue coupled thereto includes imaging the plurality of expandable elements with respect to the tissue of the native heart valve annulus and the tissue coupled thereto by viewing the plurality of expandable elements against the tissue.

In an application, viewing the tissue of the native heart valve annulus and tissue coupled thereto includes imaging the plurality of expandable elements with respect to the tissue of the native heart valve annulus and the tissue coupled thereto by viewing movement of the plurality of expandable elements responsively to movement of the tissue.

In an application, viewing the tissue of the native heart valve annulus and tissue coupled thereto includes imaging the plurality of expandable elements with respect to the tissue of the native heart valve annulus, tissue of at least one leaflet, and tissue of an atrial wall.

In an application, the annulus-marking device includes a plurality of radiopaque filaments coupled at least to a distal end of the annulus-marking device, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including placing at a ventricular surface of a native heart valve annulus of a subject a distal end portion of an annulus-marking device including a radiopaque material, the distal end portion being shaped to define a curved section that curves upward toward the ventricular surface; facilitating imaging of the heart valve annulus by imaging movement of the distal end portion of the annulus-marking device along a perimeter of the ventricular surface of the native heart valve annulus; and implanting an implant along the native heart valve annulus of the subject using the annulus-marking device as a guide for implantation of the implant along the annulus under imaging. The method can also include retrieving the annulus-marking device following the implanting.

In an application, placing the distal end portion of the annulus-marking device at the ventricular surface includes placing the distal end portion of the annulus-marking device at the ventricular surface of a native mitral valve.

In an application, placing the distal end portion of the annulus-marking device at the ventricular surface includes placing the distal end portion of the annulus-marking device at the ventricular surface of a native tricuspid valve.

In an application, implanting includes implanting in conjunction with the imaging movement of the distal end portion of the annulus-marking device.

In an application, the method further includes generating a map of the native heart valve annulus by imaging movement of the distal end of the annulus-marking device along the perimeter of the ventricular surface of the native heart valve annulus. In an application, generating the map includes generating the map prior to the implanting.

This method can be performed on a living animal or on a simulation, such as on a cadaver, cadaver heart, simulator (e.g. with the body parts, tissue, etc. being simulated), etc.

There is further provided, in accordance with some applications, a method, including placing at a surface of a native heart valve annulus of a subject an annulus-marking device including a toroidal stent including a radiopaque material, facilitating imaging of the heart valve annulus by imaging movement of the distal end portion of the annulus-marking device along a perimeter of the ventricular surface of the native heart valve annulus, and implanting an implant along the native heart valve annulus of the subject using the annulus-marking device as a guide for implantation of the implant along the annulus under imaging. The method can also include retrieving the annulus-marking device following the implanting.

In an application, implanting the implant includes implanting the implant between an external surface of the toroidal stent and tissue of an atrial wall.

In an application, placing at the surface includes placing the annulus-marking device at an atrial surface of the native heart valve annulus.

In an application, placing includes placing the annulus-marking device at a surface of a native mitral valve. In an application, placing includes placing the annulus-marking device at a surface of a native tricuspid valve.

In an application, the method further includes viewing tissue of the native heart valve annulus and tissue coupled thereto under imaging the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus includes imaging the annulus-marking device with respect to the tissue of the native heart valve annulus and the tissue coupled thereto by viewing movement of the annulus-marking device responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

In an application, toroidal stent includes a plurality of radiopaque filaments coupled at an inner surface of the toroidal stent, and placing the annulus-marking device includes placing the toroidal stent along the annulus in a manner in which the plurality of radiopaque filaments project toward an orifice of the valve, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including placing at a surface of a native heart valve annulus of a subject an annulus-marking device including an implant-leading device including a radiopaque material, facilitating imaging of the heart valve annulus by imaging movement of the implant-leading device along a perimeter of a surface of the native heart valve annulus, and in conjunction with the placing, implanting an implant along the native heart valve annulus of the subject using the implant-leading device as a guide for implantation of the implant along the annulus under imaging. The method can also include retrieving the annulus-marking device following the implanting.

In an application, placing the annulus-marking device includes advancing the annulus-marking device along an implantation path upstream of the implant.

In an application, placing includes placing the annulus-marking device at a surface of a native mitral valve. In an application, placing includes placing the annulus-marking device at a surface of a native tricuspid valve.

In an application, placing includes placing the annulus-marking device in a manner in which a portion of the annulus-marking device spans a portion of an orifice of the valve.

In an application, the method further includes viewing tissue of the native heart valve annulus and tissue coupled thereto under imaging the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus includes imaging the annulus-marking device with respect to the tissue of the native heart valve annulus and the tissue coupled thereto by viewing movement of the annulus-marking device responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

In an application, implant-leading device includes a plurality of radiopaque filaments coupled thereto, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including placing at a surface of a native heart valve annulus of a subject an annulus-marking device including a loop-shaped wire including a radiopaque material, facilitating imaging of the heart valve annulus by imaging movement of the wire along at least a portion of a perimeter of a surface of the native heart valve annulus, in conjunction with the placing, implanting an implant along the native heart valve annulus of the subject using the wire as a guide for implantation of the implant along the annulus under imaging. The method can also include retrieving the annulus-marking device following the implanting.

In an application, implanting under imaging includes implanting using fluoroscopy.

In an application, placing the annulus-marking device includes advancing the annulus-marking device along an implantation path upstream of the implant.

In an application, placing includes placing the annulus-marking device at a surface of a native mitral valve. In an application, placing includes placing the annulus-marking device at a surface of a native tricuspid valve.

In an application, placing includes pushing a first portion of the annulus-marking device against a first portion of the annulus of the valve and thereby, pushing a second portion of the annulus-marking device that is opposite the first portion of the annulus-marking device against a second portion of the annulus of the valve.

In an application, implanting the implant includes implanting the implant at an external perimeter of the annulus-marking device responsively to the pushing.

In an application, the method further includes viewing tissue of the native heart valve annulus and tissue coupled thereto under imaging the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus includes imaging the annulus-marking device with respect to the tissue of the native heart valve annulus and the tissue coupled thereto by viewing movement of the annulus-marking device responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

In an application, annulus-marking device includes a plurality of radiopaque filaments coupled thereto, and the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including deploying within tissue of a native heart valve annulus of a subject an annulus-marking device including a plurality of radiopaque pins including a radiopaque material, facilitating imaging of the heart valve annulus by imaging the plurality of pins, and subsequently, implanting an implant along the native heart valve annulus of the subject using the plurality of pins as a guide for implantation of the implant along the annulus under imaging.

In an application, each one of the plurality of pins has a barb configured for anchoring to tissue of the annulus.

In an application, each one of the plurality of pins has a longest width of 0.5-3.0 mm.

In an application, facilitating imaging of the heart valve annulus by imaging the plurality of pins includes facilitating imaging movement of the plurality of pins responsively to movement of the annulus.

In an application, implanting the implant includes deploying a plurality of tissue anchors to fasten the implant to tissue of the annulus.

In an application, deploying the plurality of tissue anchors includes deploying a larger number of tissue anchors than a number of pins.

This method can be performed on a living animal or on a simulation, such as on a cadaver, cadaver heart, simulator (e.g. with the body parts, tissue, etc. being simulated), etc.

There is further provided, in accordance with some applications, a method, including positioning within tissue of a native heart valve annulus of a native heart valve of a subject an annulus-marking device including a plurality of radiopaque pins that are moveable proximally and distally in response to variations in a topography of tissue of the valve, facilitating imaging of the heart valve annulus and tissue coupled thereto by moving the plurality of pins along the native heart valve and imaging the plurality of pins in order to generate an image of the topography of the heart valve, and implanting an implant along the native heart valve annulus of the subject using the image as a guide for implantation of the implant along the annulus under imaging. The method can further include retrieving the plurality of radiopaque pins from the subject.

In an application, retrieving includes retrieving subsequently to the implanting. In an application, retrieving includes retrieving prior to the implanting.

In an application, facilitating imaging of the heart valve annulus by imaging the plurality of pins includes facilitating imaging movement of the plurality of pins responsively to movement of the annulus. In an application, implanting includes implanting during the facilitating of the imaging. In an application, facilitating imaging includes viewing movement of the plurality of pins proximally in response to movement of the plurality of pins over a peak in tissue of the annulus.

In an application, facilitating imaging includes viewing movement of at least a first portion of the plurality of pins proximally in response to movement of the plurality of pins over tissue of the annulus, and viewing at least a second portion of the plurality of pins not moving in response to movement of the plurality of pins over tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus for use with a subject, the system/apparatus including a multilumen tube, at least a first annulus-marking device expandable from within the multilumen tube.

In some applications, the at least a first annulus-marking device includes a distal frame wire, the distal frame wire, when the annulus-marking device is in an expanded state, having an expanded shape in which it assumes a generally linear configuration. In some applications, the at least a first annulus-marking device includes a plurality of radiopaque filaments coupled to the distal frame wire, the plurality of radiopaque filaments including radiopaque material and projecting away from the distal frame wire in the expanded state of the annulus-marking device.

In some applications, at least one central rod is coupled to a middle portion of the distal frame wire and disposed primarily and slidable within a primary sublumen of the multilumen tube, the central rod being configured to constrain the distal frame wire and the plurality of radiopaque filaments from the expanded state of the annulus-marking device and pull the distal frame wire and the plurality of radiopaque filaments within the primary sublumen of the multilumen tube.

In some applications, at least two peripheral wires are coupled to the distal frame wire at opposite end portions thereof, the at least two peripheral wires being disposed primarily and slidable within respective secondary sublumens of the multilumen tube, the at least two peripheral wires being configured to stabilize the distal frame wire in the expanded state of the annulus-marking device.

In some applications, the annulus-marking device is compressible during delivery toward the native heart valve, and expandable from a compressed state for positioning along the native heart valve annulus.

In some applications, the system/apparatus further comprises an implant for implantation along the native heart valve annulus of the subject, and the annulus-marking device is configured to provide a guide for implantation of the implant along the annulus during implantation.

In some applications, the annulus-marking device is retrievable following the implantation of the implant.

In an application, the multilumen tube is shaped so as to define a central lumen, and the implant is configured for delivery to the heart valve annulus via the central lumen.

In an application, the peripheral wires are configured to trail behind the distal frame wire as the central rod pulls the distal frame wire the and the plurality of radiopaque filaments within the primary sublumen of the multilumen tube.

In an application, each one of the plurality of radiopaque filaments and the distal frame wire include a material that is flexible.

In an application, the at least the first annulus-marking device includes at least first and second annulus-marking devices, the multilumen tube is shaped so as to define first and second primary sublumens, the multilumen tube is shaped to as to define four secondary sublumens.

In some applications, the apparatus includes first and second central rods configured to respectively constrain the first and second annulus-marking devices within the respective first and second primary sublumens. In some applications, the apparatus includes four peripheral wires configured to respectively stabilize the distal frame wires of the respective first and second annulus-marking devices, the four peripheral wires being slidable within the four secondary sublumens.

In an application, the first and second annulus-marking devices are independently controllable by the respective first and second control rods.

In an application, the at least the first annulus-marking device includes first, second, third, and fourth annulus-marking devices, the multilumen tube is shaped so as to define first, second, third, and fourth primary sublumens, the multilumen tube is shaped to as to define eight secondary sublumens, the apparatus includes first, second, third, and fourth central rods configured to respectively constrain the first, second, third, and fourth annulus-marking devices within the respective first, second, third, and fourth primary sublumens, and the apparatus includes eight peripheral wires configured to respectively stabilize the distal frame wires of the respective first, second, third, and fourth annulus-marking devices, the eight peripheral wires being slidable within the eight secondary sublumens.

In an application, the first, second, third, and fourth annulus-marking devices are independently controllable by the respective first, second, third, and fourth control rods.

There is further provided, in accordance with some applications, a method, including delivering within a heart chamber of a subject a distal end portion of a central multilumen tube, expanding from within the multilumen tube at least a first annulus-marking device, and implanting an implant along the native heart valve annulus of the subject using the annulus-marking device as a guide for implantation of the implant along the annulus under imaging. The method can include retrieving the annulus-marking device following the implanting.

In some applications, the at least a first annulus-marking device includes a distal frame wire, the distal frame wire, when the annulus-marking device is in an expanded state, having an expanded shape in which it assumes a generally linear configuration. In some applications, a plurality of radiopaque filaments are coupled to the distal frame wire, the plurality of radiopaque filaments including radiopaque material and projecting away from the distal wire in the expanded state of the annulus-marking device.

In some applications, the method includes controlling a position of the at least first annulus-marking device by sliding primary sublumen of the multilumen tube at least one central rod coupled to a middle portion of the distal frame wire and disposed primarily within the primary sublumen of the multilumen tube.

In some applications, the method includes stabilizing the distal frame wire by at least two peripheral wires coupled to the distal frame wire at opposite end portions thereof, the at least two peripheral wires being disposed primarily and slidable within respective secondary sublumens of the multilumen tube, the at least two peripheral wires being configured to stabilize the distal frame wire in the expanded state of the annulus-marking device.

In some applications, the method includes constraining the annulus-marking device by pulling on the central rod to constrain the distal frame wire and the plurality of radiopaque filaments from the expanded state of the annulus-marking device, and by the pulling, pulling the distal frame wire and the plurality of radiopaque filaments within the primary sublumen of the multilumen tube.

In some applications, the annulus-marking device is compressible during delivery toward the native heart valve, and expandable from a compressed state for positioning along the native heart valve annulus;

In an application, the multilumen tube is shaped so as to define a central lumen, and the method further includes delivering the implant to the heart valve annulus via the central lumen.

In an application, the constraining the annulus-marking device by pulling on the central rod includes allowing the peripheral wires to trail behind the distal frame wire as the central rod pulls the distal frame wire the and the plurality of radiopaque filaments within the primary sublumen of the multilumen tube.

In an application, each one of the plurality of radiopaque filaments and the distal frame wire include a material that is flexible.

In an application, controlling the position of the at least first annulus-marking device includes placing the at least first annulus-marking device along an annulus of a mitral valve.

In an application, controlling the position of the at least first annulus-marking device includes placing the at least first annulus-marking device along an annulus of a tricuspid valve.

In an application, the at least the first annulus-marking device includes at least first and second annulus-marking devices, the multilumen tube is shaped so as to define first and second primary sublumens, the multilumen tube is shaped to as to define four secondary sublumens, and the method further includes respectively constraining the first and second annulus-marking devices within the respective first and second primary sublumens by pulling respective first and second control rods. In some applications, the method further includes respectively stabilizing the wires of the respective first and second annulus-marking devices using four peripheral wires that are slidable within the four secondary sublumens.

In an application, the method further includes independently controlling the first and second annulus-marking devices using the respective first and second control rods.

In an application, the at least the first annulus-marking device includes first, second, third, and fourth annulus marking devices, the multilumen tube is shaped so as to define first, second, third, and fourth primary sublumens, the multilumen tube is shaped to as to define eight secondary sublumens, and the method further includes respectively constraining the first, second, third, and fourth annulus-marking devices within the respective second, third, and fourth primary sublumens by pulling respective first, second, third, and fourth control rods. In some applications, the method further includes respectively stabilizing the distal frame wires of the respective second, third, and fourth annulus-marking devices using eight peripheral wires that are slidable within the eight secondary sublumens.

The method can further include independently controlling the first, second, third, and fourth annulus-marking devices using the respective first and second control rods.

In an application, the method further includes viewing tissue of the native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the plurality of radiopaque filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including placing at a native heart valve annulus of a subject an annulus-marking device including a radiopaque material shaped to define a plurality of inflatable fingers, the annulus-marking device being in a compressed state during delivery toward the native heart valve, and expandable from the compressed state for positioning along the native heart valve annulus, and implanting an implant along the native heart valve annulus of the subject using the annulus-marking device as a guide for implantation of the implant along the annulus under imaging. The method can include retrieving the annulus-marking device following the implanting.

In an application, placing the annulus-marking device includes delivering the annulus-marking device using a delivery tool, the annulus-marking device surrounds the tool, and implanting the implant includes delivering the implant through a lumen of the tool around which the annulus-marking device surrounds.

In an application, placing the annulus-marking device includes measuring a height of the annulus using the annulus-marking device.

In an application, implanting under imaging includes implanting using fluoroscopy.

In an application, retrieving the annulus-marking device following the implanting includes deflating the annulus-marking device and constraining the annulus-marking device within a tool and extracting the annulus-marking device from the subject.

In an application, placing includes placing the annulus-marking device along an annulus of a mitral valve. In an application, placing includes placing the annulus-marking device along an annulus of a tricuspid valve.

In an application, implanting using the annulus-marking device as the guide includes viewing a shape of each one of the plurality of fingers.

In an application, viewing the shape includes determining that the annulus-marking device is at the annulus responsively to viewing a bend in at least one of the plurality of fingers.

In an application, viewing the shape includes determining that the annulus-marking device is at at least a portion of a leaflet responsively to viewing a movement of at least one of the plurality of fingers responsively to movement of the at least one of the plurality of fingers.

In an application, the method further includes inflating the plurality of fingers prior to the placing. In an application, inflating includes inflating the plurality of fingers with a radiopaque fluid.

In an application, the method further includes viewing tissue of the native heart valve annulus and tissue coupled thereto under imaging the plurality of fingers.

In an application, viewing the tissue of the native heart valve annulus and tissue coupled thereto includes imaging the plurality of fingers with respect to the tissue of the native heart valve annulus and the tissue coupled thereto by viewing the plurality of fingers against the tissue.

In an application, viewing the tissue of the native heart valve annulus includes imaging the plurality of fingers with respect to the tissue of the native heart valve annulus and the tissue coupled thereto by viewing movement of the plurality of fingers responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus for use with a subject, the system/apparatus including an annulus-marking device including a radiopaque material shaped to define: (1) a plurality of concentric wire loops connected by a scaffolding configured for placement at an orifice of a native heart valve of the subject; and (2) a wire loop frame coupled to the scaffolding and concentric with respect to the plurality of concentric wire loops, the wire loop frame configured for placement along at least a part of a circumference of an annulus of the native heart valve.

In some applications, the annulus-marking device is compressible during delivery toward the native heart valve, and expandable from a compressed state for positioning in the native heart valve.

In some applications, the system/apparatus further includes an implant for implantation along the annulus of the valve of the subject.

In some applications, the annulus-marking device is configured to provide a guide for implantation of the implant along the annulus and within a space defined by the frame. In some applications, the annulus-marking device is retrievable following the implantation of the implant.

In an application, the annulus-marking device includes a superelastic material. In an application, the plurality of concentric wire loops, the scaffolding, and the wire loop frame are fabricated from a single piece.

In an application, the annulus-marking device includes a plurality of radiopaque filaments coupled at least to the plurality of concentric wire loops, each one of the plurality of filaments being configured to sway responsively to movement of blood through the orifice of the valve to provide an indication of a location of leaflets of the valve.

In an application, the annulus-marking device includes a locking ring in a center of the plurality of concentric wire loops, the locking ring being pushable distally in order to lock the annulus-marking device in the expanded state.

In an application, the apparatus further includes a plurality of radiopaque filaments coupled to the plurality of concentric wire loops, the plurality of radiopaque filaments including radiopaque material.

In an application, the plurality of radiopaque filaments are configured to provide an indication of a location of leaflets of the valve by moving responsively to movement of the native heart valve.

There is further provided, in accordance with some applications, a method, including placing at a native heart valve of a subject an annulus-marking device including a radiopaque material shaped to define: (1) a plurality of concentric wire loops connected by a scaffolding; and (2) a wire loop frame coupled to the scaffolding and concentric with respect to the plurality of concentric wire loops, the wire loop frame configured for placement along at least a part of a circumference of an annulus of the native heart valve.

In some applications, the annulus-marking device is compressible to a compressed state during delivery toward the native heart valve, and expandable from a compressed state for positioning in the native heart valve to an expanded state.

In some applications, the method includes, under imaging, implanting an implant along the annulus using the annulus-marking device as a guide for implantation of the implant along the annulus and within a space defined by the frame. In some applications, the method includes retrieving the annulus-marking device following the implanting.

In an application, the method further includes locking the annulus-marking device in the expanded state by pushing distally a locking ring that is disposed in a center of the plurality of concentric wire loops.

In an application, the method further includes transitioning the annulus-marking device from the compressed state to the expanded state by pushing distally a locking ring that is disposed in a center of the plurality of concentric wire loops.

In an application, implanting under imaging includes implanting using fluoroscopy.

In an application, placing includes placing the annulus-marking device at a mitral valve, placing the plurality of concentric wire loops at an orifice of the valve, and placing the wire loop frame along at least a part of a circumference of the annulus of the mitral valve.

In an application, placing includes placing the annulus-marking device at a tricuspid valve, placing the plurality of concentric wire loops at an orifice of the valve, and placing the wire loop frame along at least a part of a circumference of the annulus of the tricuspid valve.

In an application, retrieving the annulus-marking device following the implanting includes sliding the frame around the implant and proximally away from the annulus.

In an application, the method further includes viewing tissue of the native heart valve annulus and tissue coupled thereto using the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus and tissue coupled thereto includes imaging the annulus-marking device with respect to the tissue of the native heart valve annulus and the tissue coupled thereto by viewing movement of the annulus-marking device responsively to movement of the tissue.

In an application, the annulus-marking device includes a plurality of radiopaque filaments coupled to the plurality of concentric wire loops, and the method further includes determining that the annulus-marking device is at at least a portion of a leaflet responsively to viewing a movement of at least some of the plurality of radiopaque filaments responsively to movement of the valve.

In an application, the method further includes determining that the annulus-marking device is at at least a portion of the annulus responsively to viewing a lack of movement of at least a first of the plurality of radiopaque filaments while a second portion of the plurality of radiopaque filaments move with responsively to movement of the valve.

In an application, retrieving the annulus-marking device following the implanting includes constraining the annulus-marking device within a tool and extracting the annulus-marking device from the subject.

In an application, retrieving the annulus-marking device includes transitioning the annulus-marking device from the expanded state to the compressed state by pulling proximally a locking ring that is disposed in a center of the plurality of concentric wire loops.

This method can be performed on a living animal or on a simulation, such as on a cadaver, cadaver heart, simulator (e.g. with the body parts, tissue, etc. being simulated), etc.

There is further provided, in accordance with some applications, a method, including placing at a native heart valve annulus of a subject an annulus-marking device including a radiopaque material shaped to define a plurality of radiopaque petals or loops, the annulus-marking device being in a compressed state during delivery toward the native heart valve, and expandable from the compressed state for positioning along the native heart valve annulus, and implanting an implant along the native heart valve annulus of the subject using the annulus-marking device as a guide for implantation of the implant along the annulus under imaging. The method can include retrieving the annulus-marking device following the implanting.

In an application, placing the annulus-marking device includes delivering the annulus-marking device using a delivery tool, the annulus-marking device surrounds the tool, and implanting the implant includes delivering the implant through a lumen of the tool around which the annulus-marking device surrounds.

In an application, placing the annulus-marking device includes measuring a height of the annulus using the annulus-marking device.

In an application, implanting under imaging includes implanting using fluoroscopy.

In an application, retrieving the annulus-marking device following the implanting includes constraining the annulus-marking device within a tool and extracting the annulus-marking device from the subject.

In an application, placing includes placing the annulus-marking device along an annulus of a mitral valve.

In an application, placing includes placing the annulus-marking device along an annulus of a tricuspid valve.

In an application, at least one of the plurality of petals or loops is a larger petal or loop than the other petals or loops, and placing includes placing the annulus-marking device in the valve in manner which the larger petal or loop is positioned between leaflets of the valve.

In an application, implanting using the annulus-marking device as the guide includes viewing a shape of each one of the plurality of petals or loops.

In an application, viewing the shape includes determining that the annulus-marking device is at the annulus responsively to viewing a bend in at least one of the plurality of petals or loops.

In an application, viewing the shape includes determining that the annulus-marking device is at at least a portion of a leaflet responsively to viewing a movement of at least one of the plurality of petals or loops responsively to movement of the at least one of the plurality of petals or loops.

In an application, the method further includes viewing tissue of the native heart valve annulus and tissue coupled thereto under imaging the plurality of petals or loops.

In an application, viewing the tissue of the native heart valve annulus and tissue coupled thereto includes imaging the plurality of petals or loops with respect to the tissue of the native heart valve annulus and the tissue coupled thereto by viewing the plurality of petals or loops against the tissue.

In an application, viewing the tissue of the native heart valve annulus includes imaging the plurality of petals or loops with respect to the tissue of the native heart valve annulus and the tissue coupled thereto by viewing movement of the plurality of petals or loops responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus, including a guidewire having a distal end portion that is configured to assume a shape in an expanded state of the guidewire; and an annulus-marking device including a plurality of radiopaque filaments coupled to the distal end portion of the guidewire.

In an application, each one of the plurality of radiopaque filaments includes a material that is flexible.

In an application, the apparatus further includes a tube, and the distal end portion of the guidewire surrounds a portion of the tube at least in part in the expanded state of the guidewire.

In an application, the apparatus further includes an implant deliverable through a lumen of the tube, and the plurality of radiopaque filaments are configured to guide implantation of the implant.

There is further provided, in accordance with some applications, a method, including positioning a distal end portion of a guidewire within a chamber of a heart of a subject, the guidewire being configured to assume a shape in an expanded state of the guidewire, and the distal end portion of the guidewire being coupled to an annulus-marking device including a plurality of radiopaque filaments; and moving the distal end portion of the guidewire along tissue surrounding the chamber of the heart; and imaging the tissue surrounding the chamber of the heart by viewing the moving of the distal end portion of the guidewire and by viewing the plurality of radiopaque filaments.

In an application, moving the distal end portion of the guidewire along tissue includes measuring a height of a native annulus of a valve of the heart using the annulus-marking device.

In an application, imaging includes imaging using fluoroscopy.

In an application, positioning the distal end portion of the guidewire includes positioning the distal end portion of the guidewire along an annulus of a mitral valve. In an application, positioning the distal end portion of the guidewire includes positioning the distal end portion of the guidewire along an annulus of a tricuspid valve.

In an application, positioning the distal end portion of the guidewire includes positioning the distal end portion of the guidewire in a subannular space of a native heart valve of the subject.

In an application, imaging the tissue surrounding the chamber includes viewing tissue of a native heart valve annulus and tissue coupled thereto using the plurality of radiopaque filaments.

In an application, viewing the tissue of the native heart valve annulus and tissue coupled thereto includes imaging the annulus-marking device with respect to the tissue of the native heart valve annulus and the tissue coupled thereto by viewing the plurality of radiopaque filaments against the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

In an application, the method further includes implanting an implant along a native heart valve annulus of the subject using the annulus-marking device as a guide for implantation of the implant along the annulus under imaging. In an application, the method includes retrieving the annulus-marking device following the implanting.

In an application, the implant is delivered through a tube, the distal end portion of the guidewire surrounds a portion of the tube, and implanting an implant along a native heart valve annulus of the subject includes guiding the portion of the tube along the annulus using the annulus-marking device.

This method can be performed on a living animal or on a simulation, such as on a cadaver, cadaver heart, simulator (e.g. with the body parts, tissue, etc. being simulated), etc.

There is further provided, in accordance with some applications, a method, including expanding within an atrium of a heart of a subject an annulus-marking device including a radiopaque material shaped to define: (1) a first radiopaque loop, and (2) a second radiopaque loop configured to pivot and tilt with respect to the first radiopaque loop. The method can include tilting the second radiopaque loop with respect to the first radiopaque loop and allowing the second radiopaque loop to pivot along a plane that is at a non-zero angle with respect to a plane of the first radiopaque loop.

In some applications, the method includes positioning the annulus-marking device in its fully expanded state at least in part within a native heart valve of the heart in a manner in which (1) the first radiopaque loop is disposed between leaflets of the native heart valve, an upper portion of the first radiopaque loop is disposed within the atrium and a lower portion of the first radiopaque is disposed within a ventricle of the heart, and (2) the second radiopaque loop is disposed along an atrial surface of an annulus of the valve.

In some applications, the annulus-marking device is compressible to a compressed state during delivery toward the native heart valve, and expandable from a compressed state for positioning in the native heart valve to an expanded state, and implanting an implant along the annulus using the annulus-marking device as a guide for implantation of the implant along the annulus under imaging. In some applications, the method includes retrieving the annulus-marking device following the implanting.

In an application, implanting under imaging includes implanting using fluoroscopy.

In an application, positioning includes positioning the annulus-marking device at a mitral valve. In an application, positioning includes positioning the annulus-marking device at a tricuspid valve.

In an application, retrieving the annulus-marking device following the implanting includes pivoting and tilting the second radiopaque loop with respect to the first radiopaque loop.

In an application, positioning includes positioning the first radiopaque loop between the leaflets and by the positioning, applying a force to commissures of the valve by the first radiopaque loop.

In an application, the first and second radiopaque loops each include wire frames surrounded at least in part by a respective radiopaque spring, and positioning the annulus-marking device includes allowing the springs to compress and expand.

In an application, retrieving the annulus-marking device following the implanting includes constraining the annulus-marking device within a tool and extracting the annulus-marking device from the subject.

In an application, the method further includes viewing tissue of the native heart valve annulus and tissue coupled thereto using the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus and tissue coupled thereto includes imaging the annulus-marking device with respect to the tissue of the native heart valve annulus and the tissue coupled thereto by viewing movement of the annulus-marking device responsively to movement of the tissue.

In an application, the method further includes, in the fully expanded state of the annulus-marking device, moving the second radiopaque loop vertically along a portion of the first radiopaque loop.

In an application, moving the second radiopaque loop vertically along a portion of the first radiopaque loop includes measuring a height of the annulus.

This method can be performed on a living animal or on a simulation, such as on a cadaver, cadaver heart, simulator (e.g. with the body parts, tissue, etc. being simulated), etc.

There is further provided, in accordance with some applications, a system and/or an apparatus including an annulus-marking device, the annulus-marking device including: a central pole; two or more expandable wires connected at their respective proximal and distal ends to the central pole, the two or more expandable wires each shaped to define an indented section to fit a native heart valve annulus of a valve of a subject; and at least one ultrasound transducer slidable along and rotational with respect to the central pole. In some applications, the annulus-marking device is compressible to a compressed state during delivery toward the native heart valve, and expandable from a compressed state for positioning in the native heart valve to an expanded state.

In an application, the apparatus further includes an implant implantable at the annulus under guidance from imaging using the annulus-marking device.

In an application, the central pole is hollow, and the at least one ultrasound transducer is disposed within the central pole.

In an application, the apparatus further includes at least one radiopaque marker slidable along the two or more expandable elements until the radiopaque marker abuts the annulus.

In an application, the at least one radiopaque marker includes a wire ring.

In an application, the at least one radiopaque marker includes a plurality of radiopaque filaments coupled to the wire ring.

There is further provided, in accordance with some applications, a method, including expanding within a native heart valve of a subject an annulus-marking device shaped to define two or more expandable wires connected at their respective proximal and distal ends to a central pole, the two or more expandable wires each shaped to define an indented section to fit a native heart valve annulus of the valve.

In some applications, the annulus-marking device is compressible to a compressed state during delivery toward the native heart valve, and expandable from a compressed state for positioning in the native heart valve to an expanded state.

In some applications, the method includes sliding at least one ultrasound transducer along and rotationally with respect to the central pole, imaging the annulus of the valve using the ultrasound transducer, and implanting an implant along the annulus using the annulus-marking device as a guide for implantation of the implant along the annulus under the imaging. In some applications, the method includes retrieving the annulus-marking device following the implanting.

In an application, imaging includes measuring a height of the annulus.

In an application, expanding includes expanding the annulus-marking device at a mitral valve.

In an application, expanding includes expanding the annulus-marking device at a tricuspid valve.

In an application, expanding includes expanding the two or more expandable wires between leaflets of the valve and by the expanding, applying a force to commissures of the valve by the two or more expandable wires.

In an application, retrieving the annulus-marking device following the implanting includes constraining the annulus-marking device within a tool and extracting the annulus-marking device from the subject.

In an application, expanding includes positioning the annulus-marking device within the native heart valve of the heart in a manner in which the two or more expandable wires are disposed between leaflets of the native heart valve, an upper portion of each expandable wire being disposed within an atrium, and a lower portion of each expandable wire being disposed within a ventricle.

In an application, the method further includes:
sliding a radiopaque marker vertically along the two or more expandable elements until the radiopaque marker abuts the annulus; and
imaging the annulus under fluoroscopy.

In an application, sliding the radiopaque marker includes measuring a height of the annulus.

In an application, the method further includes viewing tissue of the native heart valve annulus and tissue coupled thereto using the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus and tissue coupled thereto includes imaging the annulus-marking device with respect to the tissue of the native heart valve annulus and the tissue coupled thereto by viewing movement of the annulus-marking device responsively to movement of the tissue.

This method can be performed on a living animal or on a simulation, such as on a cadaver, cadaver heart, simulator (e.g. with the body parts, tissue, etc. being simulated), etc.

There is further provided, in accordance with some applications, a method, including positioning an annulus-marking device including a clip within a ventricle of a heart of a subject, the clip including: radiopaque material, first and second jaws coupled together at a hinge point, each one of the first and second jaws having an end, and first and second filaments extending from the respective ends of the first and second jaws.

The method can include clipping together first and second leaflets of a heart valve of the subject using the clip, and by the clipping, allowing the first filament to abut an atrial surface of at least one of the first and second leaflets in a manner in which an end of the first filament is positioned in a vicinity of a hinge of an annulus of the valve in a vicinity of an atrial wall, and the second filament to abut a ventricular surface of at the least one of the first and second leaflets in a manner in which an end of the second filament is positioned in a subannular groove of the valve in a vicinity of a ventricular wall.

The method can further include implanting an implant along the native heart valve annulus of the subject using the annulus-marking device as a guide for implantation of the implant along the annulus under imaging.

In an application, the method further includes retrieving the annulus-marking device following the implanting.

In an application, the first and second filaments include material that is superelastic.

In an application, clipping includes implanting the annulus-marking device.

In an application, implanting includes affixing at least one of the first and second filaments to the valve.

In an application, implanting under imaging includes implanting using fluoroscopy.

In an application, positioning the annulus-marking device in the ventricle includes positioning the annulus-marking device in a right ventricle, and clipping together the leaflets includes clipping the leaflets of a tricuspid valve. In an application, positioning the annulus-marking device in the ventricle includes positioning the annulus-marking device in a left ventricle, and clipping together the leaflets includes clipping the leaflets of a mitral valve.

In an application, clipping includes creating a double orifice of the mitral valve.

In an application, the method further includes viewing tissue of the native heart valve annulus and tissue coupled thereto using the first and second filaments.

In an application, viewing the tissue of the native heart valve annulus and tissue coupled thereto includes imaging the annulus-marking device with respect to the tissue of the native heart valve annulus and the tissue coupled thereto by viewing the first and second filaments against the tissue.

In an application, viewing the tissue of the native heart valve annulus and tissue coupled thereto includes imaging the annulus-marking device with respect to the tissue of the native heart valve annulus and the tissue coupled thereto by viewing movement of the first and second filaments responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including positioning an annulus-marking device including a clamp within a ventricle of a heart of a subject, the clamp including radiopaque material, first and second arms coupled together at a hinge point, each one of the first and second arms having an end, and first and second curved elements coupled to the respective ends of the first and second arms.

The method can further comprise clamping a leaflet of a heart valve of the subject between the first and second arms using the clamp, and by the clamping, allowing: the first curved element to abut an atrial surface of the leaflet in a vicinity of a hinge of an annulus of the valve in a vicinity of an atrial wall; and the second curved element to abut a ventricular surface of at the leaflet in a subannular groove of the valve in a vicinity of a ventricular wall.

The method can further include implanting an implant along the native heart valve annulus of the subject using the annulus-marking device as a guide for implantation of the implant along the annulus under imaging.

In an application, the method further includes retrieving the annulus-marking device following the implanting.

In an application, implanting under imaging includes implanting using fluoroscopy.

In an application, positioning the annulus-marking device in the ventricle includes positioning the annulus-marking device in a right ventricle, and clamping includes clamping the leaflet of a tricuspid valve.

In an application, positioning the annulus-marking device in the ventricle includes positioning the annulus-marking device in a left ventricle, and clamping includes clamping the leaflet of a mitral valve.

In an application, the method further includes viewing tissue of the native heart valve annulus and tissue coupled thereto using the first and second curved elements.

In an application, viewing the tissue of the native heart valve annulus and tissue coupled thereto includes imaging the annulus-marking device with respect to the tissue of the native heart valve annulus and the tissue coupled thereto by viewing the first and second curved elements against the tissue.

In an application, viewing the tissue of the native heart valve annulus and tissue coupled thereto includes imaging the annulus-marking device with respect to the tissue of the native heart valve annulus and the tissue coupled thereto by viewing movement of the first and second curved elements responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including delivering an annulus-marking device including a balloon within a native heart valve of a heart of a subject and implanting an implant along a native heart valve annulus of the subject using the annulus-marking device as a guide for implantation of the implant along the annulus under imaging.

The balloon can be the same as or similar to other inflatable elements and/or balloons described herein. In some applications, the balloon includes an upper inflatable section inflatable to assume a generally paddle shape, a lower inflatable section inflatable to assume a spherical shape, and a central waist between the upper and lower inflatable sections.

In some applications, the method includes positioning the balloon such that the upper inflatable section is disposed within an atrium of the heart, the lower inflatable section is disposed within a ventricle of the heart, and the central waist is disposed between leaflets of the valve.

In some applications, the method includes inflating the balloon such that the upper inflatable section expands to assume the generally paddle shape, and the lower inflatable section expands to assume the spherical shape.

In an application, implanting includes implant the implant between an external surface of the upper inflatable element and an atrial wall of the heart.

In an application, the method further includes retrieving the annulus-marking device following the implanting.

In an application, an upper surface of the upper inflatable section is slanted.

In an application, implanting under imaging includes implanting using fluoroscopy.

In an application, the balloon is shaped so as to define an hourglass shape at at least one cross-section thereof.

In an application, positioning the annulus-marking device in the valve includes positioning the annulus-marking device in a mitral valve. In an application, positioning the annulus-marking device in the valve includes positioning the annulus-marking device in a tricuspid valve.

In an application, the upper inflatable section is less compliant than the lower inflatable section. In an application, the upper inflatable section is noncompliant.

In an application, the method further includes viewing tissue of the native heart valve annulus and tissue coupled thereto using the balloon.

In an application, the balloon includes radiopaque material. In an application, inflating the balloon includes inflating the balloon with radiopaque fluid.

In an application, viewing the tissue of the native heart valve annulus and tissue coupled thereto includes imaging the annulus-marking device with respect to the tissue of the native heart valve annulus and the tissue coupled thereto by viewing the upper and lower inflatable elements against the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including delivering an annulus-marking device including a balloon within a ventricle of a native heart valve of a heart of a subject, inflating the balloon within the ventricle, and implanting an implant along a native heart valve annulus of the subject using the annulus-marking device as a guide for implantation of the implant along the annulus under imaging. In some applications, the method includes retrieving the annulus-marking device following the implanting.

In an application, inflating includes inflating the balloon such that it assumes a spherical shape. In an application, inflating includes inflating the balloon such that it assumes a toroidal shape.

In an application, implanting under imaging includes implanting using fluoroscopy.

In an application, delivering the annulus-marking device within the ventricle includes positioning the annulus-marking device in a left ventricle. In an application, delivering the annulus-marking device within the ventricle includes positioning the annulus-marking device in a right ventricle.

In an application, the balloon includes a magnetic substance within a space defined by the balloon and implanting under imaging includes drawing the magnetic substance to an upper surface of the balloon and marking the annulus of the valve from a ventricular surface of the valve.

In an application, delivering the annulus-marking device includes delivering the annulus-marking device using a delivery tool including a magnet, and drawing the magnetic substance to the upper surface of the balloon includes using the magnet of the delivery tool.

In an application, the magnet includes a circular magnet, delivering the annulus-marking device using the delivery tool includes positioning the magnet at an atrial surface of the valve, and implanting the implant includes implanting the implant between an external surface of the magnet and an atrial wall.

In an application, the method further includes viewing tissue of the native heart valve annulus and tissue coupled thereto using the balloon.

In an application, the balloon includes radiopaque material. In an application, inflating the balloon includes inflating the balloon with radiopaque fluid.

In an application, viewing the tissue of the native heart valve annulus and tissue coupled thereto includes imaging the annulus-marking device with respect to the tissue of the native heart valve annulus and the tissue coupled thereto by viewing the balloon against the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including delivering an annulus-marking device within a native heart valve of a heart of a subject and implanting an implant along a native heart valve annulus of the subject using the annulus-marking device as a guide for implantation of the implant along the annulus under imaging. The annulus-marking device can be the same as or similar to other annulus-marking devices described herein.

In some applications, the annulus-marking device includes an upper inflatable element inflatable to assume a first toroidal shape and a lower inflatable element inflatable to assume a second toroidal shape. In some applications, the method includes positioning the annulus-marking device such that the upper inflatable element is disposed within an atrium of the heart and the lower inflatable element is disposed within a ventricle of the heart, and inflating the upper and lower inflatable elements such that the upper inflatable element expands to assume the first toroidal shape, and the lower inflatable element expands to assume the second toroidal shape.

In an application, implanting includes implant the implant between an external surface of the upper inflatable element and an atrial wall of the heart.

In an application, the method further includes retrieving the annulus-marking device following the implanting.

In an application, implanting under imaging includes implanting using fluoroscopy.

In an application, positioning the annulus-marking device in the valve includes positioning the annulus-marking device in a mitral valve. In an application, positioning the annulus-marking device in the valve includes positioning the annulus-marking device in a tricuspid valve.

In an application, the upper and lower inflatable elements include compliant material. In an application, the upper and lower inflatable elements include noncompliant material.

In an application, the upper and lower inflatable elements are discrete.

In an application, the annulus-marking device includes a single balloon including the upper and lower inflatable elements coupled together. In an application, the balloon includes a central waist between the upper and lower inflatable elements. In an application, the balloon is shaped so as to define an hourglass shape at at least one cross-element thereof.

In an application, positioning the annulus-marking device includes positioning the central waist between leaflets of the valve.

In an application, the method further includes viewing tissue of the native heart valve annulus and tissue coupled thereto using the annulus-marking device.

In an application, the annulus-marking device includes radiopaque material.

In an application, inflating the annulus-marking device includes inflating the annulus-marking device with radiopaque fluid.

In an application, viewing the tissue of the native heart valve annulus and tissue coupled thereto includes imaging the annulus-marking device with respect to the tissue of the native heart valve annulus and the tissue coupled thereto by viewing the upper and lower inflatable elements against the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including delivering an annulus-marking device including at least a first magnetic element to one or more surfaces of a native heart valve of a heart of a subject, the one or more surfaces selected from the group consisting of: an atrial surface and a ventricular surface, generating a magnetic field around the at least the first magnetic element, and implanting an implant along a native heart valve annulus of the subject using the annulus-marking device as a guide for implantation of the implant along the annulus under imaging.

The method can also include retrieving the annulus-marking device following the implanting.

In an application, the at least the first magnetic element includes a circular wire. In an application, the at least the first magnetic element includes a flat disc. In an application, the at least the first magnetic element includes a toroid.

In an application, generating the magnetic field includes preventing movement of the magnetic element with respect to tissue of the valve.

In an application, generating the magnetic field includes positioning the magnetic element at a suitable position with respect to tissue of the valve.

In an application, implanting under imaging includes implanting using fluoroscopy.

In an application, delivering the annulus-marking device includes delivering the annulus-marking device to a mitral valve. In an application, delivering the annulus-marking device includes delivering the annulus-marking device to a tricuspid valve.

In an application, generating the magnetic field around the at least the first magnetic element includes providing an external magnetic field.

In an application, delivering the annulus-marking device includes positioning the at least the first magnetic element at the atrial surface, and generating the magnetic field includes generating the magnetic field from within a ventricle of the heart.

In an application, delivering the annulus-marking device includes positioning the at least the first magnetic element at the ventricular surface, and generating the magnetic field includes generating the magnetic field from within an atrium of the heart.

In an application, delivering the at least the first magnetic element includes delivering the first magnetic element to the atrial surface of the valve. In an application, the method further includes delivering a second magnetic element to the ventricular surface of the valve, and generating the magnetic field includes generating the magnetic field responsively to the delivering the second magnetic element.

In an application, implanting the implant includes implanting the implant between an external surface of the first magnetic element and an atrial wall.

In an application, the method further includes viewing tissue of the native heart valve annulus and tissue coupled thereto using the at least the first magnetic element.

In an application, viewing the tissue of the native heart valve annulus and tissue coupled thereto includes imaging the annulus-marking device with respect to the tissue of the native heart valve annulus and the tissue coupled thereto by viewing the first magnetic element against the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including placing at a surface of a native heart valve annulus of a subject an annulus-marking device including a coil-shaped wire including a radiopaque material, facilitating imaging of the heart valve annulus by imaging movement of the coil-shaped wire along at least a portion of a perimeter of a surface of the native heart valve annulus, and in conjunction with the placing, implanting an implant along the native heart valve annulus of the subject using the coil-shaped wire as a guide for implantation of the implant along the annulus under imaging. The method can also include retrieving the annulus-marking device following the implanting.

In an application, implanting under imaging includes implanting using fluoroscopy.

In an application, placing includes placing the annulus-marking device at a surface of a native mitral valve. In an application, placing includes placing the annulus-marking device at a surface of a native tricuspid valve.

In an application, placing includes (1) anchoring a first end portion of the coil-shaped wire to a first commissure of the valve, (2) allowing the coil-shaped wire to expand along a portion of the circumference of the valve, and (3) anchoring a second end portion of the coil-shaped wire to a second commissure of the valve.

In an application, allowing the coil-shaped wire to expand along the portion of the circumference of the valve includes applying a pushing force to a portion of the annulus at the portion of the circumference of the valve.

In an application, placing includes placing the annulus-marking device along an atrial surface of the valve, and (1) anchoring the first end portion of the coil-shaped wire to the first commissure of the valve includes anchoring the first end portion to the first commissure using a first anchor that locks in place at the first commissure in a ventricle of the heart of the subject, and (2) anchoring the second end portion of the coil-shaped wire to the second commissure of the valve includes anchoring the second end portion to the second commissure using a second anchor that locks in place at the second commissure in the ventricle of the heart of the subject.

In an application, the valve includes a mitral valve, and (1) anchoring the first end portion of the coil-shaped wire to the first commissure of the valve includes anchoring the first end portion to an anterolateral commissure of the valve, (2) allowing the coil-shaped wire to expand along the portion of the circumference of the valve includes allowing the coil-shaped wire to expand along the posterior circumference of the valve, and (3) anchoring the second end portion of the coil-shaped wire to the second commissure of the valve includes anchoring the second end portion of the coil-shaped wire to a posteromedial commissure of the valve.

In an application, implanting the implant includes implanting the implant at an external perimeter of the annulus-marking device responsively to the pushing.

In an application, the method further includes viewing tissue of the native heart valve annulus and tissue coupled thereto under imaging the annulus-marking device.

In an application, viewing the tissue of the native heart valve annulus and tissue coupled thereto includes imaging the annulus-marking device with respect to the tissue of the native heart valve annulus and the tissue coupled thereto by viewing the annulus-marking device against the tissue.

In an application, viewing the tissue of the native heart valve annulus includes imaging the annulus-marking device with respect to the tissue of the native heart valve annulus and the tissue coupled thereto by viewing movement of the annulus-marking device responsively to movement of the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with some applications, a method, including placing within a native heart valve of a heart of a subject an annulus-marking device including a radiopaque material shaped to define an expandable element which expands within the heart valve that the expandable element provides an indication as to a location of a native heart valve annulus of the native heart valve of the subject.

In some applications, the annulus-marking device is compressible during delivery toward the native heart valve, and expandable from a compressed state for positioning at least within the heart valve. The method can further include expanding the annulus-marking device to an expanded state.

The method can further include implanting an implant along the native heart valve annulus of the subject using the annulus-marking device as a guide for implantation of the implant along the annulus under imaging.

The method can also include retrieving the annulus-marking device following the implanting.

In an application, implanting under imaging includes implanting using fluoroscopy.

In an application, retrieving the annulus-marking device following the implanting includes constraining the annulus-marking device within a tool and extracting the annulus-marking device from the subject.

In an application, placing includes placing the annulus-marking device in a mitral valve. In an application, placing includes placing the annulus-marking device in a tricuspid valve.

In an application, the expanding the expandable device includes expanding the expandable device to assume a generally spherical shape, and implanting the implant includes positioning the implant between the annulus-marking device and tissue of an atrial wall.

In an application, the expandable element includes a plurality of expandable elements including a plurality of woven radiopaque fabric fibers assuming a mesh.

In an application, the expandable element includes a plurality of expandable elements including a plurality of woven radiopaque metal fibers assuming a mesh.

In an application, the expandable element includes a balloon.

In an application, the method further includes viewing tissue of the native heart valve annulus and tissue coupled thereto by viewing the annulus-marking device.

In an application, viewing the tissue of the native heart valve annulus and tissue coupled thereto includes imaging the expandable element with respect to the tissue of the native heart valve annulus and the tissue coupled thereto by viewing the expandable element against the tissue.

In an application, viewing the tissue of the native heart valve annulus and tissue coupled thereto includes imaging the expandable element with respect to the tissue of the native heart valve annulus and the tissue coupled thereto by viewing movement of the expandable element responsively to movement of the tissue.

In an application, viewing the tissue of the native heart valve annulus and tissue coupled thereto includes imaging the expandable element with respect to the tissue of the native heart valve annulus, tissue of at least one leaflet, and tissue of an atrial wall.

This method can be performed on a living animal or on a simulation, such as on a cadaver, cadaver heart, simulator (e.g. with the body parts, tissue, etc. being simulated), etc.

There is further provided, in accordance with an application of the present invention, a system for use with a subject, the system including an implant configured for placement along a native heart valve annulus of a native heart valve of the subject and an annulus-marking device.

In some applications, the implant includes a body portion including flexible material, the body portion having a longitudinal axis that runs along a length of the body portion The annulus-marking device can be the same as or similar to any of the annulus-marking devices described herein. In some applications, the annulus-marking device includes a scaffolding including radiopaque material, the scaffolding being collapsible and expandable and configured, when expanded, to laterally push against tissue of the heart valve. A plurality of radiopaque elements can be coupled to the scaffolding, the plurality of radiopaque elements being configured to mark the native heart valve annulus and tissue coupled thereto.

In an application, the body portion includes a plurality of radiopaque markings configured to indicate placement of anchors along the body portion. In an application, each one of the plurality of radiopaque elements includes a material that is flexible. In an application, each one of the plurality of radiopaque elements includes a radiopaque filament.

In an application, when the scaffolding is expanded, the scaffolding is configured to push against tissue of a leaflet of the valve in a manner in which the leaflet assumes two subcusps.

In an application, the annulus-marking device is coupled to a delivery tool, and the annulus-marking device is retrievable upon removal of the delivery tool from the subject.

In an application, the scaffolding includes at least one a rod having a vertical orientation when the scaffolding is expanded. In an application, when the scaffolding is expanded, the rod extends from an atrial surface of the heart valve toward a ventricular surface of the heart valve.

In an application, the plurality of radiopaque elements includes a plurality of radiopaque filaments and the rod is coupled to the plurality of radiopaque filaments such that, when the scaffolding is expanded, the plurality of radiopaque filaments are configured to be pressed against tissue of the native heart valve annulus and tissue coupled thereto in a manner in which the plurality of radiopaque filaments provide an indication of the native heart valve annulus and tissue coupled thereto.

In an application, the at least one rod includes a plurality of rods and the scaffolding includes an expandable basket coupled to the plurality of rods such that the scaffolding expands circumferentially with respect to the native heart valve in a manner in which the plurality of rods are disposed circumferentially with respect to the native heart valve.

In an application, the scaffolding includes a central rod, an upper laterally-expandable element configured to expand laterally away from the central rod, a lower laterally-expandable element configured to expand laterally away from the central rod; and at least one flexible wire coupled to and extending between the upper and lower laterally-expandable elements, and when the scaffolding is expanded, the at least one flexible wire is configured to push against the tissue of the heart valve.

In an application, the upper and lower laterally-expandable elements are moveable longitudinally with respect to the central rod to control a tension of the at least one flexible wire.

In an application, when the scaffolding is expanded, the upper laterally-expandable element is configured to be disposed in an atrium of a heart of the subject and the lower laterally-expandable element is configured to be disposed in a ventricle of the heart of the subject.

In an application, the upper laterally-expandable element includes a first expandable and collapsible ring, the lower laterally-expandable element includes a second expandable and collapsible ring, the at least one wire includes at least two wires coupled at corresponding locations circumferentially along the first and second rings, and when the scaffolding is expanded, the first and second rings are in an expanded state.

In an application, the upper laterally-expandable element includes a first expandable and collapsible cross-beam that extends laterally away from the central rod, the lower laterally-expandable element includes a second expandable and collapsible cross-beam that extends laterally away from the central rod, the at least one wire includes at least two wires coupled at corresponding locations along the first and second cross-beams, and when the scaffolding is expanded, the first and second cross-beams are in an expanded state.

In an application, the scaffolding includes a central rod, a first loop element configured to expand laterally away from the central rod, a second loop element configured to expand laterally away from the central rod, at least one curved, flexible wire coupled to and extending from the rod at least within a space defined by the first and second loop elements; and a first magnet coupled to an end of the flexible wire, the first magnet being moveable by a second magnet that is not coupled to the scaffolding. When the scaffolding is expanded, the first and second loop elements are configured to push against the tissue of the heart valve.

In an application, the first and second loop elements are moveable longitudinally with respect to the central rod to control a tension of the first and second loop elements.

In an application, a delivery tool is configured to deliver the implant, the system includes the second magnet, and the delivery tool is coupled to the second magnet.

In an application, when the scaffolding is expanded, a first half of each of the first and second loop elements is configured to be disposed in an atrium of a heart of the subject and a second half of each of the first and second loop elements is configured to be disposed in a ventricle of the heart of the subject.

In an application, the first and second loop elements include radiopaque material. In an application, the first and second loop elements are coupled to radiopaque material.

In an application, the scaffolding includes a central rod, at least one curved, flexible wire coupled to and extending from the rod, and a first magnet coupled to an end of the flexible wire, the first magnetic element being moveable by a second magnetic element that is not coupled to the scaffolding.

In an application, when the scaffolding is expanded, (1) the at least one curved, flexible wire is configured to be disposed within a ventricle of a heart of the subject, and (2) the first magnetic element is configured to be disposed within a subannular space of the heart.

In an application, the at least one curved, flexible wire is moveable longitudinally with respect to the central rod.

In an application, the second magnetic element is configured to be positioned within vasculature surrounding the native heart valve.

In an application, the at least one curved, flexible wire is coupled to radiopaque material. In an application, the at least one curved, flexible wire includes radiopaque material.

In an application, the scaffolding includes a central rod, at least one cross-beam coupled to and extending laterally from the rod, and a first magnetic element coupled to an end of the least one cross-beam, the first magnetic element being moveable by a second magnetic element that is not coupled to the scaffolding.

In an application, when the scaffolding is expanded, the at least one least one cross-beam is configured to be disposed within an atrium of a heart of the subject.

In an application, the at least one least one cross-beam is moveable longitudinally with respect to the central rod.

In an application, the second magnetic element is configured to be positioned within vasculature surrounding the native heart valve.

In an application, the at least one least one cross-beam is coupled to radiopaque material. In an application, the at least one least one cross-beam includes radiopaque material.

There is further provided, in accordance with an application of the present invention, a system for use with a subject, the system including an implant configured for placement along a native heart valve annulus of a native heart valve of the subject and an annulus-marking device discrete from the implant and removable from within the subject following implantation of the implant. The annulus-marking device can be the same as or similar to any annulus-marking devices described herein.

In some applications, the annulus-marking device includes a plurality of radiopaque markers juxtaposing each other at a given distance from each other, the plurality of radiopaque markers each being deformable by tissue at different intervals indicating proximity of tissue to the implant.

In some applications, the implant includes a body portion including flexible material, the body portion having a longitudinal axis that runs along a length of the body portion.

In an application, the plurality of radiopaque markers are sized differently from each other. In an application, the plurality of radiopaque markers include concentric loops. In an application, the plurality of radiopaque markers include concentric petals or loops. In an application, the plurality of radiopaque markers include a plurality of radiopaque strips.

In an application, the plurality of radiopaque markers include wire.

In an application, each one of the plurality of radiopaque markers includes a radiopaque sail extending therefrom.

In an application, each one of the plurality of radiopaque markers includes a radiopaque filament extending therefrom.

There is further provided, in accordance with an application of the present invention, a system for use with a subject, the system including an implant configured for placement along a native heart valve annulus of a native heart valve of the subject and an annulus-marking device including an elongate radiopaque element and a plurality of flexible radiopaque filaments coupled to the elongate radiopaque element configured to mark the native heart valve annulus and tissue coupled thereto.

In some applications, the elongate radiopaque element is slidable along the body portion of the implant and along the longitudinal axis, and the plurality of radiopaque filaments.

In some applications, the implant includes a body portion including flexible material, the body portion having a longitudinal axis that runs along a length of the body portion.

In an application, the annulus-marking device is removable from the subject following implantation of the implant.

In an application, the body portion includes a plurality of radiopaque markings configured to indicate placement of anchors along the body portion. In an application, each one of the plurality of radiopaque filaments includes a material that is flexible. In an application, the elongate radiopaque element includes a wire. In an application, the elongate radiopaque element includes a rod.

In an application, the plurality of radiopaque filaments are disposed at a distal end of the elongate radiopaque element, the annulus-marking device includes a tube coupled to a proximal end of the elongate radiopaque element, and the tube surrounds the body portion and slides with respect to the body portion to move the plurality of radiopaque filaments with respect to the implant.

In an application, the plurality of radiopaque filaments are disposed at a distal end of the elongate radiopaque element, the body portion includes a plurality of eyelets, and the elongate radiopaque element is slidable with respect to the plurality of eyelets to move the plurality of radiopaque filaments with respect to the implant.

In an application, the plurality of radiopaque filaments are collapsible as they pass through each one of the plurality of eyelets.

There is further provided, in accordance with an application of the present invention, a method, including placing at a native heart valve annulus of a subject, at a first angle of delivery with respect to a planar surface of a leaflet of the valve, an annulus-marking device including a radiopaque material, implanting an implant along the native heart valve annulus of the subject using the annulus-marking device as a guide for implantation of the implant along the annulus under imaging. In some applications, the method further includes retrieving the annulus-marking device following the implanting.

The annulus-marking device can be the same as or similar to any of the annulus-marking devices described herein.

In some applications, the annulus-marking device comprises (1) a wire radiopaque extension, and (2) at least one radiopaque distal curved tip disposed at a nonzero angle with respect to the wire extension.

In some applications, the method includes, subsequently to the placing, enabling the annulus marking device to move incrementally along the leaflet, and by the moving, changing the angle of delivery of the annulus-marking device with respect to the planar surface of the leaflet of the valve.

The method can further include, by the changing the angle, determining a position of an annulus of the valve by visualizing the changing of the angle.

In an application, determining the position includes determining that the curved distal tip is disposed along the leaflet responsively to visualizing beating of the annulus-marking device.

In an application, determining the position includes determining that the curved distal tip is disposed at the annulus responsively to visualizing that the annulus-marking device does not move.

This method can be performed on a living animal or on a simulation, such as on a cadaver, cadaver heart, simulator (e.g. with the body parts, tissue, etc. being simulated), etc.

There is further provided, in accordance with an application of the present invention, a system for use with a subject, the system including an implant configured for placement along a native heart valve annulus of a native heart valve of the subject and an annulus-marking device including an expandable radiopaque braided mesh that is expandable from a collapsed state to an expanded state.

In some applications, the expanded state comprises a frustoconical shape. In some applications, two or more pull wires are coupled to the expandable braided mesh, the two or more pull wires being configured to be pulled in order to transition the braided mesh from the frustoconical shape to a shape in which the mesh assumes (1) a sloped upper portion configured for positioning within an atrium of a heart of the subject, (2) a bulging ledge portion configured for positioning above the heart valve, (3) a narrow portion for positioning within the heart valve, and (4) a trumpet portion configured for expanding within a ventricle of the heart of the subject.

In some applications, the implant including a body portion including flexible material, the body portion having a longitudinal axis that runs along a length of the body portion.

In an application, the annulus-marking device is removable from the subject following implantation of the implant.

In an application, the body portion includes a plurality of radiopaque markings configured to indicate placement of anchors along the body portion.

In an application, the one two or more pull wires includes three pull wires.

In an application, the bulging portion has a greater diameter than the other portion of the annulus-marking device. In an application, the implant is slidable along the sloped upper portion toward the annulus.

There is further provided, in accordance with an application of the present invention, a system for use with a subject, the system including an implant configured for placement along a native heart valve annulus of a native heart valve of the subject and an annulus-marking device. The annulus-marking device can be the same as or similar to other annulus-marking devices described herein.

In some applications, the annulus-marking device comprises an expandable radiopaque braided mesh that is expandable from a collapsed state to an expanded state, in the expanded state, the mesh assumes (1) a sloped upper portion configured for positioning within an atrium of a heart of the subject, and (2) an asymmetrical portion for positioning within the heart valve.

In an application, the annulus-marking device is removable from the subject following implantation of the implant.

In some applications, the implant including a body portion including flexible material, the body portion having a longitudinal axis that runs along a length of the body portion.

In an application, the body portion includes a plurality of radiopaque markings configured to indicate placement of anchors along the body portion.

In an application, the implant is slidable along the sloped upper portion toward the annulus.

In an application, the system includes a stabilizing rod and a tissue anchor coupled to an end of the stabilizing rod and configured to be reversibly coupled to tissue of the heart of the subject, the annulus-marking device is slidably coupled to the stabilizing rod, and the stabilizing rod is configured to stabilize and guide positioning of the annulus-marking device.

In an application, in the expanded state, the mesh assumes a trumpet portion configured for expanding within a ventricle of the heart of the subject.

In an application, the trumpet portion has a greater diameter than the other portions of the annulus-marking device.

In an application, the system includes a plurality of expandable snares coupled to a distal end portion of the expandable radiopaque braided mesh, the plurality of expandable radiopaque snares being configured to ensnare one or more native leaflets of the native valve of the subject.

In an application, the plurality of expandable snares includes a rigid material. In an application, the plurality of expandable snares includes a flexible material. In an application, the plurality of expandable snares includes a radiopaque material.

In an application, the plurality of expandable snares extend distally from a distal end of the expandable radiopaque braided mesh and then curve proximally.

In an application, the system includes a plurality of expandable radiopaque elements which are coupled to a distal end portion of the expandable radiopaque braided mesh and configured to expand radially such that the plurality of expandable elements provides an indication as to a location of the native heart valve annulus of the native heart valve of the subject.

In an application, the plurality of radiopaque expandable elements collectively form the annulus-marking device into a generally spherical shape.

In an application, the plurality of expandable radiopaque elements include a plurality of woven radiopaque fibers assuming a mesh. In an application, the plurality of expandable radiopaque elements include a plurality of curved wires.

In an application, the system includes an inflatable annular element coupled to a distal end portion of the expandable radiopaque braided mesh, the inflatable annular element being configured to position the expandable radiopaque braided mesh within the native valve of the subject.

In an application, the inflatable annular element includes a radiopaque material.

In an application, the inflatable annular element includes a prosthetic valve.

In an application, the expandable radiopaque braided mesh is positionable within the native heart valve, and the inflatable annular element is positionable below the native heart valve.

There is further provided, in accordance with an application of the present invention, a system for use with a subject, the system including an implant configured for placement along a native heart valve annulus of a native heart valve of the subject and an annulus-marking device including a temporary valve.

In some applications, the temporary valve is an inflatable temporary valve that is inflatable from a collapsed state to an inflated state or expanded state. In some applications, in the expanded state, the inflatable temporary valve includes (1) a proximal non-compliant balloon configured for positioning within the native heart valve and partially within an atrium of a heart of the subject, and (2) a distal compliant balloon configured for positioning in a subannular space of the native heart valve.

In an application, two or more prosthetic leaflets are coupled to the temporary valve.

In some applications, the implant includes a body portion including flexible material, the body portion having a longitudinal axis that runs along a length of the body portion.

There is further provided, in accordance with an application of the present invention, a method, including delivering an annulus-marking device including at least a first magnetic element to one or more surfaces of a native heart valve of a heart of a subject, the one or more surfaces selected from the group consisting of: an atrial surface and a ventricular surface, delivering a second magnetic element to vasculature surrounding the heart valve, generating a magnetic field around the at least the first magnetic element; and implanting an implant along a native heart valve annulus of the subject using the annulus-marking device as a guide for implantation of the implant along the annulus under imaging.

In some applications, the method further includes retrieving the annulus-marking device following the implanting.

In an application, the at least the first magnetic element is coupled to a curved wire and delivering the annulus-marking device includes delivering the first magnetic element to the ventricular surface.

In an application, the at least the first magnetic element is coupled to an end of at least one cross-beam, and delivering the annulus-marking device includes delivering the first magnetic element to the atrial surface.

In an application, generating the magnetic field includes positioning the magnetic elements at a suitable position with respect to tissue of the valve.

In an application, implanting under imaging includes implanting using fluoroscopy.

In an application, delivering the annulus-marking device includes delivering the annulus-marking device to a mitral valve. In an application, delivering the annulus-marking device includes delivering the annulus-marking device to a tricuspid valve.

In an application, the method further includes viewing tissue of the native heart valve annulus and tissue coupled thereto using the at least the first magnetic element.

In an application, viewing the tissue of the native heart valve annulus and tissue coupled thereto includes imaging the annulus-marking device with respect to the tissue of the native heart valve annulus and the tissue coupled thereto by viewing the first magnetic element against the tissue.

In an application, viewing the tissue of the native heart valve annulus and tissue coupled thereto includes imaging the annulus-marking device with respect to the tissue of the native heart valve annulus, tissue of at least one leaflet, and tissue of an atrial wall.

This and other methods herein can be performed on a living animal or on a simulation, such as on a cadaver, cadaver heart, simulator (e.g. with the body parts, tissue, etc. being simulated), etc.

The present invention will be more fully understood from the following detailed description of embodiments thereof, taken together with the drawings, in which:

BRIEF DESCRIPTION OF THE DRAWINGS

FIGS. 2A-F are schematic illustrations of a method for implanting the annulus-marking devices of FIGS. 1A-C, in accordance with some applications;

FIGS. 4A-B are schematic illustrations of an implant comprising an annulus-marking device, in accordance with some applications;

FIGS. 5A-B are schematic illustrations of an implant comprising an annulus-marking device, in accordance with some applications;

FIGS. 6A-B are schematic illustrations of respective tissue anchors comprising an annulus-marking device, in accordance with some applications;

FIGS. 7A-C are schematic illustrations of an implant comprising an annulus-marking device, in accordance with some applications;

FIGS. 9A-B are schematic illustrations of a navigational-based guidance system, which employs one or more longitudinal guides configured to facilitate guidance of an implant to specific portions of the mitral valve by the guides contacting a surface of the mitral valve, in accordance with some applications;

FIGS. 33A-B are schematic illustrations of annulus-marking devices comprising inflatable elements for aiding implantation of cardiac devices under the guidance of imaging, in accordance with some applications;

FIGS. 37A-G are schematic illustrations of an annulus-marking device comprising first and second radiopaque loops for aiding implantation of cardiac devices under the guidance of imaging, in accordance with some applications;

FIG. 43 is a schematic illustration of an annulus-marking device comprises a balloon having upper and lower inflatable sections for aiding implantation of cardiac devices under the guidance of imaging, in accordance with some other applications;

FIGS. 44-46 are schematic illustrations of an annulus-marking device comprises magnetic elements for aiding implantation of cardiac devices under the guidance of imaging, in accordance with respective applications;

FIGS. 51A-C are schematic illustrations of an annulus-marking device comprising a scaffolding comprising an expandable basket for aiding implantation of cardiac devices under the guidance of imaging, in accordance with some applications;

FIGS. 52A-B are schematic illustrations of an annulus-marking device comprising a plurality of radiopaque markers for aiding implantation of cardiac devices under the guidance of imaging, in accordance with some applications;

FIGS. 57A-B, 58A-B, 59A-B, 60A-B, and 61A-B are schematic illustrations of respective annulus-marking device comprising a radiopaque asymmetrical mesh for aiding implantation of cardiac devices under the guidance of imaging, in accordance with respective applications;

DETAILED DESCRIPTION OF EMBODIMENTS

Figure 1A:
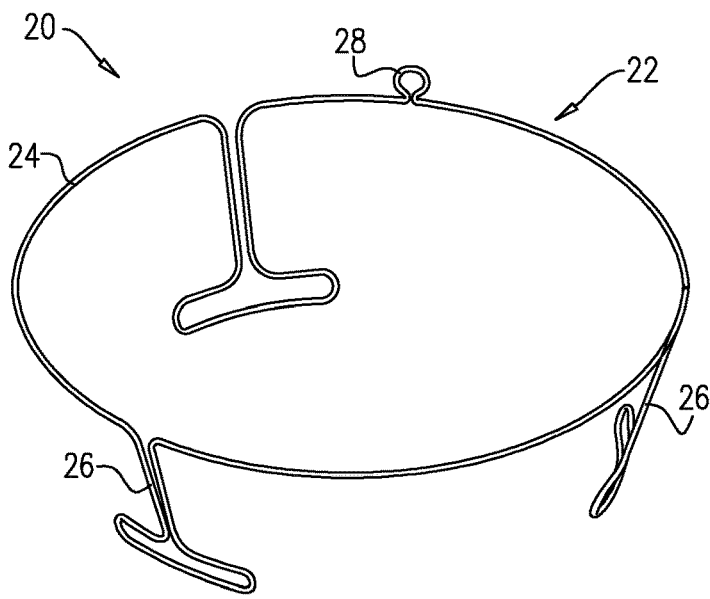
FIGS. 1A-C are schematic illustrations of examples of respective annulus-marking devices for aiding implantation of cardiac devices under the guidance of imaging, in accordance with some applications.
Figure 1B:
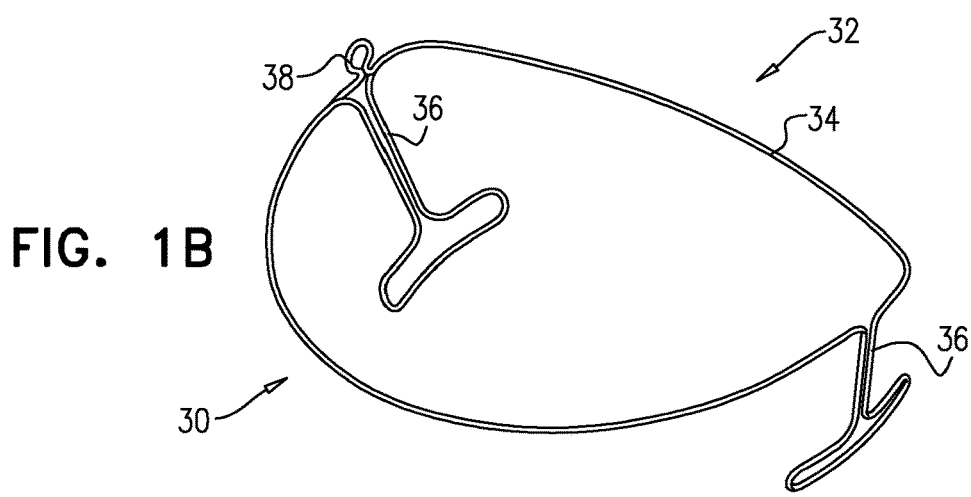
Figure 1C:
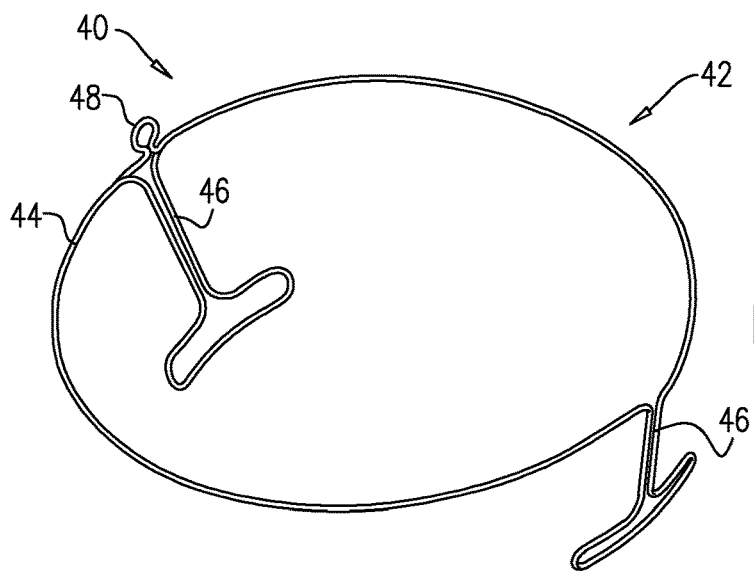

Reference is now made to FIGS. 1A-C, which are schematic illustrations of respective annulus-marking devices for aiding implantation of cardiac devices under the guidance of imaging, in accordance with some applications of the present invention. The steering procedure can be performed with the aid of imaging, such as fluoroscopy, transesophageal echo, and/or echocardiography.

FIG. 1A shows a system 20 comprising an annulus-marking device 22 comprising a radiopaque material shaped so as to define a base frame 24 having a shape such that it tracks a circumference of a native heart valve annulus and approximates the shape of the annulus. That is, frame 24 has a circular shape that tracks the circumference of the native heart valve. Device 22 comprises one or more struts 26 (e.g., three as shown by way of illustration and not limitation). Struts 26 project away from a plane define by base frame 24 and are shaped so as to be placed in the commissures of the native valve. Struts 26 thereby provide an indicator of the location, height, and orientation of the commissures under imaging. Struts 26 are desirably sized and configured to contact tissue near or within the heart valve annulus to brace base frame 24 against migration within the annulus. Struts 26 are spaced apart to rest in engagement with tissue at or near the leaflet commissures (or wherever tissue contact with the struts 26 is intended to occur). For some applications, frame 24 and struts 26 are fabricated from a single piece. Optionally, frame 24 and struts 26 can be fabricated as separate pieces and coupled together by welding, clamping, etc., for example. Struts 26 can provide an indication as to the height of the annulus of the valve, so that when placing device 22, a height of the annulus can be measured, for example by imaging the struts when in contact with the annulus.

Device 22 can be delivered percutaneously, thoracoscopically through the chest, or using open heart surgical techniques. To help with percutaneous delivery and/or for other reasons, the device 22 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 22 comprises a wire.

Device 22 is configured for placement along a native tricuspid valve. As such, frame 24 of device 22 is generally circular. For some applications, device 22 comprises an adjustment mechanism 28 which expands and contracts a perimeter of base frame 24. For some applications, base frame 24 is hollow and is shaped so as to define a lumen, and adjustment mechanism 28 comprises a wire that runs at least partially within the lumen of base frame 24. In such applications, the wire is pullable and/or twistable to adjust the perimeter of base frame 24. For some applications, a portion of base frame 24 is collapsible telescopically in response to pulling of the wire of adjustment mechanism 28.

Device 22 is compressible during delivery toward the native heart valve. During delivery of device 22, device 22 is constrained in a collapsed condition. A flexible push rod can be used to expel the device 22 from a delivery catheter. Free of the catheter, device 22 will self-expand from its compressed state to its preordained configuration, e.g., like that shown in FIG. 1A.

FIG. 1B shows a system 30 comprising an annulus-marking device 32 comprising a radiopaque material shaped so as to define a base frame 34 having a shape such that it tracks a circumference of a native heart valve annulus and approximates the shape of the annulus. That is, frame 34 has a "D"-shape that tracks the circumference of the native heart valve. Device 32 comprises one or more struts 36 (e.g., three as shown by way of illustration and not limitation). Struts 36 project away from a plane define by base frame 34 and are shaped so as to be placed in the commissures of the native valve. Struts 36 thereby provide an indicator of the location, height, and orientation of the commissures under imaging. Struts 36 are desirably sized and configured to contact tissue near or within the heart valve annulus to brace base frame 34 against migration within the annulus. Struts 36 are spaced apart to rest in engagement with tissue at or near the leaflet commissures (or wherever tissue contact with the struts 36 is intended to occur). For some applications, frame 34 and struts 36 are fabricated from a single piece, or as separate pieces coupled to each other, as mentioned above with respect to device 22. Also, as mentioned above, struts 36 can provide an indication as to the height of the annulus of the valve, so that when placing device 32, a height of the annulus can be measured, for example by imaging the struts when in contact with the annulus.

Device 32 can be delivered percutaneously, thoracoscopically through the chest, or using open heart surgical techniques. If delivered percutaneously, the device 32 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 32 comprises a wire.

Device 32 is configured for placement along a native mitral valve. As such, frame 34 of device 32 is substantially D-shaped and struts 36 are oppositely spaced so as to fit within the commissures of the native mitral valve. For some applications, frame 34 of device 32 is substantially saddle-shaped, such that frame 43 looks like the undulated outer circumference line of a saddle. For some applications, device 32 comprises an adjustment mechanism 38 which expands and contracts a perimeter of base frame 34. For some applications, base frame 34 is hollow and is shaped so as to define a lumen, and adjustment mechanism 38 comprises a wire that runs at least partially within the lumen of base frame 34. In such applications, the wire is pullable and/or twistable to adjust the perimeter of base frame 34. For some applications, a portion of base frame 34 is collapsible telescopically in response to pulling of the wire of adjustment mechanism 38.

Device 32 is compressible during delivery toward the native heart valve. During delivery of device 32, device 32 is constrained in a collapsed condition. A flexible push rod can be used to expel the device 32 from a delivery catheter. Free of the catheter, device 32 will self-expand from its compressed state to its preordained configuration, e.g., like that shown in FIG. 1B.

FIG. 1C shows a system 40 comprising an annulus-marking device 42 comprising a radiopaque material shaped so as to define a base frame 44 having a shape such that it tracks a circumference of a native heart valve annulus and approximates the shape of the annulus. That is, frame 44 has a circular shape that tracks the circumference of the native heart valve. Device 42 comprises one or more struts 46 (e.g., three as shown by way of illustration and not limitation). Struts 46 project away from a plane define by base frame 44 and are shaped so as to be placed in the commissures of the native valve. Struts 46 thereby provide an indicator of the location, height, and orientation of the commissures under imaging. Struts 46 are desirably sized and configured to contact tissue near or within the heart valve annulus to brace base frame 44 against migration within the annulus. Struts 46 are spaced apart to rest in engagement with tissue at or near the leaflet commissures (or wherever tissue contact with the struts 46 is intended to occur). For some applications, frame 44 and struts 46 are fabricated from a single piece, or as separate pieces coupled to each other, as mentioned above with respect to device 22. Also, struts 46 can provide an indication as to the height of the annulus of the valve, so that when placing device 42, a height of the annulus can be measured, for example by imaging the struts when in contact with the annulus.

Device 42 can be delivered percutaneously, thoracoscopically through the chest, or using open heart surgical techniques. The device 42 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 42 comprises a wire.

Device 42 is configured for placement along a native mitral valve. As shown, frame 44 of device 42 is generally circular and struts 46 are oppositely spaced so as to fit within the commissures of the native mitral valve. For some applications, frame 44 of device 42 is substantially saddle-shaped. For some applications, device 42 comprises an adjustment mechanism 48 which expands and contracts a perimeter of base frame 44. For some applications, base frame 44 is hollow and is shaped so as to define a lumen, and adjustment mechanism 48 comprises a wire that runs at least partially within the lumen of base frame 44. In such applications, the wire is pullable and/or twistable to adjust the perimeter of base frame 44. For some applications, a portion of base frame 44 is collapsible telescopically in response to pulling of the wire of adjustment mechanism 48.

Device 42 is compressible during delivery toward the native heart valve. During delivery of device 42, device 42 is constrained in a collapsed condition. A flexible push rod can be used to expel the device 42 from a delivery catheter. Free of the catheter, device 42 will self-expand from its compressed state to its preordained configuration, e.g., like that shown in FIG. 1C.

Reference is now made to FIGS. 1A-C. Devices 22, 32, and 42 are made, for example by machining, bending, shaping, joining, molding, or extrusion, from a biocompatible metallic or polymer material, or a metallic or polymer material that is suitably coated, impregnated, or otherwise treated with a material to impart biocompatibility, or a combination of such materials. The material is also desirably radiopaque to facilitate fluoroscopic visualization.

Reference is now made to FIGS. 2A-F, which are schematic illustrations of a method and a system 60 for implanting the annulus-marking devices of FIGS. 1A-C, in accordance with some applications.

In FIG. 2A, device 22 is positioned along an annulus 66 of a native tricuspid valve 62 and device 32 is positioned along an annulus 68 of a native mitral valve 64. It is to be noted that device 42 can be implanted along mitral valve 64. As described hereinabove, devices 22 and 32 can be delivered in a constrained configuration into the atrium and then expanded within the atrium. For example, percutaneous vascular access can be achieved by conventional methods into the femoral or jugular vein.

In FIG. 2B, devices 22 and 32 are adjusted by respective adjusting mechanisms 28 and 38. In some applications, an adjustment tool 70 engages with a portion of adjusting mechanisms 28 and 38 and pulls and or twists the portion of the adjusting mechanisms 28 and 38 (e.g., a wire of mechanism 28 and 38). Frames 24 and 34 are adjusted by tool 70 so as to achieve the desired positioning of devices 22 and 32 respectively along the annulus.

Figure 2C:
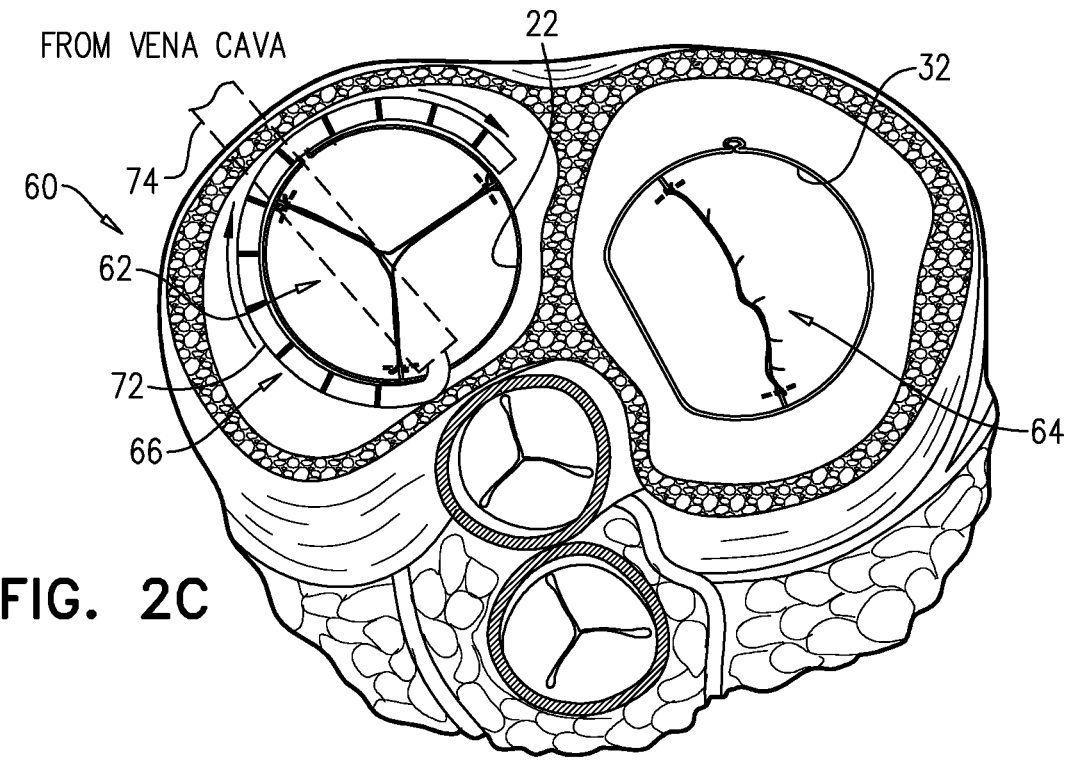

In FIG. 2C, an implant, e.g., an annuloplasty structure 72, is positioned along annulus 66 of tricuspid valve 62 using a delivery tool 74 which passes structure 72 into the right atrium via the superior vena cava or the inferior vena cava. Structure 72 can comprise a flexible body portion. For some applications, the body portion of structure 72 is shaped so as to define a tubular sleeve through which a plurality of anchors is implanted. The body portion of structure 72 comprises a plurality of radiopaque markers 75, which are positioned along structure 72 at respective longitudinal sites. The markers provide an indication in a radiographic image (such as a fluoroscopy image) of how much of the body portion has been deployed at any given point during an implantation procedure, in order to enable setting a desired distance between the tissue anchors along the body portion. For some applications, the markers comprise a radiopaque ink. For some applications the markers comprise a radiopaque material or additional radiopaque material, markers, etc. attached to or incorporated in structure 72.

Structure 72 is delivered within a delivery tool 74. Delivery tool 74 is guided and steered in accordance with imaging guided by annulus-marking device 22. That is, structure 72 is positioned along annulus 66 and anchored thereto under imaging using annulus-marking device 22 to mark tissue of the annulus and the commissures.

In some applications, at least a portion (e.g., at least three, some, all, etc.) of the longitudinal sites of radiopaque markers 75 are longitudinally spaced at a constant interval. In some applications, the longitudinal distance between the distal edges of adjacent markers, and/or the distance between the proximal edges of adjacent markers, is set equal to the desired distance between adjacent anchors. For example, the markers can comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance can be between 3 and 15 mm, such as 6 mm, and the longitudinal length of each marker can be between 0.1 and 14 mm, such as 2 mm. (If, for example, the distance were 6 mm and the length were 2 mm, the longitudinal gaps between adjacent markers would have lengths of 4 mm.)

Annuloplasty structure 72 is used to repair a dilated valve annulus of tricuspid valve 62. For some applications, the annuloplasty structure is configured to be placed only partially around the valve annulus (e.g., to assume a C-shape), and, once anchored in place, to be contracted so as to circumferentially tighten the valve annulus.

For some applications, structure 72 further comprises an adjusting mechanism, which facilitates contracting and expanding of annuloplasty structure 72 so as to facilitate adjusting of a perimeter of the annulus and leaflets of the cardiac valve. For some applications, the adjusting mechanism comprises a contracting member such as a wire, line, suture, elongate member, etc. extending along the annuloplasty structure 72 and a rotatable structure (e.g., a spool, wheel, spindle, etc.) configured to apply a contracting force to the contracting member so as to longitudinally contract annuloplasty structure 72.

Figure 2D:
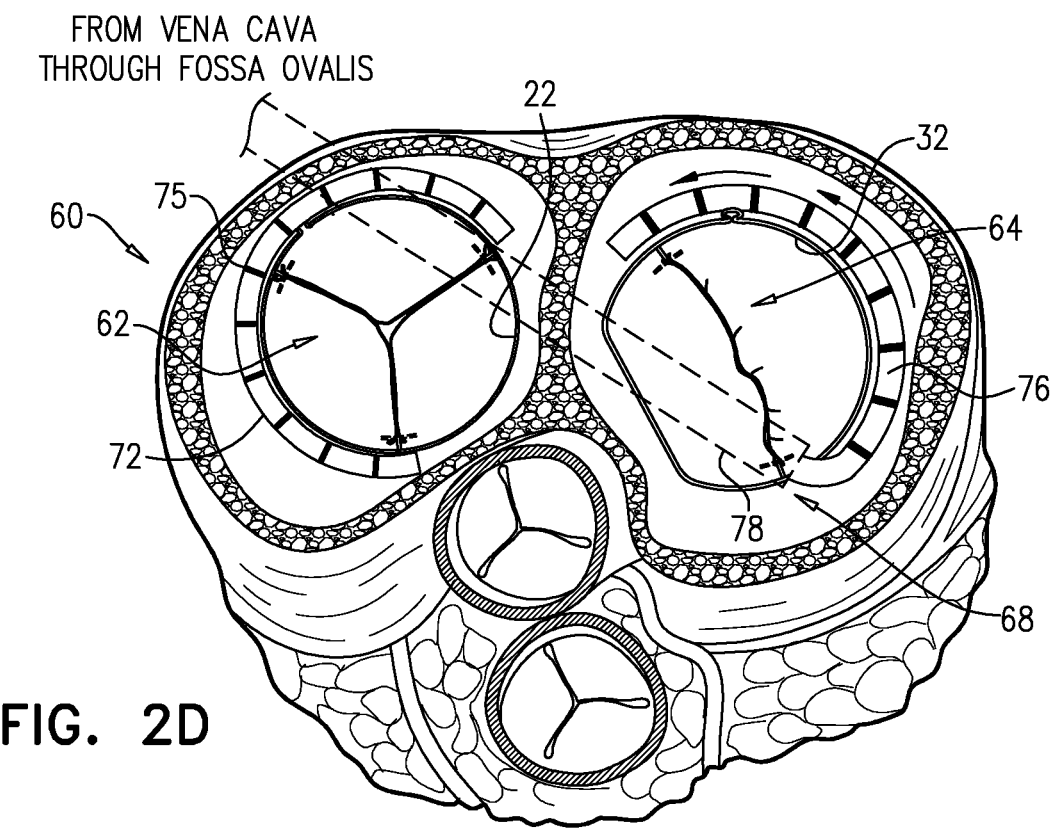

In FIG. 2D, an implant, e.g., an annuloplasty structure 76, is positioned along annulus 68 of mitral valve 64 using a delivery tool 74 which passes structure 76 into the left atrium via the superior vena cava or the inferior vena cava and subsequently through the fossa ovalis. In some applications, structure 76 comprises a flexible body portion. For some applications, the body portion of structure 76 is shaped so as to define a tubular sleeve through which a plurality of anchors is implanted. The body portion of structure 76 comprises a plurality of radiopaque markers 75, which are positioned along structure 76 at respective longitudinal sites. The markers provide an indication in a radiographic image (such as a fluoroscopy image) of how much of the body portion has been deployed at any given point during an implantation procedure, in order to enable setting a desired distance between the tissue anchors along the body portion. For some applications, the markers comprise a radiopaque ink. For some applications the markers comprise a radiopaque material or additional radiopaque material, markers, etc. attached to or incorporated in structure 76.

Structure 76 is delivered within a delivery tool 78. Delivery tool 78 is guided and steered in accordance with imaging guided by annulus-marking device 32. That is, structure 76 is positioned along annulus 68 and anchored thereto under imaging using annulus-marking device 32 to mark tissue of the annulus and the commissures.

For some applications, at least a portion (e.g., at least three, such as all) of the longitudinal sites of radiopaque markers 75 are longitudinally spaced at a constant interval. For some applications, the longitudinal distance between the distal edges of adjacent markers, and/or the distance between the proximal edges of adjacent markers, is set equal to the desired distance between adjacent anchors. For example, the markers can comprise first, second, and third markers, which first and second markers are adjacent, and which second and third markers are adjacent, and the distance between the proximal and/or distal edges of the first and second markers equal the corresponding distance between the proximal and/or distal edges of the second and third markers. For example, the distance may be between 3 and 15 mm, such as 6 mm, and the longitudinal length of each marker may be between 0.1 and 14 mm, such as 2 mm. (If, for example, the distance were 6 mm and the length were 2 mm, the longitudinal gaps between adjacent markers would have lengths of 4 mm.)

Annuloplasty structure 76 is used to repair a dilated valve annulus of mitral valve 64. For some applications, the annuloplasty structure is configured to be placed only partially around the valve annulus (e.g., to assume a C-shape), and, once anchored in place, to be contracted so as to circumferentially tighten the valve annulus. For some application, annuloplasty structure 76 is implemented using techniques described in U.S. application Ser. No. 12/437,103, filed May 7, 2009 which published as US 2010/0286767, and/or U.S. application Ser. No. 12/689,635, filed Jan. 19, 2010 which published as US 2010/0280604, both of which are assigned to the assignee of the present application and are incorporated herein by reference.

For some applications, structure 76 further comprises an adjusting mechanism, which facilitates contracting and expanding of annuloplasty structure 76 so as to facilitate adjusting of a perimeter of the annulus and leaflets of the cardiac valve. For some applications, the adjusting mechanism comprises a contracting member such as a wire, line, suture, elongate member, etc. extending along the annuloplasty structure 76 and a rotatable structure (e.g., a spool, wheel, spindle, etc.) configured to apply a contracting force to the contracting member so as to longitudinally contract annuloplasty structure 76.

Figure 2E:
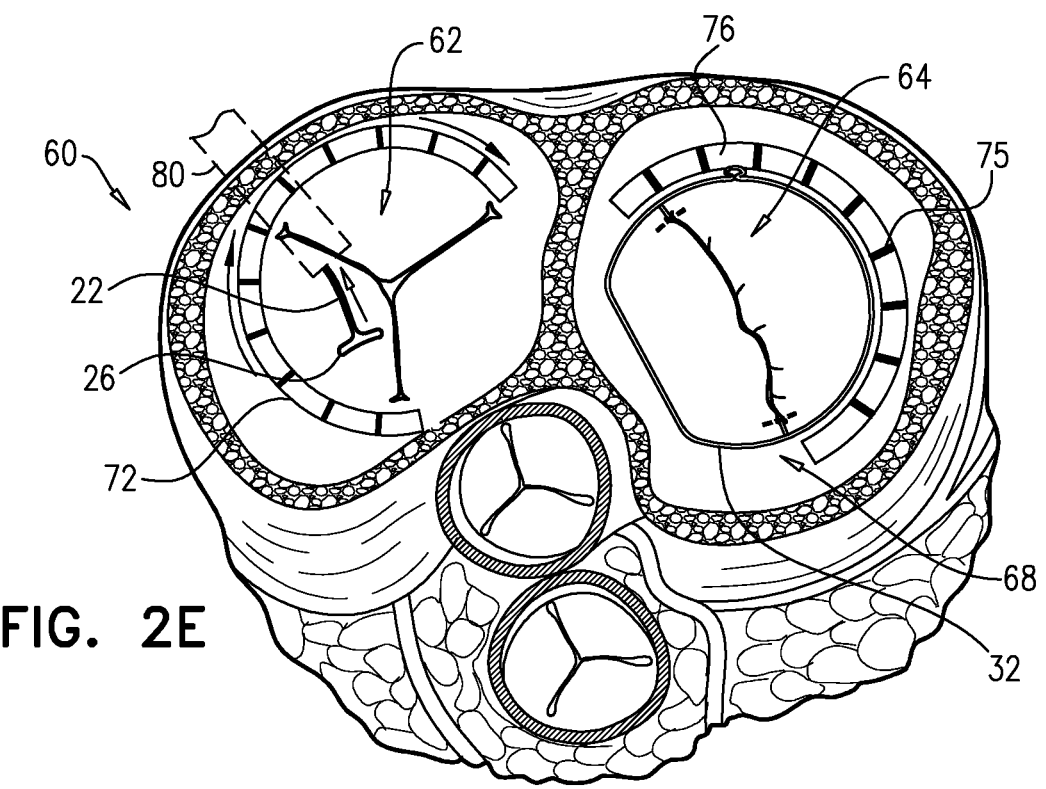

FIG. 2E shows retrieval of annulus-marking device 22 following implantation of annuloplasty structure 72 at annulus 66 of tricuspid valve 62. Since device 22 is flexible and compressible, device 22 is constrained by pulling device 22 within an extraction tool 80 during the retrieval of device 22 and subsequent removal of device 22 from the body of the subject. That is, device 22 does not function as an implant for such embodiments and is used only to guide implantation of annuloplasty structure 72 (i.e., the implant); rather, device 22 acts as a guide for implantation while placed temporarily within the body of the patient to be subsequently removed therefrom following the implantation of annuloplasty structure 72.

Figure 2F:
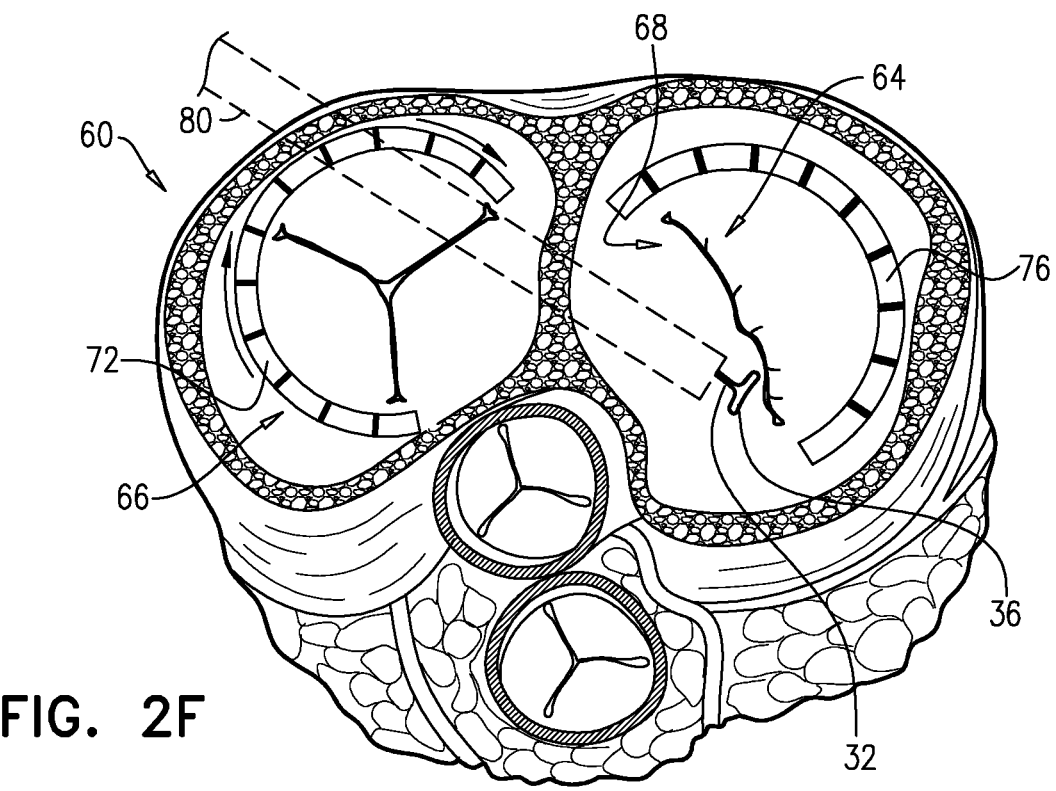

FIG. 2F shows retrieval of annulus-marking device 32 following implantation of annuloplasty structure 76 at annulus 68 of mitral valve 64. Since device 32 is flexible and compressible, device 32 is constrained by pulling device 32 within an extraction tool 80 during the retrieval of device 32 and subsequent removal of device 32 from the body of the subject. That is, device 32 does not function as an implant for such embodiments and is used only to guide implantation of annuloplasty structure 76 (i.e., the implant); rather, device 32 acts as a guide for implantation while placed temporarily within the body of the patient to be subsequently removed therefrom following the implantation of annuloplasty structure 76.

Reference is now made to FIGS. 1A-C and 2A-F. It is to be noted that annulus-marking devices 22, 32, and 42 can be used as a rail for mechanically guiding implantation of the annuloplasty structures described herein. When implanting annuloplasty structure 76 along the annulus, structure 76 can be pushed against the annulus while an anchor is implanted into the annulus, so that the frame of annulus-marking devices 22, 32, and 42 which is less compliant than the annulus tissue provides tactile feedback to an operating physician, and moreover, can also act as a rail at which structure 76 is deflected to the more compliant annulus tissue. That is, the delivery tool which deliver the annuloplasty structure uses the frame of devices 22, 32, and 42 as a tactile and mechanical guide in addition to being a visual guide for moving the delivery tool along the annulus.

Figure 3A:
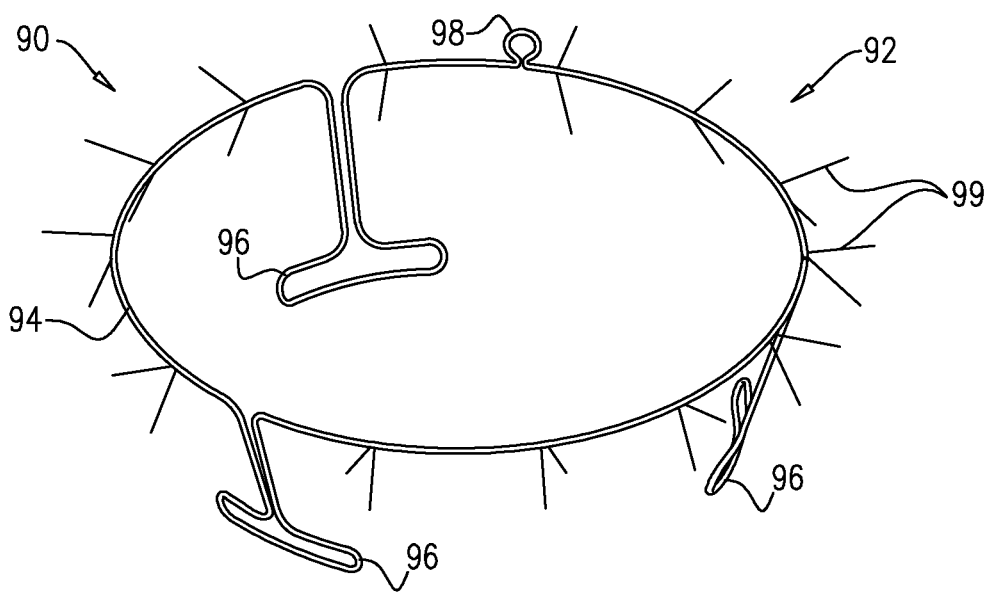
FIGS. 3A-C are schematic illustrations of examples of respective annulus-marking devices, in accordance with some applications.
Figure 3B:
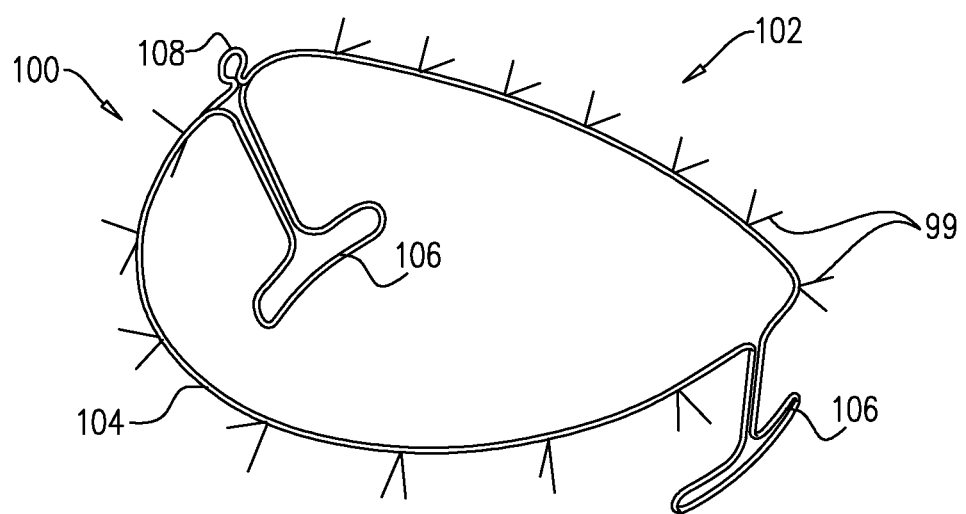
Figure 3C:
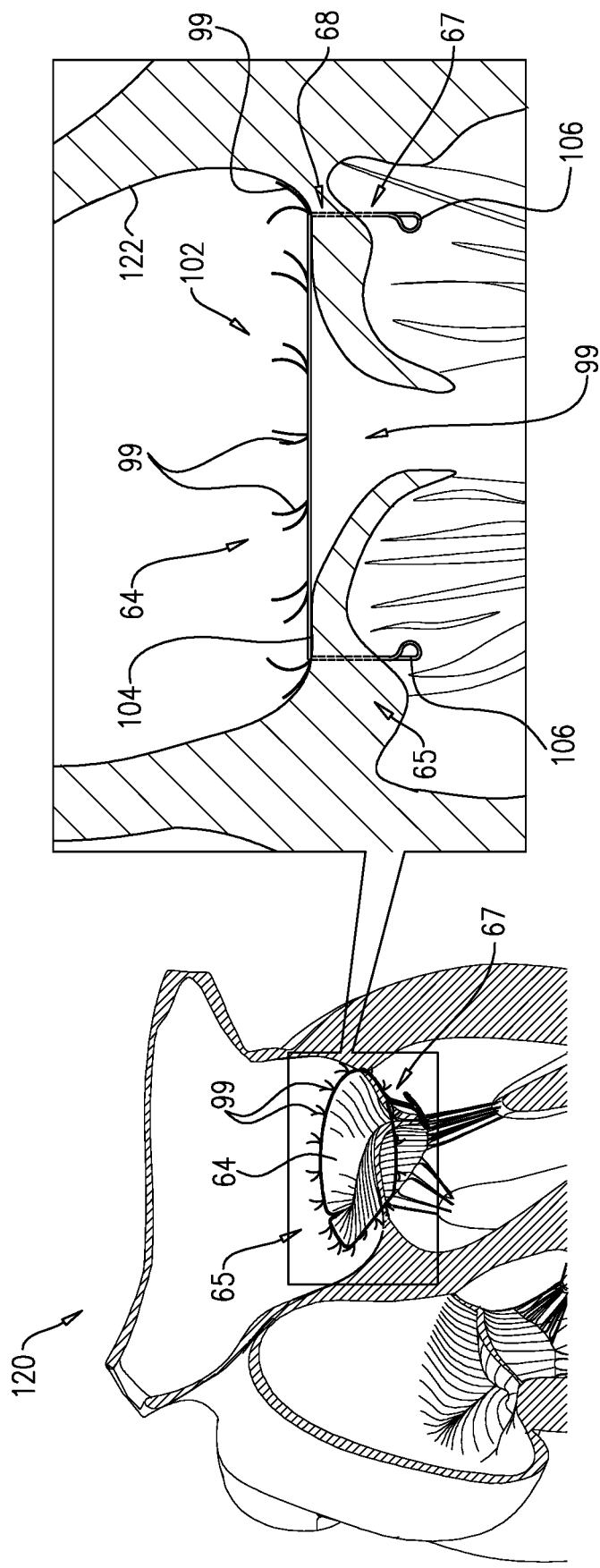

Reference is now made to FIGS. 3A-C, which are schematic illustrations of respective annulus-marking devices 92 and 102 which are similar to devices 22 and 32 of FIGS. 1A-B, respectively, with the exception that devices 92 and 102 each comprise a plurality of radiopaque elements 99 (e.g., radiopaque markers, filaments, wires, extensions, beads, etc.), which are described for example, but are not limited to, radiopaque filaments 99 herein. The plurality of radiopaque filaments 99 function as additional annulus-marking devices. Annulus-marking devices 92 and 102 are configured for aiding implantation of cardiac devices under the guidance of imaging, in accordance with some applications. The steering procedure is often performed with the aid of imaging, such as fluoroscopy, transesophageal echo, and/or echocardiography.

FIG. 3A shows a system 90 comprising an annulus-marking device 92 comprising a radiopaque material shaped so as to define a base frame 94 having a shape such that it tracks a circumference of a native heart valve annulus and approximates the shape of the annulus. Device 92 comprises one or more struts 96 (e.g., three as shown by way of illustration and not limitation). Struts 96 project away from a plane define by base frame 94 and are shaped so as to be placed in the commissures of the native valve. Struts 96 thereby provide an indicator of the location, height, and orientation of the commissures under imaging. Struts 96 are desirably sized and configured to contact tissue near or within the heart valve annulus to brace base frame 94 against migration within the annulus. Struts 96 are spaced apart to rest in engagement with tissue at or near the leaflet commissures (or wherever tissue contact with the struts 96 is intended to occur). For some applications, frame 94 and struts 96 are fabricated from a single piece, or as separate pieces coupled to each other, as mentioned above with respect to device 22. Also, struts 96 can provide an indication as to the height of the annulus of the valve, so that when placing device 92, a height of the annulus can be measured, for example by imaging the struts when in contact with the annulus.

Device 92 can be delivered percutaneously, thoracoscopically through the chest, and/or using open heart surgical techniques. Device 92 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 92 comprises a wire.

Device 92 is configured for placement along a native tricuspid valve. As such, frame 94 of device 92 is generally circular. For some applications, device 92 comprises an adjustment mechanism 98 which expands and contracts a perimeter of base frame 94. For some applications, base frame 94 is hollow and is shaped so as to define a lumen, and adjustment mechanism 98 comprises a wire that runs at least partially within the lumen of base frame 94. In such applications, the wire is pullable and/or twistable to adjust the perimeter of base frame 94. For some applications, a portion of base frame 94 is collapsible telescopically in response to pulling of the wire of adjustment mechanism 98.

Device 92 is compressible during delivery toward the native heart valve. During delivery of device 92, device 92 is constrained in a collapsed condition. A flexible push rod can be used to expel the device 92 from a delivery catheter. Free of the catheter, device 92 will self-expand from its compressed state to its preordained configuration, e.g., like that shown in FIG. 3A.

FIG. 3B shows a system 100 comprising an annulus-marking device 102 comprising a radiopaque material shaped so as to define a base frame 104 having a shape such that it tracks a circumference of a native heart valve annulus and approximates the shape of the annulus. Device 102 comprises one or more struts 106 (e.g., three as shown by way of illustration and not limitation). Struts 106 project away from a plane define by base frame 104 and are shaped so as to be placed in the commissures of the native valve. Struts 106 thereby provide an indicator of the location, height, and orientation of the commissures under imaging. Struts 106 are desirably sized and configured to contact tissue near or within the heart valve annulus to brace base frame 104 against migration within the annulus. Struts 106 are spaced apart to rest in engagement with tissue at or near the leaflet commissures (or wherever tissue contact with the struts 106 is intended to occur). For some applications, frame 104 and struts 106 are fabricated from a single piece, or as separate pieces coupled to each other, as mentioned above with respect to device 22. Also, struts 106 can provide an indication as to the height of the annulus of the valve, so that when placing device 102, a height of the annulus can be measured, for example by imaging the struts when in contact with the annulus.

Device 102 can be delivered percutaneously, thoracoscopically through the chest, and/or using open heart surgical techniques. Device 102 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 102 comprises a wire.

Device 102 is configured for placement along a native mitral valve. As such, frame 104 of device 102 is substantially D-shaped and struts 106 are oppositely spaced so as to fit within the commissures of the native mitral valve. For some applications, frame 104 of device 102 is substantially saddle-shaped. For some applications, device 102 comprises an adjustment mechanism 108 which expands and contracts a perimeter of base frame 104. For some applications, base frame 104 is hollow and is shaped so as to define a lumen, and adjustment mechanism 108 comprises a wire that runs at least partially within the lumen of base frame 104. In such applications, the wire is pullable and/or twistable to adjust the perimeter of base frame 104. For some applications, a portion of base frame 104 is collapsible telescopically in response to pulling of the wire of adjustment mechanism 108.

Device 102 is compressible during delivery toward the native heart valve. During delivery of device 102, device 102 is constrained in a collapsed condition. A flexible push rod can be used to expel the device 102 from a delivery catheter. Free of the catheter, device 102 will self-expand from its compressed state to its preordained configuration, e.g., like that shown in FIG. 3B.

Frame 104 of device 102 can be circular or another shape.

Reference is now made to FIGS. 3A-C, the plurality of radiopaque filaments 99 comprise radiopaque material (e.g., nitinol or stainless steel) and can be configured to be extremely flexible. Filaments 99 project radially away from base frames 94 and 104.

For some applications, filaments 99 sway with movement of the blood. For some applications, filaments 99 press against tissue of the annulus and tissue coupled thereto (as shown in FIG. 3C), such as tissue of an atrial wall 122 as well as tissue of the leaflets of the native valve. Within the entire present disclosure, the term "press against" has the same or a similar meaning as the terms "push against", "place against" or "align against", irrespective of a strength of the exerted force. Filaments 99 thus provide enhanced imaging of tissue of valve 64. That is, when filaments 99 appear bent or pressed, this imaging detects annulus tissue, while when filaments 99 are straight, this could indicate the orifice of the valve. FIG. 3C shows a system, 120 in which device 102 is positioned in the native mitral valve 64. Frame 104 is positioned along the annulus 68 while struts 106 are each placed at commissures 65 and 67. As mentioned above, struts 106 provide an indication as to the height of the annulus of valve 64. During positioning of device 102, the native valve 64 functions normally.

Reference is now made to FIGS. 4A-B, which are schematic illustrations of a system 140 comprising an implant comprising an annuloplasty structure 142 which comprises a body portion 144 and an annulus-marking device which comprises a plurality of radiopaque projections distributed along and attached to body portion 144 and shaped so as to define a plurality of tubular elements 148, in accordance with some applications. Body portion 144 comprises a flexible material, e.g., a braided fabric mesh. For some applications, body portion 144 is shaped so as to define a sleeve shaped so as to define a lumen therethrough, as shown. For some applications, body portion 144 is flat. Body portion 144 extends along a central longitudinal axis 141 of structure 142, and the radiopaque projections comprising tubular elements 148 project away from longitudinal axis 141.

Body portion 144 can comprise a braided fabric mesh, e.g., comprising DACRON™. Body portion 144 can be configured to be placed only partially around a cardiac valve annulus (e.g., to assume a C-shape), and, once anchored in place, to be contracted so as to circumferentially tighten the valve annulus. Optionally, structure 142 can be configured to be placed entirely around the valve annulus (e.g., as a closed circle or other closed shape). In order to tighten the annulus, annuloplasty structure 142 comprises a flexible elongated contracting member 145 that extends along body portion 144. Elongated contracting member 145 comprises a wire, a ribbon, a rope, or a band, which often comprises a flexible and/or superelastic material, e.g., nitinol, polyester, stainless steel, or cobalt chrome. For some applications, contracting member 145 comprises a radiopaque material. For some applications, contracting member 145 comprises a braided polyester suture (e.g., Ticron). For some applications, contracting member 145 is coated with polytetrafluoroethylene (PTFE). For some applications, contracting member 145 comprises a plurality of wires that are intertwined to form a rope structure.

The plurality of radiopaque projections comprising tubular elements 148 that comprise a flexible fabric. In some applications, tubular elements 148 and body portion 144 comprise the same material. Tubular elements 148 can be tapered away from axis 141, as shown. As shown, the distal ends of each element 148 (i.e., the ends of the elements 148 furthest from body portion 144) are closed, such that elements 148 are shaped as a pocket. For some applications, elements 148 are each shaped so as to define a windsock.

Body portion 144 of structure 142 comprises a plurality of radiopaque markers 146, which are positioned along structure 142 at respective longitudinal sites. The markers can provide an indication in a radiographic image (such as a fluoroscopy image) of how much of the body portion has been deployed at any given point during an implantation procedure, in order to enable setting a desired distance between tissue anchors 147 along body portion 144, and thus to indicate placement of anchors 147. For some applications, the markers comprise a radiopaque ink. For some applications the markers comprise a radiopaque material attached to or incorporated in body portion 144.

As shown, contracting member 145 is coupled to body portion 144 and extends along body portion 144 and through the plurality of tubular elements 148 in a manner in which during application of tension to contracting member 145, contracting member 145 is configured to change a structural configuration of the plurality of radiopaque projections comprising tubular elements 148. As shown in FIG. 4B, contracting member 145 is configured to change the structure configuration of elements 148 by closing an opening 149 (opening 149 is shown in FIG. 4A) of each one of tubular elements 148. In such embodiments, as shown, contracting member 145 extends along the perimeter of each opening 149 of each tubular element 148. For some applications, contracting member 145 runs along a perimeter of each tubular element 148 such that during application of tension to contracting member 145, member 145 is configured to compress each tubular element 148 radially toward axis 141 of structure 142. For some applications, contracting member is configured to change a spatial configuration of tubular elements 148 in sequence.

For some applications, contracting member 145 is configured to additionally apply a contracting force to body portion 144 of structure 142 so as to facilitate adjustment of the perimeter of annuloplasty structure 142. Adjustment of annuloplasty structure 142 can be performed by an adjusting mechanism similar to that described above with respect to annuloplasty structure 72, for example. For some applications, system 140 comprises an additional contracting member (not shown) configured to adjust a perimeter of body portion 144 while contracting member 145 adjusts the spatial configuration of the plurality of radiopaque projections comprising tubular elements 148.

For some applications, the plurality of radial projections comprising tubular elements 148 are each fully radiopaque. For some applications at least 50% of each projection is radiopaque. The plurality of radial projections comprising tubular elements 148 help facilitate viewing of the tissue of the native heart valve annulus and tissue coupled thereto under imaging. For some applications, the plurality of radial projections comprising tubular elements 148 are placed against and abut the tissue of the annulus and/or tissue coupled thereto (e.g., atrial wall tissue and/or tissue of the leaflets of the native valve). For some applications, at least some of the plurality of radial projections comprising tubular elements 148 are positioned in the path of blood flow. The plurality of radial projections can provide information relating to tissue and/or blood flow responsively to movement of tubular elements 148.

Reference is now made to FIGS. 5A-B, which are schematic illustrations of a system 160 comprising an implant comprising an annuloplasty structure 162 which comprises a body portion 164 and an annulus-marking device which comprises a plurality of radiopaque projections distributed along and attached to body portion 164 and shaped so as to define a plurality of flat and planar elements 168, in accordance with some applications. Body portion 164 comprises a flexible material, e.g., a braided fabric mesh. For some applications, body portion 164 is shaped so as to define a sleeve shaped so as to define a lumen therethrough, as shown. For some applications, body portion 164 is flat. Body portion 164 extends along a central longitudinal axis 161 of structure 162, and the radiopaque projections comprising flat and planar elements 168 project away from longitudinal axis 161.

Body portion 164 can comprise a braided fabric mesh, e.g., comprising DACRON™. Body portion 164 can be configured to be placed only partially around a cardiac valve annulus (e.g., to assume a C-shape), and, once anchored in place, to be contracted so as to circumferentially tighten the valve annulus. Optionally, structure 162 can be configured to be placed entirely around the valve annulus (e.g., as a closed circle or other closed shape). In order to tighten the annulus, annuloplasty structure 162 comprises a flexible elongated contracting member 165 that extends along body portion 164. Elongated contracting member 165 comprises a wire, a ribbon, a rope, or a band, which can comprise a flexible and/or superelastic material, e.g., nitinol, polyester, stainless steel, or cobalt chrome. For some applications, the contracting member 165 comprises a radiopaque material. For some applications, contracting member 165 comprises a braided polyester suture (e.g., Ticron). For some applications, contracting member 165 is coated with polytetrafluoroethylene (PTFE). For some applications, contracting member 165 comprises a plurality of wires that are intertwined to form a rope structure.

The plurality of radiopaque projections comprising flat and planar elements 168 that comprise a flexible fabric. For some applications, flat and planar elements 168 and body portion 164 comprise the same material. Flat and planar elements 168 each have a longest dimension that is measured along an axis that is at a nonzero angle (i.e. not parallel) with respect to longitudinal axis 161 of body portion 164.

Body portion 164 of structure 162 comprises a plurality of radiopaque markers 166, which are positioned along structure 162 at respective longitudinal sites. The markers can provide an indication in a radiographic image (such as a fluoroscopy image) of how much of the body portion has been deployed at any given point during an implantation procedure, in order to enable setting a desired distance between tissue anchors 167 along body portion 164, and thus to indicate placement of anchors 167. For some applications, the markers comprise a radiopaque ink. For some applications the markers comprise a radiopaque material or additional radiopaque material, markers, etc. attached to or incorporated in body portion 164.

As shown, contracting member 165 is coupled to body portion 164 and extends along body portion 164 and through the plurality of flat and planar elements 168 in a manner in which during application of tension to contracting member 165, contracting member 165 is configured to change a structural configuration of the plurality of radiopaque projections comprising flat and planar elements 168. As shown in FIG. 5B, contracting member 165 is configured to change the structure configuration of elements 168 by compressing and/or folding elements 168. In such embodiments, as shown, contracting member 165 runs along a perimeter of each flat and planar element 168 such that during application of tension to contracting member 165, member 165 is configured to compress each flat and planar element 168 radially toward axis 161 of structure 162. For some applications, contracting member is configured to change a spatial configuration of flat and planar elements 168 in sequence.

For some applications, contracting member 165 is configured to additionally apply a contracting force to body portion 164 of structure 162 so as to facilitate adjustment of the perimeter of annuloplasty structure 162. Adjustment of annuloplasty structure 162 can be performed by an adjusting mechanism similar to that described above with respect to annuloplasty structure 72 (contracting member and spool, wheel, spindle, etc.), for example. For some applications, system 160 comprises an additional contracting member (not shown) configured to adjust a perimeter of body portion 164 while contracting member 165 adjusts the spatial configuration of the plurality of radiopaque projections comprising flat and planar elements 168.

For some applications, the plurality of radial projections comprising flat and planar elements 168 are each fully radiopaque. For some applications at least 50% of each projection is radiopaque. The plurality of radial projections comprising flat and planar elements 168 help facilitate viewing of the tissue of the native heart valve annulus and tissue coupled thereto under imaging. For some applications, the plurality of radial projections comprising flat and planar elements 168 are placed against and abut the tissue of the annulus and/or tissue coupled thereto (e.g., atrial wall tissue and/or tissue of the leaflets of the native valve). For some applications, at least some of the plurality of radial projections comprising flat and planar elements 168 are positioned in the path of blood flow. The plurality of radial projections can provide information relating to tissue and/or blood flow responsively to movement of flat and planar elements 168.

In some applications, anchors 167 comprise a biocompatible material such as stainless steel 316 LVM. For some applications, anchors 167 comprise nitinol. For some applications, anchors 167 are coated fully or partially with a non-conductive material.

Figure 6A:
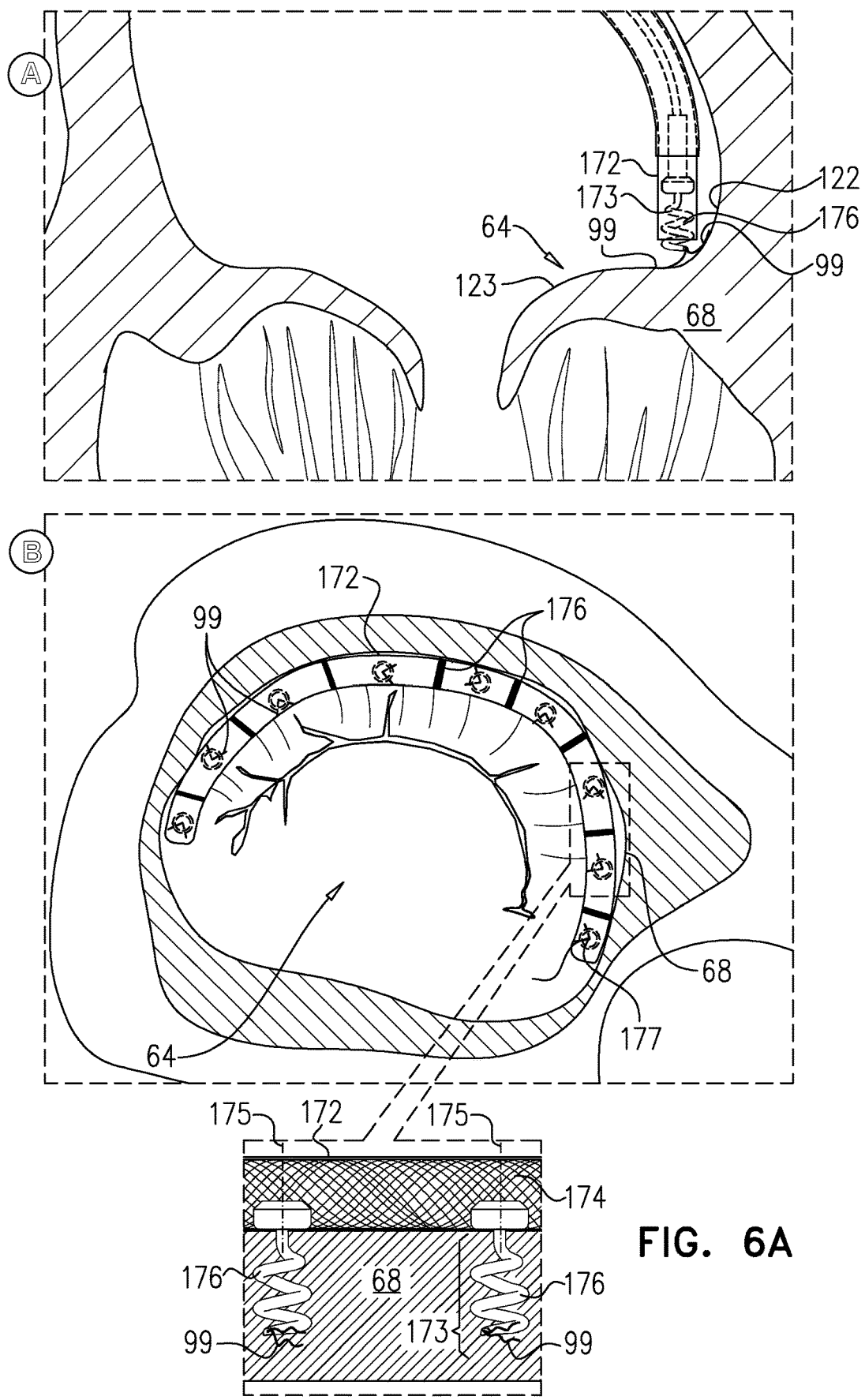

Reference is now made to FIG. 6A, which is a schematic illustration of a system 170 comprising a tissue anchor 176 comprising a distal tissue-coupling element 173 having a longitudinal axis 175 measured from a distal end to a proximal end of distal tissue-coupling element 173 and an annulus-marking device having a plurality of radiopaque elements, e.g., filaments 99, coupled to the tissue anchor 176. The filaments 99 or other radiopaque elements comprise a radiopaque material and project away from axis 175, in accordance with some applications. Distal tissue-coupling element 173 is configured for anchoring into tissue of a native heart valve annulus 68.

In some embodiments, the plurality of radiopaque filaments 99 comprise radiopaque material (e.g., nitinol or stainless steel) and are configured to be extremely flexible. Filaments 99 project away from anchor 176. Filaments 99 are configured for aiding implantation of cardiac devices, e.g., an annuloplasty structure 172, under the guidance of imaging, in accordance with some applications. Implantation of anchors 176 and annuloplasty structure 172 is often performed with the aid of imaging, such as fluoroscopy, transesophageal echo, and/or echocardiography.

For some applications, filaments 99 sway with movement of the blood. For some applications, filaments 99 press against tissue of the annulus and tissue coupled thereto (e.g., such as tissue of an atrial wall 122 as well as tissue of leaflet 123 of the native valve) prior to placement of a portion of structure 172 along annulus 68 and prior to puncturing of tissue of annulus 68 by the distal tip of anchor 176, as shown in view A of FIG. 6A. That is, the distal tip of anchor 176 punctures through a portion of a body portion 174 of structure 172 and brings filaments 99 through fabric of body portion 174 such that filaments 99 can be pressed against tissue of the annulus and tissue coupled thereto. As such, filaments 99 thus provide enhanced imaging of tissue of the cardiac valve 64.

It is to be noted that although system 170 is shown on mitral valve 64, system 170 can be used on any cardiac valve, e.g., a tricuspid valve, or any other tissue of the subject.

In some applications, anchors 176 comprise a biocompatible material such as stainless steel 316 LVM. For some applications, anchors 176 comprise nitinol. For some applications, anchors 176 are coated fully or partially with a non-conductive material.

For some applications, each distal tissue-coupling element 173 of anchors 176 is hollow and filaments 99 can be compressed in a lumen of the hollow element 173 during delivery of anchor 176 to the atrium of the heart and expand from within the lumen once inside the atrium.

Annuloplasty structure 172 can comprise a braided fabric mesh, e.g., comprising DACRON™. Annuloplasty structure 172 can be configured to be placed only partially around a cardiac valve annulus (e.g., to assume a C-shape), and, once anchored in place, to be contracted so as to circumferentially tighten the valve annulus. Optionally, structure 172 can be configured to be placed entirely around the valve annulus (e.g., as a closed circle or other closed shape).

As shown, for some applications, the annulus-marking device comprising filaments 99 is coupled to the distal end of distal tissue-coupling element 173. Structure 172 comprises a fabric, and the annulus-marking device comprising filaments 99 is configured to pass through the fabric of structure 172. It is to be noted that additional filaments 99 can be coupled to distal tissue-coupling element 173 or to any other portion of anchor 176.

It is to be noted that for some applications, filaments 99 can be coupled to the anchor driver used to drive the anchor into tissue.

Reference is now made to FIG. 6B, which is a schematic illustration of a system 180 comprising a tissue anchor 176 comprising a distal tissue-coupling element 173 having a longitudinal axis 175 measured from a distal end to a proximal end of distal tissue-coupling element 173 and an annulus-marking device having a plurality of radiopaque filaments 99 coupled to the tissue anchor 176, filaments 99 comprise a radiopaque material and project away from axis 175, in accordance with some applications. Distal tissue-coupling element 173 is configured for anchoring into tissue of a native heart valve annulus 68.

The plurality of radiopaque filaments 99 comprise radiopaque material (e.g., nitinol or stainless steel) and can be configured to be extremely flexible. Filaments 99 are coupled to a proximal head 177 of anchor 176 and project away from anchor 176. Filaments 99 are configured for aiding implantation of cardiac devices, e.g., an annuloplasty structure 182, under the guidance of imaging, in accordance with some applications. Implantation of anchors 176 and annuloplasty structure 172 is often performed with the aid of imaging, such as fluoroscopy, transesophageal echo, and/or echocardiography.

For some applications, filaments 99 sway with movement of the blood. Filaments 99 thus provide enhanced imaging of tissue of the cardiac valve 64.

Annuloplasty structure 182 comprises a flat band by way of illustration and not limitation. Structure 182 comprises a braided fabric or braided metal and is not tubular in shape.

It is to be noted that although system 180 is shown on mitral valve 64, system 180 can be used on any cardiac valve, e.g., a tricuspid valve, or any other tissue of the subject.

For some applications, anchors 176 comprise a biocompatible material such as stainless steel 316 LVM. For some applications, anchors 176 comprise nitinol. For some applications, anchors 176 are coated fully or partially with a non-conductive material.

Annuloplasty structure 182 can comprise a braided fabric mesh, e.g., comprising DACRON™. Annuloplasty structure 182 can be configured to be placed only partially around a cardiac valve annulus (e.g., to assume a C-shape), and, once anchored in place, to be contracted so as to circumferentially tighten the valve annulus. Optionally, structure 182 can be configured to be placed entirely around the valve annulus (e.g., as a closed circle or other closed shape).

As shown, structure 182 is flat, and head 177 is disposed above the flat band following implantation of anchor 176. Once implanted in the tissue, filaments 99 provide an indication of their placement above the band of structure 182.

Reference is now made to FIGS. 7A-C, which are schematic illustrations of a system 190 comprising an implant comprising an annuloplasty structure 192 which comprises a body portion 194 and an annulus-marking device which comprises one or more (e.g., two, as shown) planar radiopaque fins 196, in accordance with some applications. Body portion 194 comprises a flexible material, e.g., a braided fabric mesh. For some applications, body portion 194 is shaped so as to define a sleeve shaped so as to define a lumen therethrough, as shown. For some applications, body portion 194 is flat. Body portion 194 extends along a central longitudinal axis 191 of structure 192, and radiopaque fins 196 project away from longitudinal axis 191. Radiopaque fins 196 each have a longest dimension that is measured along longitudinal axis 191.

Body portion 194 can comprise a braided fabric mesh, e.g., comprising DACRON™. Body portion 194 can be configured to be placed only partially around a cardiac valve annulus (e.g., to assume a C-shape), and, once anchored in place, to be contracted so as to circumferentially tighten the valve annulus. Optionally, structure 192 can be configured to be placed entirely around the valve annulus (e.g., as a closed circle or other closed shape). In order to tighten the annulus, annuloplasty structure 192 comprises a flexible elongated contracting member (not shown) that extends along body portion 194. The contracting member comprises a wire, a ribbon, a rope, or a band, which often comprises a flexible and/or superelastic material, e.g., nitinol, polyester, stainless steel, or cobalt chrome. For some applications, the contracting member comprises a radiopaque material. For some applications, contracting the member comprises a braided polyester suture (e.g., Ticron). For some applications, the contracting member is coated with polytetrafluoroethylene (PTFE). For some applications, the contracting member comprises a plurality of wires that are intertwined to form a rope structure.

Planar radiopaque fins 196 comprise a flexible fabric. In some applications, fins 196 and body portion 194 comprise the same material.

Body portion 194 of structure 192 comprises a plurality of radiopaque markers 195, which are positioned along structure 192 at respective longitudinal sites. The markers may provide an indication in a radiographic image (such as a fluoroscopy image) of how much of the body portion has been deployed at any given point during an implantation procedure, in order to enable setting a desired distance between tissue anchors 198 along body portion 194. For some applications, the markers comprise a radiopaque ink. For some applications the markers comprise a radiopaque material or additional radiopaque material, markers, etc. attached to or incorporated in body portion 164.

FIG. 7B shows a transverse cross-section of structure 172 showing body portion 194 and fins 196.

In some applications, fins 196 are each fully radiopaque. For some applications at least 50% of each fin 196 is radiopaque. Fins 196 help facilitate viewing of the tissue of the native heart valve annulus and tissue coupled thereto under imaging. For some applications, as shown in FIG. 7C, fins 196 are placed against and abut the tissue of the annulus and/or tissue coupled thereto (e.g., tissue of atrial wall 122 and/or tissue of the leaflets of the native valve). For some applications, fins 196 are positioned in the path of blood flow and provide information relating to tissue and/or blood flow responsively to movement of fins 196.

As shown in FIG. 7C, anchors 198 that anchor structure 192 to tissue of annulus 68 are designated for implantation in-between fins 196.

For some applications, fins 196 comprise shape-memory wires which help them expand to assume their shape. For some applications, the fabric of fins 196 is thinner than the fabric of body portion 194.

It is to be noted that although system 190 is shown on mitral valve 64, system 190 can be used on any cardiac valve, e.g., a tricuspid valve, or any other tissue of the subject.

Figure 8A:
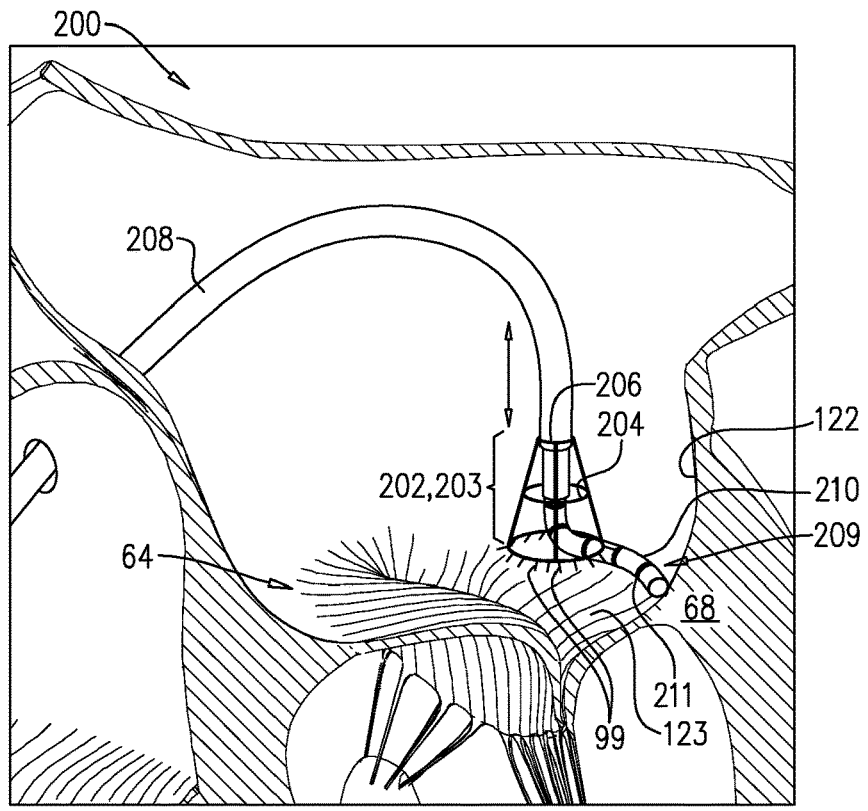
FIGS. 8A-B are schematic illustrations of an annulus-marking device for aiding implantation of cardiac devices under the guidance of imaging, in accordance with some applications.
Figure 8B:
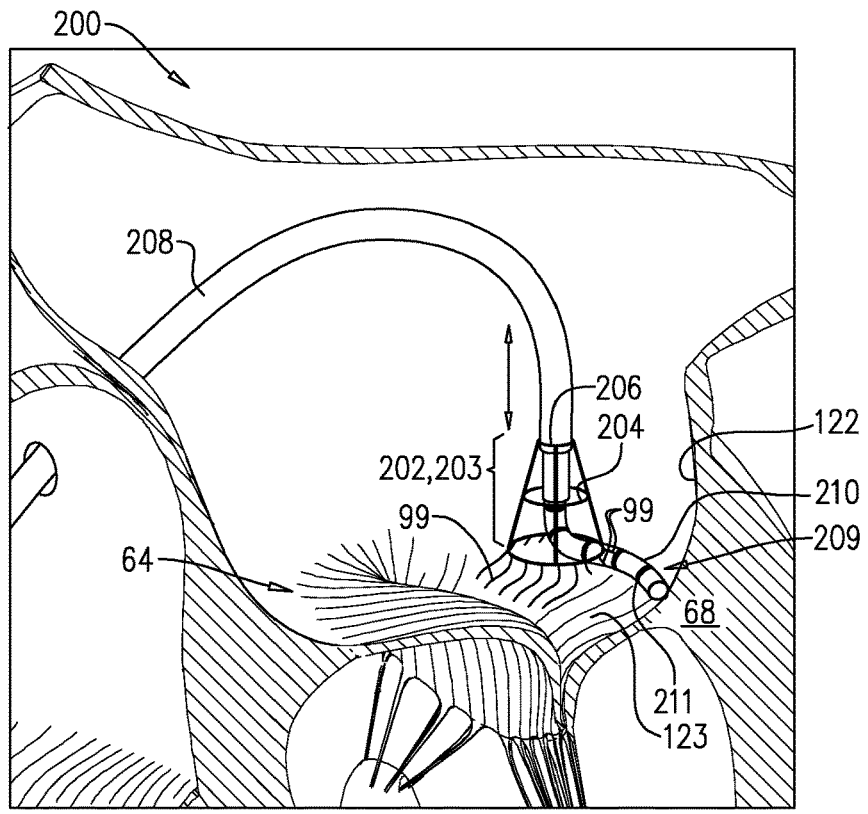

Reference is now made to FIGS. 8A-B, which are schematic illustrations of a system 200 comprising an annulus-marking device 202 for aiding implantation of cardiac devices under the guidance of imaging, in accordance with some applications. Device 202 comprises a frustoconical scaffolding 203 having a plurality of struts 204 collectively arranged in a frustoconical shape. Scaffolding 203 is collapsible and expandable. Annulus-marking device 202 is configured to run alongside at least one side of body portion 210 of an implant 209 (e.g., an annuloplasty structure, as shown) configured for placement along a native heart valve annulus 68 of a mitral valve 64 of the subject. As shown, device 202 surrounds a given portion of body portion 210, as it is frustoconical in shape. Body portion 210 of implant 209 comprises a flexible material and has a longitudinal axis that runs along the length of body portion 210 (e.g., when the body portion is straightened). Body portion 210 comprises radiopaque markings 211 to aid in imaging for accurate delivery of anchors to annulus 68 in order to anchor implant 209 to tissue of annulus 68.

Scaffolding 203 comprises radiopaque material (e.g., nitinol or stainless steel) and is flexible. Scaffolding 203 is coupled to a proximal ring 206 at a proximal end of scaffolding 203. For some applications, scaffolding 203 comprises ring 206. Ring 206 surrounds at least a portion of body portion 210 of implant 209 and is moveable proximally and distally with respect to body portion 210 in a manner in which scaffolding 203 is moveable to multiple locations along body portion 210 of implant 209.

Annulus-marking device 202 is coupled to a delivery tool 208 which is configured to deliver implant 209 to annulus 68. Annulus-marking device 202 is retrievable upon removal of delivery tool 208 from the subject. For some applications, scaffolding 203 and ring 206 slide with respect to tool 208. For some applications, ring 206 is fixedly coupled to tool 208, and scaffolding 203 moves proximally and distally with respect to body portion 210 responsively to movement of tool 208. Delivery tool 208 is configured to surround a portion of body portion 210 of implant 209, and annulus-marking device 202 is configured to surround body portion 210 of implant 209 at least in part, e.g., entirely surround a portion of body portion 210.

For some applications, a plurality of radiopaque elements, such as radiopaque filaments 99 (or other radiopaque markers, wires, extensions, beads, etc.), are coupled to scaffolding 203 at a distal portion thereof. The plurality of radiopaque elements or filaments 99 function as additional annulus-marking devices. Annulus-marking device 202 is configured for aiding implantation of cardiac devices under the guidance of imaging, in accordance with some applications. The steering procedure is performed with the aid of imaging, such as fluoroscopy, transesophageal echo, and/or echocardiography.

Device 202 can be delivered percutaneously, thoracoscopically through the chest, or using open heart surgical techniques. If delivered percutaneously, device 202 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 202 comprises a wire.

The plurality of radiopaque filaments 99 comprise radiopaque material (e.g., nitinol or stainless steel) and can be configured to be extremely flexible. For some applications, filaments 99 sway with movement of the blood. For some applications, filaments 99 press against tissue of the annulus and tissue coupled thereto (as shown in FIG. 8), such as tissue of an atrial wall 122 as well as tissue of leaflets 123 of the native valve. Filaments 99 thus provide enhanced imaging of tissue of valve 64.

For some applications, delivery tool 208 comprises a fin (not shown, but shown as fin 227 in FIG. 10B) that is coupled to a distal portion of delivery tool 208 and to a portion of scaffolding 203 in a manner in which movement of the fin responsively to blood flow rotationally orients scaffolding 203 with respect to body portion 210 of implant 209. In such a manner, the operating physician is able to discern between tissue of the atrial wall and leaflet tissue under the aid of imaging.

Reference is now made to FIG. 8B. For some applications, the plurality of radiopaque elements or radiopaque filaments 99 comprise a first subset of radiopaque filaments having a first length and a second subset of filaments having a second length that is greater than the first length. The first and second subsets are configured to rotationally orient scaffolding 203 with respect to implant 209. That is, the second subset of filaments 99 having a longer length will orient scaffolding 203 in a manner in which the second subset of longer filaments 99 will align against tissue of leaflet 123 and the first subset of shorter filaments 99 will align against tissue of atrial wall 122. For some applications, the plurality of radiopaque filaments 99 comprises a first subset of radiopaque filaments having a first rigidity and a second subset of filaments having a second rigidity that is greater than the first length. The first and second subsets are configured to rotationally orient scaffolding 203 with respect to implant 209. That is, the second subset of filaments 99 having a greater rigidity will orient scaffolding 203 in a manner in which the second subset of more rigid filaments 99 will align against tissue of leaflet 123 and the first subset of less rigid filaments 99 will align against tissue of atrial wall 122.

Subsequently to implanting of implant 209, annulus-marking device 202 is retrieved. Since device 202 is flexible and compressible, device 202 is constrained within the tool during the retrieval of device 202 and subsequent removal of device 202 from the body of the subject. That is, device 202 does not function as an implant for such embodiments and is used only to guide implantation of implant 209; rather, device 202 acts as a guide for implantation while placed temporarily within the body of the patient to be subsequently removed therefrom following the implantation of implant 209.

It is to be noted that although system 200 is shown on mitral valve 64, system 200 can be used on any cardiac valve, e.g., a tricuspid valve, or any other tissue of the subject.

Reference is made to FIGS. 9A-B, which are schematic illustrations of a navigational-based guidance system 230, which employs one or more longitudinal guides 232 configured to facilitate guidance of an implant 231 to specific portions of annulus 68 by the guides contacting a surface of the valve (e.g., the annulus, commissure, and/or leaflets of the valve), in accordance with some applications. Guide 232 comprises a flexible material (e.g., a flexible metal such as nitinol or stainless steel), and each guide 232 is radiopaque. A plurality of eyelets 234 are disposed along a lateral outer surface of a body portion 233 of implant 231, and each guide 232 (e.g., a distal portion thereof) is disposed within at least some of the eyelets (e.g., the guide is threaded through the eyelets). Eyelets 234 can comprise suture or fabric.

In some applications, eyelets 234 are arranged in longitudinal rows along the length of body portion 233, and each guide 232 is disposed within the eyelets of a respective row. In some applications, the eyelets of each row are disposed at the same longitudinal site as a corresponding eyelet of each other row. For some applications body portion 233 comprises a plurality of radiopaque markers 235, which are positioned along the body portion at respective longitudinal sites. For some applications the eyelets of each row are disposed at the same longitudinal site as a corresponding radiopaque marker. Though, optionally, the eyelets can be disposed between radiopaque markers. Guides 232 are disposed at respective circumferential positions around body portion 233 (e.g., the longitudinal axis thereof). In FIGS. 9A-B, each of the three guides is shown as being disposed at about 120 degrees around body portion 233 from the adjacent guides, but the scope includes other arrangements, such as two guides disposed opposite each other.

For some applications, each guide 232 comprises a wire with a looped portion 238 such that the guide has (1) two parallel linear portions of the wire, and (2) the looped portion at a distal end portion 236 of the guide.

For some applications, distal end portion 236 of each guide 232 is biased (e.g., shape-set) to protrude radially outward from body portion 233. Such biasing may confer a desired behavior on the guide, e.g., during distal movement of the guide. For example, when the guide is moved distally against tissue, the biasing may facilitate splaying of the guide over the tissue (e.g., as described hereinbelow). Alternatively or additionally, after the guide has been withdrawn proximally from a given eyelet, when the guide is subsequently moved distally again, the biasing may inhibit (e.g., prevent) re-threading of the guide into the given eyelet.

Body portion 233 is configured to be advanced distally out of delivery tool 208 and anchored to annulus 68 using anchors.

Guides 232 are placed (e.g., pushed) against tissue of the valve, e.g., by virtue of being already disposed distally to a distal end of body portion 233, or by being advanced distally after the distal end of the body portion has itself been placed against tissue of the valve. Each guide 232 (e.g., looped portion 238 thereof) thereby comprises a tissue-engaging portion that is configured to be placed in contact with tissue of the subject.

In one or more ways, the behavior of guides 232 in response to being placed against the tissue of the valve facilitates guidance by viewing of body portion 233 (e.g., positioning of the body portion on the annulus). For example:

Resistance of a guide to being pushed further distally may indicate that the guide is in contact with tissue that resists forces applied by the guide. For example, the distal end of the guide may be abutting annulus 68 and/or a wall 122 of the atrium (as shown in FIG. 9B). Conversely, lack of resistance of a guide to being pushed further distally may indicate that the distal end of the guide is not in contact with tissue that resists forces applied by the guide. For example, the distal end of the guide may be moving between leaflets 123 of the valve (e.g., at a commissure), and/or may be pushing a leaflet 123 downward (e.g., into the ventricle). Such resistance (or lack thereof) can be detected mechanically (e.g., as tactile feedback to the operating physician and/or by an extracorporeal control unit). Since guides 232 comprise radiopaque material, such resistance (or lack thereof) can be detected via imaging (e.g., fluoroscopically).

Similarly, the position, orientation and/or shape of a guide (e.g., with respect to one or more other guides, body portion 233 of implant 231, tissue of the valve, etc.) may indicate against what, if anything, the guide is disposed. Imaging techniques such as fluoroscopy can be used to identify this position, orientation and/or shape of the guide. For example, if the distal end of a guide is positioned at the same height (i.e., at the same place on a superior-inferior axis of the subject) as the distal end of body portion 233, this may indicate that body portion 233 and guide 232 abut the same surface (e.g., annulus 68). Conversely, if the distal end of guide 232 is positioned lower than body portion 233, this may indicate that the body portion 233 is disposed against annulus 68, while guide 232 has passed toward or into the ventricle. Movement (e.g., beating) of the guide may indicate that the guide is disposed against a leaflet of the valve, and that the leaflet is moving the guide as the heart beats. Such imaging may be facilitated by one or more components comprising radiopaque markings. For some applications, each guide 232 has different radiopaque markings, so as to facilitate identification during imaging.

One or more of the guides 232 may inhibit movement of body portion 233 of implant 231. For example, if a guide extends between leaflets at a commissure, the guide may inhibit movement of body portion 233 away from the commissure.

Guides 232 may be configured and/or selected, either collectively or individually, such that the guides behave in a particular manner upon interaction with tissue. For example, the guides may be configured and/or selected to be (1) sufficiently rigid so as to provide tactile feedback upon abutting tissue, and/or (2) sufficiently flexible so as to splay over tissue, not to damage tissue, and/or to be movable by beating leaflets.

FIG. 9B shows body portion 233 having been placed against annulus 68 of the subject in a vicinity of left fibrous trigone. Guides 232 have been pushed distally, and have splayed across annulus 68, e.g., due to resistance of the annulus (see view A of FIG. 9B). As described hereinabove, this can be detected mechanically and/or by imaging. Guide 232a, which has also been pushed distally, extends between leaflets 123 at the commissure (see view B of FIG. 9B). As described hereinabove, this can be detected mechanically and/or using imaging. The position, orientation and/or shape of each guide, alone and/or in combination with the other guides and/or elements indicates that the portion of body portion 233 is positioned against firm tissue that is close to the commissure, which for some applications is the preferred position for anchoring of the portion of body portion 233. Identification (e.g., mechanically and/or by imaging) of which guide is in which position may further indicate the rotational orientation of body portion 233.

Once the desired position has been identified, an anchor (e.g., a first anchor) is used to anchor body portion 233. For some applications, one or more of guides 232 can be withdrawn slightly proximally before anchoring, e.g., so as to reduce a likelihood of inadvertently anchoring the guide to the tissue. Subsequently, additional portions of body portion 233 are anchored to annulus 68. In some applications, guides 232 are moved proximally with respect to body portion 233. This process can be repeated for each anchor until implant 231 is fully implanted.

It is to be noted that although system 230 is shown on mitral valve 64, system 230 can be used on any cardiac valve, e.g., a tricuspid valve, or any other tissue of the subject.

Figure 10A:
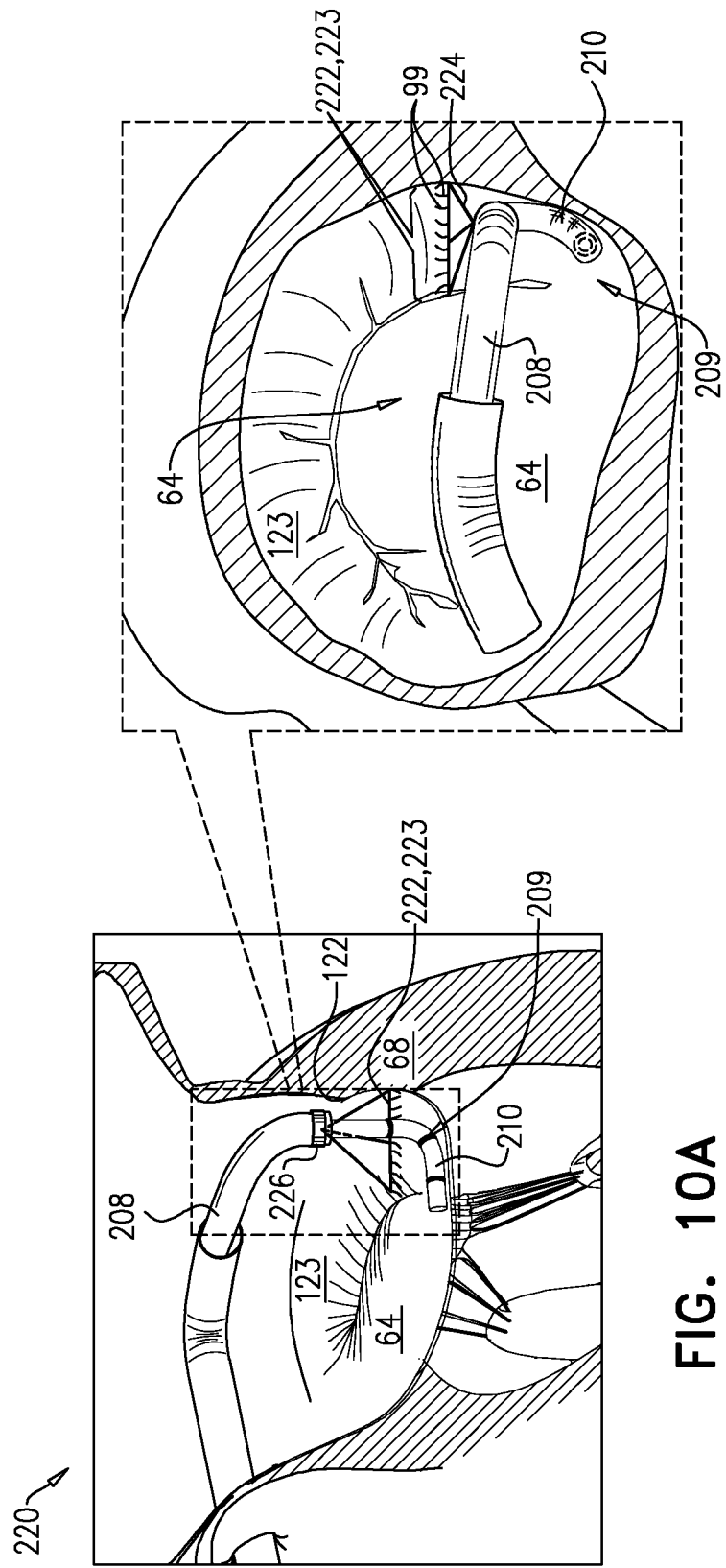
FIGS. 10A-B are schematic illustrations of an annulus-marking device for aiding implantation of cardiac devices under the guidance of imaging, in accordance with some applications.
Figure 10B:
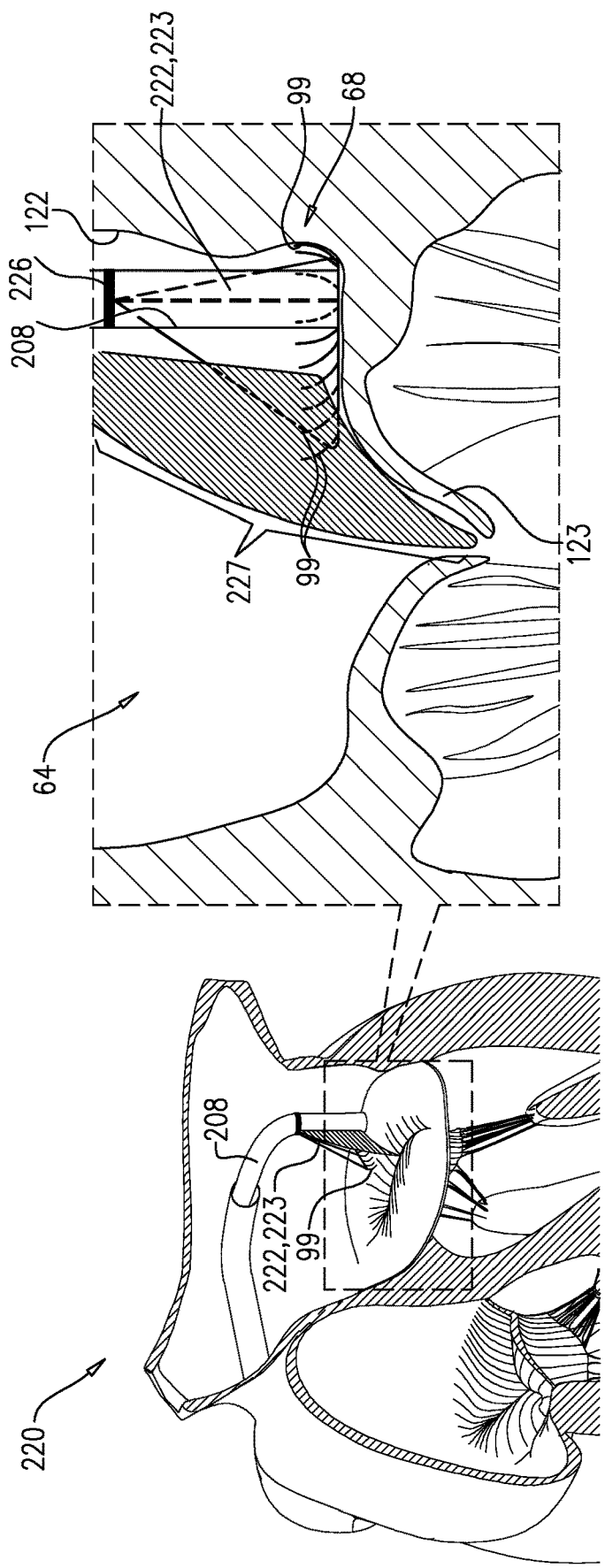

Reference is now made to FIGS. 10A-B, which are schematic illustrations of a system 220 comprising an annulus-marking device 222 for aiding implantation of cardiac devices under the guidance of imaging, in accordance with some applications. Device 222 comprises a generally-triangular scaffolding 223 having a plurality of struts 204 collectively arranged in a generally triangular shape. Scaffolding 223 is collapsible and expandable. Annulus-marking device 222 is configured to run alongside at least one side of body portion 210 of an implant 209 (e.g., an annuloplasty structure, as shown) configured for placement along a native heart valve annulus 68 of a mitral valve 64 of the subject. As shown, device 222 is positioned ahead and in advance of body portion 210. Device 222 leads implant 209. Body portion 210 of implant 209 comprises a flexible material and has a longitudinal axis that runs along the length of body portion 210 (e.g., when the body portion is straightened). Body portion 210 comprises radiopaque markings to aid in imaging for accurate delivery of anchors to annulus 68 in order to anchor implant 209 to tissue of annulus 68.

Scaffolding 223 comprises radiopaque material (e.g., nitinol or stainless steel) and is flexible. Scaffolding 223 is coupled to a proximal ring 226 at a proximal end of scaffolding 223. For some applications, scaffolding 223 comprises ring 226. Ring 226 surrounds at least a portion of body portion 210 of implant 209 and is moveable proximally and distally with respect to body portion 210 in a manner in which scaffolding 223 is moveable to multiple locations along body portion 210 of implant 209. For some applications, scaffolding 223 is semitubular.

Annulus-marking device 222 is coupled to a delivery tool 208 which is configured to deliver implant 209 to annulus

68. Annulus-marking device 222 is retrievable upon removal of delivery tool 208 from the subject. For some applications, scaffolding 223 and ring 226 are configured to slide with respect to tool 208. For some applications, scaffolding 223 and ring 226 are configured to rotate with respect to delivery tool 208. For some applications, ring 226 is fixedly coupled to tool 208, and scaffolding 223 moves proximally and distally with respect to body portion 210 responsively to movement of tool 208. Delivery tool 208 is configured to surround a portion of body portion 210 of implant 209, and annulus-marking device 222 is configured to surround body portion 210 of implant 209 at least in part, e.g., a single side of body portion 210, as shown.

For some applications, scaffolding 223 is planar and triangular, as shown. For some applications, scaffolding 223 is semi-tubular.

For some applications, a plurality of radiopaque elements, such as radiopaque filaments 99 (or other radiopaque markers, wires, extensions, beads, etc.) are coupled to scaffolding 223 at a distal portion thereof. The plurality of radiopaque elements or filaments 99 function as additional annulus-marking devices. Annulus-marking device 222 is configured for aiding implantation of cardiac devices under the guidance of imaging, in accordance with some applications. The steering procedure is performed with the aid of imaging, such as fluoroscopy, transesophageal echo, and/or echocardiography. In some embodiments, a first subset of filaments 99 touch atrial wall 122, a second subset of filaments 99 touch annulus 68, a third subset of filaments 99 touch leaflet 123, while a fourth subset of filaments 99 extend over the orifice of the valve and between leaflets 123.

Device 222 may be delivered percutaneously, thoracoscopically through the chest, or using open heart surgical techniques. If delivered percutaneously, device 222 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 222 comprises a wire.

The plurality of radiopaque filaments 99 comprise radiopaque material (e.g., nitinol or stainless steel) and can be configured to be extremely flexible. For some applications, filaments 99 sway with movement of the blood. For some applications, filaments 99 press against tissue of the annulus and tissue coupled thereto (as shown in FIG. 10), such as tissue of an atrial wall 122. Filaments 99 thus provide enhanced imaging of tissue of valve 64.

Reference is now made to FIG. 10B. For some applications, delivery tool 208 comprises a fin 227 that is coupled to a distal portion of delivery tool 208 and to a portion of scaffolding 223 in a manner in which movement of fin 227 responsively to blood flow rotationally orients scaffolding 223 with respect to body portion 210 of implant 209. In such a manner, the operating physician is able to discern between tissue of the atrial wall and leaflet tissue under the aid of imaging. For some applications, fin 227 is radiopaque. For some applications, a distal portion of fin 227 extends into the ventricle.

Reference is now made to FIGS. 8B and 10A-B. For some applications, the plurality of radiopaque filaments 99 comprises a first subset of radiopaque filaments having a first length and a second subset of filaments having a second length that is greater than the first length. The first and second subsets are configured to rotationally orient scaffolding 223 with respect to implant 209. That is, the second subset of filaments 99 having a longer length will orient scaffolding 223 in a manner in which the second subset of longer filaments 99 will align against tissue of leaflet 123 and the first subset of shorter filaments 99 will align against tissue of atrial wall 122. For some applications, the plurality of radiopaque filaments 99 comprises a first subset of radiopaque filaments having a first rigidity and a second subset of filaments having a second rigidity that is greater than the first length. The first and second subsets are configured to rotationally orient scaffolding 223 with respect to implant 209. That is, the second subset of filaments 99 having a greater rigidity will orient scaffolding 223 in a manner in which the second subset of more rigid filaments 99 will align against tissue of leaflet 123 and the first subset of less rigid filaments 99 will align against tissue of atrial wall 122.

For some applications, a first subset of filaments 99 touch atrial wall 122, a second subset of filaments 99 touch annulus 68, a third subset of filaments 99 touch leaflet 123, while a fourth subset of filaments 99 extend over the orifice of the valve and between leaflets 123.

Reference is again made to FIGS. 10A-B. In some applications, device 222 is configured for placement between implant 209 and tissue of atrial wall 122, as shown.

Subsequently to implanting of implant 209, annulus-marking device 222 is retrieved. Since device 222 is flexible and compressible, device 222 is constrained within the tool during the retrieval of device 222 and subsequent removal of device 222 from the body of the subject. That is, device 222 does not function as an implant for such embodiments and is used only to guide implantation of implant 209; rather, device 222 acts as a guide for implantation while placed temporarily within the body of the patient to be subsequently removed therefrom following the implantation of implant 209.

It is to be noted that although system 220 is shown on mitral valve 64, system 220 can be used on any cardiac valve, e.g., a tricuspid valve, or any other tissue of the subject.

Figure 11A:
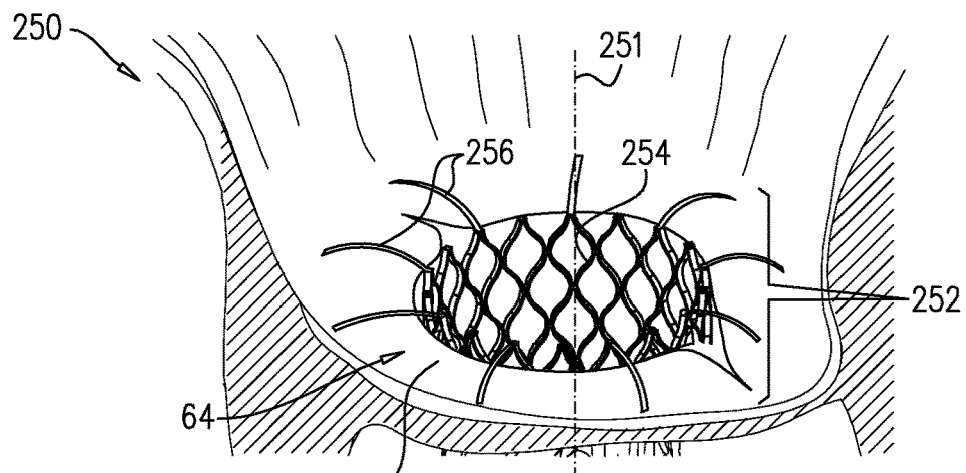
FIGS. 11A-C are schematic illustrations of respective annulus-marking devices for aiding implantation of cardiac devices under the guidance of imaging, in accordance with some applications.
Figure 11B:
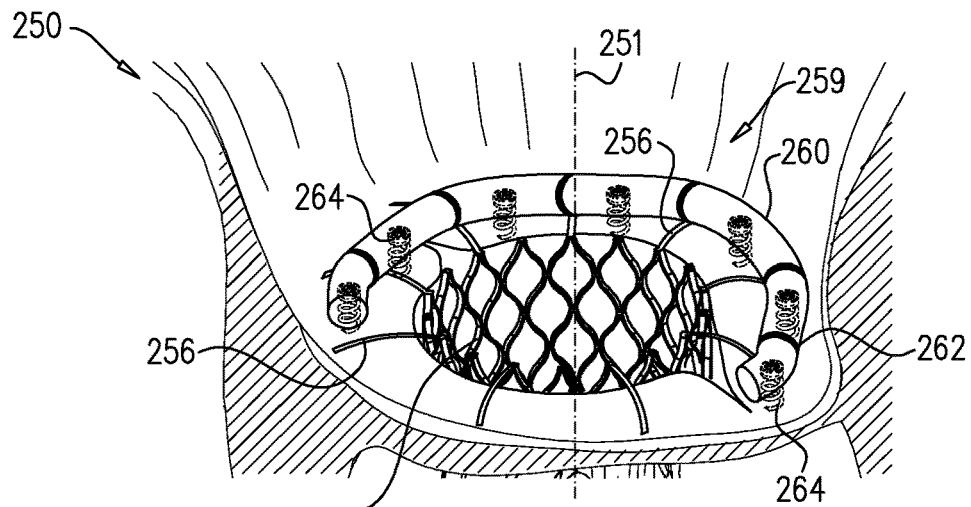
Figure 11C:
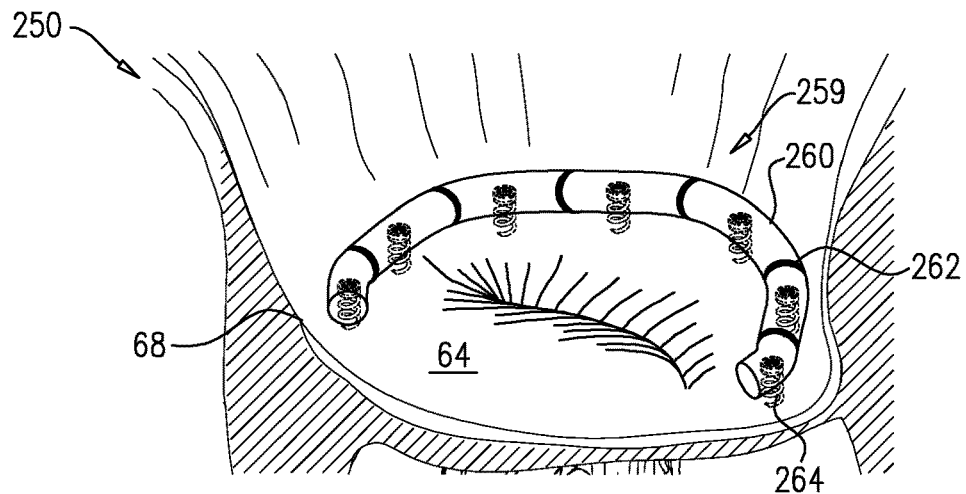

Reference is now made to FIGS. 11A-C, which are schematic illustrations of a system 250 comprising an annulus-marking device 252 comprising a tubular stent body 254 having a central longitudinal axis 251 and a plurality of extensions 256 coupled to a proximal end of tubular stent body 254 and projecting away from longitudinal axis 251 of stent body 254, in accordance with some applications. Annulus-marking device 252 is configured for placement within a native heart valve of the subject, e.g., mitral valve 64, as shown, the tricuspid valve, or any other cardiac valve.

The plurality of extensions 256 are configured for placement along a circumference of annulus 68 of valve 64. In some applications, prior to implantation of an implant along annulus 68, annulus-marking device is positioned within valve 64 and thus configured to provide a guide for implantation of the implant along the annulus during implantation. For some applications, tubular stent body 254 comprises two or more leaflets in order to regulate blood flow while device 252 is positioned in valve 64. Device 252 is compressible during delivery toward valve 64 and expandable from a compressed state for positioning in the native heart valve 64. Once device 252 is positioned within valve 64, the valve is imaged using imaging, e.g., fluoroscopy. Extensions 256 provide an indication as to the circumference of annulus 68.

Device 252 may be made from a superelastic material (e.g., nitinol or stainless steel) enabling it to be folded and collapsed such that it can be delivered in a catheter. Additionally, device 252 is made from radiopaque material to facilitate fluoroscopic visualization. In some applications, tissue of valve annulus 68 and tissue coupled thereto is viewed using the plurality of extensions 256. Additionally, the tissue of the native heart valve annulus 68 and tissue coupled thereto is viewed by imaging annulus-marking device 252 with respect to the tissue of the native heart valve annulus and the tissue coupled thereto by viewing the plurality of extensions 256 against the tissue. For some applications, the tissue of the native heart valve annulus 68 and tissue coupled thereto is viewed by imaging annulus-marking device 252 with respect to the tissue of the native heart valve annulus and the tissue coupled thereto by viewing movement of the plurality of extensions 256 responsively to movement of the tissue.

Subsequently to the positioning of device 252 within valve 64, and under imaging, an implant comprising an annuloplasty structure 259 is positioned along annulus 68, as shown in FIG. 11B. Structure 259 comprises a body portion 260, e.g., a tubular body portion, through which a plurality of anchors 264 are deployed. Structure 259 comprises a plurality of a plurality of radiopaque markers 262, which are positioned along structure 259 at respective longitudinal sites. The markers may provide an indication in a radiographic image (such as a fluoroscopy image) of how much of the body portion has been deployed at any given point during an implantation procedure, in order to enable setting a desired distance between the tissue anchors along the body portion. For some applications, the markers comprise radiopaque ink. For some applications the markers comprise a radiopaque material attached to or incorporated in body portion 164.

Anchors 264 are delivered to valve 64 in order to anchor structure 259 to annulus 68 by deploying each anchor 264 of the plurality of anchors 264 between adjacent extensions 256 of device 252. In addition to the guidance under imaging provided by radiopaque extensions 256, markers 262 of structure 259 aid in deployment of anchors 264.

Following anchoring of structure 259 to annulus 68, annulus-marking device 252 is constrained within a catheter such that tubular stent body 254 collapses and extensions 256 trail behind body 254 in a manner in which extensions 256 slide from under annuloplasty structure 259 implanted along annulus 68. Annulus-marking device 252 is retrieved and removed from the body of the subject.

Subsequently to implanting of structure 259, annulus-marking device 252 is retrieved. Since device 252 is flexible and compressible, device 252 is constrained within a tool during the retrieval of device 252 and subsequent removal of device 252 from the body of the subject. That is, device 252 does not function as an implant for such embodiments and is used only to guide implantation of annuloplasty structure 259 (i.e., the implant); rather, device 252 acts as a guide for implantation while placed temporarily within the body of the patient to be subsequently removed therefrom following the implantation of annuloplasty structure 259.

It is to be noted that although system 250 is shown on mitral valve 64, system 250 can be used on any cardiac valve, e.g., a tricuspid valve, or any other tissue of the subject.

Figure 12A:
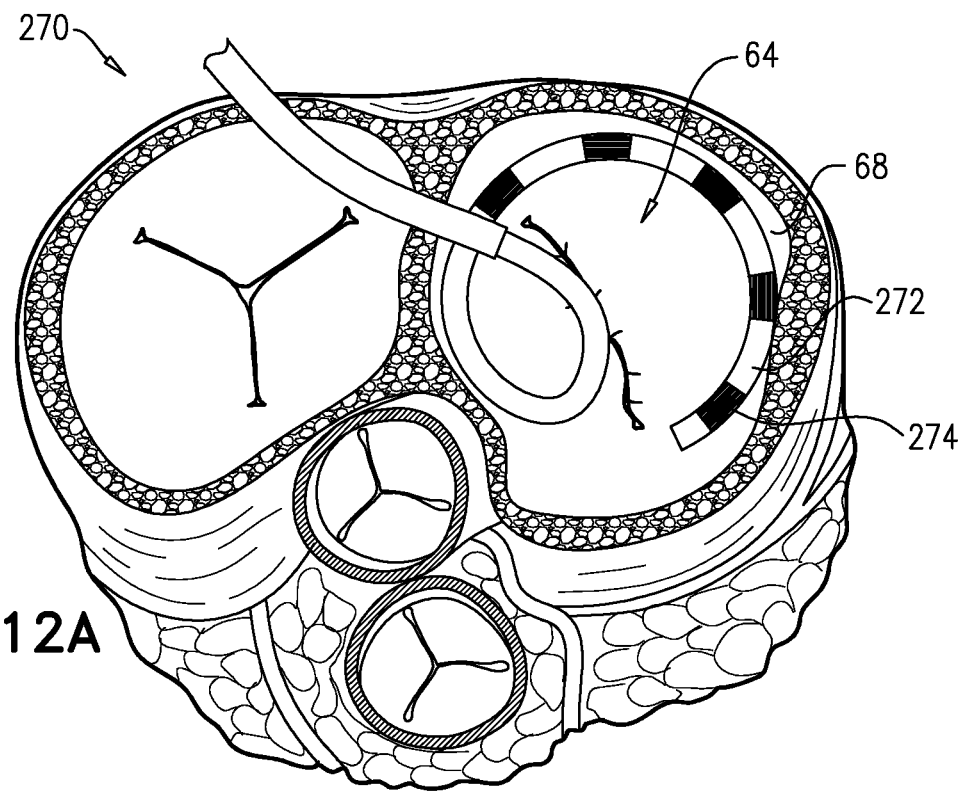
FIGS. 12A-B are schematic illustrations of a system for facilitating imaging of cardiac tissue during implantation of a cardiac implant, the system comprising a mapping catheter, in accordance with some applications.
Figure 12B:
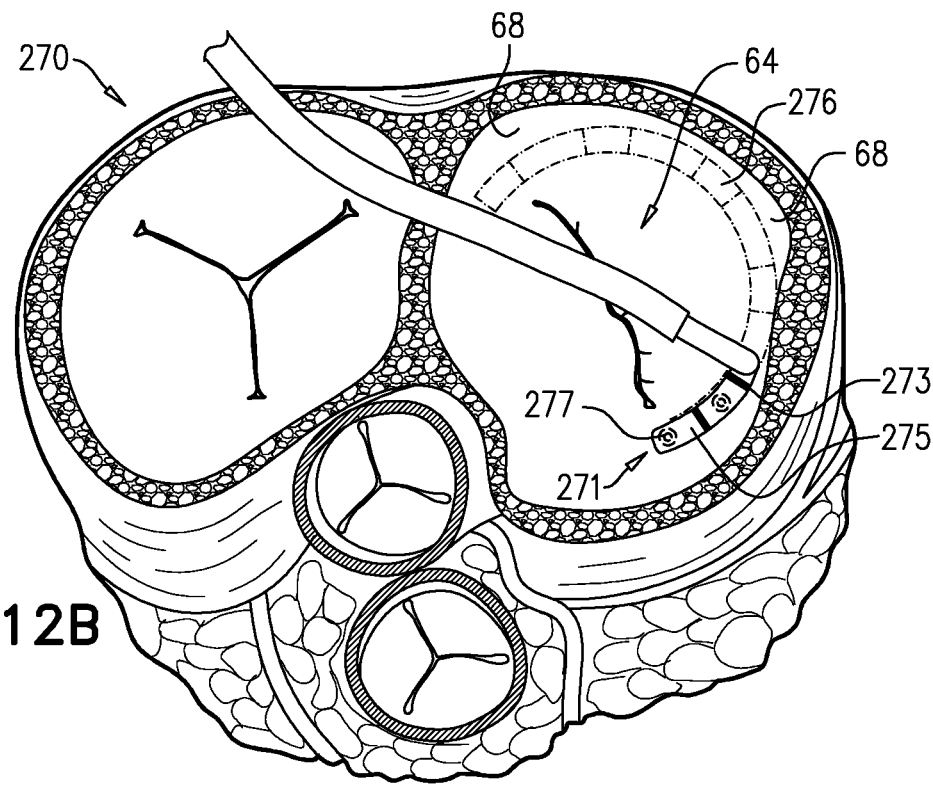

Reference is now made to FIGS. 12A-B, which are schematic illustrations of a system 270 for facilitating imaging of cardiac tissue during implantation of a cardiac implant, the system 270 comprising an annulus-marking device comprising a mapping catheter 272, in accordance with some applications. Mapping catheter 272 is introduced percutaneously (e.g., transvascularly) toward mitral valve 64, as shown. It is to be noted that catheter 272 may be advanced to the tricuspid valve and/or to any other cardiac valve. Mapping catheter 272 comprises a plurality of mapping subunits 274. For some applications, subunits 274 comprise electrodes and mapping of valve 64 is performed electrophysiologically using electroanatomic mapping systems using the electrodes. For some applications, subunits 274 comprise magnets and mapping of valve 64 is performed by generating a magnetic field and under magnetic imaging. For some applications, subunits 274 comprise radiopaque material and imaging is performed, such as under fluoroscopy.

As shown in FIG. 12B, once a map of valve 64 is generated using mapping catheter 272, an implant, e.g., an annuloplasty structure 271, is placed at valve 64 using the map as a guide. In some applications, structure 271 comprises a flexible body portion 275. For some applications, the body portion of structure 271 is shaped so as to define a tubular sleeve through which a plurality of anchors 277 is implanted. The body portion of structure 271 comprises a plurality of radiopaque markers 273, which are positioned along structure 271 at respective longitudinal sites. The markers may provide an indication in a radiographic image (such as a fluoroscopy image) of how much of the body portion has been deployed at any given point during an implantation procedure, in order to enable setting a desired distance between the tissue anchors along the body portion. For some applications, the markers comprise radiopaque ink. For some applications the markers comprise a radiopaque material or additional radiopaque material, markers, etc. attached to or incorporated in body portion 164.

For some applications, mapping catheter 272 is removed prior to implanting of structure 271 and structure 271 is implanted under the guidance of a map 276 generated by mapping catheter 272, wherein map 276 can be stored and displayed by an imaging device. For some applications, mapping catheter 272 remains at annulus 68 during implantation of structure 271 and is viewed under fluoroscopy. For some applications, mapping catheter 272 facilitates viewing and mapping of tissue of the native heart valve annulus and tissue coupled thereto using mapping catheter 272. For some applications, mapping catheter 272 facilitates viewing and mapping of tissue of the native heart valve annulus and tissue coupled thereto by viewing mapping catheter 272 against the tissue. For some applications, mapping catheter 272 facilitates viewing and mapping of tissue of the native heart valve annulus and tissue coupled thereto by viewing movement of mapping catheter 272 responsively to movement of the tissue.

It is to be noted that although system 270 is shown on mitral valve 64, system 270 can be used on any cardiac valve, e.g., a tricuspid valve, or any other tissue of the subject.

Figure 13:
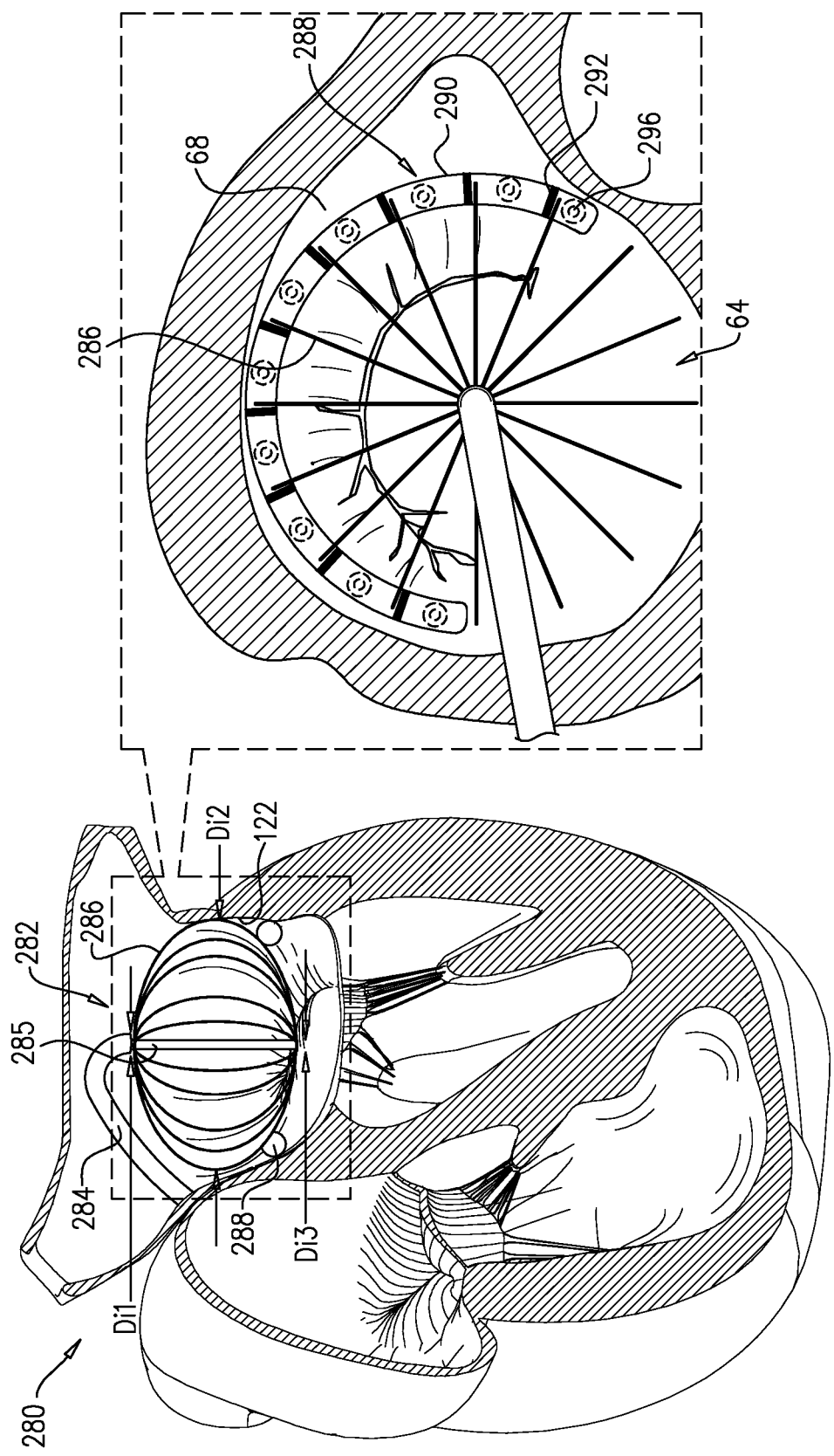
FIG. 13 is a schematic illustration of an annulus-marking device comprising a generally spherical expandable element for facilitating imaging of cardiac tissue during implantation of a cardiac implant, in accordance with some applications.

Reference is now made to FIG. 13, which is a schematic illustration of a system 280 comprising an annulus-marking device 282 comprising a plurality of expandable elements 286 which form device 282 into a generally spherical shape for facilitating imaging of cardiac tissue during implantation of a cardiac implant, in accordance with some applications. Device 282 comprises a flexible, radiopaque material, e.g., nitinol or stainless steel, which facilitates collapsing and expanding of device 282.

As shown, device 282 aids in imaging implantation of a cardiac implant, e.g., an annuloplasty structure 288, as shown. Structure 288 comprises a body portion 290 which comprises a flexible material and has a longitudinal axis that runs along the length of body portion 290 (e.g., when the body portion is straightened). Body portion 290 comprises radiopaque markings 292 to aid in imaging for accurate delivery of anchors 296 to annulus 68 in order to anchor implant 288 to tissue of annulus 68.

Annulus-marking device 282 is delivered using a delivery tool 284 which is configured to deliver device 282 to the left atrium in a compressed state. Device 282 is configured to be expanded from its compressed state once deployed from within a lumen of tool 284. Annulus-marking device 282 is retrievable upon removal of delivery tool 284 from the subject. That is, device 282 is constrained within the lumen of tool 284 once the cardiac implant has been implanted at annulus 68. Device 282 may be delivered percutaneously, thoracoscopically through the chest, or using open heart surgical techniques. If delivered percutaneously, device 282 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 282 comprises a wire.

Once inside the atrium, the plurality of expandable elements 286 expand radially within the atrium such that the plurality of expandable elements 286 provides an indication as to a location of the native heart valve annulus 68 of native heart valve 64. It is to be noted that although device 282 is being used in the left atrium, device 282 may be used in the right atrium, the left ventricle, and the right ventricle.

The plurality of expandable elements 286 collectively form annulus-marking device 282 into a generally spherical shape. As shown, the plurality of expandable elements 286 comprise a plurality of curved wires. For some applications, plurality of expandable elements 286 surround a central shaft 285. A proximal end and a distal end of each expandable element 286 is coupled to shaft 285.

A collective proximal diameter Di1 of the proximal ends of the plurality of expandable elements 286 is equal to a collective distal diameter Di3 of the distal ends of the plurality of expandable elements 286. A collective middle diameter Di2 of the plurality of expandable elements 286 is greater than collective proximal diameter Di1 and greater than collective distal diameter Di3.

Annulus 68 is then imaged using fluoroscopy. In some applications, annulus-marking device 282 is imaged with respect to the tissue of the native heart valve annulus 68 and the tissue coupled thereto by viewing the plurality of expandable elements 286 against the tissue. For some applications, annulus-marking device 282 is imaged with respect to the tissue of the native heart valve annulus 68 and the tissue coupled thereto by viewing movement of the plurality of expandable elements 286 responsively to movement of the tissue. For either application, annulus-marking device 282 is imaged with respect to the tissue of the native heart valve annulus 68, tissue of at least one leaflet, and tissue of an atrial wall 122.

Reference is now made to FIGS. 3A-B and 13. For some applications, annulus-marking device 282 is coupled to a plurality of radiopaque elements or filaments 99. In some applications, annulus-marking device 282 and elements or filaments 99 are imaged with respect to the tissue of the native heart valve annulus 68 and the tissue coupled thereto by viewing the plurality of expandable elements 286 and radiopaque elements or filaments 99 against the tissue. For some applications, annulus-marking device 282 is imaged with respect to the tissue of the native heart valve annulus 68 and the tissue coupled thereto by viewing movement of the plurality of expandable elements 286 and of filaments 99 responsively to movement of the tissue. For either application, annulus-marking device 282 and radiopaque element or filaments 99 are imaged with respect to the tissue of the native heart valve annulus 68, tissue of at least one leaflet, and tissue of an atrial wall 122.

Reference is again made to FIG. 13. Annuloplasty structure 288 is implanted under the guidance of fluoroscopy using annulus-marking device 282 as a guide. Annuloplasty structure 288 is positioned between annulus-marking device 282 and atrial wall 122. A respective anchor 296 is deployed to anchor structure 288 at a site along annulus 68 that is marked between successive curved wires of elements 286.

Once annuloplasty structure 288 is implanted, device 282 is constrained within tool 284 and extracted from the subject.

Subsequently to implanting of structure 288, annulus-marking device 282 is retrieved. Since device 282 is flexible and compressible, device 282 is constrained within a tool during the retrieval of device 282 and subsequent removal of device 282 from the body of the subject. That is, device 282 does not function as an implant for such embodiments and is used only to guide implantation of annuloplasty structure 288 (i.e., the implant); rather, device 282 acts as a guide for implantation while placed temporarily within the body of the patient to be subsequently removed therefrom following the implantation of annuloplasty structure 288.

It is to be noted that although system 280 is shown on mitral valve 64, system 280 can be used on any cardiac valve, e.g., a tricuspid valve, or any other tissue of the subject.

Figure 14:
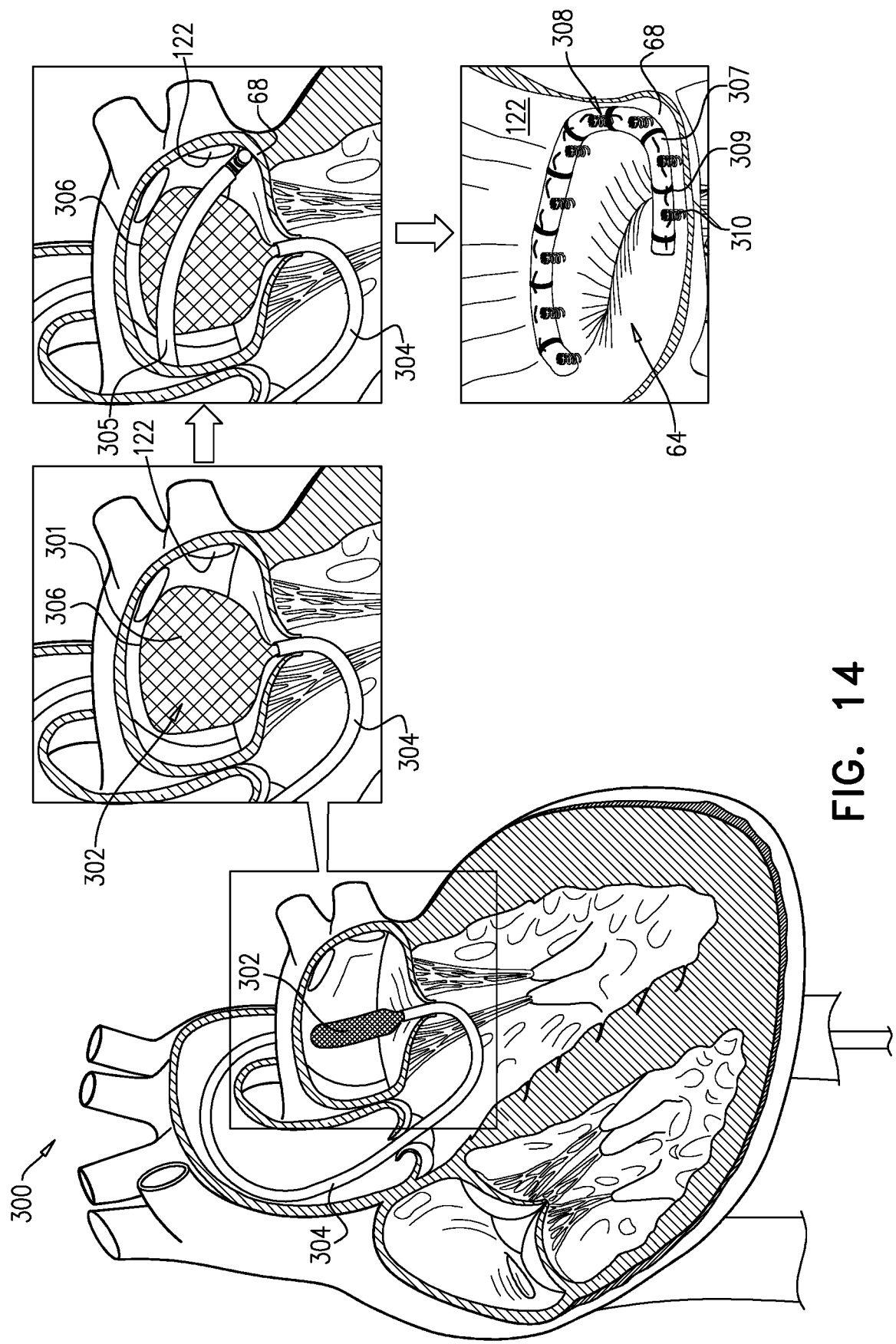
FIG. 14 is a schematic illustration of an annulus-marking device comprising a generally spherical expandable mesh for facilitating imaging of cardiac tissue during implantation of a cardiac implant, in accordance with some.

Reference is now made to FIG. 14, which is a schematic illustration of a system 300 comprising an annulus-marking device 302 comprising a plurality of expandable elements 301 which form device 302 into a generally spherical, or generally bulbous shape for facilitating imaging of cardiac tissue during implantation of a cardiac implant, in accordance with some applications. The plurality of expandable elements 301 of device 302 comprise woven radiopaque fibers comprising a flexible, radiopaque material, e.g., nitinol or stainless steel, which facilitates collapsing and expanding of device 302. The plurality of expandable elements 301 of device 302 collectively assumes a mesh.

As shown, device 302 aids in imaging implantation of a cardiac implant, e.g., an annuloplasty structure 308, as shown. Structure 308 comprises a body portion 307 which comprises a flexible material and has a longitudinal axis that runs along the length of body portion 307 (e.g., when the body portion is straightened). Body portion 307 comprises radiopaque markings 309 to aid in imaging for accurate delivery of anchors 310 to annulus 68 in order to anchor structure 308 to tissue of annulus 68. Structure 308 is delivered using a delivery tool 305.

Annulus-marking device 302 is delivered using a delivery tool 304 which is configured to deliver device 302 to the left atrium in a compressed state. Device 302 is configured to be expanded from its compressed state once deployed from within a lumen of tool 304. Annulus-marking device 302 is retrievable upon removal of delivery tool 304 from the subject. That is, device 302 is constrained within the lumen of tool 304 once the cardiac implant has been implanted at annulus 68. Device 302 may be delivered percutaneously, thoracoscopically through the chest, or using open heart surgical techniques. If delivered percutaneously, device 302 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 302 comprises a wire.

It is to be noted that although device 302 is shown as being delivered via the aorta, any suitable delivery path may be used in order to deliver device 302 into the atrium.

Once inside the atrium, the plurality of expandable elements 301 expand radially within the atrium such that the plurality of expandable elements 301 provides an indication as to a location of the native heart valve annulus 68 of native heart valve 64. It is to be noted that although device 302 is being used in the left atrium, device 302 may be used in the right atrium, the left ventricle, and the right ventricle.

Annulus 68 is then imaged using fluoroscopy. In some applications, annulus-marking device 302 is imaged with respect to the tissue of the native heart valve annulus 68 and the tissue coupled thereto by viewing the plurality of expandable elements 301 against the tissue. For some applications, annulus-marking device 302 is imaged with respect to the tissue of the native heart valve annulus 68 and the tissue coupled thereto by viewing movement of the plurality of expandable elements 301 responsively to movement of the tissue. For either application, annulus-marking device 302 is imaged with respect to the tissue of the native heart valve annulus 68, tissue of at least one leaflet, and tissue of an atrial wall 122.

Reference is now made to FIGS. 3A-B and 14. For some applications, annulus-marking device 302 is coupled to a plurality of radiopaque elements, such as radiopaque filaments 99, or other radiopaque markers, wires, extensions, beads, etc. In some applications, annulus-marking device 302 and radiopaque elements or filaments 99 are imaged with respect to the tissue of the native heart valve annulus 68 and the tissue coupled thereto by viewing the plurality of expandable elements 301 and radiopaque elements or filaments 99 against the tissue. For some applications, annulus-marking device 302 is imaged with respect to the tissue of the native heart valve annulus 68 and the tissue coupled thereto by viewing movement of the plurality of expandable elements 301 and of radiopaque elements or filaments 99 responsively to movement of the tissue. For either application, annulus-marking device 302 and radiopaque elements or filaments 99 are imaged with respect to the tissue of the native heart valve annulus 68, tissue of at least one leaflet, and tissue of an atrial wall 122.

Annuloplasty structure 308 is implanted under the guidance of fluoroscopy using annulus-marking device 302 as a guide. Annuloplasty structure 308 is positioned between annulus-marking device 302 and atrial wall 122. A respective anchor 310 is deployed to anchor structure 308 at a site along annulus 68 that is marked between successive curved wires of elements 301.

Once annuloplasty structure 308 is implanted, device 302 is constrained within tool 304 and extracted from the subject.

Subsequently to implanting of structure 308, annulus-marking device 302 is retrieved. Since device 302 is flexible and compressible, device 302 is constrained within a tool during the retrieval of device 302 and subsequent removal of device 302 from the body of the subject. That is, device 302 does not function as an implant for such embodiments and is used only to guide implantation of annuloplasty structure 308 (i.e., the implant); rather, device 302 acts as a guide for implantation while placed temporarily within the body of the patient to be subsequently removed therefrom following the implantation of annuloplasty structure 308.

It is to be noted that although system 300 is shown on mitral valve 64, system 300 can be used on any cardiac valve, e.g., a tricuspid valve, or any other tissue of the subject.

Figure 15:
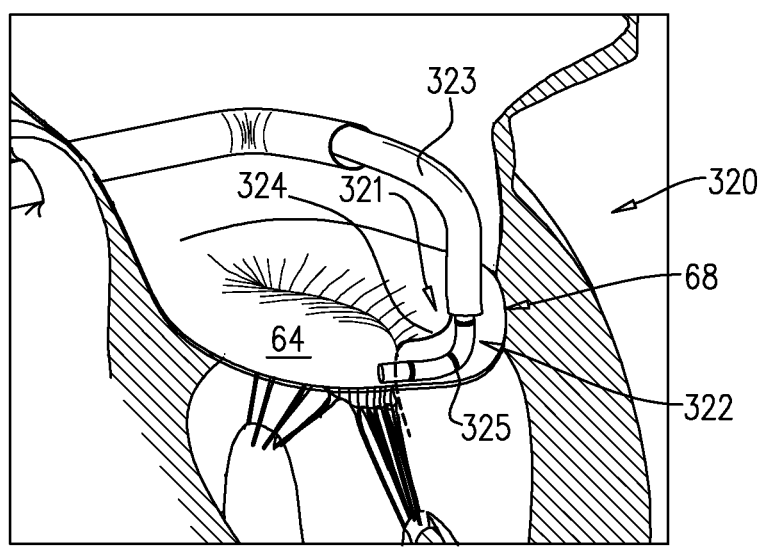
FIG. 15 is a schematic illustration of a system comprising an annulus-marking device comprising a guidewire that runs alongside an implant aiding implantation of the implant under the guidance of imaging, in accordance with some applications.

Reference is now made to FIG. 15, which is a schematic illustration of a system 320 comprising an annulus-marking device 321 comprising a guidewire 324 that runs alongside an implant, e.g., an annuloplasty structure 322, in accordance with some applications. Guidewire 324 extends from within a delivery tool 323 and is disposed between leaflets 123 (e.g., posterior leaflet and anterior leaflet), often at a commissure of the valve. Guidewire 324 is at least partly stiff, and provides resistance, which facilitates positioning of structure 322. Guidewire 324 may also provide tactile feedback to the operating physician.

Structure 322 comprises a body portion which comprises a flexible material and has a longitudinal axis that runs along the length of the body portion (e.g., when the body portion is straightened). The body portion comprises radiopaque markings 325 to aid in imaging for accurate delivery of anchors to annulus 68 in order to anchor structure 322 to tissue of annulus 68.

In addition to providing tactile feedback, guidewire 324 may also facilitate positioning of the annuloplasty structure 322 by facilitating imaging (e.g., fluoroscopy). For example, the presence of guidewire 324 and/or the shape thereof (e.g., bending due to being pressed into the commissure) is visible in fluoroscopic imaging, and can be used to facilitate identification of the position and angle of annuloplasty structure 322 with respect to tissues.

Guidewire 324 extends proximally through tool 323 and can extend to outside of the body of the subject. Guidewire 324 can be removed by pulling subsequent to the deployment of one or more tissue anchors in order to anchor structure 322.

Reference is now made to FIGS. 3A-B and 15. It is to be noted that guidewire 324 can be coupled to a plurality of filaments 99 and can be shaped in any suitable shape. For example, a distal end of guidewire 324 may be helical.

It is to be noted that although system 320 is shown on mitral valve 64, system 320 can be used on any cardiac valve, e.g., a tricuspid valve, or any other tissue of the subject.

Figure 16A:
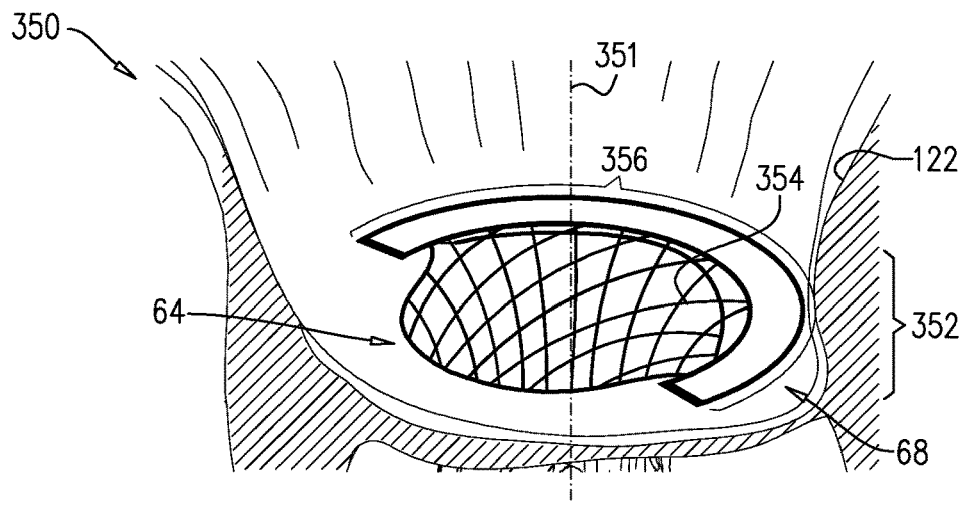
FIGS. 16A-C are schematic illustrations of respective annulus-marking devices for aiding implantation of cardiac devices under the guidance of imaging, in accordance with some applications.
Figure 16B:
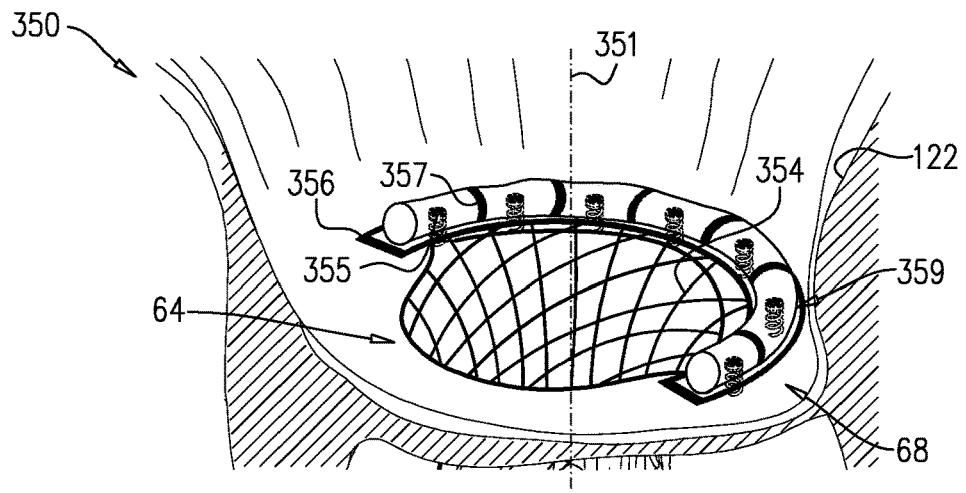
Figure 16C:
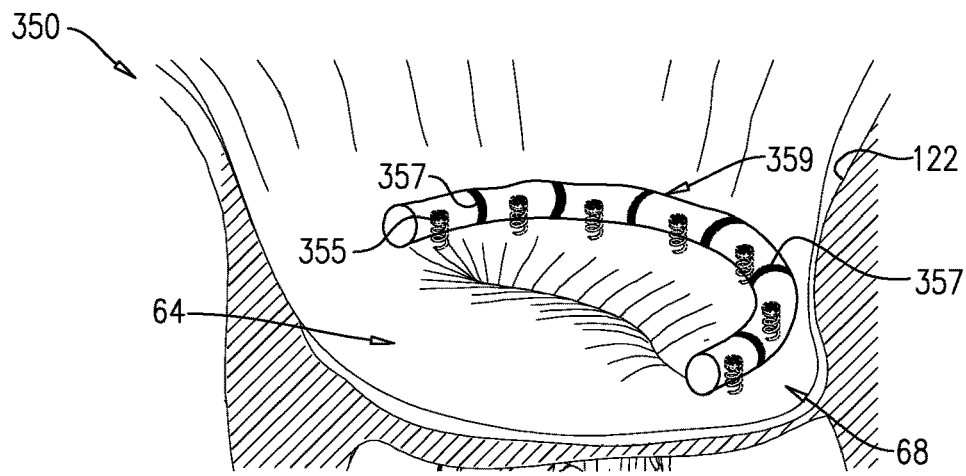

Reference is now made to FIGS. 16A-C, which are schematic illustrations of a system 350 comprising an annulus-marking device 352 comprising a tubular stent body 354 having a central longitudinal axis 251 and a frame 356 coupled to a proximal end of tubular stent body 354 and projecting away from longitudinal axis 351 of stent body 354, in accordance with some applications. Annulus-marking device 352 is configured for placement within a native heart valve of the subject, e.g., mitral valve 64, as shown, the tricuspid valve, or any other cardiac valve.

Frame 356 is configured for placement along at least a part of a circumference of annulus 68 of valve 64. In some applications, prior to implantation of an implant along annulus 68, annulus-marking device is positioned within valve 64. For some applications, tubular stent body 354 comprises two or more leaflets in order to regulate blood flow while device 352 is positioned in valve 64. Device 352 is compressible during delivery toward valve 64 and expandable from a compressed state for positioning in the native heart valve 64. Once device 352 is positioned within valve 64, the valve is imaged using imaging, e.g., fluoroscopy. Frame 356 provides an indication as to the circumference of annulus 68.

Device 352 may be made from a superelastic material (e.g., nitinol or stainless steel) enabling it to be folded and collapsed such that it can be delivered in a catheter. Additionally, device 352 is made from radiopaque material to facilitate fluoroscopic visualization. In some applications, tissue of valve annulus 68 and tissue coupled thereto is viewed using the frame 356. Additionally, the tissue of the native heart valve annulus 68 and tissue coupled thereto is viewed by imaging annulus-marking device 352 with respect to the tissue of the native heart valve annulus and the tissue coupled thereto by viewing frame 356 against the tissue. In other words, viewing the tissue of the native heart valve annulus 68 and tissue coupled thereto comprises imaging annulus-marking device 352 with respect to the tissue of the native heart valve annulus and the tissue coupled thereto when frame 356 is placed against the tissue. For some applications, the tissue of the native heart valve annulus 68 and tissue coupled thereto is viewed by imaging annulus-marking device 352 with respect to the tissue of the native heart valve annulus and the tissue coupled thereto by viewing movement of the frame 356 responsively to movement of the tissue. In other words, viewing the tissue of the native heart valve annulus 68 and tissue coupled thereto comprises imaging annulus-marking device 352 with respect to the tissue of the native heart valve annulus and the tissue coupled thereto when frame 356 is moved responsively to movement of the tissue.

Subsequently to the positioning of device 352 within valve 64, and under imaging, an implant comprising an annuloplasty structure 359 is positioned along annulus 68, as shown in FIG. 16B. Structure 359 comprises a body portion 260, e.g., a tubular body portion, through which a plurality of anchors 355 are deployed. Structure 359 comprises a plurality of radiopaque markers 357, which are positioned along structure 359 at respective longitudinal sites. The markers may provide an indication in a radiographic image (such as a fluoroscopy image) of how much of the body portion has been deployed at any given point during an implantation procedure, in order to enable setting a desired distance between the tissue anchors along the body portion. For some applications, the markers comprise radiopaque ink. For some applications the markers comprise a radiopaque material attached to or incorporated in body portion 164.

Anchors 355 are delivered to valve 64 in order to anchor structure 359 to annulus 68 by deploying each anchor 355 of the plurality of anchors 355 within frame 356 of device 352. In addition to the guidance under imaging provided by frame 356, markers 357 of structure 359 aid in deployment of anchors 355.

Following anchoring of structure 359 to annulus 68, annulus-marking device 352 is constrained within a catheter such that tubular stent body 354 collapses and frame 356 slides proximally around structure 359 and proximally away from annulus 68. Annulus-marking device 352 is retrieved and removed from the body of the subject.

Subsequently to the implanting of structure 359, annulus-marking device 352 is retrieved. Since device 352 is flexible and compressible, device 352 is constrained within a tool during the retrieval of device 352 and subsequent removal of device 352 from the body of the subject. That is, device 352 does not function as an implant for such embodiments and is used only to guide implantation of annuloplasty structure 359 (i.e., the implant); rather, device 352 acts as a guide for implantation while placed temporarily within the body of the patient to be subsequently removed therefrom following the implantation of annuloplasty structure 359.

It is to be noted that although system 350 is shown on mitral valve 64, system 350 can be used on any cardiac valve, e.g., a tricuspid valve, or any other tissue of the subject.

Figure 17A:
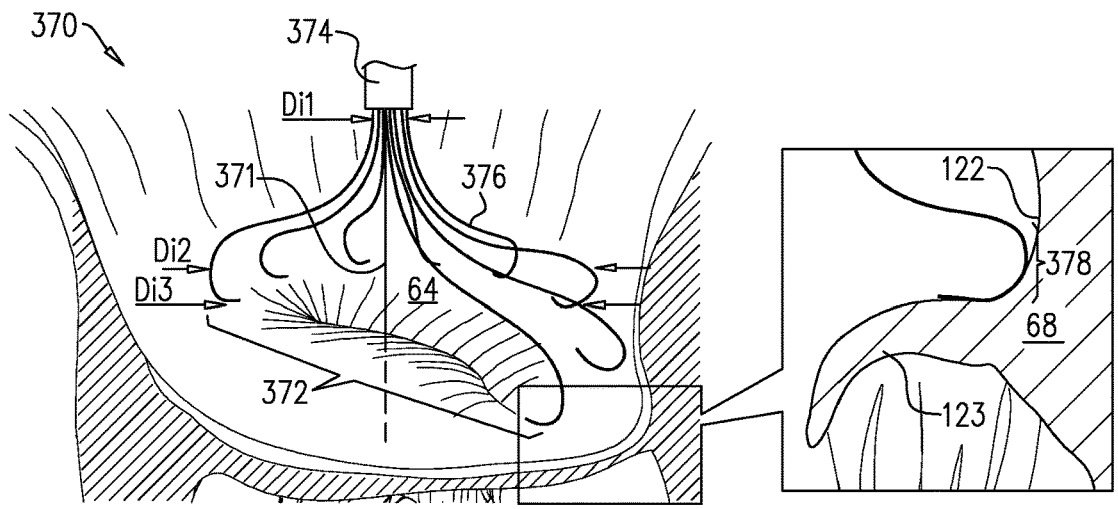
FIGS. 17A-C are schematic illustrations of respective annulus-marking devices comprising expandable elements for aiding implantation of cardiac devices under the guidance of imaging, in accordance with some applications.
Figure 17B:
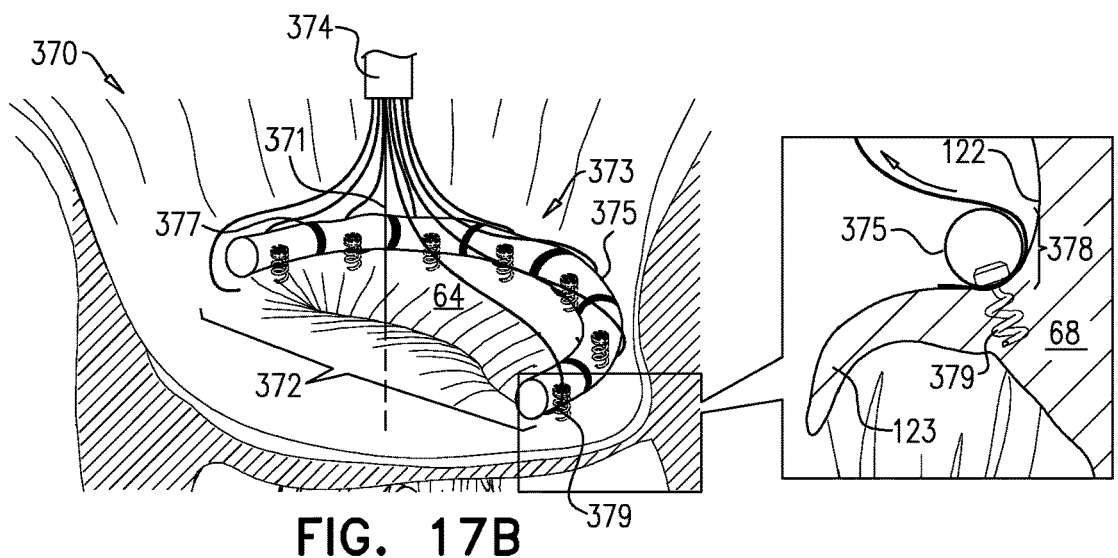
Figure 17C:
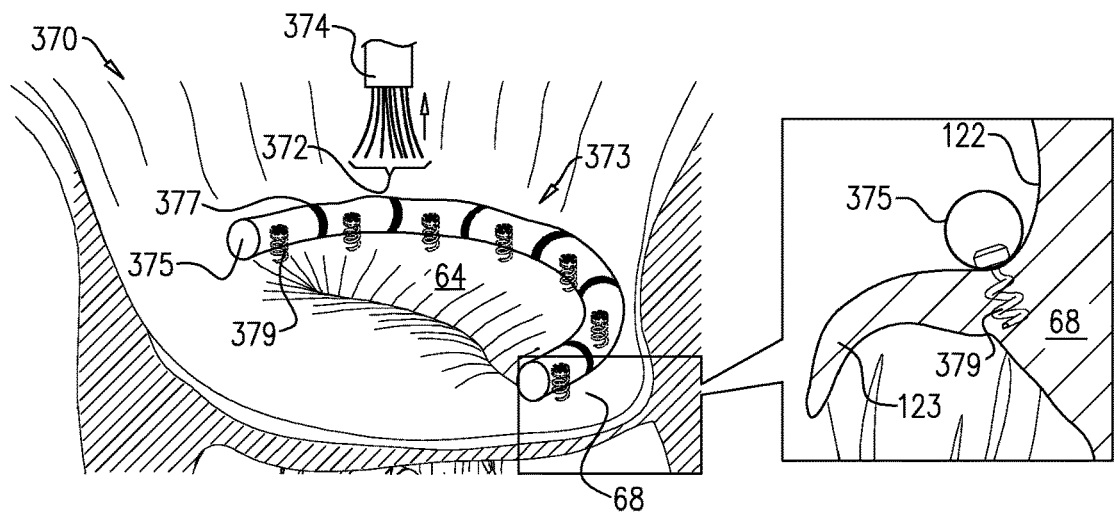

Reference is now made to FIGS. 17A-C, which are schematic illustrations of a system 370 comprising an annulus-marking device 372 comprising a plurality of expandable elements 376 which form device 372 into a generally umbrella shape for facilitating imaging of cardiac tissue during implantation of a cardiac implant, in accordance with some applications. Device 372 comprises a flexible, radiopaque material, e.g., nitinol or stainless steel, which facilitates collapsing and expanding of device 372. For some applications, the plurality of expandable elements 376 form device 372 into a generally pear shape. For some applications, the plurality of expandable elements 376 form device 372 into a partially-spherical shape. For some applications, the plurality of expandable elements 376 form device 372 into a partially-bulbous shape.

As shown, device 372 aids in imaging implantation of a cardiac implant, e.g., an annuloplasty structure 373, as shown. Structure 373 comprises a body portion 375 which comprises a flexible material and has a longitudinal axis that runs along the length of body portion 375 (e.g., when the body portion is straightened). Body portion 375 comprises radiopaque markings 377 to aid in imaging for accurate delivery of anchors 379 to annulus 68 in order to anchor structure 373 to tissue of annulus 68.

Annulus-marking device 372 is delivered using a delivery tool 374 which is configured to deliver device 372 to the left atrium in a compressed state. Device 372 is configured to be expanded from its compressed state once deployed from within a lumen of tool 374. Annulus-marking device 372 is retrievable upon removal of delivery tool 374 from the subject. That is, device 372 is constrained within the lumen of tool 374 once the cardiac implant has been implanted at annulus 68. Device 372 may be delivered percutaneously, thoracoscopically through the chest, or using open heart surgical techniques. If delivered percutaneously, device 372 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 372 comprises a wire.

Once inside the atrium, the plurality of expandable elements 376 expand radially within the atrium such that the plurality of expandable elements 376 provides an indication as to a location of the native heart valve annulus 68 of native heart valve 64. It is to be noted that although device 372 is being used in the left atrium, device 372 may be used in the right atrium, the left ventricle, and the right ventricle.

The plurality of expandable elements 376 collectively form annulus-marking device 372 into a generally umbrella shape.

Annulus 68 is then imaged using fluoroscopy. In some applications, annulus-marking device 372 is imaged with respect to the tissue of the native heart valve annulus 68 and the tissue coupled thereto by viewing the plurality of expandable elements 376 against the tissue. For some applications, annulus-marking device 372 is imaged with respect to the tissue of the native heart valve annulus 68 and the tissue coupled thereto by viewing movement of the plurality of expandable elements 376 responsively to movement of the tissue. For either application, annulus-marking device 372 is imaged with respect to the tissue of the native heart valve annulus 68, tissue of at least one leaflet, and tissue of an atrial wall 122.

For some applications, in order to facilitate positioning of the plurality of expandable elements 376, a guidewire 371 extends from within tool 374 and is disposed between leaflets 123 (e.g., posterior leaflet and anterior leaflet), often at a commissure of the valve. For some applications, a proximal section of each one of the plurality of expandable elements 376 is coupled to guidewire 371. Guidewire 371 is at least partly stiff, and provides resistance, which facilitates positioning of the plurality of expandable elements 376. Guidewire 371 may also provide tactile feedback to the operating physician.

In addition to mechanical effects such as biasing of the plurality of expandable elements 376 and providing tactile feedback, guidewire 371 may also facilitate positioning of the plurality of expandable elements 376 and/or of annuloplasty structure 373 by facilitating imaging. For example, the presence of guidewire 371 and/or the shape thereof (e.g., bending due to being pressed into the commissure) is visible in fluoroscopic imaging, and can be used to facilitate identification of the position and angle of the plurality of expandable elements 376 and/or of annuloplasty structure 373 with respect to tissues.

Guidewire 371 extends proximally through tool 374 and can extend to outside of the body of the subject. Guidewire 371 can be removed by pulling subsequent to the deployment of one or more tissue anchors 379.

As shown, the plurality of expandable elements 376 comprise a plurality of curved wires each having a curved section 378 at a distal end portion thereof, as shown in FIG. 17A. Structure 373 is placed within a concave section of each curved section 378 of the plurality of expandable elements 376.

As shown in FIGS. 17A-B, structure 373 is delivered subsequently to placement of the plurality of expandable elements 376. It is to be noted that for some applications, structure 373 is delivered together with annulus-marking device 372. For such applications, structure 373 is coupled to the plurality of expandable elements 376 in a manner in which curved sections 378 wrap around body portion 375 of structure 373, and structure 373 is delivered toward the annulus within tool 374.

A collective proximal diameter Di1 of the proximal ends of the plurality of expandable elements 376 is smaller than a collective distal diameter Di3 of the distal ends of the plurality of expandable elements 376. A collective middle diameter Di2 of the plurality of expandable elements 376 is greater than collective proximal diameter Di1 and greater than collective distal diameter Di3.

Reference is now made to FIGS. 3A-B and 17A-C. For some applications, annulus-marking device 372 is coupled to a plurality of radiopaque elements such as radiopaque filaments 99, radiopaque markers, radiopaque wires, radiopaque extensions, radiopaque beads, etc. In some applications, annulus-marking device 372 and radiopaque elements or filaments 99 are imaged with respect to the tissue of the native heart valve annulus 68 and the tissue coupled thereto by viewing the plurality of expandable elements 376 and radiopaque elements or filaments 99 against the tissue. For some applications, annulus-marking device 372 is imaged with respect to the tissue of the native heart valve annulus 68 and the tissue coupled thereto by viewing movement of the plurality of expandable elements 376 and of radiopaque elements or filaments 99 responsively to movement of the tissue. For either application, annulus-marking device 372 and radiopaque elements or filaments 99 are imaged with respect to the tissue of the native heart valve annulus 68, tissue of at least one leaflet, and tissue of an atrial wall 122.

Reference is again made to FIG. 17B. Annuloplasty structure 373 is implanted under the guidance of fluoroscopy using annulus-marking device 372 as a guide. Curved sections 378 are positioned between annuloplasty structure 373 and atrial wall 122. A respective anchor 379 is deployed to anchor structure 373 at a site along annulus 68 that is marked between successive curved wires of elements 376.

Following anchoring of structure 373 to annulus 68, annulus-marking device 372 is constrained within tool 374. As device 372 is constrained, elements 376 slide from under annuloplasty structure 373 implanted along annulus 68. Annulus-marking device 372 is retrieved and removed from the body of the subject. During the retrieving of annulus-marking device 372, curved sections 378 of elements 376 are sliding from under annuloplasty structure 373 implanted along annulus 68. Annulus-marking device 372 is retrieved and removed from the body of the subject.

Subsequently to implanting of structure 373, annulus-marking device 372 is retrieved. Since device 372 is flexible and compressible, device 372 is constrained within a tool during the retrieval of device 372 and subsequent removal of device 372 from the body of the subject. That is, device 372 does not function as an implant for such embodiments and is used only to guide implantation of annuloplasty structure 373 (i.e., the implant); rather, device 372 acts as a guide for implantation while placed temporarily within the body of the patient to be subsequently removed therefrom following the implantation of annuloplasty structure 373.

It is to be noted that although system 370 is shown on mitral valve 64, system 370 can be used on any cardiac valve, e.g., a tricuspid valve, or any other tissue of the subject.

Figure 18:
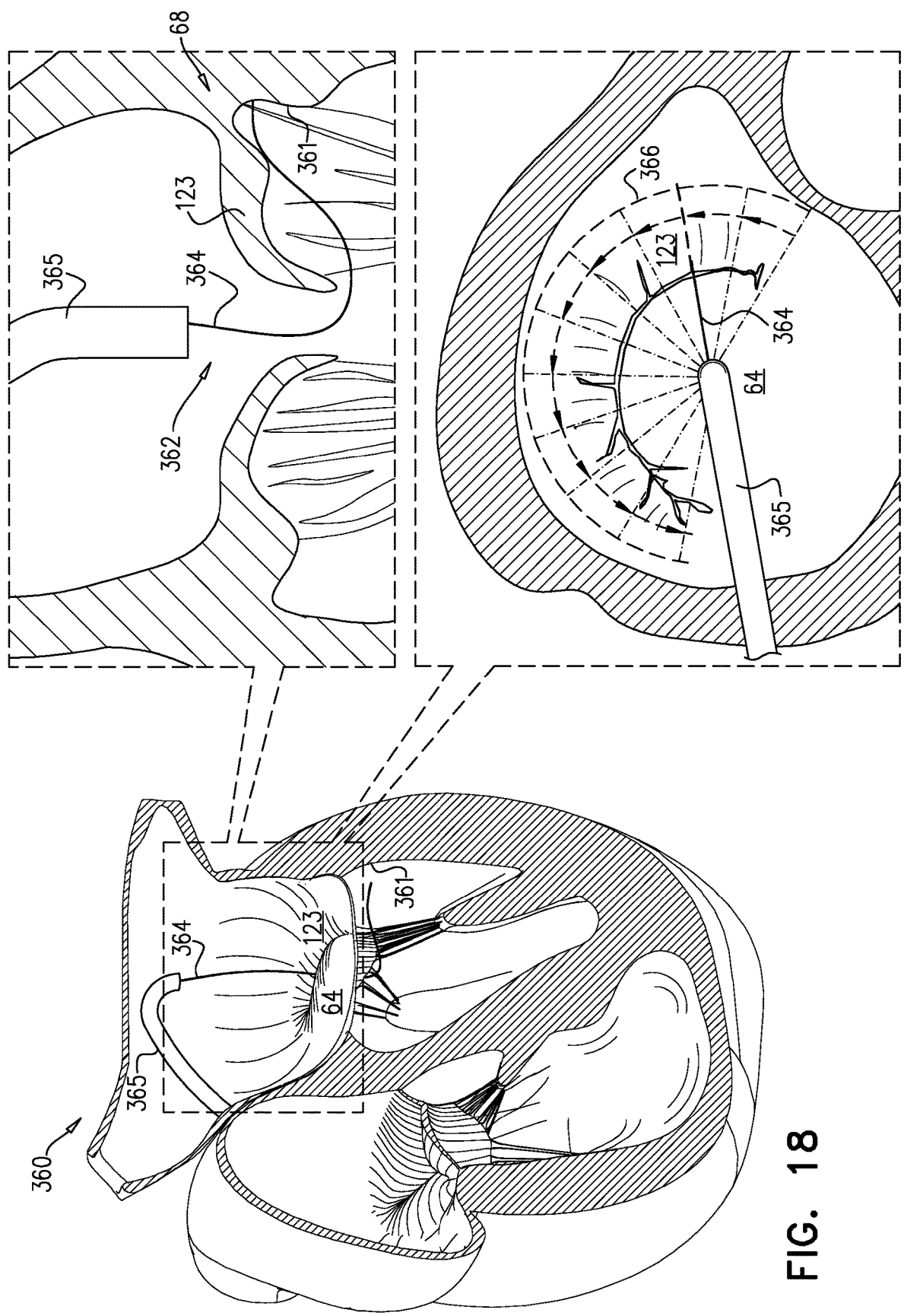
FIG. 18 is a schematic illustration of an annulus-marking device for use in a ventricle for aiding implantation of cardiac devices under the guidance of imaging, in accordance with some applications.

Reference is now made to FIG. 18, which is a schematic illustration of a system 360 comprising an annulus-marking device 362 comprising a guidewire 364 that has a distal end portion that is curved upwards and bends toward a ventricular surface 361 of valve 64, in accordance with some applications. The distal end portion of guidewire 364 is configured to contact the ventricular surface of annulus 68 and/or the ventricular wall. Guidewire 364 is configured to facilitate imaging of annulus 68 by imaging movement of the distal end portion thereof along a perimeter of the ventricular surface of annulus 68.

Guidewire 364 extends from within a delivery tool 365 and is disposed between leaflets 123 (e.g., posterior leaflet and anterior leaflet). Guidewire 364 has a distal curved section that curves upward toward ventricular surface 361. Guidewire 364 is at least partly stiff, which facilitates imaging-guided (e.g., under fluoroscopy) positioning of a cardiac device such as an annuloplasty structure (not shown). Guidewire 364 may also provide tactile feedback to the operating physician. For example, the presence of guidewire 364 and/or the shape thereof (e.g., bending due to being pressed into the commissure) is visible in fluoroscopic imaging, and can be used to facilitate identification of the position and angle of an annuloplasty structure with respect to tissues.

Guidewire 364 extends proximally through tool 365 and can extend to outside of the body of the subject. Guidewire 364 can be removed by pulling subsequent to the deployment of one or more tissue anchors in order to anchor the annuloplasty structure to annulus 68.

In some applications, guidewire 364 moves circumferentially around a ventricular surface 361 of annulus 68 in order to generate a map 366. For some applications, map 366 is generated prior to implantation of the annuloplasty structure. For some applications, guidewire 364 moves in conjunction with implantation of the annuloplasty structure at the atrial surface of annulus 68.

Reference is now made to FIGS. 3A-B and 18. It is to be noted that guidewire 364 can be coupled to a plurality of elements or filaments 99 and can be shaped in any suitable shape. For example, a distal end of guidewire 364 may be helical.

It is to be noted that although system 360 is shown on mitral valve 64, system 360 can be used on any cardiac valve, e.g., a tricuspid valve, or any other tissue of the subject.

Figures 19A, 19B, 19C:
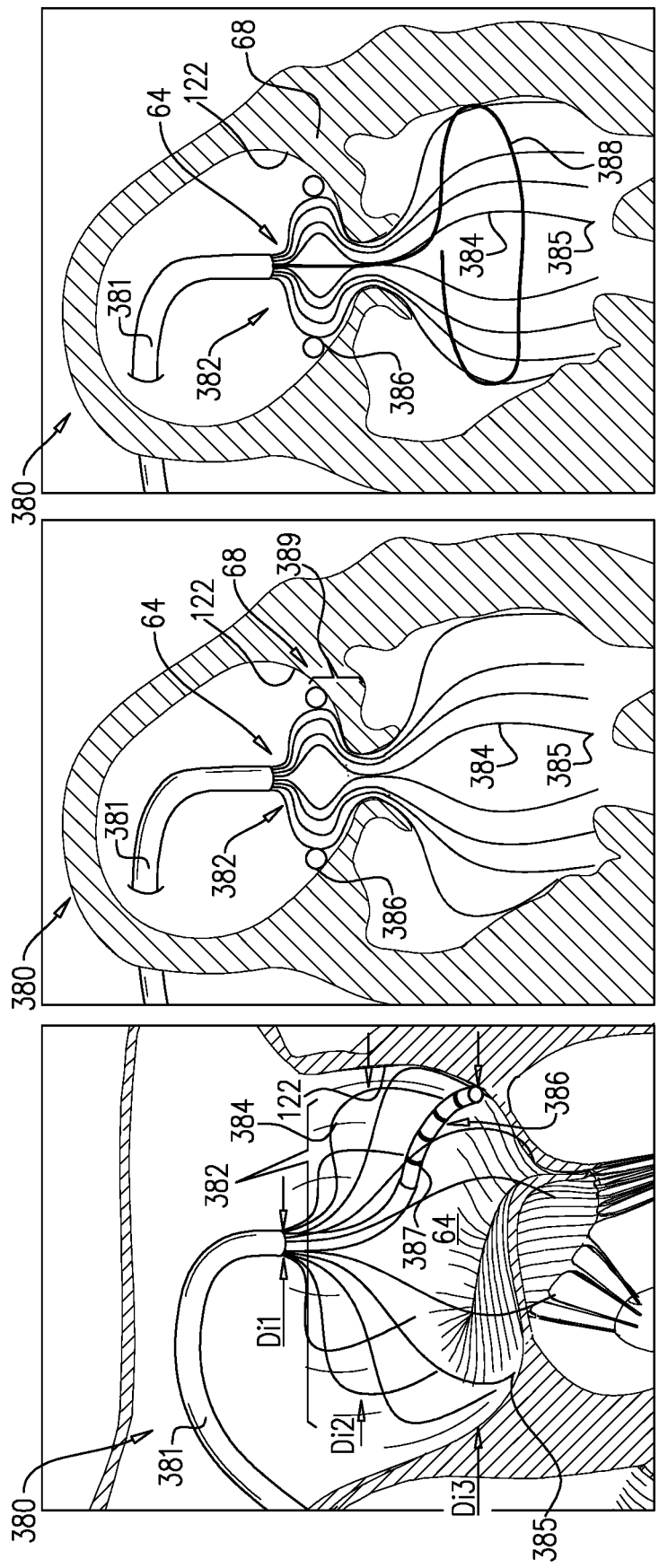
FIGS. 19A-C are schematic illustrations of respective annulus-marking devices comprising expandable elements for aiding implantation of cardiac devices under the guidance of imaging, in accordance with some applications.

Reference is now made to FIGS. 19A-C, which are schematic illustrations of a system 380 comprising an annulus-marking device 382 comprising a plurality of expandable elements 384 which form device 382 into a generally umbrella shape for facilitating imaging of cardiac tissue during implantation of a cardiac implant, in accordance with some applications. Device 382 comprises a flexible, radiopaque material, e.g., nitinol or stainless steel, which facilitates collapsing and expanding of device 382. For some applications, the plurality of expandable elements 384 form device 382 into a generally pear shape. For some applications, the plurality of expandable elements 384 form device 382 into a partially-spherical shape. For some applications, the plurality of expandable elements 384 form device 382 into a partially-bulbous shape.

As shown, device 382 aids in imaging implantation of a cardiac implant, e.g., an annuloplasty structure 386, as shown. Structure 386 comprises a body portion which comprises a flexible material and has a longitudinal axis that runs along the length of the body portion (e.g., when the body portion is straightened). The body portion comprises radiopaque markings 387 to aid in imaging for accurate delivery of anchors to annulus 68 in order to anchor structure 386 to tissue of annulus 68.

Annulus-marking device 382 is delivered using a delivery tool 381 which is configured to deliver device 382 to the left atrium in a compressed state. Device 382 is configured to be expanded from its compressed state once deployed from within a lumen of tool 381. Annulus-marking device 382 is retrievable upon removal of delivery tool 381 from the subject. That is, device 382 is constrained within the lumen of tool 381 once the cardiac implant has been implanted at annulus 68. Device 382 may be delivered percutaneously, thoracoscopically through the chest, or using open heart surgical techniques. If delivered percutaneously, device 382 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 382 comprises a wire.

For some applications, the plurality of expandable elements 384 guide tool 381 to the appropriate place along annulus 68.

Once inside the atrium, the plurality of expandable elements 384 expand radially within the atrium such that the plurality of expandable elements 384 provides an indication as to a location of the native heart valve annulus 68 of native heart valve 64. In some applications, the plurality of expandable elements 384 comprise a shape-memory material that enables elements 384 to expand to a given shape within the heart. It is to be noted that although device 382 is being used in the left atrium, device 382 may be used in the right atrium, the left ventricle, and the right ventricle.

The plurality of expandable elements 384 collectively form annulus-marking device 382 into a generally umbrella shape.

Annulus 68 is then imaged using fluoroscopy. In some applications, annulus-marking device 382 is imaged with respect to the tissue of the native heart valve annulus 68 and the tissue coupled thereto by viewing the plurality of expandable elements 384 against the tissue. For some applications, annulus-marking device 382 is imaged with respect to the tissue of the native heart valve annulus 68 and the tissue coupled thereto by viewing movement of the plurality of expandable elements 384 responsively to movement of the tissue. For either application, annulus-marking device 382 is imaged with respect to the tissue of the native heart valve annulus 68, tissue of at least one leaflet, and tissue of an atrial wall 122.

As shown in FIG. 19A, structure 386 is delivered subsequently to placement of the plurality of expandable elements 384. It is to be noted that for some applications, structure 386 is delivered together with annulus-marking device 382. Annuloplasty structure 386 is implanted under the guidance of fluoroscopy using annulus-marking device 382 as a guide. Annuloplasty structure 386 is positioned between annulus-marking device 382 and atrial wall 122. A respective anchor is deployed to anchor structure 386 at a site along annulus 68 that is marked between successive curved wires of elements 384 and in between radiopaque markings 387 of structure 386.

Reference is now made to FIG. 19A. A collective proximal diameter Di1 of the proximal ends of the plurality of expandable elements 384 is smaller than a collective distal diameter Di3 of the distal ends of the plurality of expandable elements 384. A collective middle diameter Di2 of the plurality of expandable elements 384 is greater than collective proximal diameter Di1 and greater than collective distal diameter Di3.

Reference is now made to FIGS. 19A-C. The plurality of expandable elements 384 comprise a very flexible material and design that allows elements 384 to assume the shape of the cavity that they are opened in, e.g., the left atrium, as shown.

In FIG. 19A, a respective distal end 385 of each expandable element 384 of device 382 is positioned within the atrium. That is, distal ends 385 remain at the atrial surface of annulus 68.

For some applications, distal ends 385 are pushed into the ventricle, as shown in FIG. 19B. In such applications, the plurality of expandable elements 384 are each made to bend at a middle section thereof collectively forming a bent section 389, and it is at this bent section 389 that the operating physician determines using imaging that this is the location of the annulus.

Reference is now made to FIG. 19C. For some applications, a radiopaque helical stent 388 is delivered to the ventricle between the plurality of expandable elements 384, and between leaflets 123 of valve 64. As shown, a distal end portion comprising a distal end of stent 388 is positioned within the ventricle and is sued for imaging the ventricle.

Reference is now made to FIGS. 3A-B and 19A-C. For some applications, annulus-marking device 382 is coupled to a plurality of radiopaque elements, such as radiopaque filaments 99. In some applications, annulus-marking device 382 and radiopaque elements or filaments 99 are imaged with respect to the tissue of the native heart valve annulus 68 and the tissue coupled thereto by viewing the plurality of expandable elements 384 and radiopaque elements or filaments 99 against the tissue. For some applications, annulus-marking device 382 is imaged with respect to the tissue of the native heart valve annulus 68 and the tissue coupled thereto by viewing movement of the plurality of expandable elements 384 and of radiopaque elements or filaments 99 responsively to movement of the tissue. For either application, annulus-marking device 382 and radiopaque elements or filaments 99 are imaged with respect to the tissue of the native heart valve annulus 68, tissue of at least one leaflet, and tissue of an atrial wall 122.

Following anchoring of structure 386 to annulus 68, annulus-marking device 382 is constrained within tool 381. Annulus-marking device 382 is retrieved and removed from the body of the subject.

Subsequently to implanting of structure 386, annulus-marking device 382 is retrieved. Since device 382 is flexible and compressible, device 382 is constrained within a tool during the retrieval of device 382 and subsequent removal of device 382 from the body of the subject. That is, device 382 does not function as an implant for such embodiments and is used only to guide implantation of annuloplasty structure 386 (i.e., the implant); rather, device 382 acts as a guide for implantation while placed temporarily within the body of the patient to be subsequently removed therefrom following the implantation of annuloplasty structure 386.

It is to be noted that although system 380 is shown on mitral valve 64, system 380 can be used on any cardiac valve, e.g., a tricuspid valve, or any other tissue of the subject.

Reference is now made to FIGS. 19A-C. It is to be noted that annulus-marking device 382 can comprises a braided mesh of radiopaque material, e.g., fabric or metal. For some applications, annulus-marking device 382 comprises an expandable radiopaque balloon.

Figure 20A:
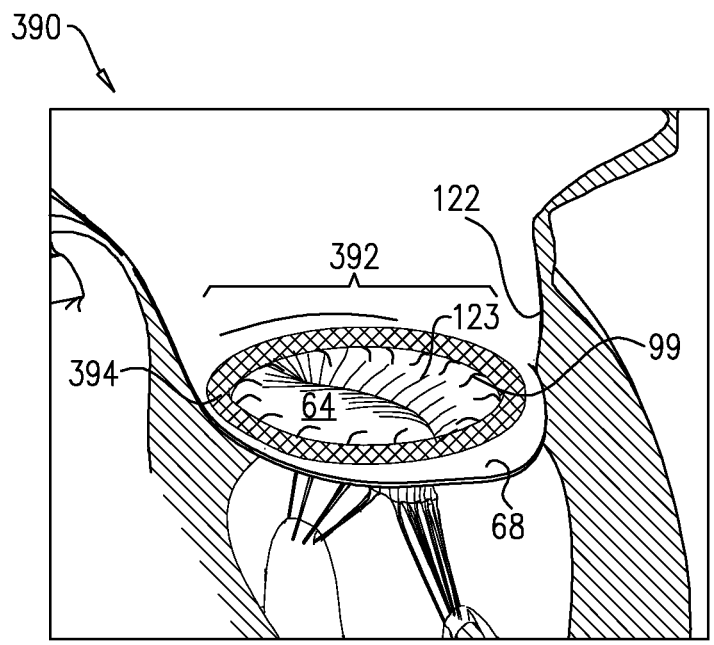
FIGS. 20A-B are schematic illustrations of an annulus-marking device comprising a toroidal stent for aiding implantation of cardiac devices under the guidance of imaging, in accordance with some applications.
Figure 20B:
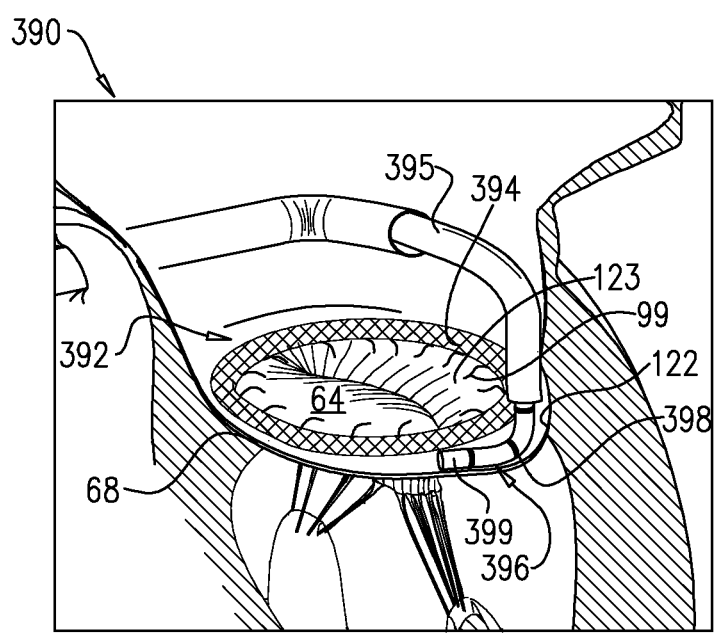

Reference is now made to FIGS. 20A-B, which are schematic illustrations of a system 390 comprising an annulus-marking device 392 comprising a toroidal stent 394, in accordance with some applications. Toroidal stent 394 is configured to be compressed and constrained within a delivery system. Stent 394 expands within the atrium and is placed against annulus tissue at a surface of valve 64. For some applications, stent 394 may be placed along an atrial surface. For some applications, stent 394 may be placed along a ventricular surface. Annulus-marking device 392 comprises radiopaque material For some applications, stent 394 is shaped so as to define a complete toroid. For some applications, stent 394 is shaped so as to define a discontinuous generally-toroidal shape. For such applications, opposing ends of stent 394 may overlap to form stent 394 into a toroid. For some applications, stent 394 can be shaped as a coil having a perimeter that corresponds to a perimeter of annulus 68 of valve 64.

Device 392 may be delivered percutaneously, thoracoscopically through the chest, or using open heart surgical techniques. If delivered percutaneously, device 392 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 392 comprises a plurality of struts, e.g., a plurality of wires.

For some applications, stent 394 comprises a plurality of radiopaque elements, such as radiopaque filaments 99, at least at an inner surface of stent 394. In some implementations, the plurality of radiopaque elements or filaments projects inwardly toward the orifice of valve 64. The plurality of radiopaque elements or filaments 99 comprise radiopaque material (e.g., nitinol or stainless steel) and can be configured to be extremely flexible. Radiopaque elements or filaments 99 are configured for aiding implantation of cardiac devices, e.g., an annuloplasty structure 396, under the guidance of imaging, in accordance with some applications. Implantation of annuloplasty structure 396 is performed with the aid of imaging, such as fluoroscopy, transesophageal echo, and/or echocardiography.

For some applications, radiopaque elements or filaments 99 sway with movement of the blood. For some applications, radiopaque elements or filaments 99 press against tissue of the annulus and tissue coupled thereto, such as tissue of an atrial wall 122 as well as tissue of leaflets 123 of the native valve (as shown). Radiopaque elements or filaments 99 thus provide enhanced imaging of tissue of valve 64. For example, in some embodiments, when radiopaque filaments 99 appear bent or pressed, this imaging detects annulus tissue, while when filaments 99 are straight, this could indicate the orifice of the valve.

Device 392 can be made from a superelastic material (e.g., nitinol or stainless steel) enabling it to be folded and collapsed such that it can be delivered in a catheter. Additionally, device 392 is made from radiopaque material to facilitate fluoroscopic visualization. In some applications, tissue of valve annulus 68 and tissue coupled thereto is viewed by imaging stent 394. Additionally, the tissue of the native heart valve annulus 68 and tissue coupled thereto is viewed by imaging annulus-marking device 392 with respect to the tissue of the native heart valve annulus and the tissue coupled thereto by viewing the stent 394 against the tissue. For some applications, the tissue of the native heart valve annulus 68 and tissue coupled thereto is viewed by imaging annulus-marking device 392 with respect to the tissue of the native heart valve annulus and the tissue coupled thereto by viewing movement of the stent 394 responsively to movement of the tissue.

Reference is now made to FIG. 20B, which shows implantation of annuloplasty structure 396 which comprises a body portion 399. Body portion 399 comprises a flexible material, e.g., a braided fabric mesh. For some applications, body portion 399 is shaped so as to define a sleeve shaped so as to define a lumen therethrough, as shown. For some applications, body portion 399 is flat.

Body portion 399 can comprise a braided fabric mesh, e.g., comprising DACRON™. Body portion 399 can be configured to be placed only partially around a cardiac valve annulus (e.g., to assume a C-shape), and, once anchored in place, to be contracted so as to circumferentially tighten the valve annulus. Optionally, structure 396 can be configured to be placed entirely around the valve annulus (e.g., as a closed circle or other closed shape). In order to tighten the annulus, annuloplasty structure 396 comprises a flexible elongated contracting member that extends along body portion 399.

Structure 396 comprises a plurality of radiopaque markers 398, which are positioned along structure 396 at respective longitudinal sites. The markers may provide an indication in a radiographic image (such as a fluoroscopy image) of how much of the body portion has been deployed at any given point during an implantation procedure, in order to enable setting a desired distance between the tissue anchors along the body portion. For some applications, the markers comprise radiopaque ink. For some applications the markers comprise a radiopaque material attached to or incorporated in body portion 164.

As shown, structure 396 is implanted between an external surface of stent 394 and tissue of atrial wall 122.

Subsequently to implanting of structure 396, annulus-marking device 392 is retrieved. Since device 392 is flexible and compressible, device 392 is constrained within a tool during the retrieval of device 392 and subsequent removal of device 392 from the body of the subject. That is, device 392 does not function as an implant for such embodiments and is used only to guide implantation of annuloplasty structure 396 (i.e., the implant); rather, device 392 acts as a guide for implantation while placed temporarily within the body of the patient to be subsequently removed therefrom following the implantation of annuloplasty structure 396.

It is to be noted that although system 390 is shown on mitral valve 64, system 390 can be used on any cardiac valve, e.g., a tricuspid valve, or any other tissue of the subject.

Reference is now made to FIGS. 21-27, which are schematic illustrations of respective annulus marking devices comprising implant-leading devices for aiding implantation of cardiac devices under the guidance of imaging, in accordance with some applications.

Figure 21:
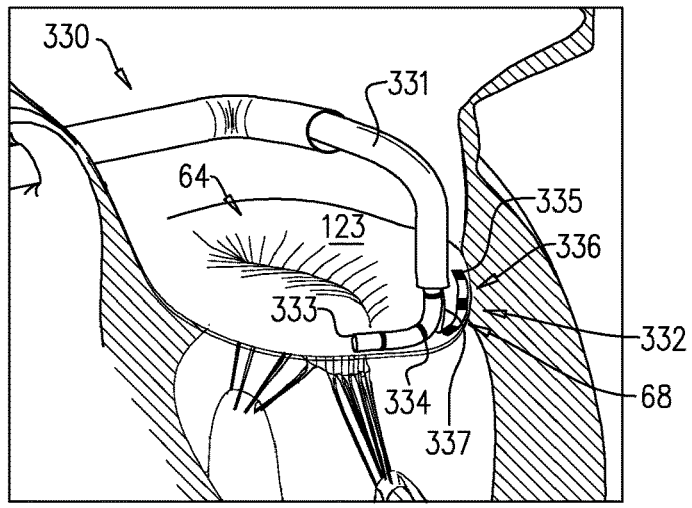
FIGS. 21-27 are schematic illustrations of respective annulus marking devices comprising implant-leading devices for aiding implantation of cardiac devices under the guidance of imaging, in accordance with some applications.

Reference is now made to FIG. 21, which is a schematic illustration of a system 330 comprising an annulus-marking device 332 comprising an implant-leading device 336 that runs in advance of an implant, e.g., an annuloplasty structure, in its implantation path, upstream thereof, in accordance with some applications. Implant-leading device 336 extends from within a delivery tool 331 and travels along a perimeter of annulus 68. As successive portions of the annuloplasty structure are extended from within delivery tool 331 and are positioned along successive portions of annulus 68, implant-leading device 336 guides the successive portions of the annuloplasty structure under imaging as implant-leading device 336 comprises a radiopaque material (e.g., nitinol or stainless steel). Implant-leading device 336 comprises a wire 337 and at least one generally flat, geometric radiopaque unit 335 at a distal end thereof, e.g., a square of radiopaque material. For some applications, as shown, implant-leading device 336 comprises wire 337 and three generally flat, geometric radiopaque units 335 at a distal end thereof.

Implant-leading device 336 is relatively small and provides an indication of a specific section of annulus 68 immediately preceding the placement of the successive portion of the annuloplasty structure along annulus 68. Implant-leading device 336 is at least partly stiff, and provides resistance, which facilitates positioning of the annuloplasty structure. Implant-leading device 336 may also provide tactile feedback to the operating physician.

The annuloplasty structure comprises a body portion 333 which comprises a flexible material and has a longitudinal axis that runs along the length of the body portion (e.g., when implant is straightened). Body portion 333 comprises radiopaque markings 334 to aid in imaging for accurate delivery of anchors to annulus 68 in order to anchor the annuloplasty structure to tissue of annulus 68.

In addition to providing tactile feedback, implant-leading device 336 may also facilitate positioning of the annuloplasty structure by facilitating imaging (e.g., fluoroscopy) and mechanical guidance. For example, the presence of implant-leading device 336 and/or the shape thereof (e.g., bending due to being pressed against an atrial wall) is visible in fluoroscopic imaging, and can be used to facilitate identification of the position and angle of the annuloplasty structure with respect to tissues.

Implant-leading device 336 extends proximally through tool 331 and can extend to outside of the body of the subject. Implant-leading device 336 can be removed by pulling subsequent to the deployment of one or more tissue anchors in order to anchor the annuloplasty structure. In some applications, implant-leading device 336 is constrained within tool 331 in order to be retrieved and removed from the body of the subject.

Reference is now made to FIGS. 3A-B and 21. It is to be noted that implant-leading device 336 can be coupled to a plurality of elements or filaments 99 and can be shaped in any suitable shape.

It is to be noted that although system 330 is shown on mitral valve 64, system 330 can be used on any cardiac valve, e.g., a tricuspid valve, or any other tissue of the subject.

Figure 22:
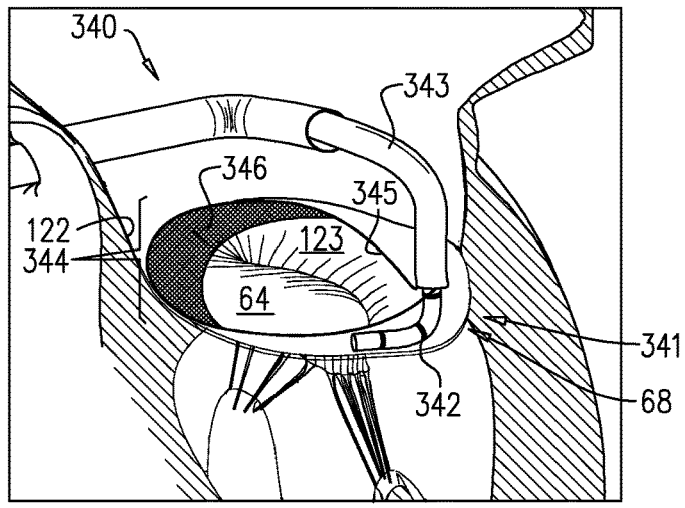

Reference is now made to FIG. 22, which is a schematic illustration of a system 340 comprising an annulus-marking device 344 comprising an implant-leading device 345 that runs in advance of an implant, e.g., an annuloplasty structure 341, in its implantation path, upstream thereof, in accordance with some applications. Annulus-marking device 344 extends from within a delivery tool 343 and travels along a perimeter of annulus 68. As successive portions of annuloplasty structure 341 are extended from within delivery tool 343 and are positioned along successive portions of annulus 68, annulus-marking device 344 guides the successive portions of structure 341 under imaging as annulus-marking device 344 comprises a radiopaque material (e.g., nitinol or stainless steel). Annulus-marking device 344 comprises (1) a wire that is shaped in a loop and, for some applications, (2) a structure comprising a mesh 346. The wire is generally deflectable to be pushed against tissue of annulus 68 and abut tissue of annulus 68 such that annulus-marking device 344 facilitates providing an image of a large percentage, e.g., at least 50% or at least 60%, of a perimeter of annulus 68. Additionally, the wire of annulus-marking device 344 pushes against a first portion of annulus 68 in order to apply a pushing force to the opposite portion of annulus 68 (i.e., the portion of annulus 68 at which delivery tool 343 is positioned) such that system 340 ensures that annuloplasty structure 341 is properly positioned at a juncture between tissue of annulus 68 and tissue of atrial wall 122. In such a manner, device 344 ensures that annuloplasty structure 341 is positioned outside the external perimeter of the wire that is shaped as a loop, responsively to the pushing of device 344 against tissue of annulus 68 such that annuloplasty structure 341 is implanted along annulus 68 and not on leaflet 123. For some applications, device 344 does not lead the implant, but rather, device 344 is positioned in conjunction with implantation of the implant.

Mesh 346 also spans a portion of the orifice of the valve at leaflets 123 and comprises a braided, radiopaque mesh that does not interfere with blood flow during implantation of annuloplasty structure 341 on a beating heart. Annulus-marking device 344 is at least partly stiff, and provides resistance, which facilitates positioning of structure 341. Annulus-marking device 344 may also provide tactile feedback to the operating physician.

It is to be noted that device 344 may be provided without mesh 346 such that device 344 comprises only the wire that is shaped in a loop.

Structure 341 comprises a body portion which comprises a flexible material and has a longitudinal axis that runs along the length of the body portion (e.g., when the body portion is straightened). The body portion comprises radiopaque markings 342 to aid in imaging for accurate delivery of anchors to annulus 68 in order to anchor structure 341 to tissue of annulus 68.

In addition to providing tactile feedback, annulus-marking device 344 may also facilitate positioning of the annuloplasty structure 341 by facilitating imaging (e.g., fluoroscopy) and mechanical guidance. For example, the presence of annulus-marking device 344 and/or the shape thereof (e.g., bending due to being pressed against an atrial wall) is visible in fluoroscopic imaging, and can be used to facilitate identification of the position and angle of annuloplasty structure 341 with respect to tissues.

Annulus-marking device 344 extends proximally through tool 343 and can extend to outside of the body of the subject. Annulus-marking device 344 can be removed by pulling subsequent to the deployment of one or more tissue anchors in order to anchor structure 341. In some applications, annulus-marking device 344 is constrained within tool 343 in order to be retrieved and removed from the body of the subject. For some applications, device 344 is delivered together with the annuloplasty structure 341 in tool 343. For some applications, device 344 is delivered in a separate tool to tool 343 used to deliver annuloplasty structure 341.

Reference is now made to FIGS. 3A-B and 22. It is to be noted that annulus-marking device 344 can be coupled to a plurality of elements or filaments 99 and can be shaped in any suitable shape.

It is to be noted that although system 340 is shown on mitral valve 64, system 340 can be used on any cardiac valve, e.g., a tricuspid valve, or any other tissue of the subject.

Figure 23:
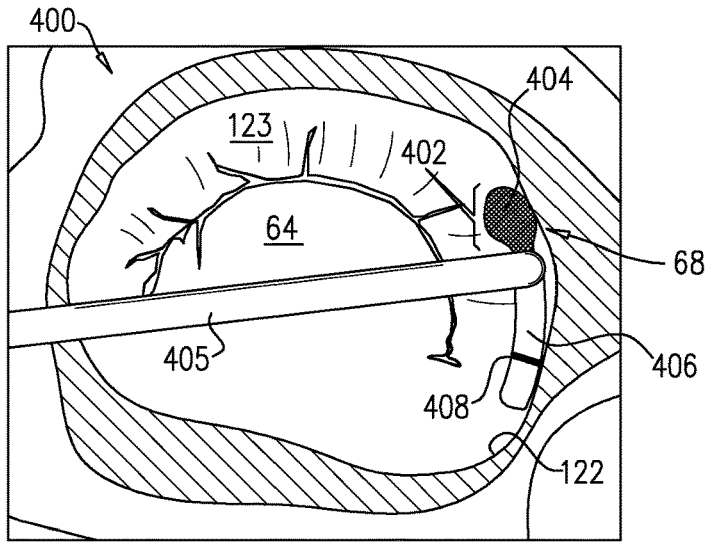

Reference is now made to FIG. 23, which is a schematic illustration of a system 400 comprising an annulus-marking device 402 comprising an implant-leading device 404 that runs in advance of an implant, e.g., an annuloplasty structure 406, in its implantation path, upstream thereof, in accordance with some applications. Implant-leading device 404 extends from within a delivery tool 405 and travels along a perimeter of annulus 68. As successive portions of annuloplasty structure 406 are extended from within delivery tool 405 and are positioned along successive portions of annulus 68, implant-leading device 404 guides the successive portions of structure 406 under imaging as implant-leading device 404 comprises a radiopaque material (e.g., nitinol or stainless steel). Implant-leading device 404 comprises a wire and a generally flat, bulbous radiopaque unit at a distal end thereof, e.g., a teardrop-shaped structure, comprising radiopaque material. For such applications, implant-leading device 404 is relatively small and provides an indication of a specific section of annulus 68 immediately preceding the placement of the successive portion of structure 406 along annulus 68. Implant-leading device 404 is at least partly stiff, and provides resistance, which facilitates positioning of structure 406. Implant-leading device 404 may also provide tactile feedback to the operating physician.

Structure 406 comprises a body portion which comprises a flexible material and has a longitudinal axis that runs along the length of the body portion (e.g., when the body portion is straightened). The body portion comprises radiopaque markings 408 to aid in imaging for accurate delivery of anchors to annulus 68 in order to anchor structure 406 to tissue of annulus 68.

In addition to providing tactile feedback, implant-leading device 404 may also facilitate positioning of the annuloplasty structure 406 by facilitating imaging (e.g., fluoroscopy) and mechanical guidance. For example, the presence of implant-leading device 404 and/or the shape thereof (e.g., bending due to being pressed against an atrial wall 122) is visible in fluoroscopic imaging, and can be used to facilitate identification of the position and angle of annuloplasty structure 406 with respect to tissues.

Implant-leading device 404 extends proximally through tool 405 and can extend to outside of the body of the subject. Implant-leading device 404 can be removed by pulling subsequent to the deployment of one or more tissue anchors in order to anchor structure 406. In some applications, implant-leading device 404 is constrained within tool 405 in order to be retrieved and removed from the body of the subject.

Reference is now made to FIGS. 3A-B and 23. It is to be noted that implant-leading device 404 can be coupled to a plurality of elements or filaments 99 and can be shaped in any suitable shape.

It is to be noted that although system 400 is shown on mitral valve 64, system 400 can be used on any cardiac valve, e.g., a tricuspid valve, or any other tissue of the subject.

Figure 24:
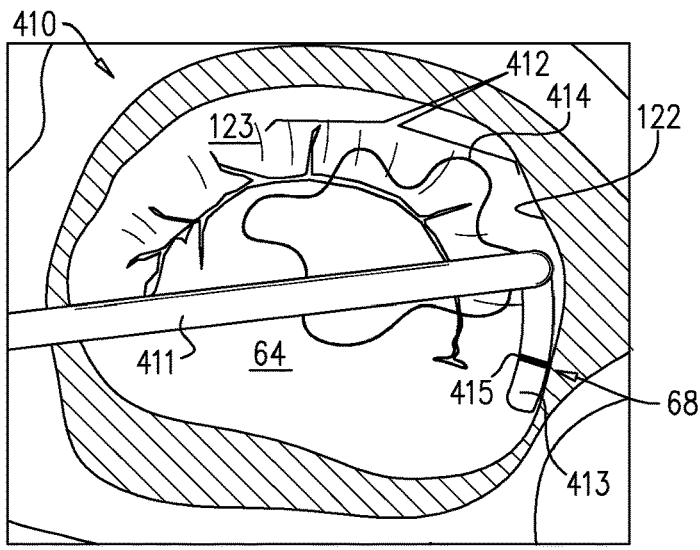

Reference is now made to FIG. 24, which is a schematic illustration of a system 410 comprising an annulus-marking device 412 comprising an implant-leading device 414 that runs in advance of an implant, e.g., an annuloplasty structure 413, in its implantation path, upstream thereof, in accordance with some applications. Implant-leading device 414 extends from within a delivery tool 411 and travels along a perimeter of annulus 68. As successive portions of annuloplasty structure 413 are extended from within delivery tool 411 and are positioned along successive portions of annulus 68, implant-leading device 414 guides the successive portions of structure 413 under imaging as implant-leading device 414 comprises a radiopaque material (e.g., nitinol or stainless steel). Implant-leading device 414 comprises a deflectable wire shaped in a petal-shaped loop, e.g., a puddle-shaped structure, comprising radiopaque material. For such applications, implant-leading device 414 facilitates providing an image of a large percentage, e.g., at least 30% or at least 40%, of valve 64. Device 414 spans a portion of the orifice of the valve at leaflets 123, and the wireframe of device 414 does not interfere with blood flow during implantation of annuloplasty structure 413 on a beating heart. Implant-leading device 414 is at least partly stiff, and provides resistance, which facilitates positioning of structure 413. Implant-leading device 414 may also provide tactile feedback to the operating physician.

Structure 413 comprises a body portion which comprises a flexible material and has a longitudinal axis that runs along the length of the body portion (e.g., when the body portion is straightened). The body portion comprises radiopaque markings 415 to aid in imaging for accurate delivery of anchors to annulus 68 in order to anchor structure 413 to tissue of annulus 68.

In addition to providing tactile feedback, implant-leading device 414 may also facilitate positioning of the annuloplasty structure 413 by facilitating imaging (e.g., fluoroscopy) and mechanical guidance. For example, the presence of implant-leading device 414 and/or the shape thereof (e.g., bending due to being pressed against an atrial wall 122) is visible in fluoroscopic imaging, and can be used to facilitate identification of the position and angle of annuloplasty structure 413 with respect to tissues.

Implant-leading device 414 extends proximally through tool 411 and can extend to outside of the body of the subject. Implant-leading device 414 can be removed by pulling subsequent to the deployment of one or more tissue anchors in order to anchor structure 413. In some applications, implant-leading device 414 is constrained within tool 411 in order to be retrieved and removed from the body of the subject.

Reference is now made to FIGS. 3A-B and 24. It is to be noted that implant-leading device 414 can be coupled to a plurality of elements or filaments 99 and can be shaped in any suitable shape.

It is to be noted that although system 410 is shown on mitral valve 64, system 410 can be used on any cardiac valve, e.g., a tricuspid valve, or any other tissue of the subject.

Figure 25:
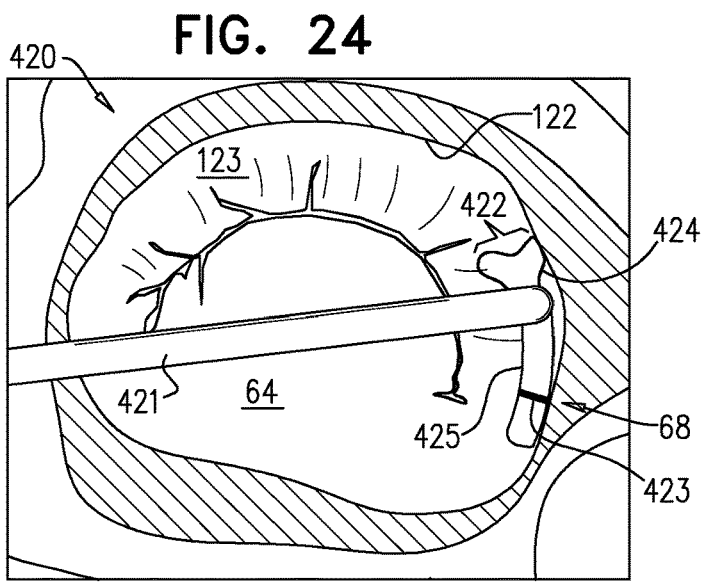

Reference is now made to FIG. 25, which is a schematic illustration of a system 420 comprising an annulus-marking device 422 comprising an implant-leading device 424 that runs in advance of an implant, e.g., an annuloplasty structure 425, in its implantation path, upstream thereof, in accordance with some applications. Implant-leading device 424 extends from within a delivery tool 421 and travels along a perimeter of annulus 68. As successive portions of annuloplasty structure 425 are extended from within delivery tool 421 and are positioned along successive portions of annulus 68, implant-leading device 424 guides the successive portions of structure 425 under imaging as implant-leading device 424 comprises a radiopaque material (e.g., nitinol or stainless steel). Implant-leading device 424 comprises a deflectable wire shaped in a petal-shaped loop, e.g., a pear-shaped structure, comprising radiopaque material. For such applications, implant-leading device 424 is relatively small and provides an indication of a specific section of annulus 68 immediately preceding the placement of the successive portion of structure 425 along annulus 68. Implant-leading device 424 is at least partly stiff, and provides resistance, which facilitates positioning of structure 425. Implant-leading device 424 may also provide tactile feedback to the operating physician.

Structure 425 comprises a body portion which comprises a flexible material and has a longitudinal axis that runs along the length of the body portion (e.g., when the body portion is straightened). The body portion comprises radiopaque markings 423 to aid in imaging for accurate delivery of anchors to annulus 68 in order to anchor structure 425 to tissue of annulus 68.

In addition to providing tactile feedback, implant-leading device 424 may also facilitate positioning of the annuloplasty structure 425 by facilitating imaging (e.g., fluoroscopy) and mechanical guidance. For example, the presence of implant-leading device 424 and/or the shape thereof (e.g., bending due to being pressed against an atrial wall 122) is visible in fluoroscopic imaging, and can be used to facilitate identification of the position and angle of annuloplasty structure 425 with respect to tissues.

Implant-leading device 424 extends proximally through tool 421 and preferably to outside of the body of the subject. Implant-leading device 424 can be removed by pulling subsequent to the deployment of one or more tissue anchors in order to anchor structure 425. In some applications, implant-leading device 424 is constrained within tool 421 in order to be retrieved and removed from the body of the subject.

Reference is now made to FIGS. 3A-B and 25. It is to be noted that implant-leading device 424 can be coupled to a plurality of elements or filaments 99 and can be shaped in any suitable shape.

It is to be noted that although system 420 is shown on mitral valve 64, system 420 can be used on any cardiac valve, e.g., a tricuspid valve, or any other tissue of the subject.

Figure 26:
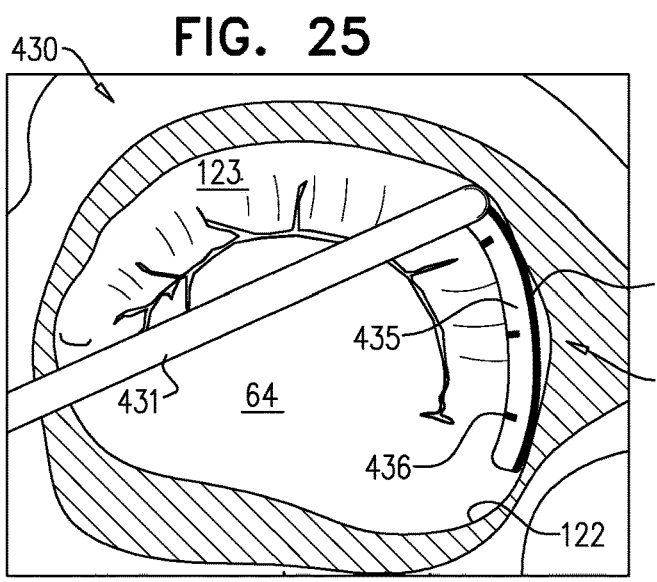

Reference is now made to FIG. 26, which is a schematic illustration of a system 430 comprising an annulus-marking device 432 comprising an implant-leading device 434 that runs alongside an implant, e.g., an annuloplasty structure 435, in accordance with some applications. For some applications, device 432 is integral with the body portion of structure 435. Implant-leading device 434 extends from within a delivery tool 431 and travels along a perimeter of annulus 68. As successive portions of annuloplasty structure 435 are extended from within delivery tool 431 and are positioned along successive portions of annulus 68, implant-leading device 434 guides the successive portions of structure 435 under imaging as implant-leading device 434 comprises a radiopaque material (e.g., nitinol or stainless steel). Implant-leading device 434 comprises a deflectable radiopaque wire or a radiopaque fabric. Implant-leading device 434 may also provide tactile feedback to the operating physician.

Structure 435 comprises a body portion which comprises a flexible material and has a longitudinal axis that runs along the length of the body portion (e.g., when body portion is straightened). The body portion comprises radiopaque markings 436 to aid in imaging for accurate delivery of anchors to annulus 68 in order to anchor structure 435 to tissue of annulus 68.

In addition to providing tactile feedback, implant-leading device 434 may also facilitate positioning of the annuloplasty structure 435 by facilitating imaging (e.g., fluoroscopy) and mechanical guidance. For example, the presence of implant-leading device 434 and/or the shape thereof (e.g., bending due to being pressed against an atrial wall 122) is visible in fluoroscopic imaging, and can be used to facilitate identification of the position and angle of annuloplasty structure 435 with respect to tissues.

Reference is now made to FIGS. 3A-B and 26. It is to be noted that implant-leading device 434 can be coupled to a plurality of elements or filaments 99 and can be shaped in any suitable shape.

It is to be noted that although system 430 is shown on mitral valve 64, system 430 can be used on any cardiac valve, e.g., a tricuspid valve, or any other tissue of the subject.

Figure 27:
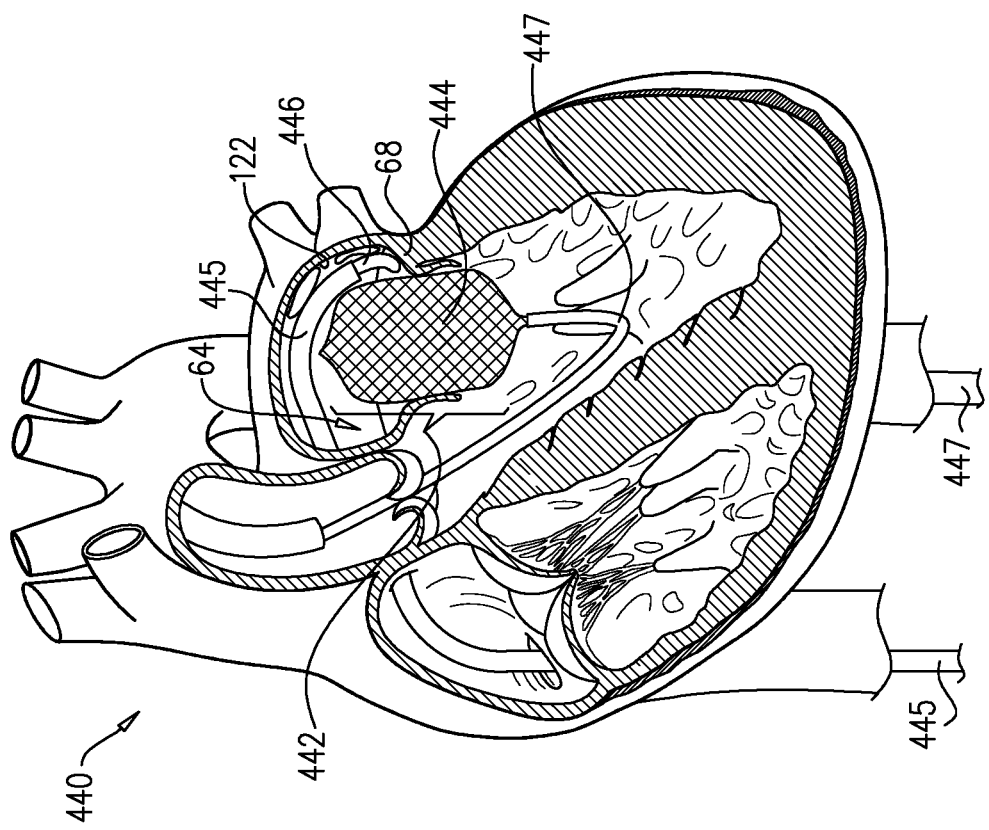

Reference is now made to FIG. 27, which is a schematic illustration of a system 440 comprising an annulus-marking device 442 that is positioned in the orifice of valve 64 in advance of an implant, e.g., an annuloplasty structure 446, in accordance with some applications. For some applications, annulus-marking device 442 leads and is placed in advance of the implant such that device 442 functions as an implant-leading device 444. Annulus-marking device 442 extends from within a delivery tool 447. For some applications, annulus-marking device 442 comprises a stent-like mesh, e.g., a fabric or metal mesh, that is positioned partially within the orifice of valve 64 and does not significantly interfere with function of valve 64. For some applications, annulus-marking device 442 comprises a tubular stent. As successive portions of annuloplasty structure 446 are extended from within its delivery tool 445 and are positioned along successive portions of annulus 68, annulus-marking device 442 guides the successive portions of structure 446 under imaging as annulus-marking device 442 comprises a radiopaque material (e.g., nitinol or stainless steel). For some applications, annulus-marking device 442 comprises a balloon made of nylon.

Annulus-marking device 442 provides an indication of a specific section of annulus 68 immediately preceding the placement of the successive portion of structure 446 along annulus 68. Annulus-marking device 442 is at least partly stiff, and provides resistance, which facilitates positioning of structure 446. Annulus-marking device 442 may also provide tactile feedback to the operating physician.

Annuloplasty structure 446 comprises a body portion which comprises a flexible material and has a longitudinal axis that runs along the length of the body portion (e.g., when the body portion is straightened). The body portion comprises radiopaque markings to aid in imaging for accurate delivery of anchors to annulus 68 in order to anchor structure 446 to tissue of annulus 68.

In addition to providing tactile feedback, annulus-marking device 442 may also facilitate positioning of the annuloplasty structure 446 by facilitating imaging (e.g., fluoroscopy) and mechanical guidance. For example, the presence of annulus-marking device 442 and/or the shape thereof (e.g., bending due to being pressed against an atrial wall) is visible in fluoroscopic imaging, and can be used to facilitate identification of the position and angle of annuloplasty structure 446 with respect to tissues. Additionally, annulus-marking device 442 ensures that tool 445 is positioned at an external perimeter of annulus-marking device 442 such that it is positioned between device 442 and atrial wall 122.

Annulus-marking device 442 can be removed by being pulled and constrained within tool 447 in order to be retrieved and removed from the body of the subject.

In some applications, as shown, annulus-marking device 442 is delivered toward valve 64 in a delivery tool 447 that is separate from delivery tool 445 used to deliver the implant. For some applications, annulus-marking device 442 and the implant may be delivered from the same delivery tool.

Reference is now made to FIGS. 3A-B and 27. It is to be noted that annulus-marking device 442 can be coupled to a plurality of elements or filaments 99 and can be shaped in any suitable shape.

It is to be noted that although system 440 is shown on mitral valve 64, system 440 can be used on any cardiac valve, e.g., a tricuspid valve, or any other tissue of the subject. It is to be further noted that although device 442 is shown as being delivered via the ventricle, device 442 may be delivered to the valve using any suitable delivery method into the atrium, e.g., transvascularly or using a minimally-invasive approach.

Reference is again made to FIGS. 21-27. It is to be noted that all implant-leading devices can be coupled to an electronic beeping gauge, e.g., a multimeter. For some applications, the implant-leading devices may be delivered to and removed from the valve using the same delivery tool as that which delivers the annuloplasty structure. For some applications, the implant-leading devices may be delivered to and removed from the valve using a separate delivery tool to the delivery tool that delivers the annuloplasty structure. For some applications, the implant-leading devices move responsively to movement of cardiac tissue such as tissue of annulus 68, tissue of atrial wall 122, and/or tissue of leaflets 123. Under imaging, such movement of the respective implant-leading devices responsively to movement of a given tissue, provides an indication as to the tissue types and an indication as to the layout of valve 64 in order to more efficiently facilitate implantation of the cardiac device.

Figure 28A:
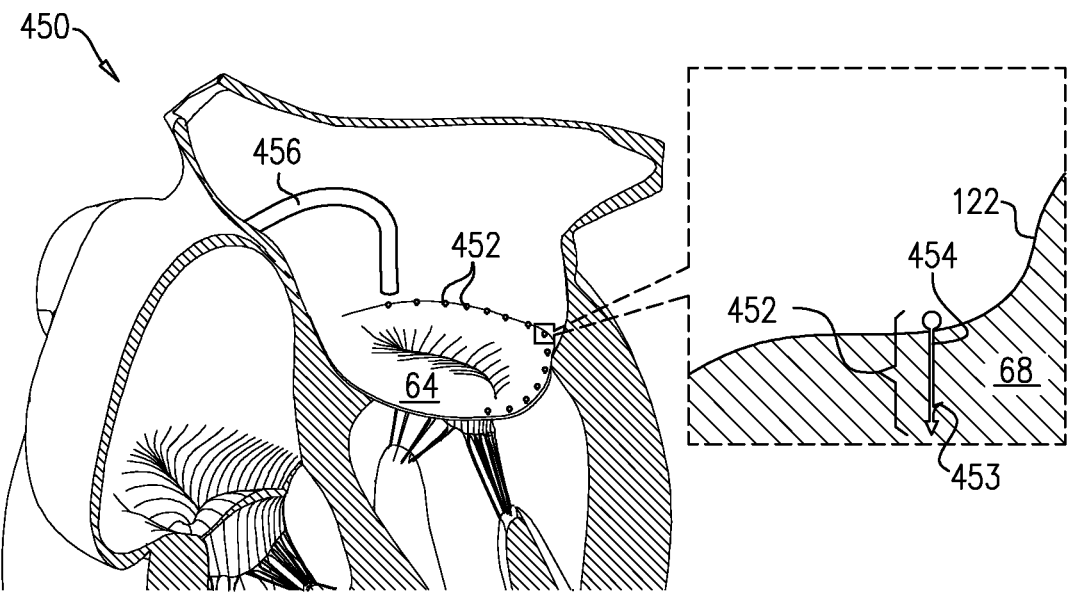
FIGS. 28A-B are schematic illustrations of an annulus marking device comprising a plurality of implantable radiopaque pins for aiding implantation of cardiac devices under the guidance of imaging, in accordance with some applications.
Figure 28B:
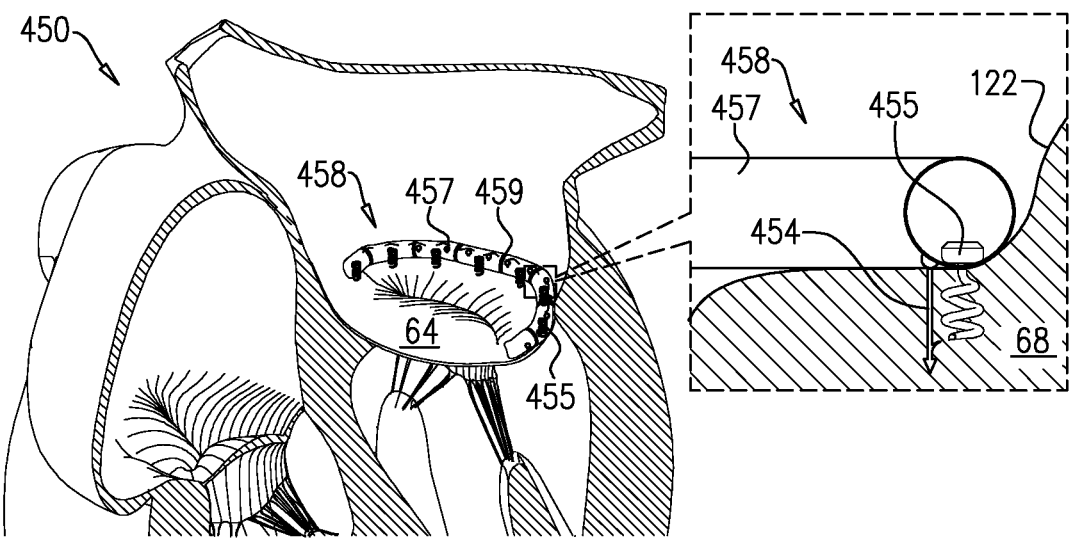

Reference is now made to FIGS. 28A-B, which are schematic illustrations of a system 450 comprising an annulus-marking device 452 comprising a plurality of radiopaque pins 454 which facilitate implantation of an implant, e.g., an annuloplasty structure 458, in accordance with some applications. Pins 454 comprise flexible, radiopaque material, e.g., nitinol or stainless steel. Each pin 454 comprises a respective barb 453 in order to ensure pin 454 remains within tissue of annulus 68. Each one of the plurality of pins has a longest width of 0.5-3.0 mm. It is to be noted that pins 454 function as indicator pins and the function of barb 453 is to anchor only themselves to tissue. Pins 454 do not function to anchor any device to tissue except for themselves; therefore, pins 454 function only as radiopaque indicator pins.

Pins 454 are implanted using a delivery system 456 which operates under imaging, e.g., echocardiography or fluoroscopy, and using tactile feedback in order to deploy a plurality of pins 454 along annulus 68. For some applications, as shown, a proximal portion of each pin 454 is exposed from tissue of annulus. For some applications, pins 454 are deployed fully within tissue of annulus 68.

Once the plurality of pins 454 have been deployed, a map is generated under imaging. For some applications, a map is not generated, but rather, pins 454 function as markers real-time during placement of the implant along annulus 68. In either embodiment, pins 454 facilitate imaging of valve 64. For some applications, pins 454 facilitate imaging of the heart valve annulus by facilitating imaging of movement of the plurality of pins responsively to movement of the annulus.

It is to be noted that although system 450 is shown on mitral valve 64, system 450 can be used on any cardiac valve, e.g., a tricuspid valve, or any other tissue of the subject.

FIG. 28B shows implantation of annuloplasty structure 458 at annulus 68. Structure 458 comprises a body portion 457 which comprises a flexible material and has a longitudinal axis that runs along the length of body portion 457 (e.g., when the body portion is straightened). Body portion 457 comprises radiopaque markings 459 to aid in imaging for accurate delivery of anchors to annulus 68 in order to anchor structure 458 to tissue of annulus 68. A plurality of tissue anchors 455 are deployed in order to fasten and anchor structure 458 to tissue of annulus 68. Pins 454 do not interfere with placement of structure 458 and/or with deploying of anchors 455. For some applications, each anchor 455 is deployed in a vicinity of pin 454 and between markings 459 of structure 458. For some applications, a larger number of tissue anchors 455 are deployed than the number of pins 454 deployed in annulus 68.

Once structure 458 is implanted at annulus 68, pins 454 remain within tissue of annulus 68.

Figure 29:
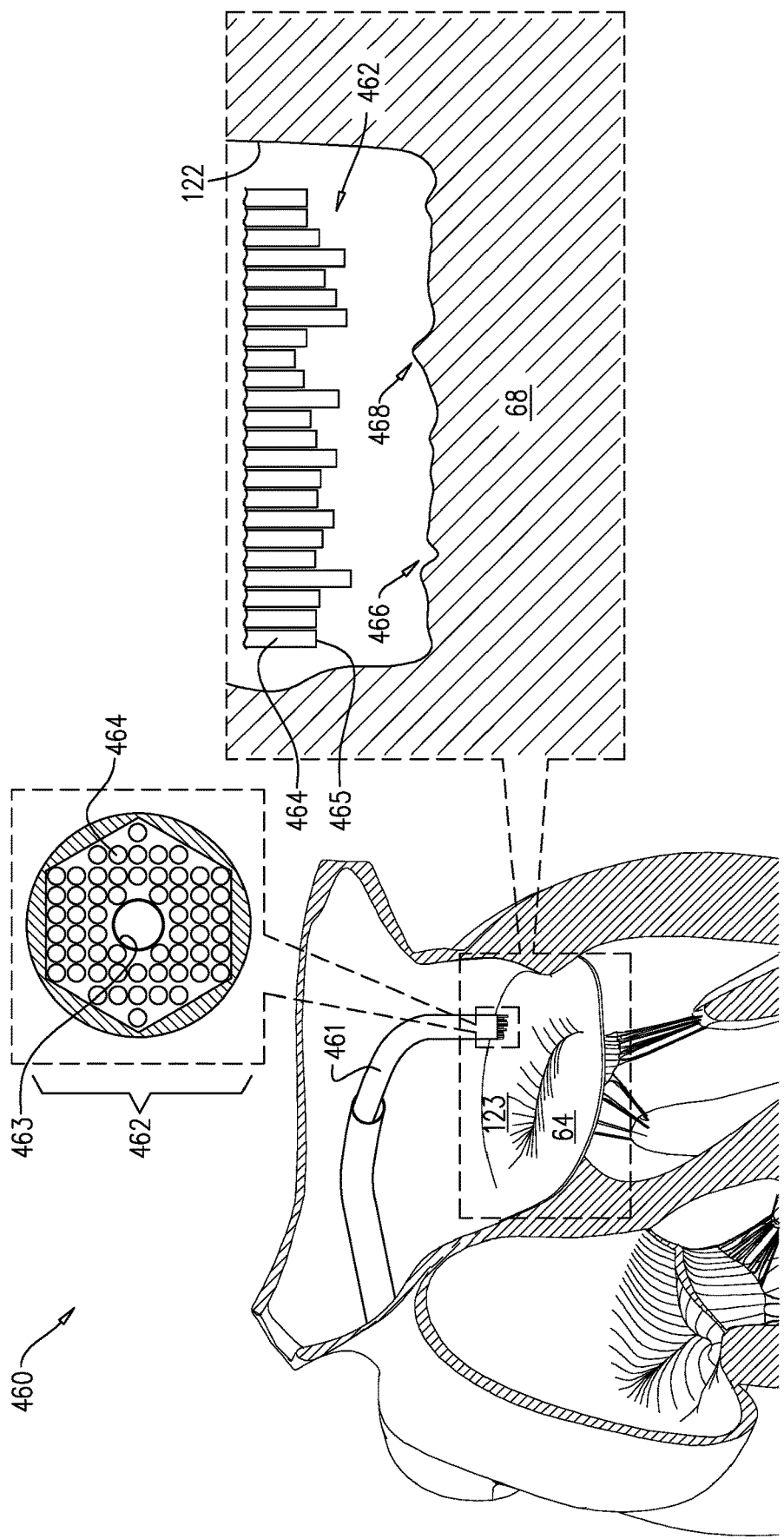
FIG. 29 is a schematic illustration of an annulus-marking device comprising a plurality of radiopaque pins which move proximally and distally for aiding implantation of cardiac devices under the guidance of imaging, in accordance with some applications.

Reference is now made to FIG. 29, which is a schematic illustration of a system 460 for facilitating imaging of annulus 68 of heart valve 64 using an annulus-marking device 462 comprising a plurality of radiopaque pins 464, in accordance with some applications. Pins 464 are disposed within a distal end of a catheter 461 and move proximally in response to a force applied thereto. Pins 464 move distally once that force is removed. If no force is applied to pins 464, they remain static. Pins 464 comprise a radiopaque material that is visible under imaging, e.g., fluoroscopy. Pins 464 move proximally and distally in response to variations in the topography of the tissue of annulus 68.

The movement of pins 464 indicated valleys 466 and peaks 468 in tissue of annulus 68. That is, each pin 464 has a distal end 465 that pushes against tissue of annulus 68. In response, tissue of annulus 68 applied a force to pins 464. For some applications, an image of annulus 68 is generated, and based on that image, an implant, e.g., an annuloplasty structure, is implanted using the image pins 464 generated as a guide. For some applications, the implant is implanted during movement of pins 464 along annulus 68. For some applications, the implant is implanted only once pins 464 have moved fully around annulus 68 and have generated a map of the topography of valve 64. In either embodiment, the implant is implanted under the guidance of imaging.

For some applications, the implant is delivered using the same catheter 461 that delivers pins 464 to annulus 68. That is, as shown, there is a central lumen 463 within catheter 461 between the plurality of radiopaque pins 464.

For some applications, pins 464 move proximally in response to movement of pins 464 against hard tissue of annulus 68 and remain static when pins 464 move around softer tissue such as tissue of atrial wall 122 and tissue of leaflets 123.

Pins 464 and catheter 461 are retrieved and removed from the body of the subject following the imaging. For some applications, pins 464 are retrieved subsequently to implantation of the implant. For example, for embodiments in which the implant is implanted while pins 464 move around annulus 68, pins 464 are removed only subsequently to implantation of the implant. For some applications, pins 464 are retrieved prior to implantation of the implant. For example, for some embodiments, an image and/or map of the topography of valve 64 is generated in advance of implantation, and the implant is implanted using the map as a guide.

For some applications, the position of pins 464 and/or the contact of each pin 464 with tissue of annulus 68 is detected electronically, e.g., from an extracorporeal location. For example, each pin 464 comprises an electronic position detector, e.g., a piezoelectric sensor.

It is to be noted that although system 460 is shown on mitral valve 64, system 460 can be used on any cardiac valve, e.g., a tricuspid valve, or any other tissue of the subject.

Figure 30:
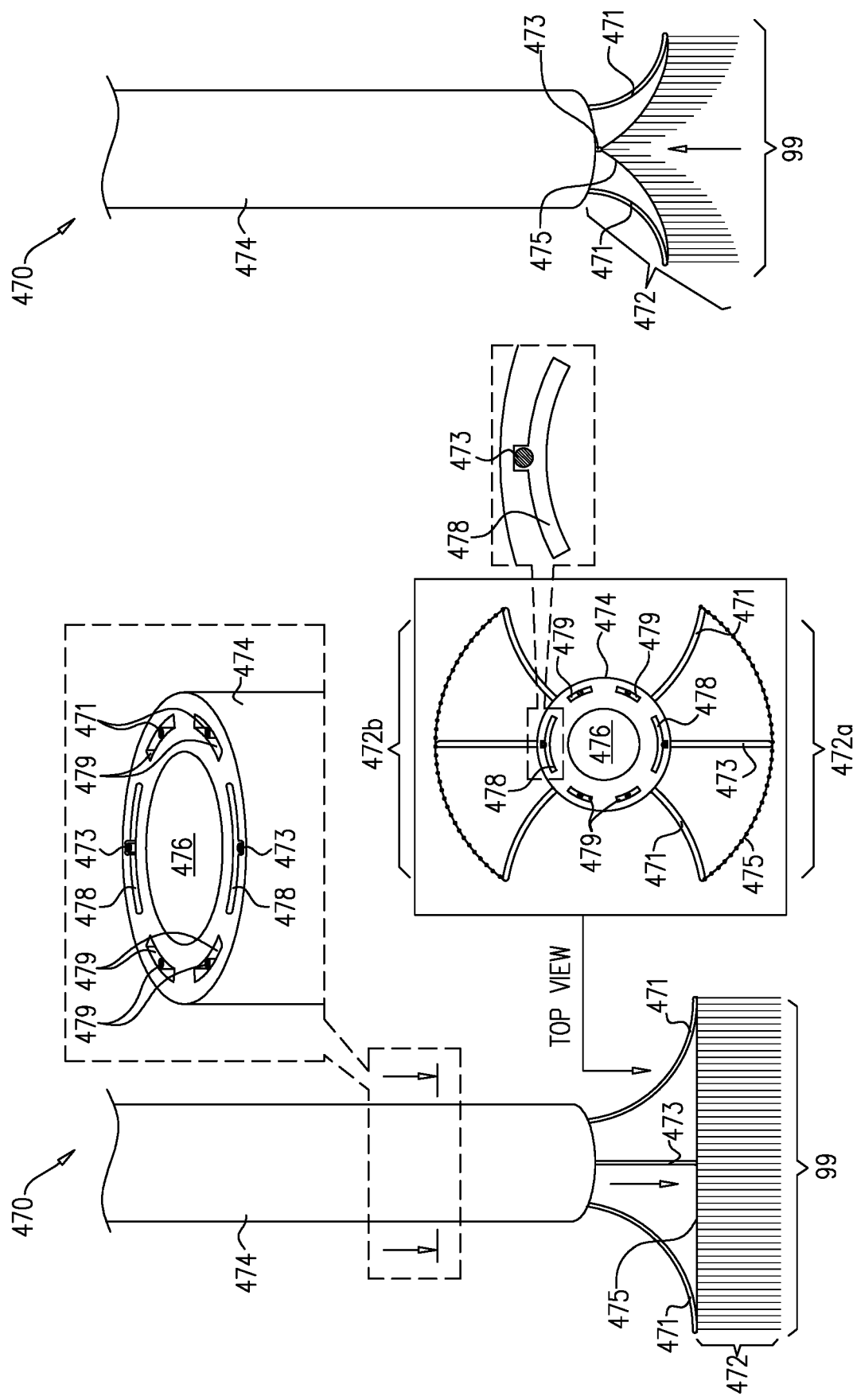
FIGS. 30A-B and 31 are schematic illustrations of respective annulus marking devices each comprising a plurality of radiopaque filaments deliverable through a multilumen tube and aid implantation of cardiac devices under the guidance of imaging, in accordance with some applications.

Reference is now made to FIGS. 30A-B, which are schematic illustrations of a system 470 for facilitating imaging of cardiac tissue using at least one annulus-marking device 472 comprising a distal frame wire 475 and a plurality of radiopaque elements, such as radiopaque filaments 99 or other radiopaque markers, radiopaque wires, radiopaque extension, etc. System 470 comprises a multilumen tube 474 from which annulus-marking device 472 expands. FIG. 30A shows annulus-marking device 472 in an expanded state and exposed from within tube 474. In the expanded state of device 472, distal frame wire 475 assumes an expanded shape in which it assumes a generally linear configuration. The plurality of radiopaque elements or filaments 99 coupled to the distal frame wire 475 comprise radiopaque material and project away from distal frame wire 475 in the expanded state of annulus-marking device 472.

For some applications, elements or filaments 99 sway with movement of the blood. For some applications, elements or filaments 99 press against tissue of the annulus and tissue coupled thereto, such as tissue of an atrial wall as well as tissue of the leaflets of the native valve. Elements or filaments 99 thus provide enhanced imaging of tissue of the valve. For example, in some implementations, when filaments 99 appear bent or pressed, this imaging detects annulus tissue, while when filaments 99 are straight, this could indicate the orifice of the valve.

For each annulus-marking device 472, at least one central rod 473 is coupled to a middle portion of distal frame wire 475 and disposed primarily and slidable within a primary sublumen 478, or a collecting lumen, of multilumen tube 474. Central rod 473 is configured to constrain distal frame wire 475 and the plurality of radiopaque filaments 99 from the expanded state of the annulus-marking device 472 (shown in FIG. 30A) and pull distal frame wire 475 and the plurality of radiopaque elements or filaments 99 within primary sublumen 478 of multilumen tube 474 during constraining of annulus-marking device 472 (shown in FIG. 30B).

For each annulus-marking device 472, at least two peripheral wires 471 are coupled to distal frame wire 475 at opposite end portions thereof. Peripheral wires 471 are disposed primarily and slidable within respective secondary sublumens 479 of multilumen tube 474. Peripheral wires 471 are configured to stabilize distal frame wire 475 in the expanded state of annulus-marking device 472 by applying a downward pushing force to the ends of distal frame wire 475 in order to ensure that wire 475 assumes the generally linear state and is in a tense state.

Annulus-marking device 472 is compressible during delivery toward the native heart valve, and expandable from a compressed state for positioning along the native heart valve annulus. Annulus-marking device 472 guides implantation of an implant, e.g., an annuloplasty structure, by providing a guide for implantation of the implant along the annulus during implantation since the plurality of elements or filaments 99 are positioned along the annulus and are radiopaque and visible under imaging, e.g., fluoroscopy. The implant can be delivered through a central lumen 476 of multilumen tube 474. Once the implant has been implanted along the annulus, annulus-marking device 472 is retrieved as is described hereinbelow with reference to FIG. 30B.

As shown in FIG. 30A, for some applications, system 470 comprises first and second annulus-marking devices 472a and 472b. Each device 472 has a respective central rod 473 as well as respective peripheral wires 471. For embodiments in which system 470 comprises first and second annulus-marking device 472a and 472b, tube 474 has (a) first and second primary sublumens 478 for sliding therethrough of respective first and second central rods 473, and (b) four secondary sublumens 479 for sliding therethrough of a respective wire of four peripheral wires 471.

For some applications, system 470 independently controls each one of first and second annulus-marking devices 472a and 472b. That is each one of first and second annulus-marking devices 472a and 472b may be expanded from within tube 474 or constrained within tube 474, independently.

Each primary sublumen 478 is typically larger than each secondary sublumen 479 since distal frame wire 475 and the plurality of elements or filaments 99 are pulled through primary sublumen 478 as is described hereinbelow.

It is to be noted that elements or filaments 99, distal frame wire 475, central rod 473, and peripheral wires 471 are radiopaque and comprise flexible material, e.g., nitinol or stainless steel. For some applications, distal frame wire 475 is instead a textile strip.

FIG. 30B shows retrieval of annulus-marking device 472 into primary sublumen 478. Central rod 473 is pulled proximally such that the center of distal frame wire 475 is pulled toward primary sublumen 478. Peripheral wires 471 are released and slide distally within their respective secondary sublumens 479. Peripheral wires 471 trail behind distal frame wire 475 as wire 475 and radiopaque elements or filaments 99 are pulled proximally into sublumen 478. Ultimately, distal frame wire 475 and the plurality of elements or filaments are collected into primary sublumen 478, or the collecting lumen.

It is to be noted that system 470 can be used on any cardiac valve, e.g., a tricuspid valve, or any other tissue of the subject.

Figure 31:
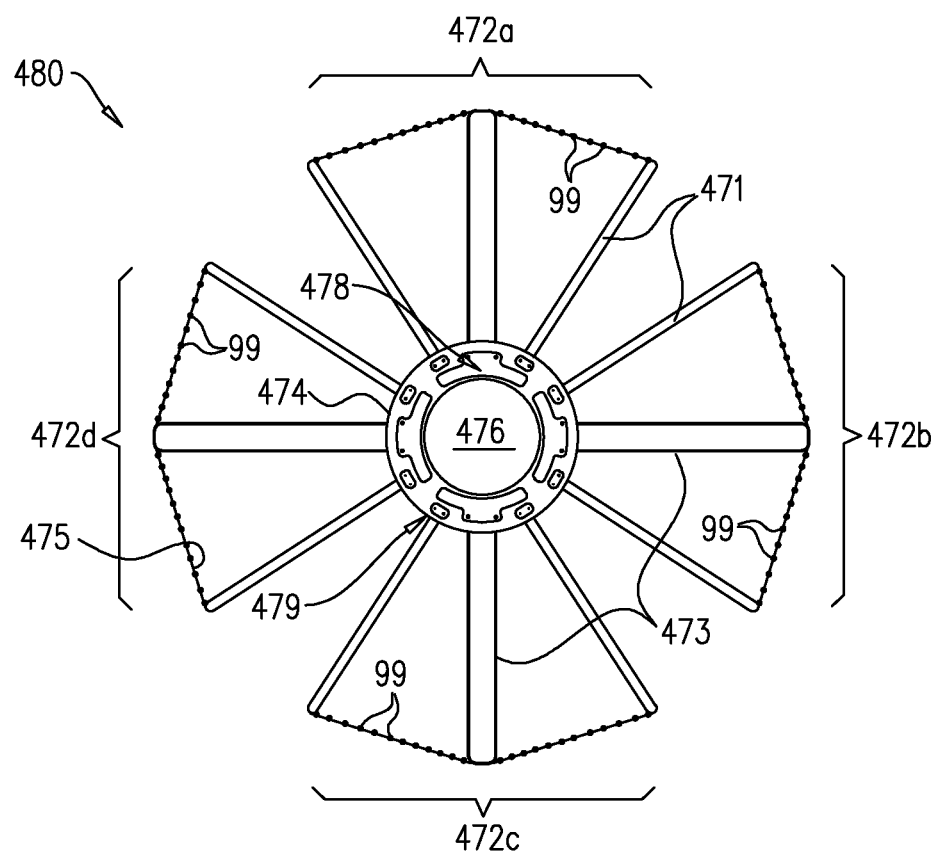

Reference is now made to FIG. 31, which is a schematic illustration of a system 480, for facilitating imaging of cardiac tissue using first, second, third, and fourth annulus-marking devices 472a, 472b, 472c, and 472d, in accordance with some applications. It is to be noted that system 480 is similar to system 470 described hereinabove with reference to FIGS. 30A-B with the exception that system 480 comprises a larger number of annulus-marking devices 472 than system 470, and like reference numbers refer to like parts. Each device 472 has a respective central rod 473 as well as respective peripheral wires 471. For embodiments in which system 480 comprises first, second, third, and fourth annulus-marking devices 472a, 472b, 472c, and 472d, tube 474 has (a) first, second, third, and fourth primary sublumens 478 for sliding therethrough of respective first, second, third, and fourth central rods 473, and (b) eight secondary sublumens 479 for sliding therethrough of a respective wire of eight peripheral wires 471.

Preferably, system 480 independently controls each one of first, second, third, and fourth annulus-marking devices 472a, 472b, 472c, and 472d. That is each one of first, second, third, and fourth annulus-marking devices 472a, 472b, 472c, and 472d may be expanded from within tube 474 or constrained within tube 474, independently.

It is to be noted that system 480 can be used on any cardiac valve, e.g., a tricuspid valve, or any other tissue of the subject.

Reference is now made to FIGS. 30A-B and 31. In some applications, once each one of annulus-marking device 472 has been positioned along the annulus, the implant is implanted over the filaments 99. When filaments 99 are configured to be very thin, they avoid interfering with and entangling with the implant and slide from underneath the implanted implant during retrieval of annulus-marking device 472 from the body of the subject. It is to be further noted that any one and any number of annulus-marking devices 472 may be expanded from within tube 474 at a given time and they can be retrieved and expanded any number of times during a single procedure.

Figure 32:
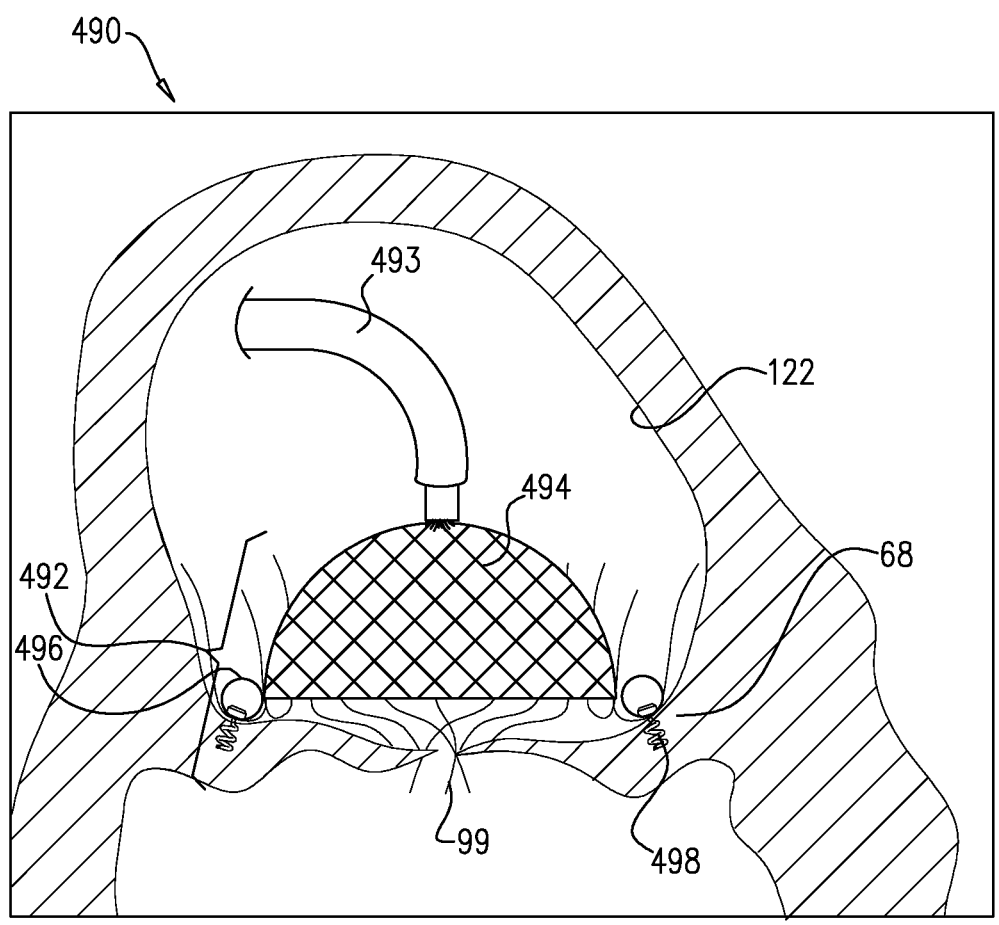
FIG. 32 is a schematic illustration of an annulus-marking devices comprising expandable elements for aiding implantation of cardiac devices under the guidance of imaging, in accordance with some applications.

Reference is now made to FIG. 32, which is schematic illustration of a system 490 comprising an annulus-marking device 492 comprising a plurality of expandable elements 494, e.g., stent struts, which form device 492 into a generally semi-spherical, or partially spherical shape for facilitating imaging of cardiac tissue during implantation of a cardiac implant, in accordance with some applications. Device 492 comprises a flexible, radiopaque material, e.g., nitinol or stainless steel, which facilitates collapsing and expanding of device 492. For some applications, the plurality of expandable elements 494 form device 492 into a partially-bulbous shape.

As shown, device 492 aids in imaging implantation of a cardiac implant, e.g., an annuloplasty structure 496, as shown. Structure 496 comprises a body portion which comprises a flexible material and has a longitudinal axis that runs along the length of the body portion (e.g., when the body portion is straightened). The body portion comprises radiopaque markings to aid in imaging for accurate delivery of anchors 498 to annulus 68 in order to anchor structure 496 to tissue of annulus 68.

Annulus-marking device 492 is delivered using a delivery tool 493 which is configured to deliver device 492 to the left atrium in a compressed state. Device 492 is configured to be expanded from its compressed state once deployed from within a lumen of tool 493. Annulus-marking device 492 is retrievable upon removal of delivery tool 493 from the subject. That is, device 492 is constrained within the lumen of tool 493 once the cardiac implant has been implanted at annulus 68. Device 492 may be delivered percutaneously, thoracoscopically through the chest, or using open heart surgical techniques. If delivered percutaneously, device 492 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 492 comprises a wire.

Once inside the atrium, the plurality of expandable elements 494 expand radially within the atrium such that the plurality of expandable elements 494 provides an indication as to a location of the native heart valve annulus 68 of native heart valve 64. For some applications, the plurality of expandable elements 494 comprise a shape-memory material that enables expandable elements 494 to expand to a given shape within the heart. It is to be noted that although device 492 is being used in the left atrium, device 492 may be used in the right atrium, the left ventricle, and the right ventricle. That is, for some applications, a distal end of device 492 enters and is positioned within the ventricle.

The plurality of expandable elements 494 collectively form annulus-marking device 492 into a generally umbrella shape.

The plurality of expandable elements 494 comprise a very flexible material and design that allows elements 494 to assume the shape of the cavity that they are opened in, e.g., the left atrium, as shown.

Annulus-marking device 492 is coupled to a plurality of radiopaque elements, such as radiopaque filaments 99 or other radiopaque markers, wires, extensions, etc. For some applications, annulus-marking device 492 and radiopaque elements or filaments 99 are imaged with respect to the tissue of the native heart valve annulus 68 and the tissue coupled thereto by viewing the plurality of expandable elements 494 and elements or filaments 99 against the tissue. For some applications, annulus-marking device 492 is imaged with respect to the tissue of the native heart valve annulus 68 and the tissue coupled thereto by viewing movement of the plurality of expandable elements 494 and of elements or filaments 99 responsively to movement of the tissue. For either application, annulus-marking device 492 and elements or filaments 99 are imaged with respect to the tissue of the native heart valve annulus 68, tissue of at least one leaflet, and tissue of an atrial wall 122.

As shown, the distal end of device 492 is positioned within the atrium. That is, the distal end remains at the atrial surface of annulus 68.

For some applications, the distal ends of device 492 is pushed into the ventricle. In such applications, the plurality of expandable elements 494 are each made to bend at a middle section thereof collectively forming a bent section, and it is at this bent section that the operating physician determines using imaging that this is the location of the annulus.

Annulus 68 is then imaged using fluoroscopy. For some applications, annulus-marking device 492 is imaged with respect to the tissue of the native heart valve annulus 68 and the tissue coupled thereto by viewing the plurality of expandable elements 494 against the tissue. For some applications, annulus-marking device 492 is imaged with respect to the tissue of the native heart valve annulus 68 and the tissue coupled thereto by viewing movement of the plurality of expandable elements 494 responsively to movement of the tissue. For either application, annulus-marking device 492 is imaged with respect to the tissue of the native heart valve annulus 68, tissue of at least one leaflet, and tissue of an atrial wall 122.

Structure 496 is delivered subsequently to placement of the plurality of expandable elements 494. It is to be noted that for some applications, structure 496 is delivered together with annulus-marking device 492. Annuloplasty structure 496 is implanted under the guidance of fluoroscopy using annulus-marking device 492 as a guide. Annuloplasty structure 496 is positioned between annulus-marking device 492 and atrial wall 122. A respective anchor 498 is deployed to anchor structure 496 at a site along annulus 68 that is marked between the radiopaque markings of structure 496.

Anchors 498 are delivered while some elements or filaments 99 may be underneath structure 496.

Subsequently to implanting of structure 496, annulus-marking device 492 is retrieved. Since device 492 is flexible and compressible, device 492 is constrained within a tool during the retrieval of device 492 and subsequent removal of device 492 from the body of the subject. That is, device 492 does not function as an implant for such embodiments and is used only to guide implantation of annuloplasty structure 496 (i.e., the implant); rather, device 492 acts as a guide for implantation while placed temporarily within the body of the patient to be subsequently removed therefrom following the implantation of annuloplasty structure 496. Annulus-marking device 492 is constrained within tool 493. Annulus-marking device 492 is retrieved and removed from the body of the subject. In some embodiments, filaments 99 are soft and flexible, such that they trail behind elements 494 in a manner in which filaments 99 slide from under annuloplasty structure 496 implanted along annulus 68.

It is to be noted that although system 490 is shown on mitral valve 64, system 490 can be used on any cardiac valve, e.g., a tricuspid valve, or any other tissue of the subject.

Reference is now made to FIGS. 33A-B, which are schematic illustrations of a system 500 comprising an annulus-marking device 502 comprising a plurality of inflatable fingers 504, which form device 502 into a glove shape, for facilitating imaging of cardiac tissue during implantation of a cardiac implant, in accordance with some applications. Device 502 comprises a flexible, radiopaque material, e.g., nitinol or stainless steel, which facilitates folding, inflating, and deflating of device 502. For some applications, device 502 is octopus-shaped. For some applications, device 502 comprises 4-10 fingers 504, e.g., 8 fingers 504. For some applications of the present invention device 502 comprises nylon. For some applications of the present invention device 502 comprises a noncompliant balloon.

For some applications, device 502 itself is radiopaque. For some applications, device 502 is inflated with radiopaque fluid.

Device 502 is delivered using a delivery tool 506. For some applications, device 502 surrounds a distal portion of tool 506. Tool 506 is shaped to define a lumen through which a cardiac implant, e.g., an annuloplasty structure 507, is delivered, as shown in FIG. 33B. That is, the implant is implanted while annulus-marking device 502 guides implantation thereof and ensures that the implant is implanted at the correct location of annulus 68 of valve 64. Since device 502 is radiopaque, implantation of the implant can be guided under fluoroscopy only, e.g., using two angles.

For some applications, during delivery of device 502, device 502 is in a deflated state and folded into a compressed state within an external catheter 508. Once inside the atrium, catheter 508 is retracted and device 502 is exposed and inflated, e.g., with saline and or with a radiopaque fluid, to assume an inflated and expanded state. For some applications, tool 506 comprises an inflation lumen for delivering fluid to device 502. Tool 506 is then advanced toward annulus 68 and using tactile feedback, device 502 is pressed against annulus 68, as shown in FIG. 33B. Under fluoroscopy, device 502 is imaged in order to determine whether tool 506 is appropriately positioned along annulus 68. That is, if the physician sees that a number of fingers 504 of device 502 are bent, the physician determines that tool 506 is in the right place along annulus 68, e.g., on annulus 68, against atrial wall 122, and/or at the hinge. If the physician detects movement of any number of fingers 504, the physician determines that tool 506 is positioned at least partially along leaflet 123 of valve 64.

If the physician detects some fingers 504 bent and some straight and moving, the physician can determine that tool is positioned partially on the annulus and partially on the leaflet.

For some applications, the physician compares an overall configuration of device 502 and its fingers 504 to an ideal configuration of device 502 which is indicative of correct positioning of tool 506 at annulus 68 in order to facilitate proper positioning of the implant along annulus 68. The physician can determine proximity of tool 506 to atrial wall 122. For some applications, device 502 is used to measure the height of annulus 68 by viewing the shape and/or movement of the fingers 504 when device 502 is placed against tissue of the annulus.

It is to be noted that inflation and deflation can occur multiple times during a single procedure.

It is to be noted that although system 500 is shown on mitral valve 64, system 500 can be used on any cardiac valve, e.g., a tricuspid valve, or any other tissue of the subject.

Figure 34A:
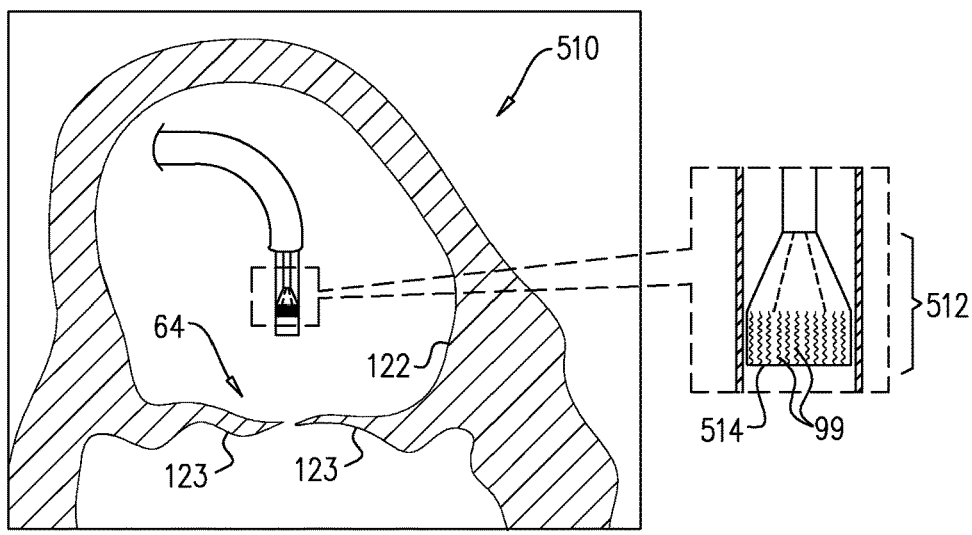
FIGS. 34A-C are schematic illustrations of annulus-marking devices comprising concentric wire loops for aiding implantation of cardiac devices under the guidance of imaging, in accordance with some applications.
Figure 34B:
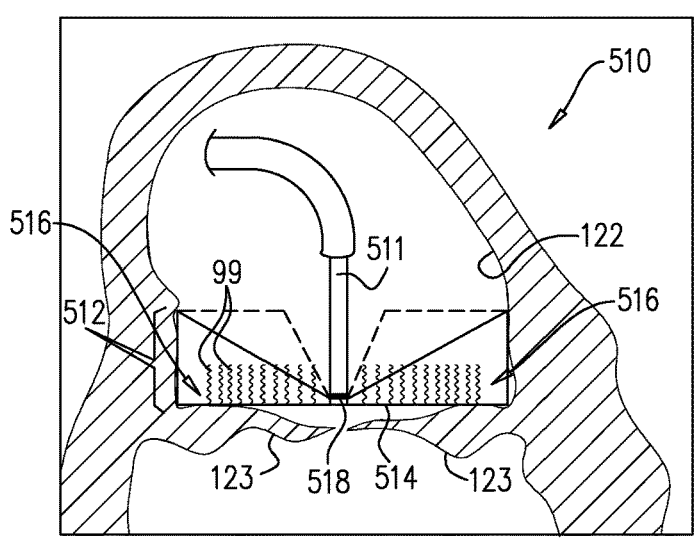
Figure 34C:
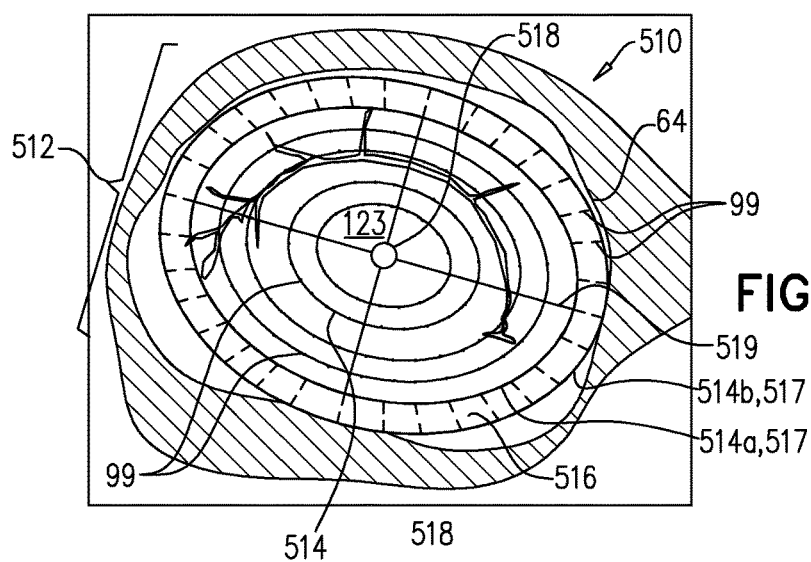

Reference is now made to FIGS. 34A-C, which are schematic illustrations of a system 510 comprising an annulus-marking device 512 comprising a radiopaque material shaped to define a plurality of concentric wire loops 514 connected by a scaffolding 519 and a wire loop frame 517 coupled to scaffolding 519 and concentric with respect to the plurality of concentric wire loops 514, in accordance with some applications. Wire loop frame 517 is configured for placement along at least a part of a circumference of annulus 68 of native heart valve 64, while the plurality of concentric wire loops 514 span the orifice of valve 64, e.g., above leaflets 123 at the atrial surface of valve 64. Annulus-marking device 512 is compressible to a compressed state during delivery toward valve 64, and expandable from a compressed state for positioning in valve 64, to an expanded state.

Frame 517 comprises the outer-most wire loops 514a and 514b. Frame 517 defines a space 516 for implanting an implant, e.g., an annuloplasty structure, along annulus 68 using annulus-marking device 512 as a guide for implantation of the implant along annulus 68 and within a space defined by frame 517, under imaging, e.g., fluoroscopy.

Annulus-marking device 512 comprises a flexible radiopaque material, e.g., nitinol or stainless steel.

Device 512 is deployed from within a delivery tool and is expanded either due to the shape-memory property of device 512 and/or using a pushing tool 511 which pushes distally on a locking ring 518 that is disposed in a center of the plurality of concentric wire loops 514 and acts via struts on wire loops 514 and/or scaffolding 519 and/or loop frame 517. Locking ring 518 helps transition device 512 from the compressed state to the expanded state by pushing distally ring 518. Pushing on locking ring 518 also locks in place the configuration of device 512. Locking ring 518 also helps transition device 512 from the expanded state to the compressed state by pulling proximally ring 518.

As shown in FIG. 34B, device 512 is expanded radially until it pushes against atrial wall 122.

As shown in FIG. 34C, device 512 is placed such that the plurality of concentric wire loops 514 are at the orifice of valve 64, wire loop frame 517 is disposed along at least a part of a circumference of annulus 68.

Once device 512 is positioned, annulus 68 is viewed under imaging annulus-marking device 512 with respect to the tissue of annulus 68 and the tissue coupled thereto by viewing annulus-marking device 512 against the tissue. For some applications, movement of annulus-marking device 512 responsively to movement of the tissue is viewed.

Annulus-marking device comprises a plurality of radiopaque elements or radiopaque filaments 99 coupled to loops 514. Under fluoroscopy, the physician is able to determine where leaflets are due to undulations of filaments 99 responsively to movement of leaflets and/or blood flowing through valve 64. For some applications, if the physician sees that some filaments 99 are not moving, the physician can determine that that portion of device 512 is positioned at annulus 68.

Once the implant is implanted along the annulus, device 512 is retrieved. During retrieval, frame 517 slides around the implant while the radiopaque filaments 99 coupled to loops 514a and 514b slide from under the implant. Device 512 is constrained within the tool and extracted from the subject. Device 512 is transitioned from the expanded state to the compressed state by pulling proximally on locking ring 518.

Since device 512 has a low profile, it does not interfere significantly with blood flow.

Subsequently to the implanting of the implant, annulus-marking device 512 is retrieved. Since device 512 is flexible and compressible, device 512 is constrained within a tool during the retrieval of device 512 and subsequent removal of device 512 from the body of the subject. That is, device 512 does not function as an implant for such embodiments and is used only to guide implantation of the implant; rather, device 512 acts as a guide for implantation while placed temporarily within the body of the patient to be subsequently removed therefrom following the implantation the implant.

It is to be noted that although system 510 is shown on mitral valve 64, system 510 can be used on any cardiac valve, e.g., a tricuspid valve, or any other tissue of the subject.

Figure 35:
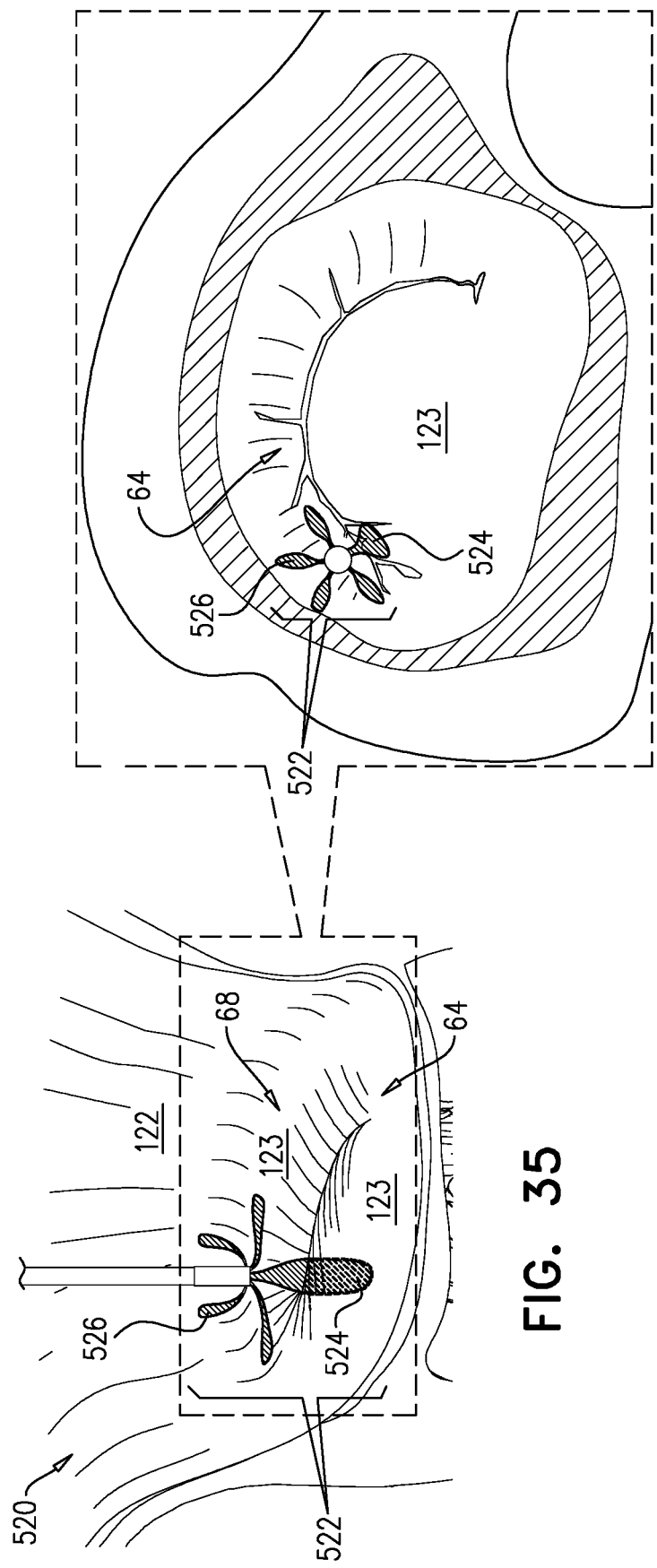
FIG. 35 is a schematic illustration of annulus-marking devices comprising a plurality of petals for aiding implantation of cardiac devices under the guidance of imaging, in accordance with some applications.

Reference is now made to FIG. 35, which is a schematic illustration of a system 520 comprising an annulus-marking device 522 comprising a plurality of inflatable petals 526, which form device 522 into a flower shape, for facilitating imaging of cardiac tissue during implantation of a cardiac implant, in accordance with some applications. Device 522 comprises a flexible, radiopaque material, e.g., nitinol or stainless steel, which facilitates expanding and compressing of device 522. For some applications, device 522 comprises 4-10 petals 526, e.g., 5 petals 526. For some applications, device 522 itself is radiopaque. For some applications, petals 526 are not inflatable.

A largest petal 524 of the plurality of petals 526 is configured for placement in between leaflets 123 of valve 64, e.g., at the commissure, as shown by way of illustration and not limitation.

Device 522 is delivered using a delivery tool. For some applications, device 522 surrounds a distal portion of the tool. For some applications, the tool is shaped to define a lumen through which a cardiac implant, e.g., an annuloplasty structure, is delivered. That is, the implant is implanted while annulus-marking device 522 guides implantation thereof and ensures that the implant is implanted at the correct location of annulus 68 of valve 64. Since device 522 is radiopaque, implantation of the implant can be guided under fluoroscopy only, e.g., using two angles.

For some applications, during delivery of device 522, device 522 is in a compressed state within an external catheter. Once inside the atrium, the external catheter is retracted and device 522 is allowed to expand to assume a shape because of its shape-memory material. The tool is then advanced toward annulus 68 and using tactile feedback, device 522 is pressed against annulus 68. Under fluoroscopy, device 522 is imaged in order to determine whether the tool is appropriately positioned along annulus 68. That is, if the physician sees that a number of petals 526 of device 522 are bent, the physician determines that the tool is in the right place along annulus 68, e.g., on annulus 68, against atrial wall 122, and/or at the hinge. If the physician detects movement of any number of petals 526, the physician determines that the tool is positioned at least partially along leaflet 123 of valve 64.

If the physician detects some petals 526 bent and some straight and moving, the physician can determine that tool is positioned partially on the annulus and partially on the leaflet.

For some applications, the physician compares an overall configuration of device 522 and its petals 526 to an ideal configuration of device 522 which is indicative of correct positioning of the tool at annulus 68 in order to facilitate proper positioning of the implant along annulus 68. The physician can determine proximity of the tool to atrial wall 122. For some applications, device 522 is used to measure the height of annulus 68 in a manner described above.

It is to be noted that although system 520 is shown on mitral valve 64, system 520 can be used on any cardiac valve, e.g., a tricuspid valve, or any other tissue of the subject.

Figure 36:
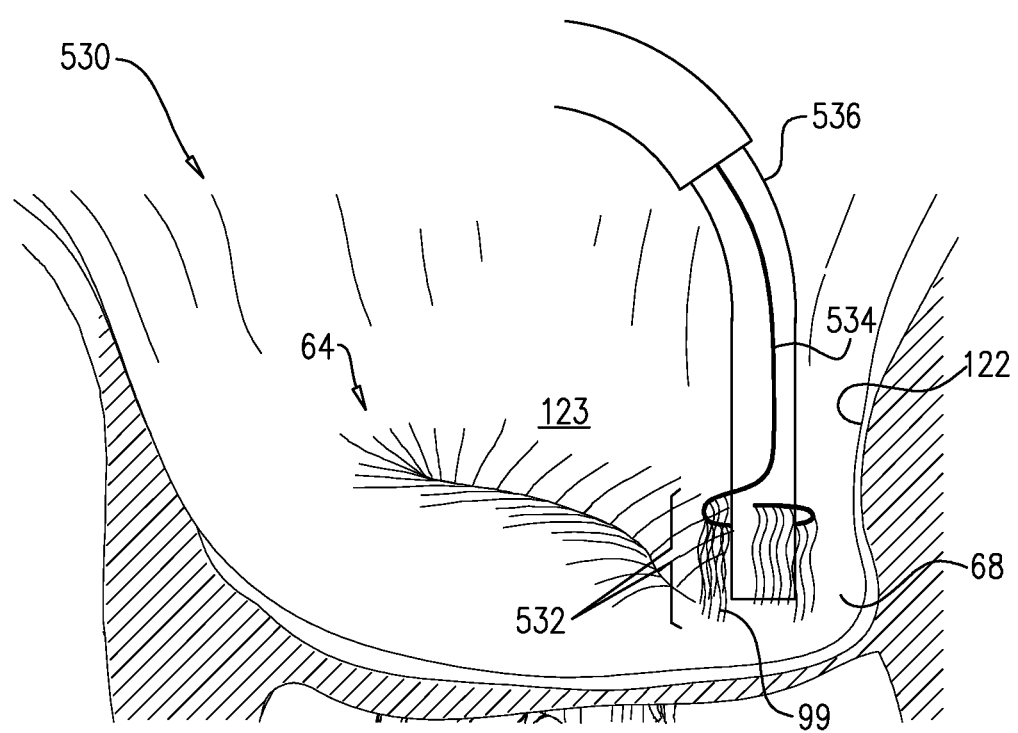
FIG. 36 is a schematic illustration of an annulus-marking device comprising a plurality of radiopaque filaments coupled to a distal end portion of a guidewire, in accordance with some applications.

Reference is now made to FIG. 36, which is a schematic illustration of a system, 530 comprising a guidewire 534 having a distal end portion that is coupled to an annulus-marking device 532 comprising a plurality of radiopaque elements, such as radiopaque filaments 99, in accordance with some applications. In some embodiments, guidewire 534 and filaments 99 comprise a flexible, radiopaque material, e.g., nitinol or stainless steel. The distal end portion of guidewire 534 has shape-memory and is configured to assume a curved or helical shape, as shown. The distal end portion of guidewire 534 may surround a delivery tube 536. Delivery tube 536 is configured to facilitate delivery and implantation of a cardiac implant, e.g., an annuloplasty structure. That is, under imaging, the plurality of filaments 99 are imaged as a concentrated fluoroscopic unit around tube 536 such that the appropriate position of tube 536 can be determined. Additionally, filaments 99 of device 532 guide implantation of the implant by facilitating guiding of tube 536 along annulus 68 under imaging. It is to be noted that the scope of the present invention includes the use of guidewire 534 and device 532 independently of tube 536.

For some applications, device 532 comprises a large number of filaments 99 such that a relatively concentrated fluoroscopic image is achieved in a given region under imaging.

For some applications, annulus-marking device 532 is imaged with respect to the tissue of the native heart valve annulus 68 and the tissue coupled thereto by viewing movement of the plurality of filaments 99 responsively to movement of the tissue. For either application, annulus-marking device 532 is imaged with respect to the tissue of the native heart valve annulus 68, tissue of at least one leaflet, and tissue of an atrial wall 122. For some applications, filaments 99 of device 532 help facilitate measuring of a height of the native heart valve annulus 68.

For some applications, if the physician sees movement of filaments 99, the physician can determine that device 532 is positioned at least partially along leaflet 123.

The distal portion of guidewire 534 and device 532 are typically advanced into a heart chamber of the subject, (e.g., a left atrium, as shown). For some applications, the distal portion of guidewire 534 and device 532 are advanced into a ventricle of the subject using a transvascular approach or a transapical approach. For some applications, the distal portion of guidewire 534 and device 532 are advanced into an atrium of the subject using a transvascular approach or a minimally-invasive approach. For applications in which the distal portion of guidewire 534 and device 532 are advanced into the ventricle, the device is positioned in a subannular space, e.g., the subannular groove of valve 64.

Device 532 and guidewire 534 and tube 536 are retrieved and extracted from the body of the subject following implantation of the cardiac implant.

It is to be noted that although system 530 is shown on mitral valve 64, system 530 can be used on any cardiac valve, e.g., a tricuspid valve, or any other tissue of the subject.

Reference is now made to FIGS. 37A-G, which are schematic illustrations of a system 540 comprising an annulus-marking device 542 comprising a first radiopaque loop 544 and a second radiopaque loop 546 configured to gyrate with respect to first radiopaque loop 544, in accordance with some applications. As shown in FIGS. 37B-C, second radiopaque loop 546 is configured to pivot and tilt with respect to first radiopaque loop 544. Device 542 comprises a flexible, radiopaque material (nitinol or stainless steel) such that it is compressible to a compressed state during delivery toward the native heart valve, and expandable from a compressed state for positioning in the native heart valve to an expanded state.

Each loop 544 and 546 comprises a wire frame surrounded at least in part by a respective spring 543 and 547 which expand and compress in order to facilitate proper positioning and alignment of loops 544 and 546 within valve 64. For some applications, springs 543 and 547 help loops 544 and 546 apply pressure to tissue of valve 64 and/or to tissue surrounding valve 64.

Device 542 is delivered within a chamber of the heart (e.g., a left atrium, as shown in FIG. 37D) and is allowed to expand due to its shape memory material.

FIG. 37E shows tilting of second radiopaque loop 546 with respect to first radiopaque loop 544 and allowing of second radiopaque loop 546 to pivot along a plane that is at a non-zero angle with respect to a plane of first radiopaque loop 544. For some applications, movement of second loop 546 is aided responsively to downward pushing of first loop 544. As shown in FIG. 37E, annulus-marking device 542 is positioned in its fully expanded state at least in part within native heart valve 64 in a manner in which (1) first radiopaque loop 544 is disposed between leaflets 123 of valve 64, an upper portion of first radiopaque loop 544 is disposed within the atrium and a lower portion of first radiopaque loop 544 is disposed within the left ventricle of the heart, and (2) second radiopaque loop 546 is disposed along an atrial surface of annulus 68 of valve 64.

For some applications, first radiopaque loop 544 is positioned between leaflets 123 such that it applies a force to commissures of valve 64.

As shown in FIG. 37E, in the fully expanded state of device 542, second radiopaque loop is moveable vertically along a portion 545 (shown in FIGS. 37A and 37E) of first radiopaque loop 544. Such moving enables proper positioning of loop 546 along annulus 68. For some applications, such moving of second radiopaque loop 546 vertically along portion 545 of the first radiopaque loop comprises measuring a height of annulus 68.

Once device 542 is in place, tissue of native heart valve annulus 68 and tissue coupled thereto is viewed under imaging annulus-marking device 542. Device 542 is imaged while placed against the tissue. For some applications, tissue of native heart valve annulus 68 and tissue coupled thereto is imaged by viewing movement of annulus-marking device 542 responsively to movement of the tissue.

FIG. 37F shows an implant, e.g., an annuloplasty structure 549, being implanted along annulus 68 using annulus-marking device 542 as a guide for implantation of the implant under imaging, e.g., fluoroscopy. The implant is positioned between loop 546 and tissue of atrial wall 122. The implant is delivered using a delivery tool 550, and a plurality of anchors 551 are used to anchor the implant to tissue of annulus 68.

Following the implantation of the implant, device 542 is retrieved by pivoting and tilting second radiopaque loop 546 with respect to first radiopaque loop 544. Device 542 is constrained within a tool and extracted from the body of the subject. That is, device 542 does not function as an implant for such embodiments and is used only to guide implantation of the implant; rather, device 542 acts as a guide for implantation while placed temporarily within the body of the patient to be subsequently removed therefrom following the implantation of the implant.

FIG. 37G shows annuloplasty structure 549 at annulus 68 in presence of annulus-marking device 542.

It is to be noted that although system 540 is shown on mitral valve 64, system 540 can be used on any cardiac valve, e.g., a tricuspid valve, or any other tissue of the subject.

Figure 38:
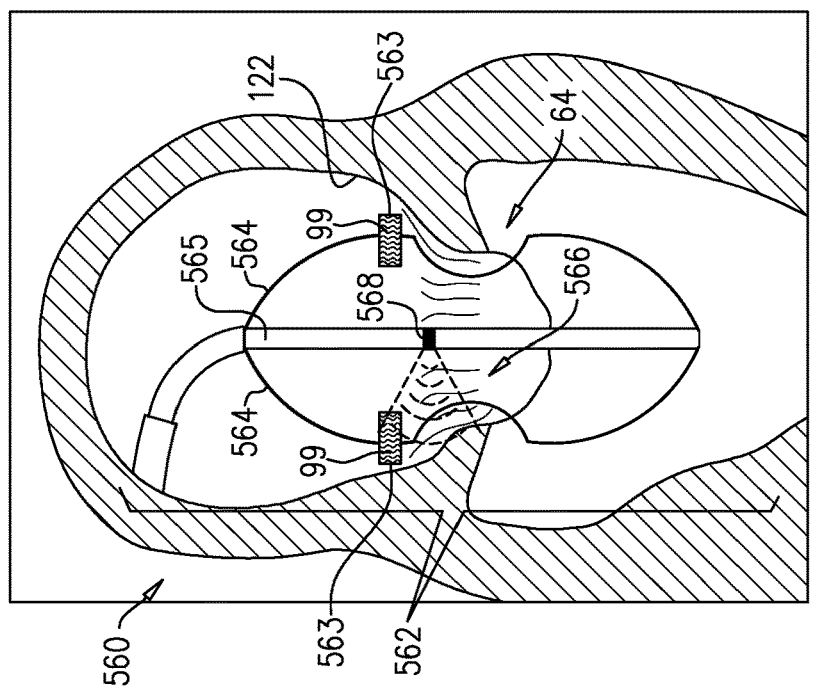
FIG. 38 is a schematic illustration of an annulus-marking device comprising two or more expandable wires and an ultrasound transducer for aiding implantation of cardiac devices under the guidance of imaging, in accordance with some applications.

Reference is now made to FIG. 38, which is a schematic illustration of a system 560 comprising an annulus-marking device 562 comprising two or more expandable wires 564, a central pole 565, and at least one ultrasound transducer 568 slidable along and rotational with respect to central pole 565, in accordance with some applications. Device 562 comprises a flexible, radiopaque material (nitinol or stainless steel) such that it is compressible to a compressed state during delivery toward the native heart valve, and expandable from a compressed state for positioning in the native heart valve to an expanded state. Wires 564 are connected at their respective proximal and distal ends to central pole 565. It is to be noted that although two wires 564 are shown, the scope of the present invention includes devices 562 comprising any suitable number of wires 564. Collectively, wires 564 form a frame of device 562.

Each wire 564 comprises a flexible metal which expands and compresses in order to facilitate proper positioning and alignment of wires 564 within valve 64. For some applications, wires 564 apply pressure to tissue of valve 64 and/or to tissue surrounding valve 64. Each wire 564 is shaped so as to define a respective indented section 566 which fits annulus 68. Wires 564 are positioned between leaflets 123 such that they apply a force to commissures of valve 64.

Device 562 is delivered within valve 64 and is allowed to expand due to its shape memory material.

Annulus-marking device 562 is positioned in its fully expanded state at least in part within native heart valve 64 in a manner in which the two or more expandable wires 564 are disposed between leaflets 123 of valve 64, an upper portion of each expandable wire 564 is disposed within the atrium, and a lower portion of each expandable wire 564 being disposed within the ventricle.

For some applications, wires 564 are positioned between leaflets 123 such that they apply a force to commissures of valve 64.

In the fully expanded state of device 562, at least one radiopaque marker 563 (e.g., two markers 563, as shown) is moveable vertically along a respective wire 564 toward annulus 68 until marker 563 abuts annulus 68. For some applications, each marker 563 comprises a wire frame and a plurality of radiopaque elements, such as radiopaque filaments 99, etc. For some applications, such moving of markers 563 vertically along wires 564 comprises measuring a height of annulus 68. Wire 564 acts as a guide for markers 563 to reach the commissures of valve 64.

Once device 562 is in place, tissue of native heart valve annulus 68 and tissue coupled thereto is viewed under imaging annulus-marking device 562. Device 562 is imaged while placed against the tissue. For some applications, tissue of native heart valve annulus 68 and tissue coupled thereto is imaged by viewing movement of annulus-marking device 562 responsively to movement of the tissue. For some applications, tissue is viewed by ultrasound transducer 568. A height of annulus 68 is also measured using transducer 568. For some applications, transducer 568 measures an inter-commissural distance. For some applications, transducer 568 faces outward, in particular radially outward.

For some applications, central pole 565 is hollow, and ultrasound transducer 568 is slidable within pole 565. It is to be noted that the scope of the present application includes any number of ultrasound transducers in device 562. For some applications, device 562 can comprise a single ultrasound transducer. For either application in which transducer 568 slides within or around pole 565, ultrasound transducer 568 is advanced along pole 565 in a vicinity of annulus 68. For some applications, ultrasound transducer 568 is advanced along pole 565 until it is in line with indented section 566 of wires 564.

An implant, e.g., an annuloplasty structure, (not shown) can be implanted along annulus 68 using annulus-marking device 562 as a guide for implantation of the implant under imaging, e.g., ultrasound and fluoroscopy. The implant is positioned between wires 564 and tissue of atrial wall 122. The implant is delivered using a delivery tool, and a plurality of anchors are used to anchor the implant to tissue of annulus 68.

Following the implantation of the implant, device 562 is retrieved by constraining device 562 within a tool and extracted from the body of the subject. That is, device 562 does not function as an implant for such embodiments and is used only to guide implantation of the implant; rather, device 562 acts as a guide for implantation while placed temporarily within the body of the patient to be subsequently removed therefrom following the implantation of the implant.

It is to be noted that although system 560 is shown on mitral valve 64, system 560 can be used on any cardiac valve, e.g., a tricuspid valve, or any other tissue of the subject.

Figure 39:
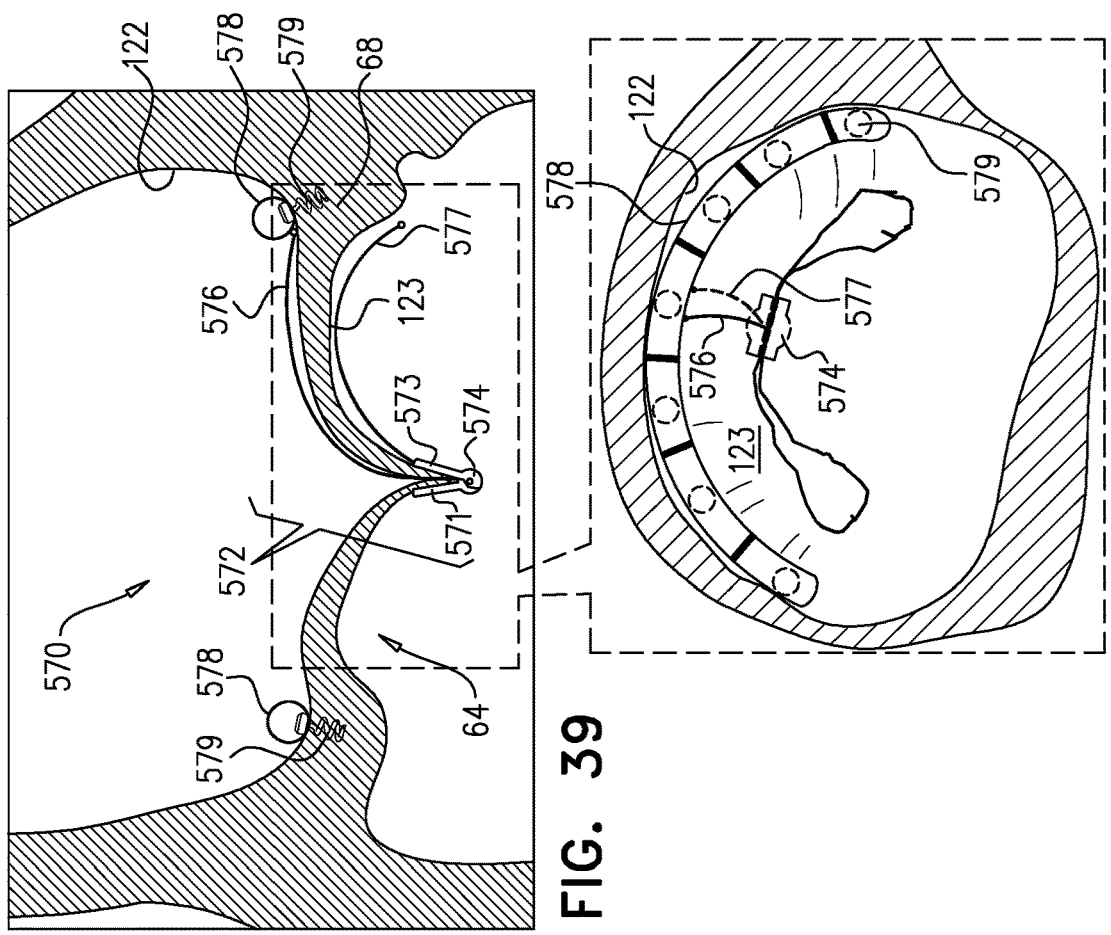
FIG. 39 is a schematic illustration of an annulus-marking device comprising a clip for aiding implantation of cardiac devices under the guidance of imaging, in accordance with some applications.

Reference is now made to FIG. 39, which is a schematic illustration of a system 570 comprising an annulus-marking device 572 comprising a clip comprising radiopaque material and first and second jaws 571 and 573 coupled together at a hinge point 574 and first and second filaments 576 and 577 extending from respective ends or from respective roots of first and second jaws 571 and 573, in accordance with some applications. For some applications, device 572 is introduced within the ventricle of the heart, either by a transapical approach or by a transaortic approach. The clip clips together both leaflets 123 of valve 64. During the clipping, first filament 576 extends along and abuts an atrial surface of one leaflet 123 in a manner in which an end of first filament 576 is positioned in a vicinity of a hinge of annulus 68 of the valve in a vicinity of atrial wall 122. Second filament 577 extends along and abuts a ventricular surface of leaflet 123 in a manner in which an end of second filament 577 is positioned in a subannular groove of the valve in a vicinity of a ventricular wall.

It is to be noted that the clip can comprise any number of filaments coupled thereto. These filaments can extend circumferentially along annulus 68.

Device 572 comprises radiopaque material, e.g., nitinol or stainless steel. Filaments 576 and 577 can be super-elastic and, for some applications, have shape-memory material.

For some applications, clipping leaflets 123 together creates a double orifice in valve 64. As shown, filament 576 extends from a ventricular space toward the atrial surface, e.g., through one of the orifices created by the clip.

Once device 572 is in place, tissue of native heart valve annulus 68 and tissue coupled thereto is viewed under imaging annulus-marking device 572. Device 572 is imaged while placed against the tissue. For some applications, tissue of native heart valve annulus 68 and tissue coupled thereto is imaged by viewing movement of annulus-marking device 572 responsively to movement of the tissue, e.g., to movement of filaments 576 and 577.

Under the guidance of imaging, e.g., fluoroscopy, using device 572, an implant, e.g., an annuloplasty structure 578 is implanted along annulus 68 of the subject. A plurality of anchors 579 are used to implant structure 578 to annulus 68.

For some applications, device 572 remains implanted within the body of the subject once structure 578 is implanted. For some applications, implanting structure 578 affixes at least one of filaments 576 and 577 to valve 64. For some applications, device 572 is retrieved following the implanting.

It is to be noted that although system 570 is shown on mitral valve 64, system 570 can be used on any cardiac valve, e.g., a tricuspid valve, or any other tissue of the subject.

Figure 40:
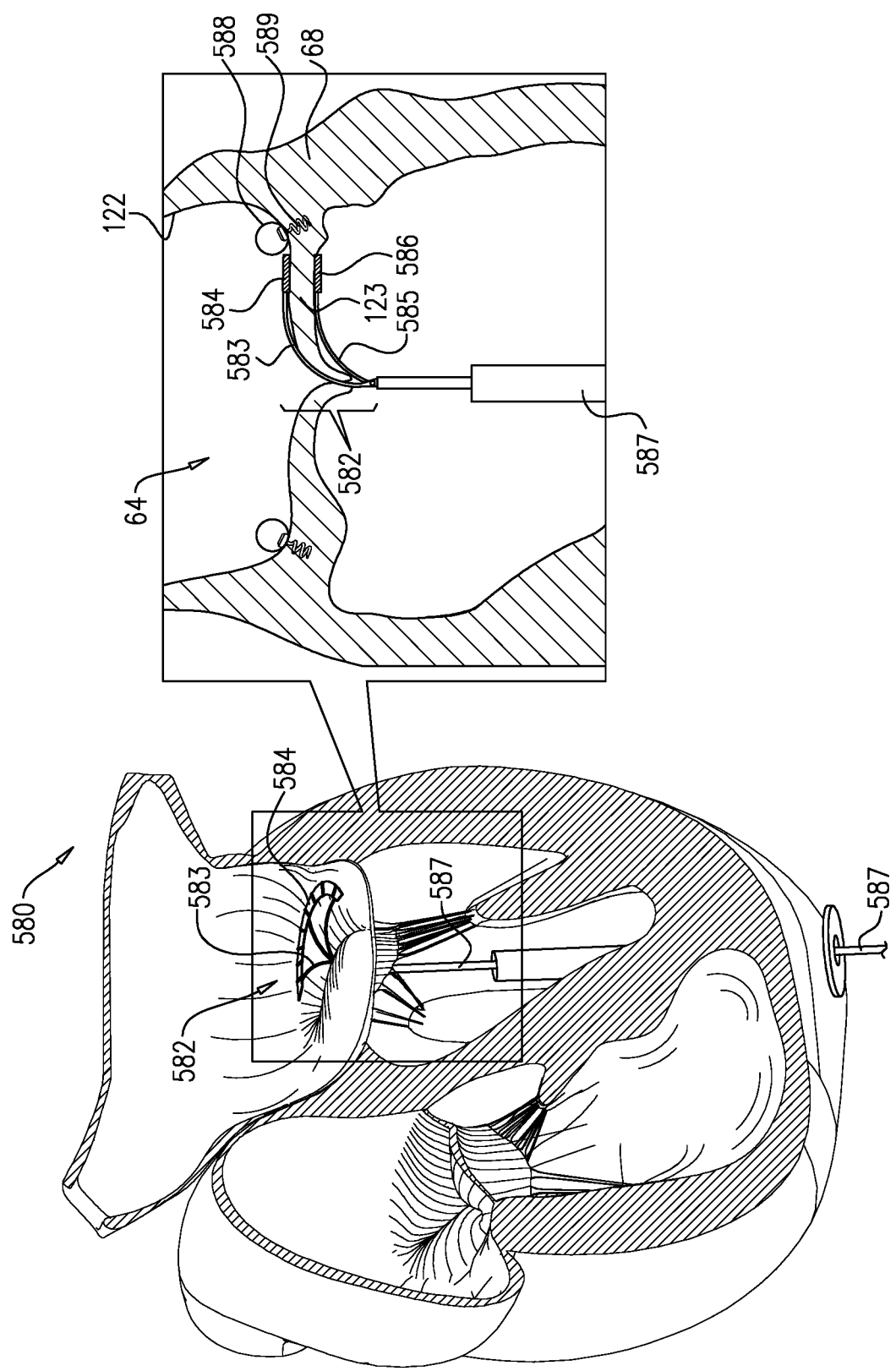
FIG. 40 is a schematic illustration of an annulus-marking device comprising a clamp for aiding implantation of cardiac devices under the guidance of imaging, in accordance with some applications.

Reference is now made to FIG. 40, which is a schematic illustration of a system 580 comprising an annulus-marking device 582 comprising a clamp comprising radiopaque material and first and second arms 583 and 585 coupled together at a hinge point, and first and second tongs, or curved elements 584 and 586 extending from respective ends of first and second arms 583 and 585, in accordance with some applications. For some applications, device 582 is introduced within the ventricle of the heart, either by a transapical approach or by a transaortic approach. The clamp clamps around a single leaflet 123 of valve 64. During the clamping, first curved element 584 extends along and abuts an atrial surface of one leaflet 123 in a manner in which curved element is positioned in a vicinity of a hinge of annulus 68 of the valve in a vicinity of atrial wall 122. Second curved element 586 extends along and abuts a ventricular surface of leaflet 123 in a manner in which second curved element 586 is positioned in a subannular groove of valve 64 in a vicinity of a ventricular wall.

It is to be noted that the clamp can comprise any number of arms 583 and 585 coupled thereto. Device 582 comprises radiopaque material, e.g., nitinol or stainless steel.

Once device 582 is in place, tissue of native heart valve annulus 68 and tissue coupled thereto is viewed under imaging annulus-marking device 582. Device 582 is imaged while placed against the tissue. For some applications, tissue of native heart valve annulus 68 and tissue coupled thereto is imaged by viewing movement of annulus-marking device 582 responsively to movement of the tissue.

Under the guidance of imaging, e.g., fluoroscopy, using device 582, an implant, e.g., an annuloplasty structure 588 is implanted along annulus 68 of the subject. A plurality of anchors 589 are used to implant structure 588 to annulus 68.

Once structure 588 is implanted, device 582 is retrieved from the body of the subject.

It is to be noted that although system 580 is shown on mitral valve 64, system 580 can be used on any cardiac valve, e.g., a tricuspid valve, or any other tissue of the subject. It is to be further noted that although device 582 is shown as being delivered transapically, device 582 may be delivered to the valve using any suitable delivery method into the atrium or into the ventricle, e.g., transvascularly or using a minimally-invasive approach.

Figure 41:
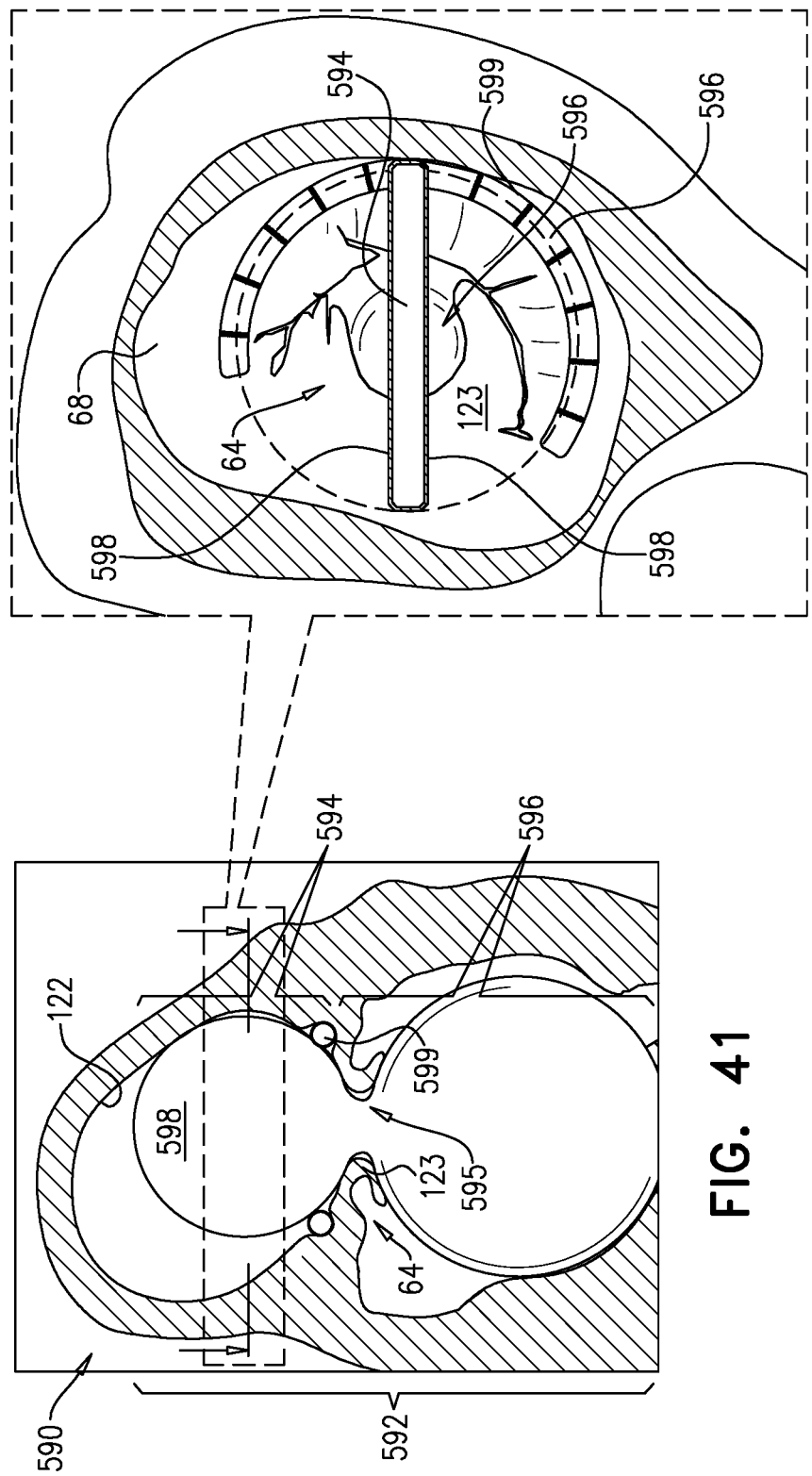
FIG. 41 is a schematic illustration of an annulus-marking device comprises a balloon having upper and lower inflatable sections for aiding implantation of cardiac devices under the guidance of imaging, in accordance with some applications.

Reference is now made to FIG. 41, which is a schematic illustration of a system 590 comprising an annulus-marking device 592 comprising a balloon having an upper inflatable section 594, a lower inflatable section 596, and a central waist 595 between the upper and lower inflatable sections 594 and 596, in accordance with some applications. Upper inflatable section 594 is inflatable to assume a generally paddle shape, or any other shape having a relatively small width and one or more flat surfaces 598, while lower inflatable section 596 is inflatable to assume a spherical shape. The balloon of device 592 is delivered to valve 64 using a catheter, such as during transvascular approach or during a minimally-invasive procedure. The balloon is positioned within the heart such that upper inflatable section 594 is disposed within an atrium of the heart, lower inflatable section 596 is disposed within a ventricle of the heart, and central waist 595 is disposed between leaflets 123 of valve 64. As shown, in one view of the balloon of device 592, the balloon assumes an hourglass shape, e.g., at at least one cross-section thereof. In a second view, as shown, upper inflatable section 594 is narrower and has a lower profile than lower inflatable section 596.

The balloon is inflated such that upper inflatable section 594 expands to assume the generally paddle shape, and lower inflatable section 596 expands to assume the spherical shape. For some applications, the balloon comprises a radiopaque material. For some applications, the balloon is inflated using radiopaque fluid. For some applications, upper inflatable section 594 is less compliant than lower inflatable section 596. For some applications, upper inflatable section 594 is noncompliant.

Once the balloon is inflated, under imaging guidance, e.g., under fluoroscopy, an implant, e.g., an annuloplasty structure 599, is implanted at annulus 68 of valve 64 using annulus-marking device 592 as a guide. For some applications, structure 599 is implanted between an external surface of upper inflatable section 594 and a surface of atrial wall 122.

For some applications, tissue of native heart valve annulus 68 and tissue coupled thereto is viewed using the balloon of device 592. The tissue is viewed by imaging annulus-marking device 592 with respect to the tissue of native heart valve annulus 68 and the tissue coupled thereto by viewing upper and lower inflatable sections 594 and 596 placed against the tissue. Annulus-marking device 592 is imaged with respect to the tissue of native heart valve annulus 68, tissue of at least one leaflet 123, and tissue of atrial wall 122.

For some applications, at least one surface, e.g., an upper surface, of upper inflatable section 594 is slanted (not shown) in order to reduce the chance that the delivery system used to deliver annuloplasty structure 599 abuts a surface of lower inflatable section 596 and reduces the chance that the delivery system drives an anchor into lower inflatable section 596.

Once structure 599 is implanted along annulus 68, annulus-marking device 592 is retrieved. For some applications, device 592 is deflated and then constrained within a tool and extracted from the body of the subject.

It is to be noted that although system 590 is shown on mitral valve 64, system 590 can be used on any cardiac valve, e.g., a tricuspid valve, or any other tissue of the subject.

Figure 42:
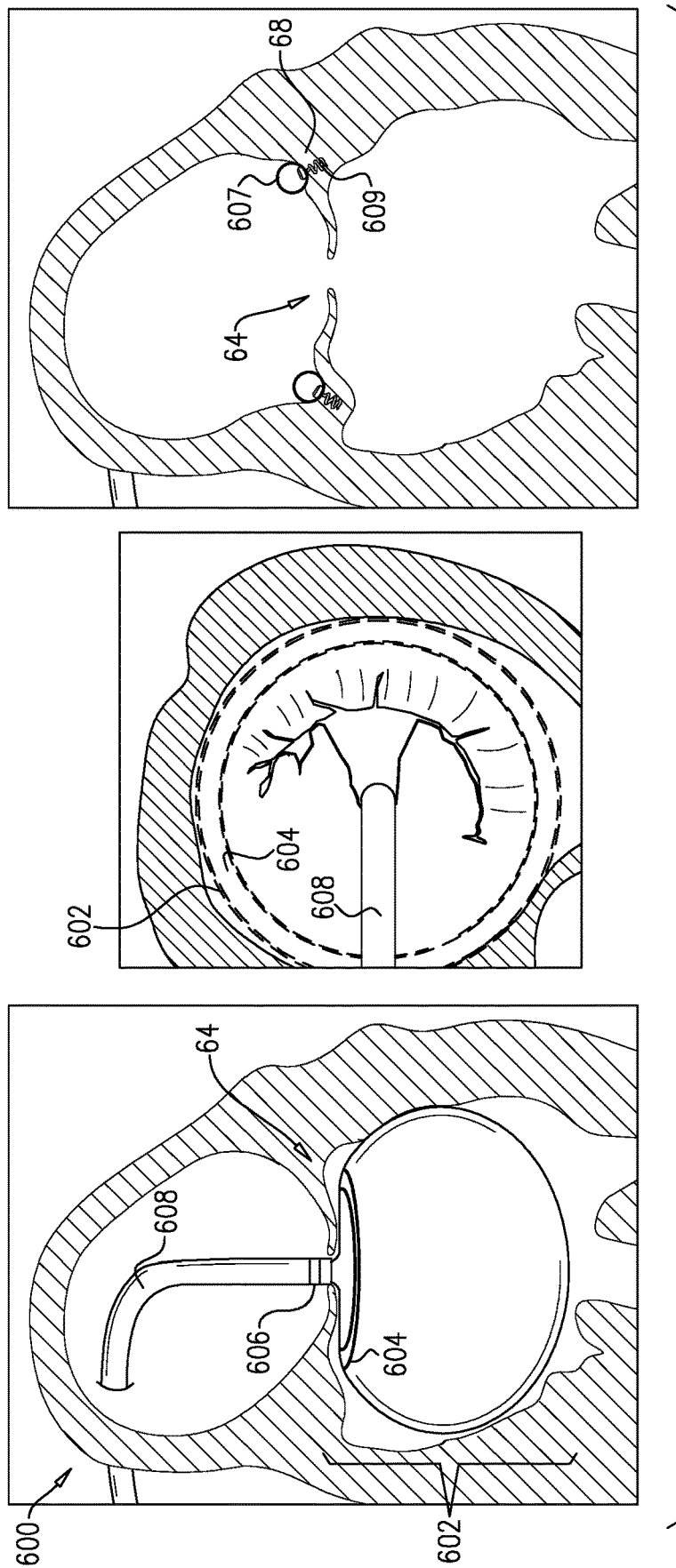
FIG. 42 is a schematic illustration of an annulus-marking device comprises a balloon for aiding implantation of cardiac devices under the guidance of imaging, in accordance with some applications.

Reference is now made to FIG. 42, which is a schematic illustration of a system 600 comprising an annulus-marking device 602 comprising a balloon configured to be positioned in the ventricle of the heart of the subject, in accordance with some applications. The balloon of device 602 is inflatable to assume a spherical shape. The balloon of device 602 is delivered to valve 64 using a catheter 608, e.g., during transvascular approach or during a minimally-invasive procedure.

The balloon is inflated such that it expands to assume the spherical shape. For some applications, the balloon comprises a radiopaque material. For some applications, the balloon includes a toroidal marking 604 which is at an upper surface of the balloon. For such applications, toroidal marking 604 is radiopaque and serves as a guide for implantation of the implant along annulus 68. For some applications, the balloon is inflated using radiopaque fluid. For some applications, the balloon of device 602 is compliant. For some applications, the balloon of device 602 is noncompliant.

For either embodiment, the balloon is inflated, and the inflation is controlled in order to prevent puncture of the balloon. The balloon is expanded toward the leaflet hinge point.

For some applications of the present invention the balloon comprises a magnetic substance, e.g., filaments, within a space defined by the balloon. For such applications, marking 604 is therefore defined by a collection of the magnetic substance at the upper surface of the balloon of device 602, thereby marking annulus 68 of valve 64 from a ventricular surface of valve 64. As such, catheter 608 comprises a magnet 606 at a distal end thereof. Magnet 606 is configured to draw the magnetic substance toward the upper surface of the balloon in order to form the magnetic substance into marking 604.

Once the balloon is inflated, under imaging guidance, e.g., under fluoroscopy, an implant, e.g., an annuloplasty structure 607, is implanted at annulus 68 of valve 64 using annulus-marking device 602 as a guide. Structure 607 is implanted using a plurality of tissue anchors 609.

For some applications, tissue of native heart valve annulus 68 and tissue coupled thereto is viewed using the balloon of device 602. The tissue is viewed by imaging annulus-marking device 602 with respect to the tissue of native heart valve annulus 68 and the tissue coupled thereto by viewing the balloon placed against the tissue. Annulus-marking device 602 is imaged with respect to the tissue of native heart valve annulus 68, tissue of at least one leaflet 123, and tissue of atrial wall 122.

For some applications, at least one surface, e.g., an upper surface, of device 602 is slanted (not shown) in order to reduce the chance that the delivery system used to deliver annuloplasty structure 607 abuts a surface of the balloon of device 602 and reduces the chance that the delivery system drives an anchor into the balloon.

Once structure 607 is implanted along annulus 68, annulus-marking device 602 is retrieved. For some applications, device 602 is deflated and then constrained within a tool and extracted from the body of the subject.

It is to be noted that although system 600 is shown on mitral valve 64, system 600 can be used on any cardiac valve, e.g., a tricuspid valve, or any other tissue of the subject.

Reference is now made to FIG. 43, which is a schematic illustration of a system 610 comprising an annulus-marking device 612 comprising one or more balloons having an upper inflatable element 614 and a lower inflatable element 616, in accordance with some applications. Upper inflatable element 614 is inflatable to assume a generally toroidal shape, and lower inflatable element 616 is inflatable to assume a toroidal shape. Device 612 is delivered to valve 64 using a catheter 613, e.g., during transvascular approach or during a minimally-invasive procedure. Device 612 is positioned within the heart such that upper inflatable element 614 is disposed within an atrium of the heart and lower inflatable element 616 is disposed within a ventricle of the heart. For some applications, upper and lower inflatable elements are discrete and are delivered and inflated separately (configuration not shown). For some applications, as shown, device 612 comprises a central waist 615 between the upper and lower inflatable elements 614 and 616, and central waist 615 is disposed between leaflets 123 of valve 64. That is, for such an embodiment, device 612 comprises a single balloon including elements 614 and 616 and waist 615 and assumes an hourglass shape at at least one cross-element thereof.

Once positioned at valve 64, upper inflatable element 614 is inflated and expands to assume the toroidal shape, and lower inflatable element 616 is inflated and expands to assume the toroidal shape. For some applications, device 612 comprises a radiopaque material. For some applications, device 612 is inflated using radiopaque fluid. For some applications, upper inflatable element 614 and lower inflatable element 616 comprise compliant material. For some applications, upper inflatable element 614 and lower inflatable element 616 comprise noncompliant material. Elements 614 and 616 are inflated to any suitable pressure depending on the compliance of the material of elements 614 and 616.

Once elements 614 and 616 are inflated, catheter 613 applies a pushing force downward to upper inflatable element 614 and/or a pulling force upward to lower inflatable element 616 in order to position device 612 properly within valve 64. Once inflated elements 614 and 616 are positioned properly, under imaging guidance, e.g., under fluoroscopy, an implant, e.g., an annuloplasty structure 618, is implanted at annulus 68 of valve 64 using annulus-marking device 612 as a guide. For some applications, structure 618 is implanted between an external surface of upper inflatable element 614 and a surface of atrial wall 122.

For some applications, tissue of native heart valve annulus 68 and tissue coupled thereto is viewed using device 612. The tissue is viewed by imaging annulus-marking device 612 with respect to the tissue of native heart valve annulus 68 and the tissue coupled thereto by viewing upper and lower inflatable elements 614 and 616 placed against the tissue. Annulus-marking device 612 is imaged with respect to the tissue of native heart valve annulus 68, tissue of at least one leaflet 123, and tissue of atrial wall 122.

For some applications, at least one surface, e.g., an upper surface, of upper inflatable element 614 is slanted (not shown) in order to reduce the chance that the delivery system used to deliver annuloplasty structure 618 abuts a surface of lower inflatable element 616 and reduces the chance that the delivery system drives an anchor into lower inflatable element 616.

Once structure 618 is implanted along annulus 68 by a plurality of anchors 619, annulus-marking device 612 is retrieved. For some applications, device 612 is deflated and then constrained within a tool and extracted from the body of the subject.

It is to be noted that although system 610 is shown on mitral valve 64, system 610 can be used on any cardiac valve, e.g., a tricuspid valve, or any other tissue of the subject.

Figure 44:
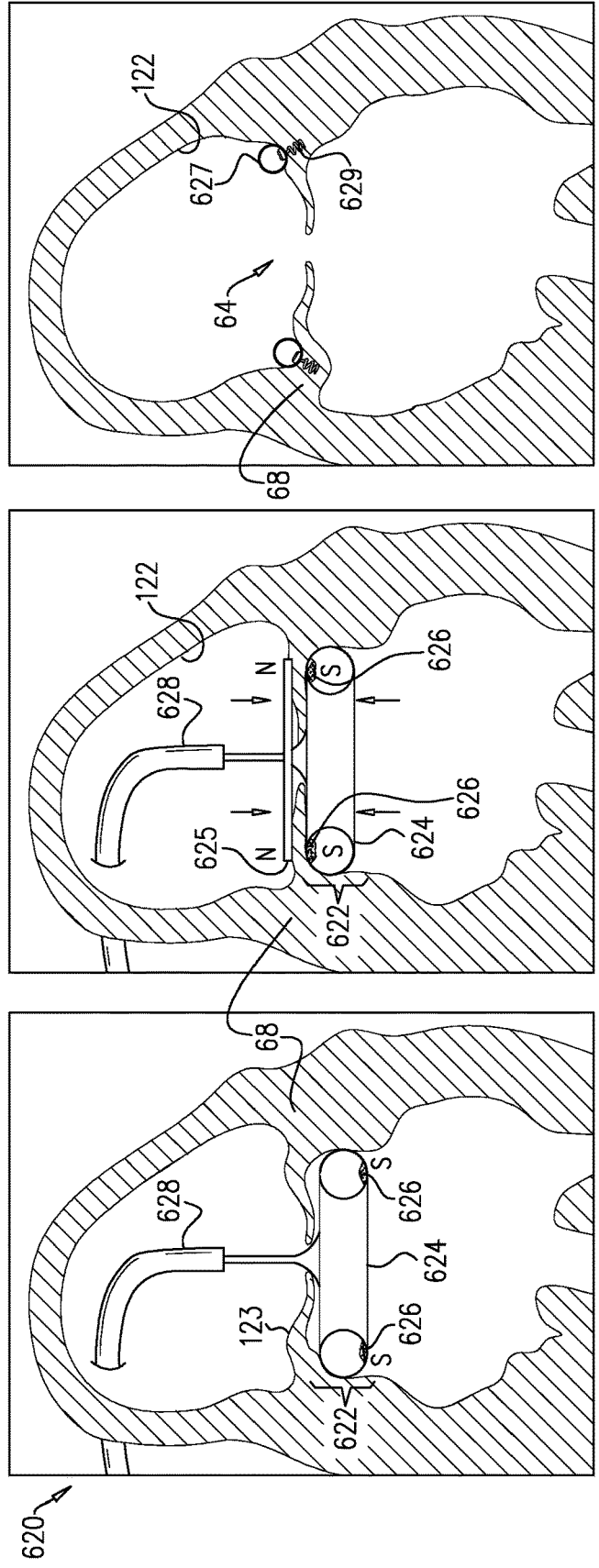

Reference is now made to FIG. 44, which is a schematic illustration of a system 620 comprising an annulus-marking device 622 comprising a balloon 624 configured to be positioned in the ventricle of the heart of the subject, in accordance with some applications. Balloon 624 of device 622 is inflatable to assume a toroidal shape. Balloon 624 of device 622 is delivered to valve 64 using a catheter 628, e.g., during transvascular approach or during a minimally-invasive procedure.

Balloon 624 is inflated such that it expands to assume the toroidal shape. For some applications, balloon 624 comprises a radiopaque material. For some applications, balloon 624 is inflated using radiopaque fluid. For some applications, balloon 624 of device 622 is compliant. For some applications, balloon 624 of device 622 is noncompliant.

For either embodiment, balloon 624 is inflated and the inflation is controlled in order to prevent puncture of the balloon. Balloon 624 is expanded toward the leaflet hinge point.

For some applications of the present invention balloon 624 comprises a magnetic substance 626, e.g., filaments, within a space defined by balloon 624. For such applications, a marker of device 622 is therefore defined by a collection of magnetic substance 626 at the upper surface of balloon 624 of device 622, thereby marking annulus 68 of valve 64 from a ventricular surface of valve 64. For such applications, magnetic substance forms a toroidal marking that serves as a guide for implantation of the implant along annulus 68. As such, catheter 628 comprises a magnet 625 at a distal end portion thereof. Magnet 625 is configured to draw magnetic substance 626 toward the upper surface of balloon 624 in order to form magnetic substance 626 into the marker. For some applications, magnet 625 is toroidal. For some applications, magnet 625 is circular and flat.

Once the balloon is inflated, under imaging guidance, e.g., under fluoroscopy, an implant, e.g., an annuloplasty structure 627, is implanted at annulus 68 of valve 64 using annulus-marking device 622 as a guide. Structure 627 is implanted using a plurality of tissue anchors 629. Structure 627 can be positioned between an external surface of magnet 625 and atrial wall 122.

For some applications, tissue of native heart valve annulus 68 and tissue coupled thereto is viewed using balloon 624 of device 622. The tissue is viewed by imaging annulus-marking device 622 with respect to the tissue of native heart valve annulus 68 and the tissue coupled thereto by viewing balloon 624 against the tissue. Annulus-marking device 622 is imaged with respect to the tissue of native heart valve annulus 68, tissue of at least one leaflet 123, and tissue of atrial wall 122.

For some applications, at least one surface, e.g., an upper surface, of device 622 is slanted (not shown) in order to reduce the chance that the delivery system used to deliver annuloplasty structure 627 abuts a surface of the balloon of device 622 and reduces the chance that the delivery system drives an anchor into balloon 624.

Once structure 627 is implanted along annulus 68, annulus-marking device 622 is retrieved. For some applications, device 622 is deflated and then constrained within a tool and extracted from the body of the subject.

It is to be noted that although system 620 is shown on mitral valve 64, system 620 can be used on any cardiac valve, e.g., a tricuspid valve, or any other tissue of the subject.

Reference is now made to FIG. 45, which is a schematic illustration of a system 630 comprising an annulus-marking device 632 comprising at least one magnetic element, e.g., first and second magnetic elements 634 and 636, configured to be positioned at respective atrial and ventricular surface of valve 64 of the subject, in accordance with some applications. For some applications, first and second magnetic elements 634 and 636 each comprise a wire. For some applications, first and second magnetic elements 634 and 636 are each circular. For some applications, first and second magnetic elements 634 and 636 are each toroidal, e.g., ring-shaped. For some applications, first and second magnetic elements 634 and 636 are partially ring-shaped, e.g., C-shaped. For some applications, first and second magnetic elements 634 and 636 each comprise flat, circular discs. For applications in which first and second magnetic elements 634 and 636 each comprise flat, circular discs, elements 634 and 636 apply pressure to leaflets 123.

Device 632 is delivered to valve 64 using a catheter, e.g., during transvascular approach or during a minimally-invasive procedure.

Positioning of second magnetic element 636 at the ventricular surface generates a magnetic field. The magnetic field helps ensure proper positioning of device 632 with respect to tissue of valve 64. The magnetic field helps prevent movement of device 632 with respect to tissue of valve 64. For some applications, the magnetic field helps adjust a size of elements 634 and 636.

Once device 632 is positioned at valve 64, under imaging guidance, e.g., under fluoroscopy, an implant, e.g., an annuloplasty structure 637, is implanted at annulus 68 of valve 64 using annulus-marking device 632 as a guide. Structure 637 is implanted using a plurality of tissue anchors 639. Structure 637 can be positioned between an external surface of magnetic element 634 and atrial wall 122.

For some applications, tissue of native heart valve annulus 68 and tissue coupled thereto is viewed using device 632, i.e., using magnetic elements 634 and 636. The tissue is viewed by imaging annulus-marking device 632 with respect to the tissue of native heart valve annulus 68 and the tissue coupled thereto by viewing elements 634 and 636 placed against the tissue. Annulus-marking device 632 is imaged with respect to the tissue of native heart valve annulus 68, tissue of at least one leaflet 123, and tissue of atrial wall 122.

Once structure 637 is implanted along annulus 68, annulus-marking device 632 is retrieved. For some applications, device 632 is constrained within a tool and extracted from the body of the subject.

It is to be noted that although system 630 is shown on mitral valve 64, system 630 can be used on any cardiac valve, e.g., a tricuspid valve, or any other tissue of the subject.

Figure 46:
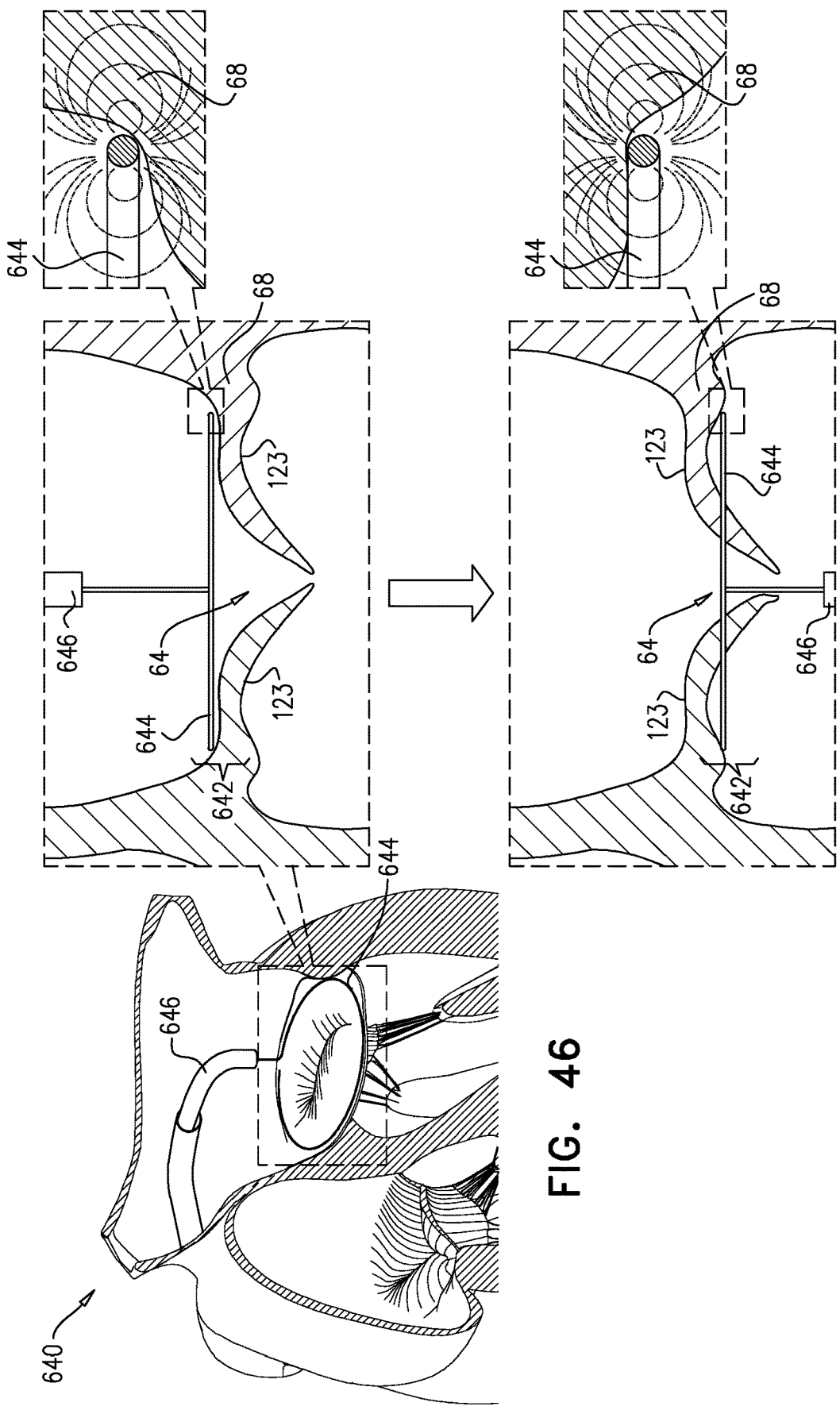

Reference is now made to FIG. 46, which is a schematic illustration of a system 640 comprising an annulus-marking device 642 comprising at least one magnetic element 644 configured to be positioned at respective atrial and ventricular surface of valve 64 of the subject, in accordance with some applications. For some applications, element 644 comprises a wire. For some applications, magnetic element 644 is circular. For some applications, magnetic element 644 is toroidal. For some applications, magnetic element 644 comprises a flat, circular disc. Device 642 is delivered to valve 64 using a catheter 646, e.g., during transvascular approach or during a minimally-invasive procedure.

Once positioned at the atrial and/or ventricular surface of valve 64, a magnetic field is generated, e.g., by an external magnetic field generator. The magnetic field helps ensure proper positioning of device 642 with respect to tissue of valve 64. The magnetic field helps prevent movement of device 642 with respect to tissue of valve 64. For some applications, the magnetic field helps adjust a size of magnetic element 644.

For applications in which magnetic element 644 is positioned at the atrial surface (e.g., approaching valve 64 via the fossa ovalis), the magnetic field is generated from the ventricle of the heart, e.g., transapically, from within the ventricle using a catheter, or from a magnet positioned outside the body of the subject.

For applications in which magnetic element 644 is positioned at the ventricular surface (e.g., approaching valve 64 via the aorta), the magnetic field is generated from the ventricle of the heart, e.g., from within the atrium using a catheter, or from a magnet positioned outside the body of the subject.

Once device 642 is positioned at valve 64, under imaging guidance, e.g., under fluoroscopy, an implant, e.g., an annuloplasty structure, is implanted at annulus 68 of valve 64 using annulus-marking device 642 as a guide. For some applications, the delivery tool used to deliver and implant the implant comprises a metallic element or a magnet which is attracted by annulus-marking device 642. For applications in which element 644 is positioned at the atrial surface, the annuloplasty structure can be positioned between an external surface of magnetic element 644 and atrial wall 122.

For some applications, tissue of native heart valve annulus 68 and tissue coupled thereto is viewed using device 642, i.e., using magnetic element 644. The tissue is viewed by imaging annulus-marking device 642 with respect to the tissue of native heart valve annulus 68 and the tissue coupled thereto by viewing element 644 placed against the tissue. Annulus-marking device 642 is imaged with respect to the tissue of native heart valve annulus 68, tissue of at least one leaflet 123, and tissue of atrial wall 122.

Once the annuloplasty structure is implanted along annulus 68, annulus-marking device 642 is retrieved. For some applications, device 642 is constrained within a tool and extracted from the body of the subject.

It is to be noted that although system 640 is shown on mitral valve 64, system 640 can be used on any cardiac valve, e.g., a tricuspid valve, or any other tissue of the subject.

Figure 47:
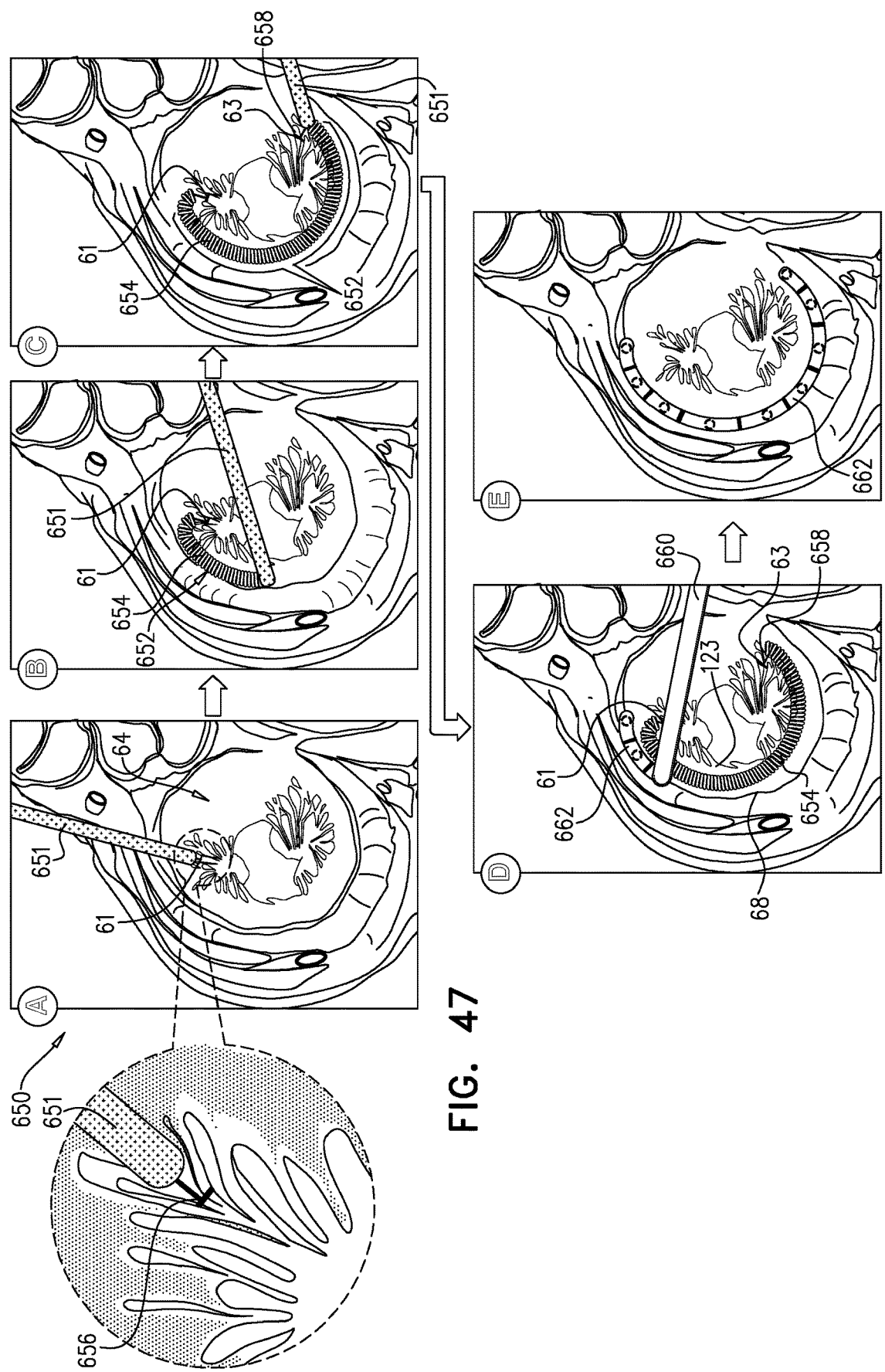
FIG. 47 is a schematic illustration of an annulus-marking device comprising a spring for aiding implantation of cardiac devices under the guidance of imaging, in accordance with some applications.

Reference is now made to FIG. 47, which is a schematic illustration of a system 650 comprising an annulus-marking device 652 comprising a coil-shaped wire 654 that is placed along annulus 68 in advance of implantation of an implant, e.g., an annuloplasty structure 662, in accordance with some applications. Annulus-marking device 652 extends from within a delivery tool 651 and travels along at least a portion of a perimeter of annulus 68 (e.g., a posterior portion of annulus 68 of mitral valve 64, as shown). Annulus-marking device 652 acts as a guide for implantation of structure 662 under imaging guidance, e.g., fluoroscopy. As successive portions of annuloplasty structure 662 are extended from within its delivery tool 660 and are positioned along successive portions of annulus 68, annulus-marking device 652 guides the successive portions of structure 662 under imaging as annulus-marking device 652 comprises a radiopaque material (e.g., nitinol or stainless steel). Annulus-marking device 652 comprises wire 654 that is shaped in a coil or spring. Wire 654 is generally deflectable to be pushed against tissue of annulus 68 and abut tissue of annulus 68 such that annulus-marking device 652 facilitates providing an image of a large percentage, e.g., at least 50% or at least 60%, of a perimeter of annulus 68. Additionally, wire 654 applies a pushing force against a portion of annulus 68 in such that system 650 ensures that annuloplasty structure 662 is properly positioned at a juncture between tissue of annulus 68 and tissue of the atrial wall at an external perimeter of annulus-marking device 652. In such a manner, device 652 ensures that annuloplasty structure 662 is positioned outside the external perimeter of wire 654 that is shaped as a coil or spring, responsively to the pushing of device 652 against tissue of annulus 68 such that annuloplasty structure 662 is implanted along annulus 68 and not on any part of the leaflets of valve 64.

Device 652 does not interfere with blood flow during implantation of annuloplasty structure 662 on a beating heart. Annulus-marking device 652 is at least partly stiff, and provides resistance, which facilitates positioning of structure 662. Annulus-marking device 652 can also provide tactile feedback to the operating physician.

For some applications, device 652 is positioned along an atrial surface of annulus 68 of valve 64. A first end portion of wire 654 of device 652 is positioned at a first commissure 61 of valve 64, e.g., an anteriolateral commissure. The first end portion of wire 654 is reversibly anchored in place at commissure 61 using a first anchor 656 which is deployed within the ventricle of the heart. For some applications, anchor 656 comprises a "T"-shaped anchor which reversibly catches tissue of the valve at the ventricular surface of the valve. Once the first end portion of wire 654 of device 652 is anchored to first commissure 61, successive portions of wire 654 of device 652 are deployed from within tool 651 and positioned along a portion of the perimeter of annulus 68 of valve 64. During the positioning of the successive portions of wire 654 of device 652, due to the shape-memory property of wire 654, device 652 assumed a curved shape and conforms to the shape of annulus 68. For some applications, device 652 applies a pushing force against tissue of annulus 68 in order to properly position device 652, and thereby annuloplasty structure 662, properly along annulus 68. For some applications, device 652 applies the pushing force due to the spring shape of coil-shaped wire 654 which has a tendency to expand radially and apply a radial pushing force against tissue of annulus 68.

Once coil-shaped wire 654 has been positioned along the posterior perimeter of valve 64, a second end portion of wire 654 of device 652 is positioned at a second commissure 63 of valve 64, e.g., a posterolateral commissure. The second end portion of wire 654 is reversibly anchored in place at commissure 63 using a second anchor 658 which is deployed within the ventricle of the heart. For some applications, anchor 656 comprises a "T"-shaped anchor which reversibly catches tissue of the valve at the ventricular surface of the valve.

Structure 662 comprises a body portion which comprises a flexible material and has a longitudinal axis that runs along the length of the body portion (e.g., when the body portion is straightened). The body portion comprises radiopaque markings to aid in imaging for accurate delivery of anchors to annulus 68 in order to anchor structure 662 to tissue of annulus 68.

In addition to providing tactile feedback, annulus-marking device 652 can also facilitate positioning of annuloplasty structure 662 by facilitating imaging (e.g., fluoroscopy) and mechanical guidance. For example, the presence of annulus-marking device 652 and/or the shape thereof (e.g., bending due to being pressed against an atrial wall) is visible in fluoroscopic imaging, and can be used to facilitate identification of the position and angle of annuloplasty structure 662 with respect to tissues.

Annulus-marking device 652 can be removed by pulling subsequent to the deployment of one or more tissue anchors in order to anchor structure 662. For some applications, annulus-marking device 652 is decoupled from commissures 61 and 63 by disengaging anchors 656 and 658 and device 652 is constrained within a tool in order to be retrieved and removed from the body of the subject. For some applications, device 652 is delivered together with the annuloplasty structure 662 in tool 660.

Following the implantation of the implant, device 652 is retrieved by constraining device 652 within a tool and extracted from the body of the subject. That is, device 652 does not function as an implant for such embodiments and is used only to guide implantation of the implant; rather, device 652 acts as a guide for implantation while placed temporarily within the body of the patient to be subsequently removed therefrom following the implantation of the implant.

Device 652 can be made from a superelastic material (e.g., nitinol or stainless steel) enabling it to be folded and collapsed such that it can be delivered in a catheter. Additionally, device 652 is made from radiopaque material to facilitate fluoroscopic visualization. For some applications, tissue of valve annulus 68 and tissue coupled thereto is viewed using device 652. Additionally, the tissue of the native heart valve annulus 68 and tissue coupled thereto is viewed by imaging annulus-marking device 652 with respect to the tissue of the native heart valve annulus and the tissue coupled thereto by viewing device 652 placed against the tissue. For some applications, the tissue of the native heart valve annulus 68 and tissue coupled thereto is viewed by imaging annulus-marking device 652 with respect to the tissue of the native heart valve annulus and the tissue coupled thereto by viewing movement of device 652 responsively to movement of the tissue.

Reference is now made to FIGS. 3A-B and 47. Annulus-marking device 652 can be coupled to a plurality of elements or filaments 99 and can be shaped in any suitable shape. Although system 650 is shown on mitral valve 64, system 650 can be used on any cardiac valve, e.g., a tricuspid valve, or any other tissue of the subject.

Figure 48:
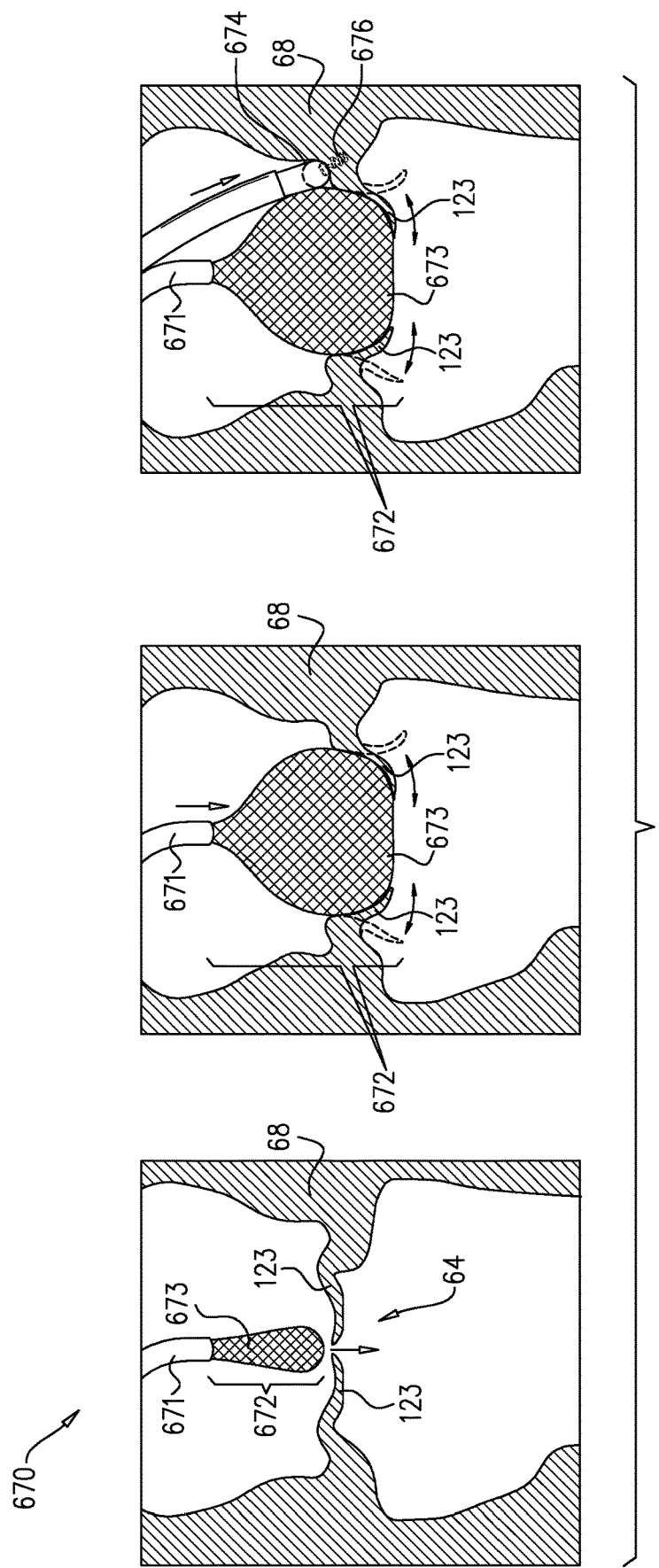
FIG. 48 is a schematic illustration of an annulus-marking device comprising an expandable element for aiding implantation of cardiac devices under the guidance of imaging, in accordance with some applications.

Reference is now made to FIG. 48, which is a schematic illustration of a system 670 comprising an annulus-marking device 672 that is positioned in the orifice of valve 64 in advance of an implant, e.g., an annuloplasty structure 674, in accordance with some applications. For some applications, annulus-marking device 672 leads and is placed in advance of the implant. Annulus-marking device 672 extends from within a delivery tool 671. For some applications, annulus-marking device 672 comprises an expandable element that assumes a spherical, generally spherical, bulbous, generally bulbous, ovoid, generally ovoid, teardrop, generally teardrop shape, etc. For some applications, annulus-marking device 672 comprises a stent-like mesh 673 comprising a plurality of expandable radiopaque elements (e.g., struts) coupled together to form a mesh (e.g., a fabric mesh or metal mesh), that is positioned partially within the orifice of valve 64 and does not significantly interfere with the function of valve 64. For some applications, annulus-marking device 672 comprises a tubular stent. For some applications, annulus-marking device 672 comprises a radiopaque balloon, e.g., a nylon balloon. As successive portions of annuloplasty structure 674 are extended from within its delivery tool and are positioned along successive portions of annulus 68, annulus-marking device 672 guides the successive portions of structure 674 under imaging as annulus-marking device 672 comprises a radiopaque material (e.g., nitinol or stainless steel).

Annulus-marking device 672 is at least partly stiff, and provides resistance, which facilitates positioning of structure 674. Annulus-marking device 672 can also provide tactile feedback to the operating physician.

Annuloplasty structure 674 comprises a body portion which comprises a flexible material and has a longitudinal axis that runs along the length of the body portion (e.g., when the body portion is straightened). The body portion comprises radiopaque markings to aid in imaging for accurate delivery of anchors 676 to annulus 68 in order to anchor structure 674 to tissue of annulus 68.

In addition to providing tactile feedback, annulus-marking device 672 can also facilitate positioning of annuloplasty structure 674 by facilitating imaging (e.g., fluoroscopy) and mechanical guidance. For example, the presence of annulus-marking device 672 and/or the shape thereof (e.g., bending due to being pressed against an atrial wall) is visible in fluoroscopic imaging, and can be used to facilitate identification of the position and angle of annuloplasty structure 674 with respect to tissues. Additionally, annulus-marking device 672 ensures that the delivery tool used to deliver structure 674 is positioned at an external perimeter of annulus-marking device 672 such that it is positioned between annulus-marking device 672 and atrial wall 122. That is, the delivery system used to deliver structure 674 is guided mechanically by the presence of the device 672.

Annulus-marking device 672 can be removed by being pulled and constrained within tool 671 in order to be retrieved and removed from the body of the subject.

For some applications, as shown, annulus-marking device 672 is delivered toward valve 64 in a delivery tool 671 that is separate from the delivery tool used to deliver the implant. For some applications, annulus-marking device 672 and the implant can be delivered from the same delivery tool.

Reference is now made to FIGS. 3A-B and 48. Annulus-marking device 672 can be coupled to a plurality of elements or filaments 99 and can be shaped in any suitable shape.

Device 672 can be made from a superelastic material (e.g., nitinol or stainless steel) enabling it to be folded and collapsed such that it can be delivered in a catheter. Device 672 can comprise a soft and compliant braid which enables mapping of the anatomy of the atrium, atrial wall, heart valve, annulus, and ventricle. For some applications, in its expanded state, device 672 contacts the atrial wall as it is configured to expand to a diameter that is greater than a dimension of the atrium. Since the material of device 672 is compliant, it does not change the natural shape of the anatomy of the atrium. Additionally, device 672 is made from radiopaque material to facilitate fluoroscopic visualization. For some applications, tissue of valve annulus 68 and tissue coupled thereto is viewed using device 672. Additionally, the tissue of the native heart valve annulus 68 and tissue coupled thereto is viewed by imaging annulus-marking device 672 with respect to the tissue of the native heart valve annulus and the tissue coupled thereto by viewing device 672 placed against the tissue. For some applications, the tissue of the native heart valve annulus 68 and tissue coupled thereto is viewed by imaging annulus-marking device 672 with respect to the tissue of the native heart valve annulus and the tissue coupled thereto by viewing movement of device 672 responsively to movement of the tissue.

It is to be noted that although system 670 is shown on mitral valve 64, system 670 can be used on any cardiac valve, e.g., a tricuspid valve, or any other tissue of the subject. It is to be further noted that although device 672 is shown as being delivered via the ventricle, device 672 may be delivered to the valve using any suitable delivery method into the atrium, e.g., transvascularly or using a minimally-invasive approach.

Figure 49A:
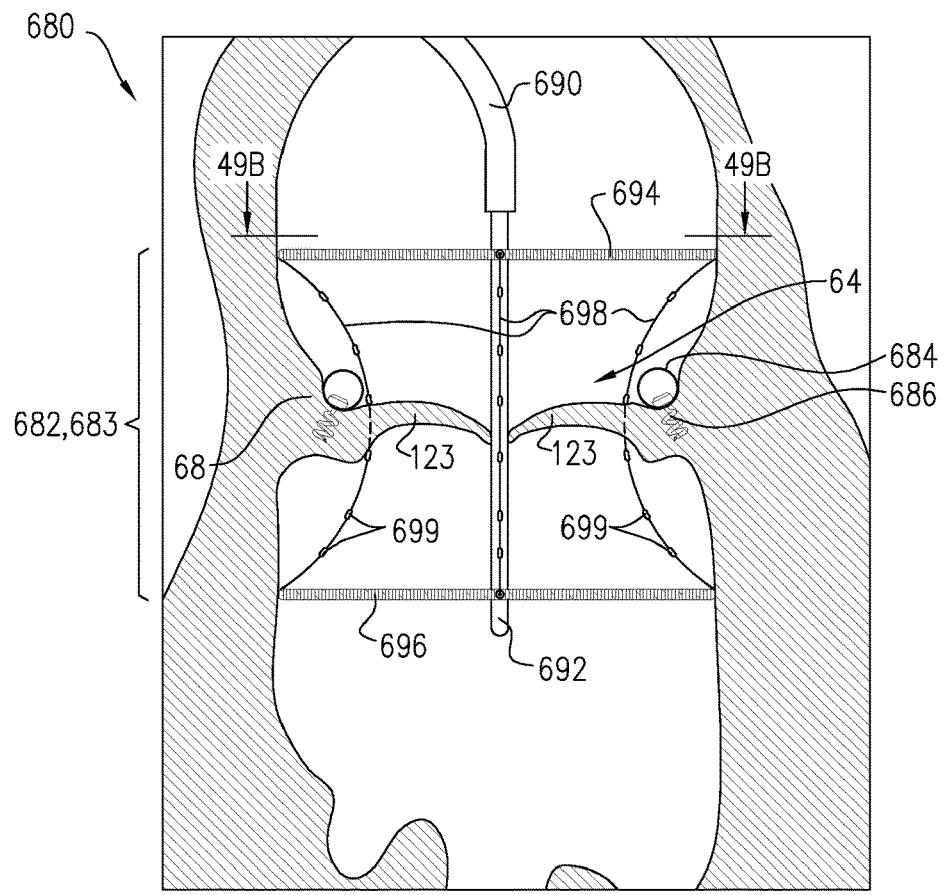
FIGS. 49A-B are schematic illustrations of an annulus-marking device comprising a scaffolding for aiding implantation of cardiac devices under the guidance of imaging, in accordance with some applications.
Figure 49B:
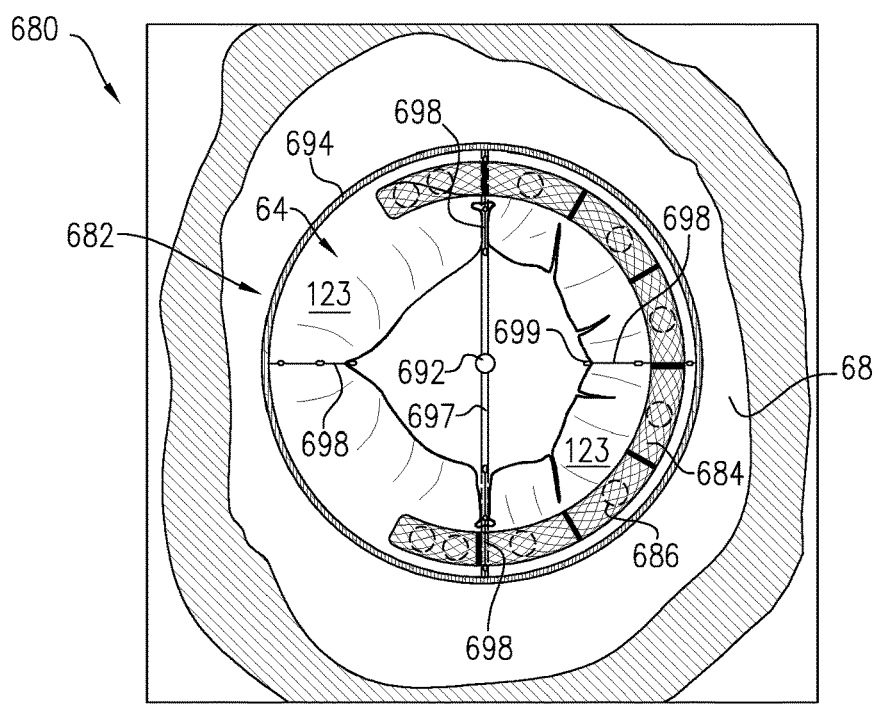

Reference is now made to FIGS. 49A-B, which are schematic illustrations of a system 680 comprising an annulus-marking device 682 for aiding implantation of cardiac devices under the guidance of imaging, in accordance with some applications. Device 682 comprises a scaffolding 683 that is collapsible and expandable. Scaffolding 683, is configured, when expanded, to laterally push against tissue of valve 64 (e.g., leaflet 123, annulus 68, or a commissure). Scaffolding 683 is radiopaque and comprises a plurality of radiopaque elements 699 which are flexible and shaped as bulbs by way of illustration and not limitation. For some applications of the present invention, radiopaque elements 699 can comprise filaments 99 described hereinabove.

In some applications, scaffolding 683 comprises a central rod 692, an upper laterally-expandable element 694 configured to expand laterally away from central rod 692, a lower laterally-expandable element 696 configured to expand laterally away from central rod 692, and at least one flexible wire 698 coupled to and extending between upper and lower laterally-expandable elements 694 and 696. For some applications, wire 698 comprises a vertical element. When scaffolding 683 is expanded, flexible wires 698 are configured to push against the tissue of valve 64 as is described hereinbelow. It is to be noted that scaffolding 683 comprises four flexible wires 698 by way of illustration and not limitation. For some applications, scaffolding 683 can comprise any number of wires 698. For some applications, scaffolding 683 can comprise a single wire 698. For some applications, scaffolding 683 can comprise two wires 698. Wires 698 comprise a flexible, radiopaque material, e.g., nitinol. A tension of wires 698 is increased by distancing upper and lower laterally-expandable elements 694 and 696 from each other. A tension of wires 698 is decreased by drawing closer upper and lower laterally-expandable elements 694 and 696. Upper and lower laterally-expandable elements 694 and 696 are moveable longitudinally proximally and distally with respect to central rod 692 to control a tension of the at least one flexible wire 698. The operating physician is able to discern whether wire 698 comes in contact with tissue of the heart (e.g., leaflet, commissure, or annulus) by observing deformation of wire 698 responsively to the presence of tissue and the force applied to wire 698 by the tissue.

When scaffolding 683 is expanded, upper laterally-expandable element 694 is configured to be disposed in an atrium of the heart, and lower laterally-expandable element 696 is configured to be disposed in a ventricle of the heart.

For some applications, scaffolding 683 comprises two wires 698 to help center device 682 and/or tool 690 as each wire 698 pushes against the tissue. It is to be noted that any suitable number of wires 698 can be coupled to elements 694 and 696. Scaffolding 683 helps stabilize device 682 in valve 64.

Upper and lower laterally-expandable elements 694 and 696 each comprise a respective expandable and collapsible ring. Wires 698 are coupled at corresponding locations circumferentially along the rings of laterally-expandable elements 694 and 696. When scaffolding 683 is expanded, the first and second rings are in an expanded state. Upper and lower laterally-expandable elements 694 and 696 each comprise a respective expandable and collapsible cross-beam 697 that extends laterally away from central rod 692. For some applications, wires 698 are coupled at corresponding locations along cross-beams 697. When scaffolding 683 is expanded, cross-beams 697 are in an expanded state. For some applications, elements 694 and 696 expand to a fixed radius. For some applications, elements 694 and 696 may expand to abut tissue of the heart such as atrial wall 122.

When scaffolding 683 is expanded and wires 698 are pulled into a tense state, wires 698 of scaffolding 683 are configured to push against tissue of the heart in order to provide an indication of the presence of the tissue. For some applications, wires 698 push against tissue of valve 64 at the commissures. For some applications, wires 698 push against tissue of leaflet 123 of valve 64. For some applications, as each wire 698 pushes against tissue of leaflet 123, wire 698 creates a bicuspidization of the leaflet in a manner in which leaflet 123 assumes two subcusps.

Annulus-marking device 682 is configured help visualize the placement of an implant 684 (e.g., an annuloplasty structure, as shown) configured for placement along annulus 68 of valve 64 of the subject.

Annulus-marking device 682 is coupled to a delivery tool 690 and is collapsible within a lumen of tool 690 during delivery of device 682 within valve 64. Annulus-marking device 682 is retrievable upon removal of delivery tool 690 from the subject.

Scaffolding 683 comprises radiopaque material (e.g., nitinol or stainless steel) and is flexible. A plurality of radiopaque elements, such as radiopaque filaments 99, (not shown) can be coupled to scaffolding 683 at any suitable portion thereof. The plurality of radiopaque elements or filaments 99 function as additional annulus-marking devices. Annulus-marking device 682 is configured for aiding implantation of cardiac devices under the guidance of imaging, in accordance with some applications. The steering procedure is performed with the aid of imaging, such as fluoroscopy, transesophageal echo, and/or echocardiography.

Device 682 may be delivered percutaneously, thoracoscopically through the chest, or using open heart surgical techniques. If delivered percutaneously, device 682 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 682 comprises a wire.

Device 682 enables mapping of the anatomy of the atrium, atrial wall, heart valve, annulus, and ventricle. Additionally, device 682 is made from radiopaque material to facilitate fluoroscopic visualization. For some applications, tissue of valve annulus 68 and tissue coupled thereto is viewed using device 682. Additionally, the tissue of the native heart valve annulus 68 and tissue coupled thereto is viewed by imaging annulus-marking device 682 with respect to the tissue of the native heart valve annulus and the tissue coupled thereto by viewing device 682 placed against the tissue. For some applications, the tissue of the native heart valve annulus 68 and tissue coupled thereto is viewed by imaging annulus-marking device 682 with respect to the tissue of the native heart valve annulus and the tissue coupled thereto by viewing movement of device 682 responsively to movement of the tissue.

Subsequently to implanting of implant 684, annulus-marking device 682 is retrieved. Since device 682 is flexible and compressible, device 682 is constrained within the tool during the retrieval of device 682 and subsequent removal of device 682 from the body of the subject. That is, device 682 does not function as an implant for such embodiments and is used only to guide implantation of implant 684; rather, device 682 acts as a guide for implantation while placed temporarily within the body of the patient to be subsequently removed therefrom following the implantation of implant 684.

It is to be noted that although system 680 is shown on mitral valve 64, system 680 can be used on any cardiac valve, e.g., a tricuspid valve, or any other tissue of the subject.

Figure 50A:
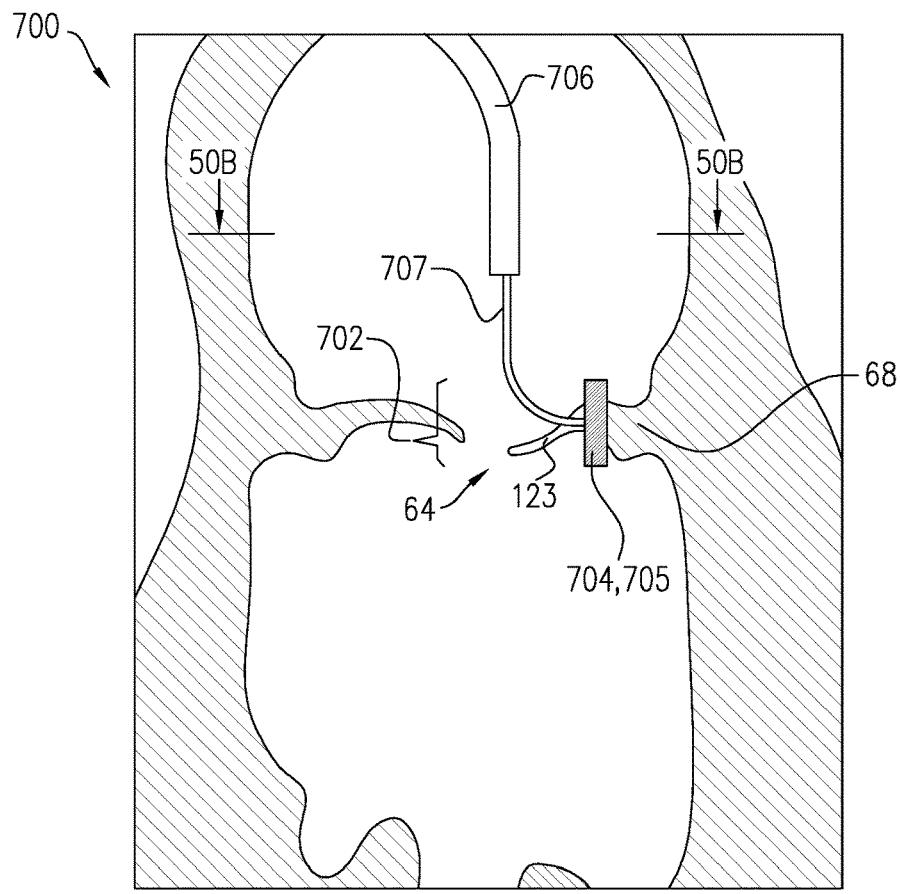
FIGS. 50A-B are schematic illustrations of an annulus-marking device comprising a scaffolding comprising a rod for aiding implantation of cardiac devices under the guidance of imaging, in accordance with some applications.
Figure 50B:
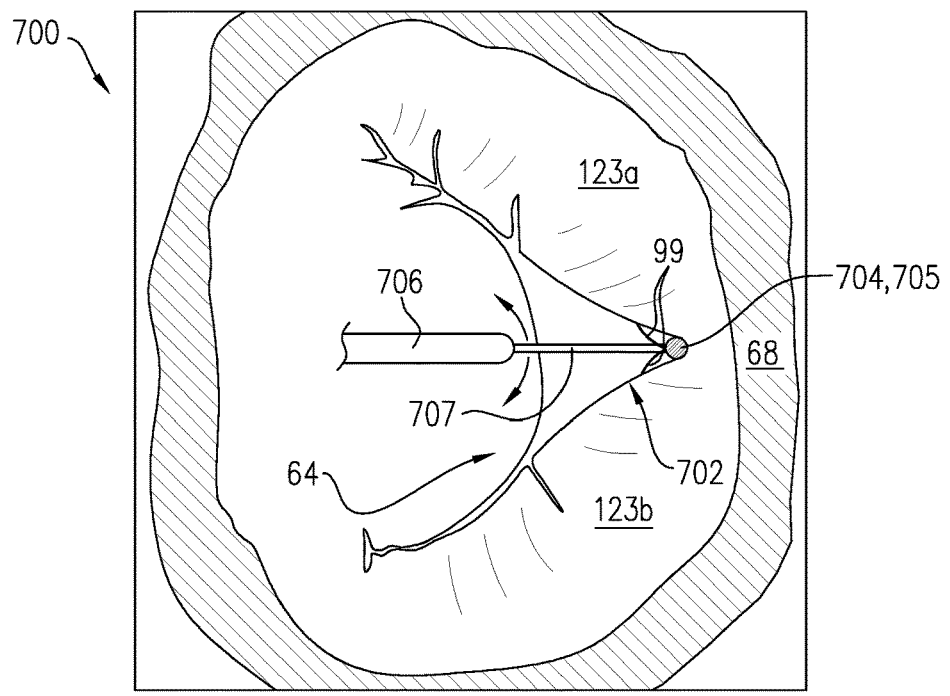

Reference is now made to FIGS. 50A-B, which are schematic illustrations of a system 700 comprising an annulus-marking device 702 for aiding implantation of cardiac devices under the guidance of imaging, in accordance with some applications. Device 702 comprises a scaffolding 705 that is collapsible and expandable. Scaffolding 705, is configured, when expanded, to laterally push against tissue of valve 64 (e.g., leaflet 123, annulus 68, or a commissure).

Scaffolding 705 comprises a radiopaque material (e.g., nitinol or stainless steel) and comprises a wire or rod 704. For some applications, rod 704 comprises a vertical element. Typically, when scaffolding 705 is expanded, rod 704 assumes a vertical orientation and extends from an atrial surface of valve 64 toward a ventricular surface of valve 64.

For some applications, as rod 704 pushes against tissue of leaflet 123, rod 704 creates a bicuspidization of the leaflet in a manner in which leaflet 123 assumes two subcusps 123a and 123b, as shown in FIG. 50B.

Annulus-marking device 702 is coupled to a delivery tool 706 and is collapsible within a lumen of tool 706 during delivery of device 702 within valve 64. Annulus-marking device 702 is retrievable upon removal of delivery tool 706 from the subject. Rod 704 is coupled to a steerable shaft 707 that is disposed and slidable within the lumen of tool 706. Shaft 707 is steerable to move rod 704 along annulus 68. Rod 704 is moved with each implantation of a tissue anchor used to implant the implant (e.g., annuloplasty structure). That is, after one anchor is implanted, rod 704 is moved to a different location of valve 64 in order to indicate a position of annulus 68 at the location such that visual feedback is provided to the operating physician as to the next location to deploy another tissue anchor.

It is to be noted that device 702 can comprise any suitable number of rods 704 and shafts 707.

For some applications of the present invention, as shown, rod 704 is coupled to a plurality of radiopaque elements (e.g., radiopaque filaments 99, etc.) described hereinabove. The plurality of radiopaque elements or filaments 99 function as additional annulus-marking devices. The radiopaque elements or filaments 99 comprise radiopaque material (e.g., nitinol or stainless steel) and can be configured to be extremely flexible. In some embodiments, filaments 99 project away from rod 704. For some applications, filaments 99 sway with movement of the blood. For some applications, filaments 99 press against tissue of annulus 68 and tissue coupled thereto (as shown in FIG. 50B), such as tissue of an atrial wall as well as tissue of leaflets 123 of the native valve. Elements or filaments 99 thus provide enhanced imaging of tissue of valve 64. For example, in some embodiments, when filaments 99 appear bent or pressed, this imaging detects annulus tissue, while when filaments 99 are straight, this could indicate the orifice of the valve.

In some embodiments, filaments 99 disposed above leaflet 123 remain static, while filaments 99 disposed at leaflets 123 move and pulse with leaflet movement. A boundary between the moving and static filaments can be observed using fluoroscopy in order to indicate the root, or base, or leaflet 123.

Annulus-marking device 702 is configured for aiding implantation of cardiac devices under the guidance of imaging, in accordance with some applications. The steering procedure is performed with the aid of imaging, such as fluoroscopy, transesophageal echo, and/or echocardiography. Device 702 may be delivered percutaneously, thoracoscopically through the chest, or using open heart surgical techniques. If delivered percutaneously, device 702 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 702 comprises a wire.

Device 702 can be made from a superelastic material (e.g., nitinol or stainless steel) enabling it to be folded and collapsed such that it can be delivered in a catheter. Device 702 enables mapping of the anatomy of the atrium, atrial wall, heart valve, annulus, and ventricle. Additionally, device 702 is made from radiopaque material to facilitate fluoroscopic visualization. For some applications, tissue of valve annulus 68 and tissue coupled thereto is viewed using device 702. Additionally, the tissue of the native heart valve annulus 68 and tissue coupled thereto is viewed by imaging annulus-marking device 702 with respect to the tissue of the native heart valve annulus and the tissue coupled thereto by viewing device 702 placed against the tissue. For some applications, the tissue of the native heart valve annulus 68 and tissue coupled thereto is viewed by imaging annulus-marking device 702 with respect to the tissue of the native heart valve annulus and the tissue coupled thereto by viewing movement of device 702 responsively to movement of the tissue.

Subsequently to implanting of the implant, annulus-marking device 702 is retrieved. Since device 702 is flexible and compressible, device 702 is constrained within the tool during the retrieval of device 702 and subsequent removal of device 702 from the body of the subject. That is, device 702 does not function as an implant for such embodiments and is used only to guide implantation of the implant; rather, device 702 acts as a guide for implantation while placed temporarily within the body of the patient to be subsequently removed therefrom following the implantation of the implant.

It is to be noted that although system 700 is shown on mitral valve 64, system 700 can be used on any cardiac valve, e.g., a tricuspid valve, or any other tissue of the subject.

Reference is now made to FIGS. 51A-C, which are schematic illustrations of a system 710 comprising an annulus-marking device 712 for aiding implantation of cardiac devices under the guidance of imaging, in accordance with some applications. Device 712 comprises a scaffolding 713 that is collapsible and expandable. Scaffolding 713, is configured, when expanded, to laterally push against tissue of valve 64 (e.g., leaflet 123, annulus 68, or a commissure). Scaffolding 713 comprises a radiopaque material (e.g., nitinol or stainless steel) and comprises a basket 714 shapes so as to define a plurality of vertical elements 716, e.g., rods as described hereinabove with reference to FIGS. 50A-B or other elongate members, wires, tubes, loops, etc. Typically, scaffolding 713 expands circumferentially with respect to valve 64 in a manner in which elements 716, or the rods, are disposed circumferentially with respect valve 64. When scaffolding 713 is expanded, elements 716 assume vertical orientations and extends from an atrial surface valve 64 toward a ventricular surface of valve 64. A radius of expansion of basket 714 is controlled by movement of structural elements 715 toward or away from each other along a central rod 717. As shown in FIG. 51A, elements 715 can be distanced from each other such that basket 714 assumes a narrower configuration. The closer elements 715 are toward each other, the more expanded and wider basket 714 is (FIG. 51B). For some applications, basket 714 is manually expanded. For some applications, basket 714 is configured to self-expand.

For some applications, as wire elements 716 push against tissue of leaflet 123, elements 716 create a multi-cuspidization of the leaflet in a manner in which leaflet 123 assumes subcusps, as shown in FIG. 51C. As shown, device 712 can be positioned within valve 64. For some applications, device 712 may rest atop valve 64. For some applications, device 712 comprises two or more leaflets in order to regulate blood flow while device 712 is positioned in valve 64.

Annulus-marking device 712 is coupled to a delivery tool 718 and is collapsible within a lumen of tool 718 during delivery of device 712 within valve 64. Annulus-marking device 712 is retrievable upon removal of delivery tool 718 from the subject.

It is to be noted that device 712 can comprise any suitable number of elements 716. For some applications, scaffolding 713 and/or basket 714 comprises 3 vertical elements 716. For some applications, scaffolding 713 and/or basket 714 comprises 5-8 vertical elements 716.

For some applications of the present invention, as shown, each vertical element 716 is coupled to a plurality of radiopaque elements, e.g., radiopaque filaments 99, etc., described hereinabove. The plurality of radiopaque elements or filaments 99 function as additional annulus-marking devices. (While often described as filaments herein, other types of radiopaque materials, markers, wires, extensions, beads, etc. can also or alternatively be used.) Elements or filaments 99 comprise radiopaque material (e.g., nitinol or stainless steel) and can be configured to be extremely flexible. In some applications, elements or filaments 99 project away from rod 704. For some applications, filaments 99 sway with movement of the blood. For some applications, filaments 99 press against tissue of annulus 68 and tissue coupled thereto (as shown in FIGS. 51B-C), such as tissue of an atrial wall as well as tissue of leaflets 123 of the native valve. Radiopaque elements or filaments 99 thus provide enhanced imaging of tissue of valve 64. For example, in some applications, when filaments 99 appear bent or pressed, this imaging detects annulus tissue, while when filaments 99 are straight, this could indicate the orifice of the valve.

Filaments 99 disposed above leaflet 123 remain static, while filaments 99 disposed at leaflets 123 move and pulse with leaflet movement. A boundary between the moving and static filaments can be observed using fluoroscopy in order to indicate the root, or base, or leaflet 123.

Annulus-marking device 712 is configured for aiding implantation of cardiac devices under the guidance of imaging, in accordance with some applications. The steering procedure is performed with the aid of imaging, such as fluoroscopy, transesophageal echo, and/or echocardiography. Device 712 can be delivered percutaneously, thoracoscopically through the chest, or using open heart surgical techniques. If delivered percutaneously, device 712 can be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic resonance, computed tomography, or combinations thereof). For some applications, device 712 comprises a wire.

Device 712 enables mapping of the anatomy of the atrium, atrial wall, heart valve, annulus, and ventricle. Additionally, device 712 is made from radiopaque material to facilitate fluoroscopic visualization. For some applications, tissue of valve annulus 68 and tissue coupled thereto is viewed using device 712. Additionally, the tissue of the native heart valve annulus 68 and tissue coupled thereto is viewed by imaging annulus-marking device 712 with respect to the tissue of the native heart valve annulus and the tissue coupled thereto by viewing device 712 placed against the tissue. For some applications, the tissue of the native heart valve annulus 68 and tissue coupled thereto is viewed by imaging annulus-marking device 712 with respect to the tissue of the native heart valve annulus and the tissue coupled thereto by viewing movement of device 712 responsively to movement of the tissue.

Subsequently to implanting of the implant, annulus-marking device 712 is retrieved. Since device 712 is flexible and compressible, device 712 is constrained within tool 718 during the retrieval of device 712 and subsequent removal of device 712 from the body of the subject. That is, device 712 does not function as an implant for such embodiments and is used only to guide implantation of the implant; rather, device 712 acts as a guide for implantation while placed temporarily within the body of the patient to be subsequently removed therefrom following the implantation of the implant.

It is to be noted that although system 710 is shown on mitral valve 64, system 710 can be used on any cardiac valve, e.g., a tricuspid valve, or any other tissue of the subject.

Reference is now made to FIGS. 52A-B, which are schematic illustrations of a system 730 comprising an annulus-marking device 732 that comprises at least one marker or radiopaque loop 734, but in some applications comprises a plurality of radiopaque markers or radiopaque loops 734, for facilitating imaging of cardiac tissue during implantation of a cardiac implant. Device 732 comprises a flexible, radiopaque material, e.g., nitinol or stainless steel, which facilitates expanding and compressing of device 732. For some applications, device 732 comprises 1-10 markers 734, e.g., 4 markers 734, 5 markers 734, etc. For some applications, device 732 itself is radiopaque. In some implementations, one or more markers or loops 734 can include one or more additional radiopaque elements thereon, e.g., radiopaque filaments, radiopaque wires, radiopaque extensions, radiopaque markers, radiopaque beads, etc., and one or more locations around the marker(s) or loop(s) 734. Further, while shown largely in the same plane in FIG. 52A-52B, in some implementations, one or more of the plurality of markers or loops 734 can be offset rotationally relative to other markers or loops 734 such that it is in a different plane (e.g., a plane rotated between 20-160 degrees from each other, such as 90 degrees or 120 degrees, etc.).

In some embodiments, the plurality of radiopaque markers 734 juxtapose each other at a given distance from each other and are each deformable by tissue at different intervals indicating proximity of tissue to the implant. The plurality of radiopaque markers can be sized differently from each other. As shown by way of illustration and not limitation, markers 734 comprise concentric loops which fan out distally and laterally from a proximal portion of device 732. For some applications, the plurality of radiopaque markers 734 can comprise and/or be configured as petals or loops which fan out distally and laterally from a proximal portion of device 732. In some embodiments, the petals or loops are concentric. For some applications, the plurality of radiopaque markers 734 comprise a plurality of radiopaque strips which fan out distally and laterally from a proximal portion of device 732. For some applications, the plurality of radiopaque markers 734 comprise a wire. For some applications, each one of the plurality of radiopaque markers 734 comprises a radiopaque sail extending therefrom in order to increase radiopacity. For some applications, each one of the plurality of radiopaque markers 734 comprises a radiopaque element (e.g., filament 99 or other element described hereinabove) extending therefrom.

Since each one of the plurality of markers 734 contacts tissue of valve 64 at different times, the physician is able to determine the position of device 732 with respect to the tissue and determine the position of implant, e.g., annuloplasty structure 738 with respect to device 732 and thereby with respect to tissue of valve 64. That is, the longest marker 734 is configured to contact tissue first, followed by the next longest. Each of markers 734 are stacked around each other.

For some applications, a largest marker 734 of the plurality of markers is configured for placement in between leaflets 123 of valve 64, e.g., at the commissure by way of illustration and not limitation.

Device 732 is delivered using a delivery tool 736. It is to be noted that device 732 is discrete from the implant and, for some applications, implant is delivered using a delivery tool other than delivery tool 736. For some applications, the tool is shaped to define a lumen through which the implant is delivered. The implant is implanted while annulus-marking device 732 guides implantation thereof and ensures that the implant is implanted at the correct location of annulus 68 of valve 64. Since device 732 is radiopaque, implantation of the implant can be guided under fluoroscopy only, e.g., using two angles.

For some applications, during delivery of device 732, device 732 is in a compressed state within an external catheter. Once inside the atrium, the external catheter is retracted and device 732 is allowed to expand to assume a shape because of its shape-memory material. The tool is then advanced toward annulus 68 and using tactile feedback, device 732 is pressed against annulus 68. Under fluoroscopy, device 732 is imaged in order to determine whether the tool is appropriately positioned along annulus 68. That is, if the physician sees that a number of markers 734 of device 732 are bent, the physician determines that the tool is in the right place along annulus 68, e.g., on annulus 68, against an atrial wall, and/or at the hinge. If the physician detects movement of any number of markers 734, the physician determines that the tool is positioned at least partially along leaflet 123 of valve 64.

If the physician detects some markers 734 bent and some straight and moving, the physician can determine that tool is positioned partially on the annulus and partially on the leaflet.

For some applications, the physician compares an overall configuration of device 732 and its markers 734 to an ideal configuration of device 732 which is indicative of correct positioning of the tool at annulus 68 in order to facilitate proper positioning of the implant along annulus 68. The physician can determine proximity of the tool to the atrial wall. For some applications, device 732 is used to measure the height of annulus 68.

It is to be noted that although system 730 is shown on mitral valve 64, system 730 can be used on any cardiac valve, e.g., a tricuspid valve, or any other tissue of the subject.

Figure 53A:
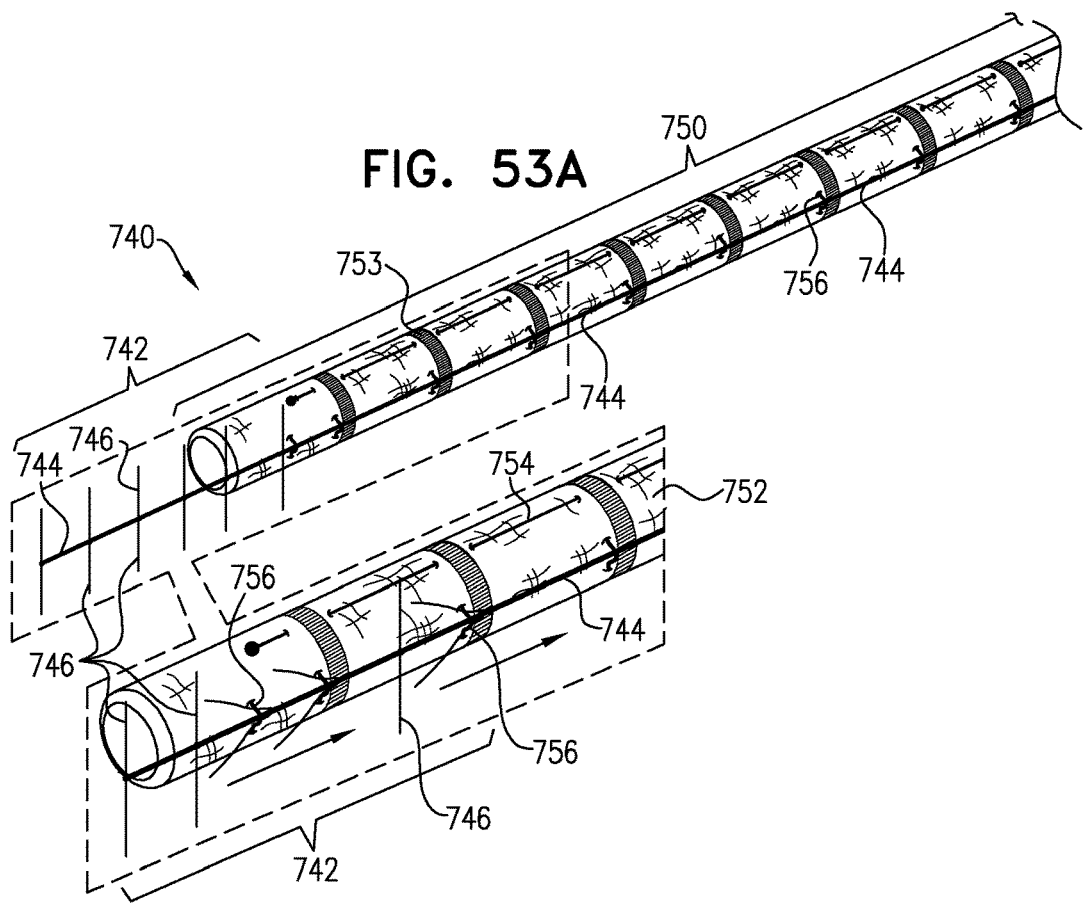
FIGS. 53A-B and 54A-B are schematic illustrations of an annulus-marking device coupled to an implant, for aiding implantation of cardiac devices under the guidance of imaging, in accordance with some applications.
Figure 53B:
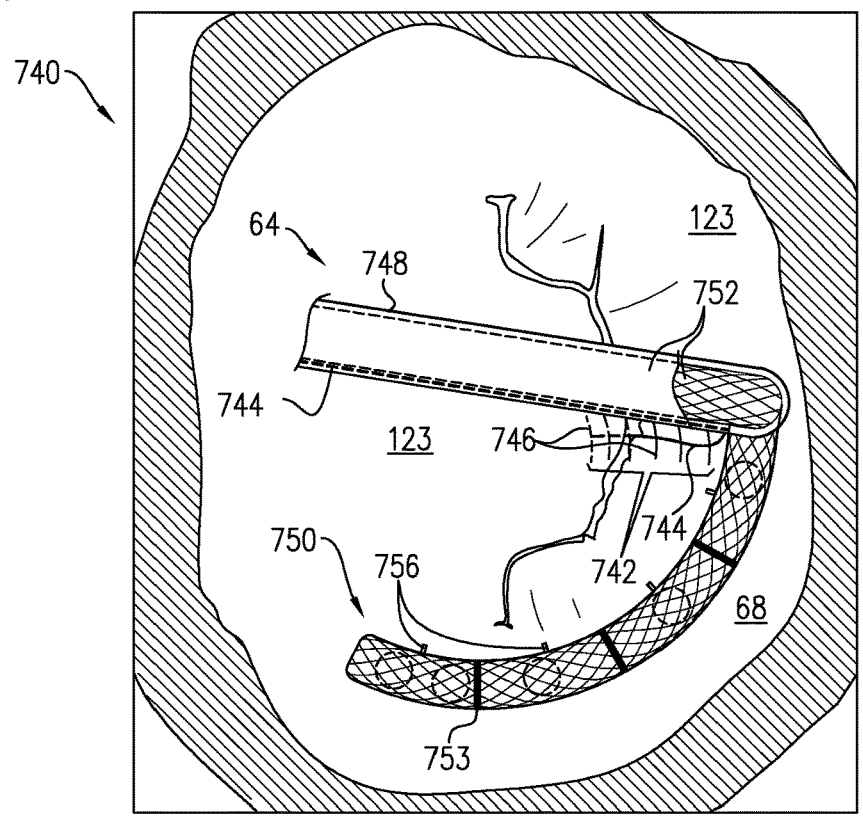

Reference is made to FIGS. 53A-B, which are schematic illustrations of a navigational-based guidance system 740, which employs one or more longitudinal guides configured to facilitate guidance of an implant 750 to specific portions of annulus 68 by the guides contacting a surface of the valve (e.g., the annulus, commissure, and/or leaflets of the valve), in accordance with some applications. The longitudinal guide comprises an annulus marking device 742 which comprises a plurality of radiopaque filaments 746 that are coupled to a distal end portion of an elongate radiopaque element 744. For some applications, elongate radiopaque element 744 comprises a flexible wire. For some applications, elongate radiopaque element 744 comprises a flexible rod. Elongate radiopaque element 744 slides with respect to body portion 752 along the longitudinal axis in order to move the plurality of radiopaque filaments 746 with respect to implant 750. The guide comprising device 742 and element 744 comprises a flexible material (e.g., a flexible metal such as nitinol or stainless steel), and each guide is radiopaque. A plurality of eyelets 756 are disposed along a lateral outer surface of a body portion 752 of implant 750, and each guide (e.g., a distal portion thereof) is disposed within at least some of the eyelets (e.g., the guide is threaded through the eyelets). Eyelets 756 can comprise suture or fabric.

In some applications, eyelets 756 are arranged in a longitudinal row along the length of body portion 752, and the guide is disposed within the eyelets of a respective row. For some applications body portion 752 comprises a plurality of radiopaque markers 753, which are positioned along the body portion at respective longitudinal sites. For some applications the eyelets are disposed at the same longitudinal site as a corresponding radiopaque marker. Though, optionally, the eyelets can be disposed between radiopaque markers.

For some applications, the distal end portion of elongate radiopaque element 744 protrudes longitudinally outward from body portion 752. Such protruding may confer a desired behavior on annulus-marking device 742, e.g., during distal movement of device 742. For example, when the device 742 is moved distally against tissue, the protrusion may facilitate splaying of device 742 over the tissue.

Body portion 752 of implant 750 is configured to be advanced distally out of a delivery tool 748 and anchored to annulus 68 using anchors. Elongate radiopaque element 744 is disposed within a lumen of and slidable with respect to delivery tool 748. For some applications, as shown, device 742 follows a path that extends distally from a distal end of delivery tool 748, touches annulus 68, and projects distally along leaflet 123 and toward the ventricle, as shown in FIG. 53B. In such a manner, device 742 functions as vertical elements 716, e.g., rods as described hereinabove with reference to FIGS. 51A-C. Optionally, for some applications, device 742 extends longitudinally along body portion 752 of implant 750.

As implant 750 is delivered within delivery tool 748, device 742 is disposed in alignment with, e.g., parallel to, body portion 752 of implant 750. As implant 750 is disposed in a linear configuration as shown in FIG. 53A, device 742 is moved linearly along and/or in parallel with a longitudinal axis of body portion 752. Once implant 750 is deployed along annulus 68, implant 750 curves, and device 742 may passively extend away from the path along which implant 750 extends. That is, device 742 extends distally from the distal end of delivery tool 748, at a nonzero angle, e.g., perpendicularly, with respect to the plane of annulus 68. As implant 750 is deployed from within delivery tool 748, it extends distally while device 742 remains in place. Alternatively, or in succession, device 742 is pulled proximally with respect to body portion 752 by pulling on elongate radiopaque element 744 with respect to body portion 752. In either application, during relative movement of device 742 and body portion 752, radiopaque filaments 746 collapse and pass through eyelets 756. During movement of filaments 746 with respect to eyelets 756, friction is generated which provides the operating physician with tactile feedback in addition to the imaging.

Annulus-marking device 742 is placed (e.g., pushed) against tissue of the valve, e.g., by virtue of being already disposed distally to a distal end of body portion 752, or by being advanced distally after the distal end of the body portion has itself been placed against tissue of the valve. Device 742 thereby comprises a tissue-engaging portion that is configured to be placed in contact with tissue of the subject.

In one or more ways, the behavior of device 742 in response to being placed against the tissue of the valve facilitates guidance by viewing of body portion 752 (e.g., positioning of the body portion on the annulus). For example:

Resistance of device 742 being pushed further distally may indicate that the device is in contact with tissue that resists forces applied by the guide. For example, the distal end of the device may be abutting annulus 68 and/or a wall of the atrium. Conversely, lack of resistance of device 742 to being pushed further distally may indicate that the distal end of the device is not in contact with tissue that resists forces applied by the guide. For example, the distal end of the device may be moving between leaflets 123 of the valve (e.g., at a commissure), and/or may be pushing a leaflet 123 downward (e.g., into the ventricle). Such resistance (or lack thereof) can be detected mechanically (e.g., as tactile feedback to the operating physician and/or by an extracorporeal control unit). Since device 742 comprise radiopaque material, such resistance (or lack thereof) can be detected via imaging (e.g., fluoroscopically).

Similarly, the position, orientation and/or shape of device 742 (e.g., with respect to body portion 752 of implant 750, tissue of the valve, etc.) may indicate against what, if anything, the device 742 is disposed. Imaging techniques such as fluoroscopy can be used to identify this position, orientation and/or shape of the device. For example, if the distal end of device 742 is positioned at the same height (i.e., at the same place on a superior-inferior axis of the subject) as the distal end of body portion 752, this may indicate that body portion 752 and device 742 abut the same surface (e.g., annulus 68). Conversely, if the distal end of device 742 is positioned lower than body portion 752, this may indicate that the body portion 752 is disposed against annulus 68, while device 742 has passed toward or into the ventricle. Movement (e.g., beating) of the device 742 may indicate that the guide is disposed against a leaflet of the valve, and that the leaflet is moving the device as the heart beats. Such imaging may be facilitated by one or more components comprising radiopaque markings. For some applications, each device 742 comprises radiopaque filaments 746, so as to facilitate identification during imaging.

Filaments 746 comprise radiopaque material (e.g., nitinol or stainless steel) and can be configured to be extremely flexible. Filaments 746 project away from elongate radiopaque element 744. For some applications, filaments 746 sway with movement of the blood. For some applications, filaments 746 press against tissue of annulus 68 and tissue coupled thereto (as shown in FIG. 53B), such as tissue of an atrial wall as well as tissue of leaflets 123 of the native valve. Filaments 746 thus provide enhanced imaging of tissue of valve 64. That is, when filaments 746 appear bent or pressed, this imaging detects annulus tissue, while when filaments 746 are straight, this could indicate the orifice of the valve.

Filaments 746 disposed above leaflet 123 remain static, while filaments 746 disposed at leaflets 123 move and pulse with leaflet movement. A boundary between the moving and static filaments can be observed using fluoroscopy in order to indicate the root, or base, or leaflet 123.

FIG. 53B shows body portion 752 having been placed against annulus 68 of the subject in a vicinity of left fibrous trigone. Device 742 is disposed distally to body portion 752, and has splayed across annulus 68, e.g., due to resistance of the annulus. As described hereinabove, this can be detected mechanically and/or by imaging. The position, orientation and/or shape of device 742, alone and/or in combination with the other elements indicates that the portion of body portion 752 is positioned against firm tissue that is close to the commissure, which for some applications is the preferred position for anchoring of the portion of body portion 752. Identification (e.g., mechanically and/or by imaging) of which guide is in which position can further indicate the rotational orientation of body portion 752.

Once the desired position has been identified, an anchor (e.g., a first anchor) is used to anchor body portion 752. For some applications, device 742 and elongate radiopaque element 744 can be withdrawn slightly proximally before anchoring, e.g., so as to reduce a likelihood of inadvertently anchoring the guide to the tissue. As element 744 is withdrawn, filaments 746 are collapsible as they pass through each one of the plurality of eyelets 756 (FIG. 53A) and expandable subsequently to passing through each eyelet 756 as filaments 746 have shape-memory. Subsequently, additional portions of body portion 752 are anchored to annulus 68. In some applications, device 742 is moved proximally with respect to body portion 752. This process can be repeated for each anchor until implant 750 is fully implanted.

Following implantation of implant 750, device 742 is removed from the body of the subject. Device 742 is removed from within the body by pulling proximally on elongate radiopaque element 744. Filaments 746 collapse within a lumen of delivery tool 748.

It is to be noted that although system 740 is shown on mitral valve 64, system 740 can be used on any cardiac valve, e.g., a tricuspid valve, or any other tissue of the subject.

Figure 54A:
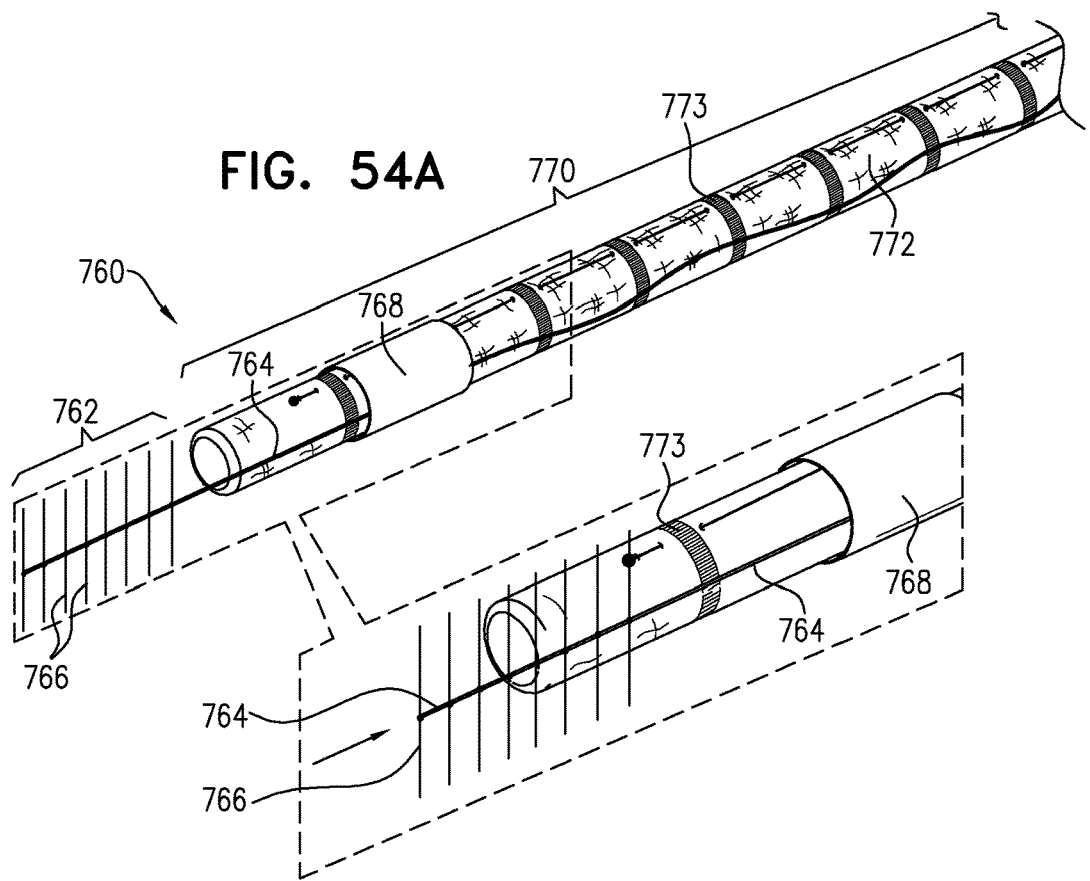
Figure 54B:
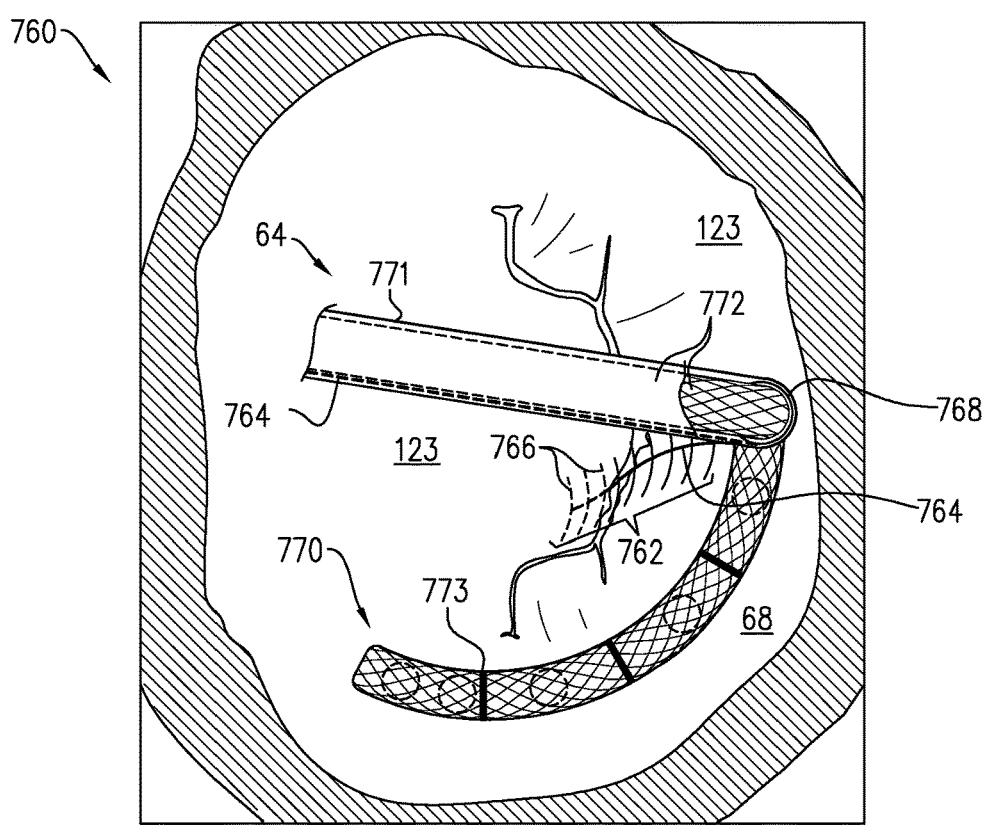

Reference is made to FIGS. 54A-B, which are schematic illustrations of a navigational-based guidance system 760, which employs one or more longitudinal guides configured to facilitate guidance of an implant 770 to specific portions of annulus 68 by the guides contacting a surface of the valve (e.g., the annulus, commissure, and/or leaflets of the valve), in accordance with some applications. The longitudinal guide comprises an annulus marking device 762 which comprises a plurality of radiopaque filaments 766 that are coupled to a distal end portion of an elongate radiopaque element 764. For some applications, elongate radiopaque element 764 comprises a flexible wire. For some applications, elongate radiopaque element 764 comprises a flexible rod. The guide comprising device 762 and element 764 comprises a flexible material (e.g., a flexible metal such as nitinol or stainless steel), and each guide is radiopaque. A proximal end of element 764 is coupled to a tube 768 which surrounds body portion 772 of implant 770 and slides with respect to body portion 772 to move the plurality of radiopaque filaments 766 with respect to implant 770.

For some applications, the distal end portion of each elongate radiopaque element 764 protrudes longitudinally outward from body portion 772. Such protruding may confer a desired behavior on annulus-marking device 762, e.g., during distal movement of device 762. For example, when the device 762 is moved distally against tissue, the protrusion may facilitate splaying of device 762 over the tissue.

Body portion 772 of implant 770 is configured to be advanced distally out of a delivery tool 771 and anchored to annulus 68 using anchors. Elongate radiopaque element 764 is disposed within a lumen of and slidable with respect to delivery tool 771. For some applications, as shown, device 762 follows a path that extends distally from a distal end of delivery tool 771, touches annulus 68, and projects distally along leaflet 123 and toward the ventricle, as shown in FIG. 54B. In such a manner, device 762 functions as vertical elements 716, e.g., rods as described hereinabove with reference to FIGS. 51A-C. Optionally, for some applications, device 762 extends longitudinally along body portion 772 of implant 770.

As implant 770 is delivered within delivery tool 771, device 762 is disposed in alignment with, e.g., parallel to, body portion 772 of implant 770. As implant 770 is disposed in a linear configuration as shown in FIG. 54A, device 762 is moved linearly along and/or in parallel with a longitudinal axis of body portion 772. Once implant 770 is deployed along annulus 68, implant 770 curves, and device 762 may passively extend away from the path along which implant 770 extends. That is, device 762 extends distally from the distal end of delivery tool 771, at a nonzero angle, e.g., perpendicularly, with respect to the plane of annulus 68. As implant 770 is deployed from within delivery tool 771, it extends distally while device 762 remains in place. Alternatively, or in succession, device 762 is pulled proximally with respect to body portion 772 by pulling on elongate radiopaque element 764 and/or pulling on tube 768 with respect to body portion 772.

Annulus-marking device 762 is placed (e.g., pushed) against tissue of the valve, e.g., by virtue of being already disposed distally to a distal end of body portion 772, or by being advanced distally after the distal end of the body portion has itself been placed against tissue of the valve. Device 762 thereby comprises a tissue-engaging portion that is configured to be placed in contact with tissue of the subject.

In one or more ways, the behavior of device 762 in response to being placed against the tissue of the valve facilitates guidance by viewing of body portion 772 (e.g., positioning of the body portion on the annulus). For example:

Resistance of device 762 being pushed further distally may indicate that the device is in contact with tissue that resists forces applied by the guide. For example, the distal end of the device may be abutting annulus 68 and/or a wall of the atrium. Conversely, lack of resistance of device 762 to being pushed further distally may indicate that the distal end of the device is not in contact with tissue that resists forces applied by the guide. For example, the distal end of the device may be moving between leaflets 123 of the valve (e.g., at a commissure), and/or may be pushing a leaflet 123 downward (e.g., into the ventricle). Such resistance (or lack thereof) can be detected mechanically (e.g., as tactile feedback to the operating physician and/or by an extracorporeal control unit). Since device 762 comprise radiopaque material, such resistance (or lack thereof) can be detected via imaging (e.g., fluoroscopically).

Similarly, the position, orientation and/or shape of device 762 (e.g., with respect to body portion 772 of implant 770, tissue of the valve, etc.) may indicate against what, if anything, the device 762 is disposed. Imaging techniques such as fluoroscopy can be used to identify this position, orientation and/or shape of the device. For example, if the distal end of device 762 is positioned at the same height (i.e., at the same place on a superior-inferior axis of the subject) as the distal end of body portion 772, this may indicate that body portion 772 and device 762 abut the same surface (e.g., annulus 68). Conversely, if the distal end of device 762 is positioned lower than body portion 772, this may indicate that the body portion 772 is disposed against annulus 68, while device 762 has passed toward or into the ventricle. Movement (e.g., beating) of the device 762 may indicate that the guide is disposed against a leaflet of the valve, and that the leaflet is moving the device as the heart beats. Such imaging may be facilitated by one or more components comprising radiopaque markings. For some applications, each device 762 comprises radiopaque filaments 766, so as to facilitate identification during imaging.

Filaments 766 comprise radiopaque material (e.g., nitinol or stainless steel) and can be configured to be extremely flexible. Filaments 766 project away from elongate radiopaque element 764. For some applications, filaments 766 sway with movement of the blood. For some applications, filaments 766 press against tissue of annulus 68 and tissue coupled thereto (as shown in FIG. 54B), such as tissue of an atrial wall as well as tissue of leaflets 123 of the native valve. Filaments 766 thus provide enhanced imaging of tissue of valve 64. That is, when filaments 766 appear bent or pressed, this imaging detects annulus tissue, while when filaments 766 are straight, this could indicate the orifice of the valve.

Filaments 766 disposed above leaflet 123 remain static, while filaments 766 disposed at leaflets 123 move and pulse with leaflet movement. A boundary between the moving and static filaments can be observed using fluoroscopy in order to indicate the root, or base, or leaflet 123.

FIG. 54B shows body portion 772 having been placed against annulus 68 of the subject in a vicinity of left fibrous trigone. Device 762 is disposed distally to body portion 772, and has splayed across annulus 68, e.g., due to resistance of the annulus. As described hereinabove, this can be detected mechanically and/or by imaging. The position, orientation and/or shape of device 762, alone and/or in combination with the other elements indicates that the portion of body portion 772 is positioned against firm tissue that is close to the commissure, which for some applications is the preferred position for anchoring of the portion of body portion 772. Identification (e.g., mechanically and/or by imaging) of which guide is in which position can further indicate the rotational orientation of body portion 772.

Once the desired position has been identified, an anchor (e.g., a first anchor) is used to anchor body portion 772. For some applications, device 762 and elongate radiopaque element 764 can be withdrawn slightly proximally before anchoring, e.g., so as to reduce a likelihood of inadvertently anchoring the guide to the tissue. Subsequently, additional portions of body portion 772 are anchored to annulus 68. In some applications, device 762 is moved proximally with respect to body portion 772. This process can be repeated for each anchor until implant 770 is fully implanted.

Following implantation of implant 770, device 762 is removed from the body of the subject. Device 762 is removed from within the body by pulling proximally on elongate radiopaque element 764. Filaments 766 collapse within a lumen of delivery tool 771.

It is to be noted that although system 760 is shown on mitral valve 64, system 760 can be used on any cardiac valve, e.g., a tricuspid valve, or any other tissue of the subject.

Figure 55A:
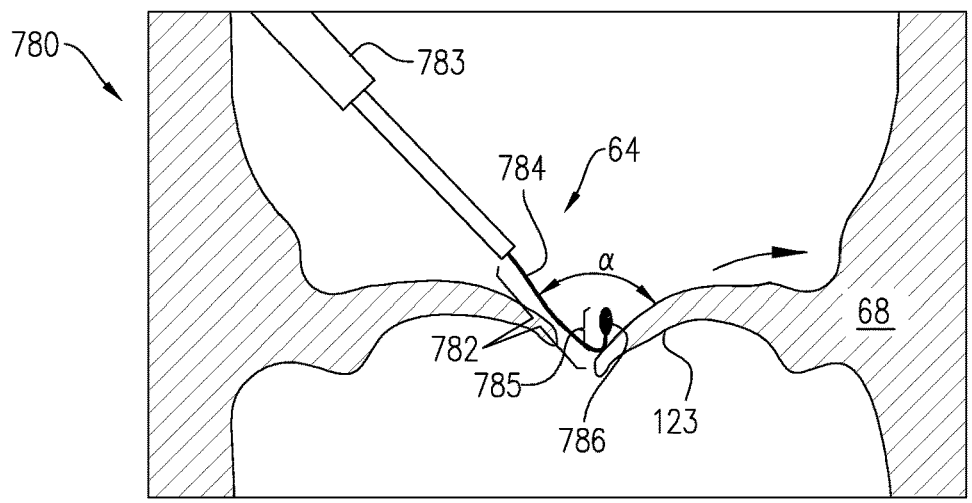
FIGS. 55A-C are schematic illustrations of an annulus-marking device comprising a radiopaque guide for aiding implantation of cardiac devices under the guidance of imaging, in accordance with some applications.
Figure 55B:
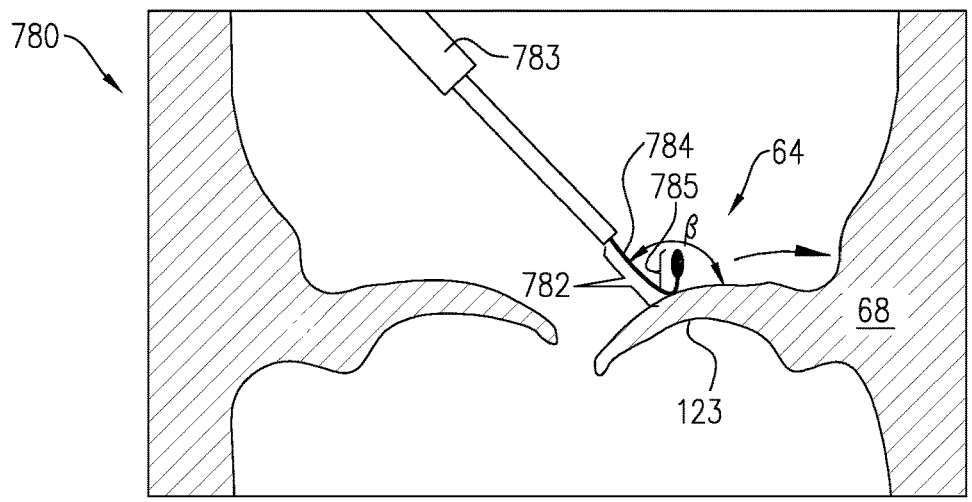
Figure 55C:
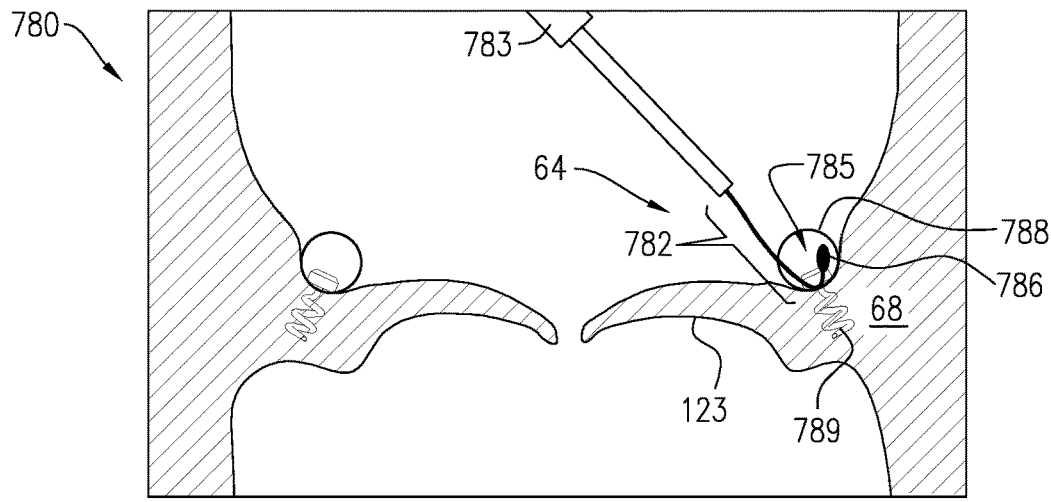

Reference is made to FIGS. 55A-C, which are schematic illustrations of a navigational-based guidance system 780, which employs one or more longitudinal guides configured to facilitate guidance of an implant 788 (e.g., an annuloplasty structure) to specific portions of annulus 68 by the guides contacting a surface of the valve (e.g., the annulus, commissure, and/or leaflets of the valve), in accordance with some applications. The longitudinal guide comprises an annulus marking device 782 which comprises a radiopaque wire extension 784 and at least one radiopaque distal curved tip 785 that is disposed at a nonzero angle with respect to wire extension 784. A radiopaque element, e.g., a bead or bulb 786 is disposed at the end of tip 785 and functions to increase radiopacity of device 782. It is to be noted that device 782 can comprise radiopaque elements or filaments 99 described hereinabove. Further, the system 780 can include features, components, elements, etc. from other systems and embodiments herein. For example, the system 780 can include and/or be used with a scaffolding 713 and/or basket 714 (e.g., as shown in FIG. 51A-C), and the scaffolding 713 and/or basket 714 can include any of the features described above, e.g., radiopaque elements, filaments, etc. As another example, the system 780 can include and/or be used with one or more radiopaque markers or loops 734 (e.g., as shown in FIG. 52A-B), and the markers or loops 734 can include any of the features described above, e.g., radiopaque elements, filaments, etc. spaced there around. Other combinations are also possible.

Device 782 comprises a tissue-engaging portion that is configured to be placed in contact with tissue of the subject. For some applications, device 782 comprises a flexible wire. For some applications, device 782 comprises a flexible rod, tube, line, etc. The device 782 comprises a flexible material (e.g., a flexible metal such as nitinol or stainless steel). A tube surrounds device 782, and device 782 slides with respect to the tube. In some embodiments, as shown, the device 782 can exit the tube at a distal end opening. In some embodiments, the device 782 can exit the tube at a side opening in a side of the tube. The tube and device 782 are delivered to valve 64 using a delivery tool 783.

As shown in FIG. 55A, tool 783 places device 782 at a first angle of delivery α (alpha) with respect to a planar surface of leaflet 123. As shown in FIG. 55B, tool 783 moves device 782 along leaflet 123 such that distal curved tip 785 moves incrementally along leaflet 123 toward annulus 68 and toward the base of leaflet 123. As tool 783 moves device 782, the angle of delivery of annulus-marking device 782 with respect to the planar surface of leaflet 123 changes. For example, in 55A, the first angle of delivery α is narrower than a second angle of delivery β (beta) shown in FIG. 55B. For some applications of the present invention, the operating physician moves device 782. For some applications of the present invention, movement of leaflet 123 moves device 782. Movement of device 782 is visualized using fluoroscopy. Once curved tip 785 stops moving, the operating physician determines that tip 785 is at the base of leaflet 123.

For some applications of the present invention, curved tip 785 is curved because it has shape-memory. For some applications of the present invention, curved tip 785 is curved because it presses against tissue of the subject.

In one or more ways, the behavior of device 782 in response to being placed against the tissue of the valve facilitates guidance by viewing of implant 788 (e.g., positioning of the implant on the annulus).

Resistance of device 782 being pushed further distally may indicate that device 782 is in contact with tissue that resists forces applied by device 782. For example, tip 785 of device 782 may be abutting annulus 68 and/or a wall of the atrium. Conversely, lack of resistance of device 782 to being pushed further distally may indicate that the distal end of the device is not in contact with tissue that resists forces applied by the guide. For example, the distal end of the device may be moving between leaflets 123 of the valve (e.g., at a commissure), and/or may be pushing a leaflet 123 downward (e.g., into the ventricle). Such resistance (or lack thereof) can be detected mechanically (e.g., as tactile feedback to the operating physician and/or by an extracorporeal control unit). Since device 782 comprise radiopaque material, such resistance (or lack thereof) can be detected via imaging (e.g., fluoroscopically). In some embodiments, the device 782 can be used under the annulus, e.g., similar to the position of wire 906 and magnet 908 shown in FIG. 65). In some embodiments, the device 782 can be configured and used similarly to wire 906 and/or bead/bulb 786 can be magnetic, include a magnet (e.g., magnet 908 or the like), or include a magnetic or ferrous material.

In some embodiments, the position, orientation and/or shape of device 782 (e.g., with respect to the body portion implant 788, tissue of the valve, etc.) may indicate against what, if anything, the device 782 is disposed. Imaging techniques such as fluoroscopy can be used to identify this position, orientation and/or shape of the device. For example, if the distal end of device 782 is positioned at the same height (i.e., at the same place on a superior-inferior axis of the subject) as implant 788, this may indicate that implant 788 and device 782 abut the same surface (e.g., annulus 68). Conversely, if the distal end of device 782 is positioned lower than implant 788, this may indicate that implant 788 is disposed against annulus 68, while device 782 has passed toward or into the ventricle. Movement (e.g., beating) of the device 782 may indicate that the guide is disposed against a leaflet of the valve, and that the leaflet is moving the device as the heart beats. Such imaging can be facilitated by one or more components comprising radiopaque markings.

Once the desired position has been identified, an anchor 789 (e.g., a first anchor) is used to anchor implant 788. For some applications, device 782 can be withdrawn slightly proximally before anchoring, e.g., so as to reduce a likelihood of inadvertently anchoring the guide to the tissue. Subsequently, additional portions of implant 788 are anchored to annulus 68 using device 782 as a guide for each anchor implantation.

Following implantation of implant 788, device 782 is removed from the body of the subject. Device 782 is removed from within the body by pulling proximally device 782 within a lumen of delivery tool 783.

It is to be noted that although system 780 is shown on mitral valve 64, system 780 can be used on any cardiac valve, e.g., a tricuspid valve, or any other tissue of the subject.

Figure 56A:
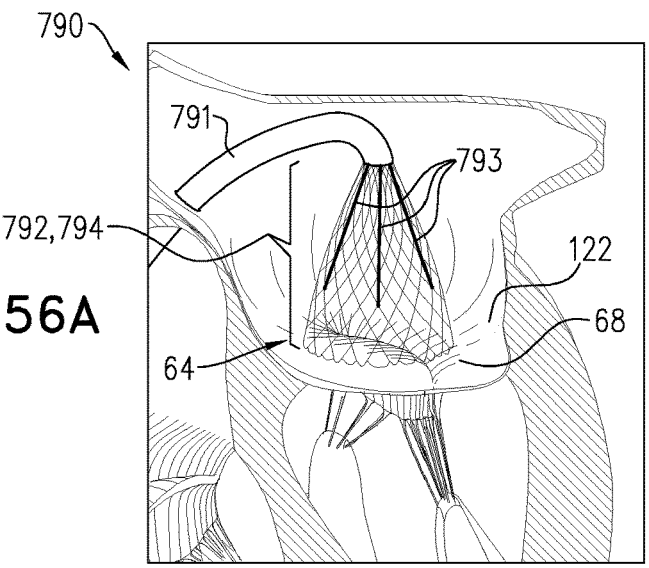
FIGS. 56A-C are schematic illustrations of an annulus-marking device comprising a radiopaque expandable mesh for aiding implantation of cardiac devices under the guidance of imaging, in accordance with some applications.
Figure 56B:
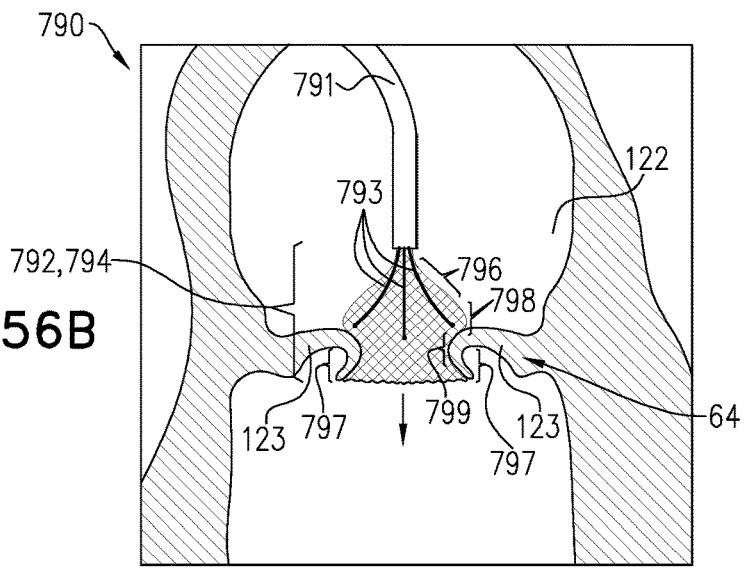
Figure 56C:
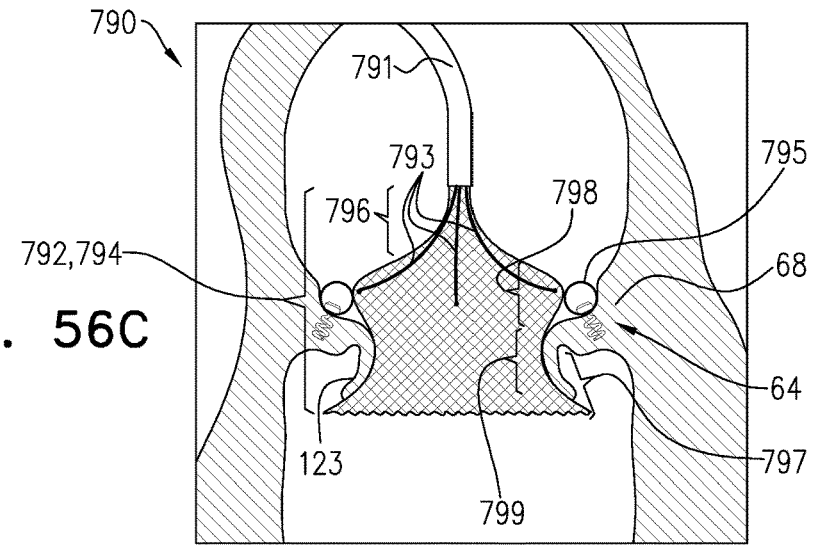

Reference is now made to FIGS. 56A-C, which are schematic illustrations of a system 790 comprising an annulus-marking device 792 that is positioned in the orifice of valve 64 in advance of an implant, e.g., an annuloplasty structure 795, in accordance with some applications. For some applications, annulus-marking device 792 is placed in advance of the implant such that device 792 guides the implantation of the implant. Annulus-marking device 792 extends from within a delivery tool 791. For some applications, annulus-marking device 792 comprises a stent-like expandable radiopaque braided mesh 794, e.g., a fabric or metal mesh, that is positioned partially within the orifice of valve 64 and does not significantly interfere with function of valve 64. For some applications, annulus-marking device 792 comprises a conical stent. As successive portions of annuloplasty structure 795 are extended from within its delivery tool and are positioned along successive portions of annulus 68, annulus-marking device 792 guides the successive portions of structure 795 under imaging as annulus-marking device 792 comprises a radiopaque material (e.g., nitinol or stainless steel). For some applications, annulus-marking device 792 comprises a balloon made of nylon that is wholly or partially radiopaque and/or is coupled to radiopaque elements.

Device 792 is delivered within tool 791 in a collapsed state. Once deployed from within tool 791, device 792 expands to assume a frustoconical shape. Device 792 comprises two or more, e.g., three as shown, pull wires 793 extending along a perimeter of mesh 794. Pull wires 793 are pullable to transition braided mesh 794 from the frustoconical shape in FIG. 56A to a shape shown in FIGS. 56B-C in which mesh 794 assumes (1) a sloped upper portion 796 configured for positioning within the atrium, (2) a bulging ledge portion 798 configured for positioning above valve 64, (3) a narrow portion 799 for positioning within valve 64, and (4) a trumpet portion 797 configured for expanding within the ventricle. Pull wires 793 are pulled by the operating physician. For some applications, sloped upper portion 796 and bulging ledge portion 798 collectively assume a pear shape.

For some applications of the present invention, alternatively or additionally to pull wires 793, mesh 794 is manufactured in a manner in which mesh 794 has a variable pitch when assuming the shapes as shown in FIGS. 56B-C. That is the mesh at each of (1) sloped upper portion 796, (2) bulging ledge portion 798, (3) narrow portion 799, and (4) a trumpet portion 797 is woven to have a different pitch which provides each portion with a diameter that is different from the other portions.

For some applications, as shown in FIG. 56B, bulging ledge portion 798 has a greater diameter than the other portions 796, 797, and 799 of the annulus-marking device 792. For some applications, as shown in FIG. 56C, trumpet portion 797 has a greater diameter than the other portions 796, 798, and 799 of the annulus-marking device 792.

Annulus-marking device 792 provides an indication of a specific section of annulus 68 immediately preceding the placement of the successive portion of structure 795 along annulus 68. Bulging ledge portion 798 rests atop annulus 68. Annulus-marking device 792 is at least partly stiff, and provides resistance, which facilitates positioning of structure 795. For some applications, structure 795 slides along sloped upper portion 796. In such applications, device 792 provides fluoroscopic and mechanical guidance of implantation of structure 795. Sloped upper portion 796 is narrow at its proximal end in order to facilitate ease of positioning of the delivery tool used to deliver annuloplasty structure between device 792 and atrial wall 122. Annulus-marking device 792 can also provide tactile feedback to the operating physician. Annulus-marking device 792 assumes a distinct shape in FIGS. 56B-C which helps the operating physician discern anatomy of the subject. For some applications, narrow portion 799 and/or bulging ledge portion 798 can comprise additional radiopaque markers to help calculate a height of annulus 68.

For some applications, mesh 794 comprises two or more leaflets in order to regulate blood flow while device 792 is positioned in valve 64.

Annuloplasty structure 795 comprises a body portion which comprises a flexible material and has a longitudinal axis that runs along the length of the body portion (e.g., when the body portion is straightened). The body portion comprises radiopaque markings at sites along the length of the body portion to aid in imaging for accurate delivery of anchors to annulus 68 in order to anchor structure 795 to tissue of annulus 68.

In addition to providing tactile feedback, annulus-marking device 792 can also facilitate positioning of the annuloplasty structure 795 by facilitating imaging (e.g., fluoroscopy) and mechanical guidance. For example, the presence of annulus-marking device 792 and/or the shape thereof (e.g., bending due to being pressed against an atrial wall) is visible in fluoroscopic imaging, and can be used to facilitate identification of the position and angle of annuloplasty structure 795 with respect to tissues. Additionally, annulus-marking device 792 ensures that the delivery tool used to deliver structure 795 is positioned at an external perimeter of annulus-marking device 792 such that it is positioned between device 792 and atrial wall 122.

Annulus-marking device 792 can be removed by being pulled and constrained within tool 791 in order to be retrieved and removed from the body of the subject.

In some applications, as shown, annulus-marking device 792 is delivered toward valve 64 in a delivery tool 791 that is separate from a delivery tool used to deliver the implant. For some applications, annulus-marking device 792 and the implant may be delivered from the same delivery tool.

It is to be noted that annulus-marking device 792 can be coupled to a plurality of radiopaque elements or filaments 99 and can be shaped in any suitable shape.

It is to be noted that although system 790 is shown on mitral valve 64, system 790 can be used on any cardiac valve, e.g., a tricuspid valve, or any other tissue of the subject.

Figure 57B:
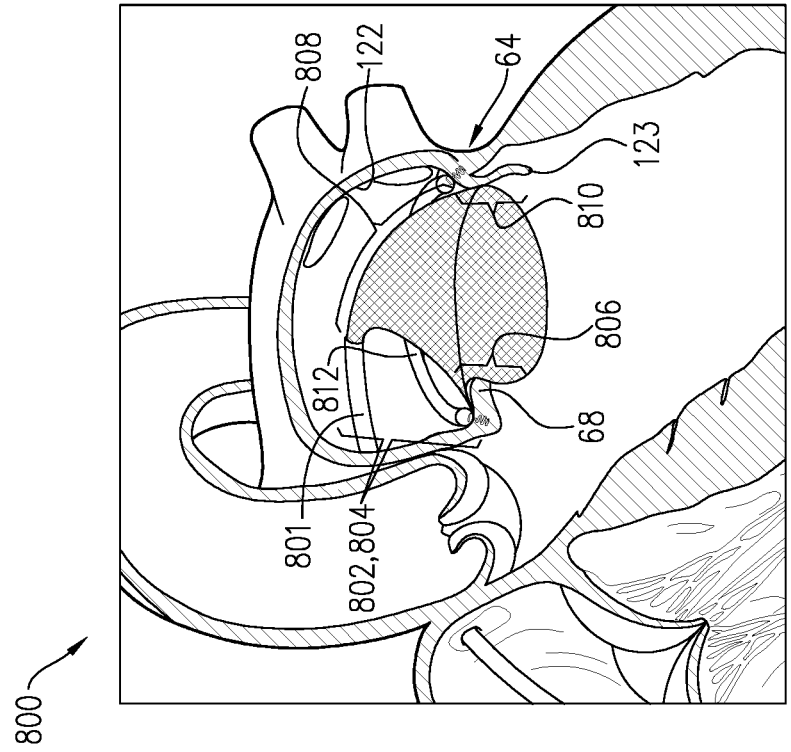
Figure 57A:
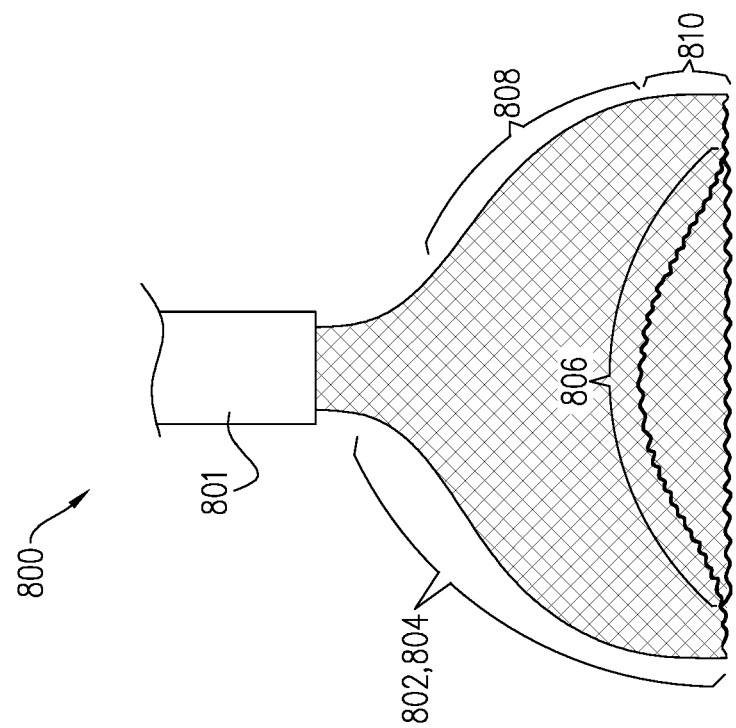

Reference is now made to FIGS. 57A-B, which are schematic illustrations of a system 800 comprising an annulus-marking device 802 that is positioned in the orifice of valve 64 in advance of an implant, e.g., an annuloplasty structure 812, in accordance with some applications. For some applications, annulus-marking device 802 is placed in advance of the implant such that device 802 guides the implantation of the implant. Annulus-marking device 802 extends from within a delivery tool 801. For some applications, annulus-marking device 802 comprises a stent-like, woven, expandable radiopaque braided mesh 804, e.g., a fabric or metal mesh, that is positioned partially within the orifice of valve 64 and does not significantly interfere with function of valve 64. For some applications, annulus-marking device 802 comprises a flexible, radiopaque material, e.g., nitinol or stainless steel. For some applications, annulus-marking device 802 comprises a conical stent. As successive portions of annuloplasty structure 812 are extended from within its delivery tool and are positioned along successive portions of annulus 68, annulus-marking device 802 guides the successive portions of structure 812 under imaging as annulus-marking device 802 comprises a radiopaque material (e.g., nitinol or stainless steel). For some applications, annulus-marking device 802 comprises a balloon made of nylon that is wholly or partially radiopaque and/or is coupled to radiopaque elements.

Device 802 is delivered within tool 801 in a collapsed state. Once deployed from within tool 801, device 802 expands to assume a frustoconical shape or a generally bulbous or generally spherical shape. In the expanded state, mesh assumes (1) a sloped upper portion 808 configured for positioning within the atrium, and (2) an asymmetrical portion 810 for positioning within valve 64. Mesh 804 of device 802 is manufactured such that it defines a curved portion 806 of asymmetrical portion 810 of device 802 that is meant to rest against the aortic valve of the heart and begins above the aortic valve in a manner in which device 802 does not interfere with or add any pressure to the aortic valve. That is, mesh 804 is manufactured such that the braid is shorter at a given distal portion (i.e., curved portion 806) of mesh 804. Mesh 804 curves upward in curved portion 806 designated for implantation against the aortic valve.

For some applications, mesh 804 comprises a trumpet portion (not shown) as described hereinabove with reference to FIGS. 56B-C, that is disposed distally to asymmetrical portion 810. For some applications, the trumpet portion has a greater diameter than the other portions 808 and 810 of the annulus-marking device 802.

Annulus-marking device 802 provides an indication of a specific section of annulus 68 immediately preceding the placement of the successive portion of structure 812 along annulus 68. Sloped upper portion 808 rests atop annulus 68. Annulus-marking device 802 is at least partly stiff, and provides resistance, which facilitates positioning of structure 812. For some applications, structure 812 slides along sloped upper portion 808. In such applications, device 802 provides fluoroscopic and mechanical guidance of implantation of structure 812. Sloped upper portion 808 is narrow at its proximal end in order to facilitate ease of positioning of the delivery tool used to deliver annuloplasty structure between device 802 and atrial wall 122. Annulus-marking device 802 may also provide tactile feedback to the operating physician. Annulus-marking device 802 assumes a distinct shape in FIGS. 57A-B which helps the operating physician discern anatomy of the subject. For some applications, asymmetrical portion 810 can comprise additional radiopaque markers to help calculate a height of annulus 68.

For some applications, mesh 804 comprises two or more leaflets in order to regulate blood flow while device 802 is positioned in valve 64.

Annuloplasty structure 812 comprises a body portion which comprises a flexible material and has a longitudinal axis that runs along the length of the body portion (e.g., when the body portion is straightened). The body portion comprises radiopaque markings to aid in imaging for accurate delivery of anchors to annulus 68 in order to anchor structure 812 to tissue of annulus 68.

In addition to providing tactile feedback, annulus-marking device 802 may also facilitate positioning of the annuloplasty structure 812 by facilitating imaging (e.g., fluoroscopy) and mechanical guidance. For example, the presence of annulus-marking device 802 and/or the shape thereof (e.g., bending due to being pressed against tissue) is visible in fluoroscopic imaging, and can be used to facilitate identification of the position and angle of annuloplasty structure 812 with respect to tissues. Additionally, annulus-marking device 802 ensures that the delivery tool used to deliver structure 812 is positioned at an external perimeter of annulus-marking device 802 such that it is positioned between device 802 and atrial wall 122.

Annulus-marking device 802 can be removed by being pulled and constrained within tool 801 in order to be retrieved and removed from the body of the subject.

In some applications, as shown, annulus-marking device 802 is delivered toward valve 64 in a delivery tool 801 that is separate from a delivery tool used to deliver the implant. For some applications, annulus-marking device 802 and the implant may be delivered from the same delivery tool.

It is to be noted that annulus-marking device 802 can be coupled to a plurality of radiopaque elements or filaments 99 and can be shaped in any suitable shape.

It is to be noted that although system 800 is shown on mitral valve 64, system 800 can be used on any cardiac valve, e.g., a tricuspid valve, or any other tissue of the subject.

Reference is now made to FIGS. 58A-B, which are schematic illustrations of a system 820 comprising an annulus-marking device 822 that is positioned in the orifice of valve 64 in advance of an implant, e.g., an annuloplasty structure 812, in accordance with some applications. Except as described hereinbelow, annulus-marking device 822 can be the same as or generally similar to annulus-marking device 802, described hereinabove with reference to FIGS. 57A-B and like reference numerals refer to like parts. Delivery tool 801 is used to deliver annulus-marking device 822. For some applications, annulus-marking device 822 comprises a flexible, radiopaque material, e.g., nitinol or stainless steel. A stabilizing rod 823 is coupled at a distal end to a tissue anchor 824 that is configured to be reversibly anchored to cardiac tissue. Annulus-marking device 822 slides around stabilizing rod 823 longitudinally. Stabilizing rod 823 is configured to stabilize and guide positioning of the annulus-marking device 822. For some applications, stabilizing rod 823 is semi-rigid. For some applications, stabilizing rod 823 functions as a track for positioning an expandable mesh 804. For some applications, annulus-marking device 822 is placed in advance of the implant such that device 822 guides implantation of the implant. Annulus-marking device 822 extends from within delivery tool 801. For some applications, annulus-marking device 822 comprises a stent-like, woven, expandable radiopaque braided mesh 804, e.g., a fabric or metal mesh, that is positioned partially within the orifice of valve 64 and does not significantly interfere with function of valve 64. For some applications, annulus-marking device 822 comprises a conical stent. As successive portions of annuloplasty structure 812 are extended from within its delivery tool and are positioned along successive portions of annulus 68, annulus-marking device 822 guides the successive portions of structure 812 under imaging as annulus-marking device 822 comprises a radiopaque material (e.g., nitinol or stainless steel). For some applications, annulus-marking device 822 comprises a balloon made of nylon that is wholly or partially radiopaque and/or is coupled to radiopaque elements.

Mesh 804 of device 822 is manufactured such that it defines a curved portion 806 of asymmetrical portion 810 of device 822 that is meant to rest against the aortic valve of the heart and begins above the aortic valve in a manner in which device 822 does not interfere with or add any pressure to the aortic valve. That is, mesh 804 is manufactured such that the braid is shorter at a given distal portion (i.e., curved portion 806) of mesh 804. Mesh 804 curves upward in curved portion 806 designated for implantation against the aortic valve.

For some applications, mesh 804 comprises a trumpet portion (not shown) as described hereinabove with reference to FIGS. 56B-C, that is disposed distally to asymmetrical portion 810. For some applications, the trumpet portion has a greater diameter than the other portions 808 and 810 of the annulus-marking device 822.

Annulus-marking device 822 can be removed by being pulled and constrained within tool 801 in order to be retrieved and removed from the body of the subject.

It is to be noted that annulus-marking device 822 can be coupled to a plurality of radiopaque elements or filaments 99 and can be shaped in any suitable shape.

It is to be noted that although system 820 is shown on mitral valve 64, system 820 can be used on any cardiac valve, e.g., a tricuspid valve, or any other tissue of the subject.

Figure 59B:
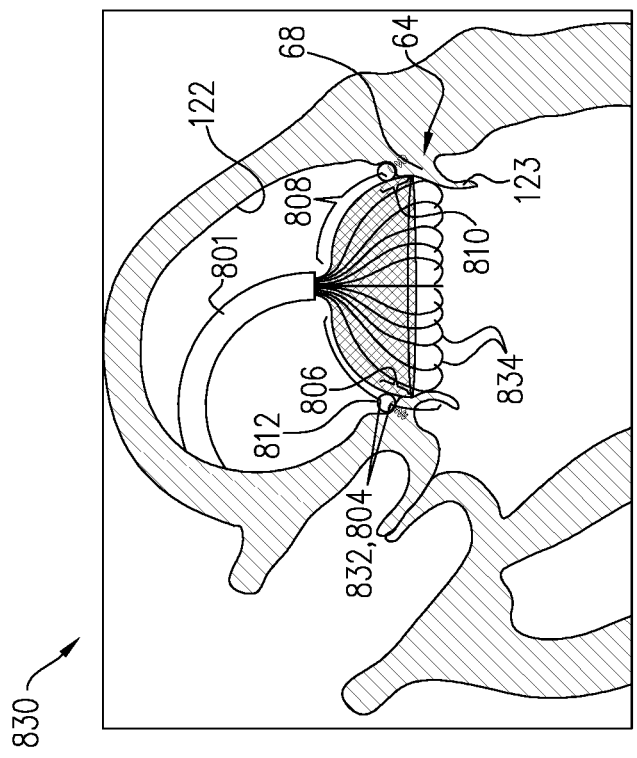
Figure 59A:
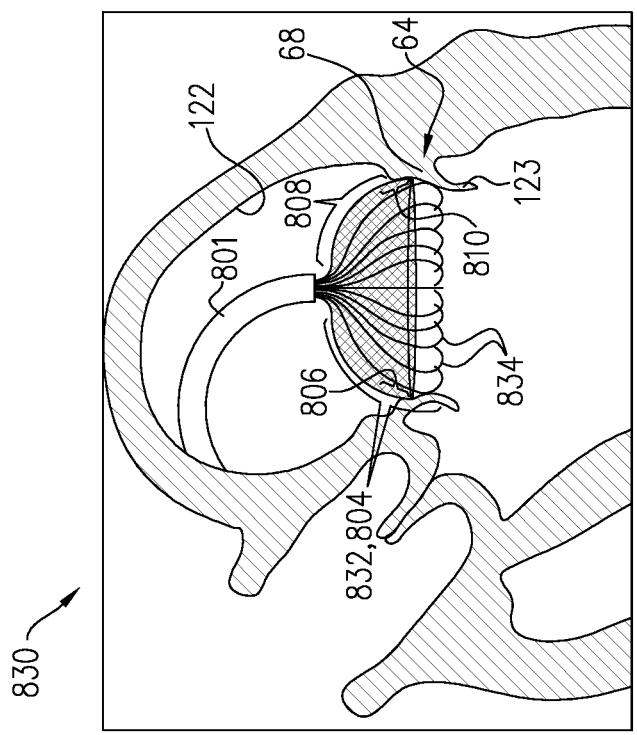

Reference is now made to FIGS. 59A-B, which are schematic illustrations of a system 830 comprising an annulus-marking device 832 that is positioned in the orifice of valve 64 in advance of an implant, e.g., an annuloplasty structure 812, in accordance with some applications. Except as described hereinbelow, annulus-marking device 832 can be the same as or generally similar to annulus-marking device 802, described hereinabove with reference to FIGS. 57A-B and like reference numerals refer to like parts. Delivery tool 801 is used to deliver annulus-marking device 832. For some applications, annulus-marking device 832 comprises a flexible, radiopaque material, e.g., nitinol or stainless steel. A plurality of expandable radiopaque elements 834 are coupled to a distal end portion of expandable radiopaque braided mesh 804 and are configured to expand radially such that the plurality of expandable radiopaque elements 834 provide an indication as to a location of heart valve annulus 68. For some applications, the plurality of expandable elements 834 comprises a flexible, radiopaque material, e.g., nitinol or stainless steel. The plurality of expandable elements 834 form device 832 into a generally umbrella shape for facilitating imaging of cardiac tissue during implantation of the implant. For some applications, the plurality of expandable elements 834 collectively form annulus-marking device 832 into a generally spherical shape. For some applications, the plurality of expandable elements 834 collectively form annulus-marking device 832 into a partially-bulbous shape. For some applications, the plurality of expandable elements 834 comprise a plurality of woven radiopaque fibers assuming a mesh. For some applications, the plurality of expandable elements 834 comprise a plurality of curved wires.

For some applications, the plurality of expandable elements 834 function as plurality of expandable elements 376 described hereinabove with reference to FIGS. 17A-C.

For some applications, the plurality of expandable elements 834 is separate from mesh 804. For such applications, the plurality of expandable elements 834 may be delivered to valve 64 in advance of delivery of mesh 804. Mesh 804 can slide over the plurality of expandable elements 834 which function as a track and a guide for the positioning of mesh 804.

For some applications, annulus-marking device 832 is placed in advance of the implant such that device 832 guides implantation of the implant. Annulus-marking device 832 extends from within delivery tool 801. For some applications, annulus-marking device 832 comprises a stent-like, woven, expandable radiopaque braided mesh 804, e.g., a fabric or metal mesh, that is positioned partially within the orifice of valve 64 and does not significantly interfere with function of valve 64. For some applications, annulus-marking device 832 comprises a conical stent. As successive portions of annuloplasty structure 812 are extended from within its delivery tool and are positioned along successive portions of annulus 68, annulus-marking device 832 guides the successive portions of structure 812 under imaging as annulus-marking device 832 comprises a radiopaque material (e.g., nitinol or stainless steel). For some applications, annulus-marking device 832 comprises a balloon made of nylon that is wholly or partially radiopaque and/or is coupled to radiopaque elements.

Mesh 804 of device 832 is manufactured such that it defines a curved portion 806 of asymmetrical portion 810 of device 832 that is meant to rest against the aortic valve of the heart and begins above the aortic valve in a manner in which device 832 does not interfere with or add any pressure to the aortic valve. That is, mesh 804 is manufactured such that the braid is shorter at a given distal portion (i.e., curved portion 806) of mesh 804. Mesh 804 curves upward in curved portion 806 designated for implantation against the aortic valve.

For some applications, mesh 804 comprises a trumpet portion (not shown) as described hereinabove with reference to FIGS. 56B-C, that is disposed distally to asymmetrical portion 810. For some applications, the trumpet portion has a greater diameter than the other portions 808 and 810 of the annulus-marking device 832.

Annulus-marking device 832 can be removed by being pulled and constrained within tool 801 in order to be retrieved and removed from the body of the subject.

It is to be noted that annulus-marking device 832 can be coupled to a plurality of radiopaque elements or filaments 99 and can be shaped in any suitable shape.

It is to be noted that although system 830 is shown on mitral valve 64, system 830 can be used on any cardiac valve, e.g., a tricuspid valve, or any other tissue of the subject.

Figure 60B:
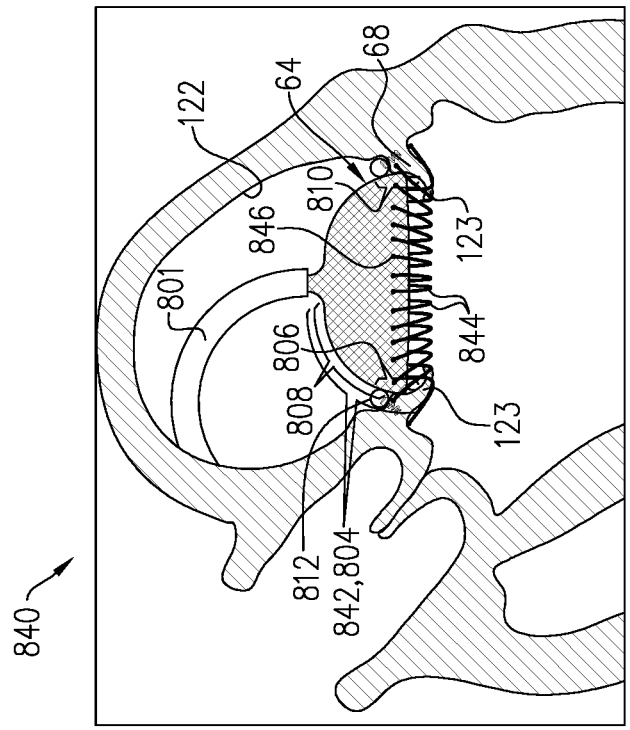
Figure 60A:
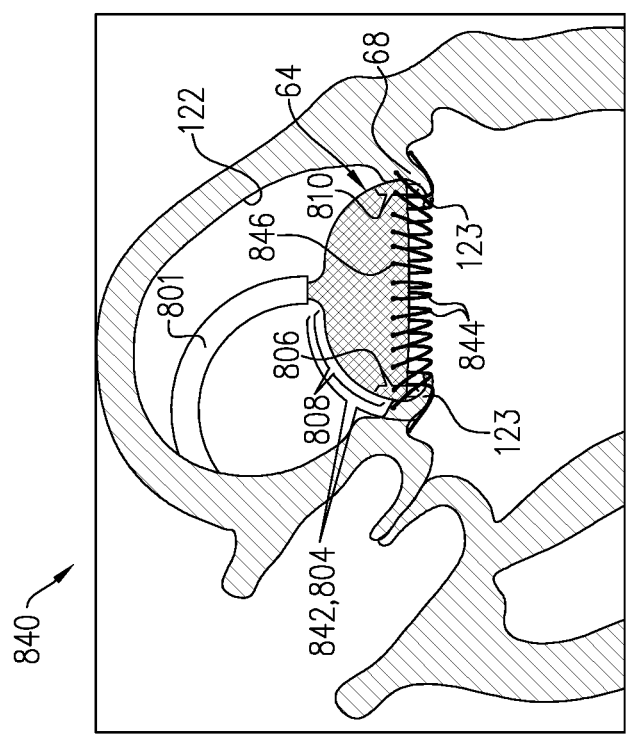

Reference is now made to FIGS. 60A-B, which are schematic illustrations of a system 840 comprising an annulus-marking device 842 that is positioned in the orifice of valve 64 in advance of an implant, e.g., an annuloplasty structure 812, in accordance with some applications. Except as described hereinbelow, annulus-marking device 842 can be the same as or generally similar to annulus-marking device 802, described hereinabove with reference to FIGS. 57A-B and like reference numerals refer to like parts. Delivery tool 801 is used to deliver annulus-marking device 842. For some applications, annulus-marking device 842 comprises a flexible, radiopaque material, e.g., nitinol or stainless steel. A plurality of expandable snares (or hooks) 844 are coupled to a distal end portion of expandable radiopaque braided mesh 804 and are configured to expand radially such that the plurality of expandable snares 844 ensnare leaflets 123 and/or tissue of valve 64. For some applications of the present invention, snares 844 comprises a radiopaque material, e.g., nitinol or stainless steel, and provide an indication as to a location of heart valve annulus 68. For some applications, the plurality of expandable snares 844 are flexible. For some applications, the plurality of expandable snares 844 are rigid. For some applications, each one of the plurality of snares 844 extend distally from a distal end of expandable radiopaque braided mesh 804 and then curve proximally to a proximal tip 846.

When mesh 804 is pulled proximally, snares 844 ensnare and engage the native leaflets 123 of valve 64. By the ensnaring of leaflets 123, snares 844 sandwich valve 64 between snares 844 and mesh 804. Such ensnaring helps temporarily anchor device 842 to valve 64.

For some applications, annulus-marking device 842 is placed in advance of the implant such that device 842 guides implantation of the implant. Annulus-marking device 842 extends from within delivery tool 801. For some applications, annulus-marking device 842 comprises a stent-like, woven, expandable radiopaque braided mesh 804, e.g., a fabric or metal mesh, that is positioned partially within the orifice of valve 64 and does not significantly interfere with function of valve 64. For some applications, annulus-marking device 842 comprises a conical stent. As successive portions of annuloplasty structure 812 are extended from within its delivery tool and are positioned along successive portions of annulus 68, annulus-marking device 842 guides the successive portions of structure 812 under imaging as annulus-marking device 842 comprises a radiopaque material (e.g., nitinol or stainless steel). For some applications, annulus-marking device 842 comprises a balloon made of nylon that is wholly or partially radiopaque and/or is coupled to radiopaque elements.

Mesh 804 of device 842 is manufactured such that it defines a curved portion 806 of asymmetrical portion 810 of device 842 that is meant to rest against the aortic valve of the heart and begins above the aortic valve in a manner in which device 842 does not interfere with or add any pressure to the aortic valve. That is, mesh 804 is manufactured such that the braid is shorter at a given distal portion (i.e., curved portion 806) of mesh 804. Mesh 804 curves upward in curved portion 806 designated for implantation against the aortic valve.

For some applications, mesh 804 comprises a trumpet portion (not shown) as described hereinabove with reference to FIGS. 56B-C, that is disposed distally to asymmetrical portion 810. For some applications, the trumpet portion has a greater diameter than the other portions 808 and 810 of the annulus-marking device 842.

Annulus-marking device 842 can be removed by being pulled and constrained within tool 801 in order to be retrieved and removed from the body of the subject.

It is to be noted that annulus-marking device 842 can be coupled to a plurality of radiopaque elements or filaments 99 and can be shaped in any suitable shape.

It is to be noted that although system 840 is shown on mitral valve 64, system 840 can be used on any cardiac valve, e.g., a tricuspid valve, or any other tissue of the subject.

Figure 61B:
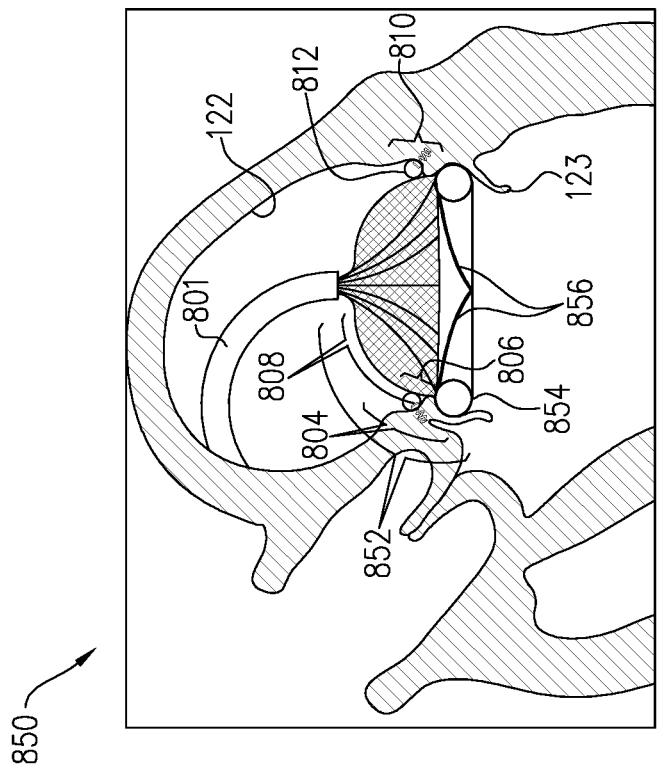
Figure 61A:
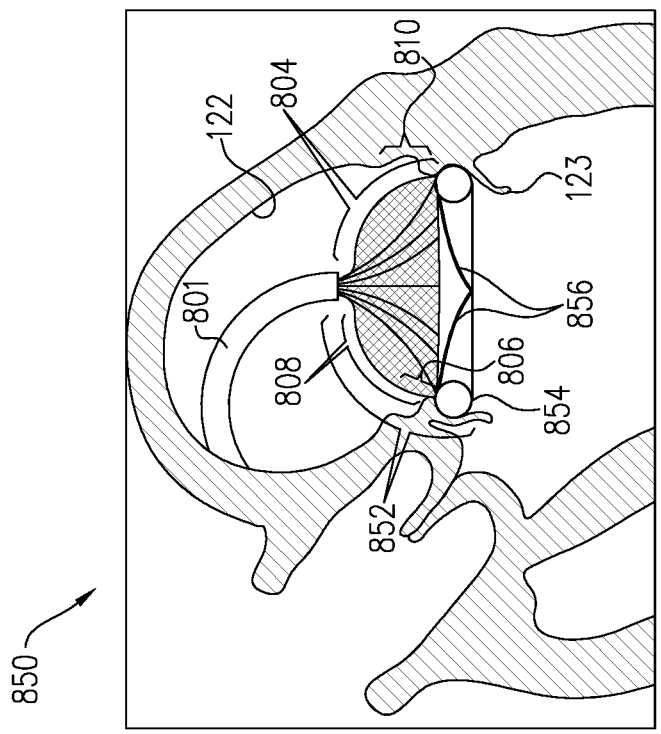

Reference is now made to FIGS. 61A-B, which are schematic illustrations of a system 850 comprising an annulus-marking device 852 that is positioned in the orifice of valve 64 in advance of an implant, e.g., an annuloplasty structure 812, in accordance with some applications. Except as described hereinbelow, annulus-marking device 852 can be the same as or generally similar to annulus-marking device 802, described hereinabove with reference to FIGS. 57A-B and like reference numerals refer to like parts. Delivery tool 801 is used to deliver annulus-marking device 852. For some applications, annulus-marking device 852 comprises a flexible, radiopaque material, e.g., nitinol or stainless steel. An inflatable annular element 854 is coupled to a distal end portion of expandable radiopaque braided mesh 804. Inflatable annular element 854 is configured to position and temporarily anchor expandable radiopaque braided mesh 804 within native valve 64. For some applications, inflatable annular element 854 comprises a radiopaque material. For some applications, inflatable annular element 854 comprises a balloon, e.g., a compliant balloon. Typically, inflatable annular element 854 comprises a prosthetic valve comprising two or more leaflets 856 which regulate blood flow while device 852 is positioned in valve 64. As shown, expandable radiopaque braided mesh 804 is positionable within valve 64, while inflatable annular element 854 is positionable below the native heart valve, e.g., in a subannular space.

When mesh 804 is pulled proximally, inflatable element 854 engages with subannular tissue thereby temporarily anchoring device 852 to valve 64.

For some applications, annulus-marking device 852 is placed in advance of the implant such that device 852 guides implantation of the implant. Annulus-marking device 852 extends from within delivery tool 801. For some applications, annulus-marking device 852 comprises a stent-like, woven, expandable radiopaque braided mesh 804, e.g., a fabric or metal mesh, that is positioned partially within the orifice of valve 64 and does not significantly interfere with function of valve 64. For some applications, annulus-marking device 852 comprises a conical stent. As successive portions of annuloplasty structure 812 are extended from within its delivery tool and are positioned along successive portions of annulus 68, annulus-marking device 852 guides the successive portions of structure 812 under imaging as annulus-marking device 852 comprises a radiopaque material (e.g., nitinol or stainless steel). For some applications, annulus-marking device 852 comprises a balloon made of nylon that is wholly or partially radiopaque and/or is coupled to radiopaque elements.

Mesh 804 of device 852 is manufactured such that it defines a curved portion 806 of asymmetrical portion 810 of device 852 that is meant to rest against the aortic valve of the heart begins above the aortic valve in a manner in which device 852 does not interfere with or add any pressure to the aortic valve. That is, mesh 804 is manufactured such that the braid is shorter at a given distal portion (i.e., curved portion 806) of mesh 804. Mesh 804 curves upward in curved portion 806 designated for implantation against the aortic valve.

For some applications, mesh 804 comprises a trumpet portion (not shown) as described hereinabove with reference to FIGS. 56B-C, that is disposed distally to asymmetrical portion 810. For some applications, the trumpet portion has a greater diameter than the other portions 808 and 810 of the annulus-marking device 852.

Annulus-marking device 852 can be removed by deflating inflatable element 854 and then pulling and constraining device 852 within tool 801 in order to be retrieved and removed from the body of the subject.

It is to be noted that annulus-marking device 852 can be coupled to a plurality of radiopaque elements or filaments 99 and can be shaped in any suitable shape.

It is to be noted that although system 850 is shown on mitral valve 64, system 850 can be used on any cardiac valve, e.g., a tricuspid valve, or any other tissue of the subject.

Reference is now made to FIGS. 58A-61B. It is to be noted that any device described herein used to stabilize, temporarily anchor, and/or enhance the radiopacity of the annulus-marking devices, e.g., stabilizing rod 823, expandable radiopaque elements 834, expandable snares 844 and/or inflatable annular element 854 can be used in combination with any annulus-marking device described herein.

Figure 62B:
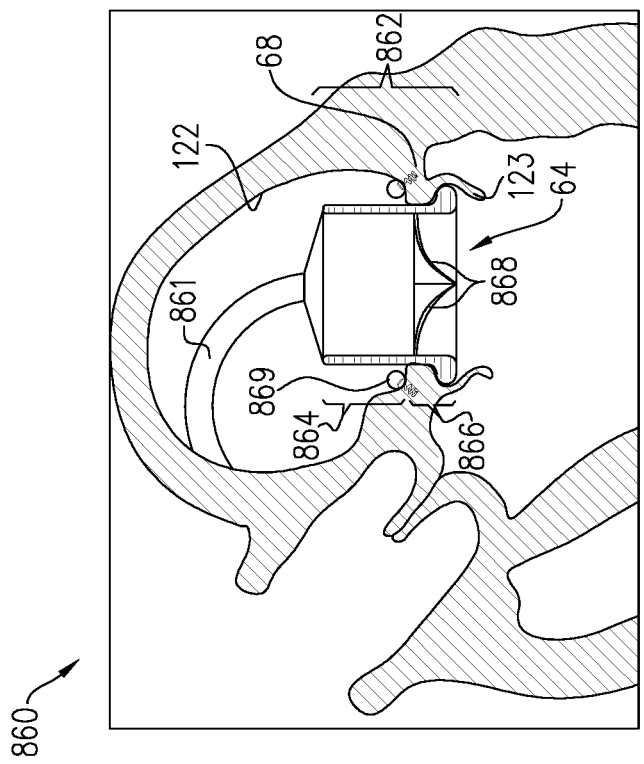
FIGS. 62A-B are schematic illustrations of an annulus-marking device comprising an inflatable prosthetic valve for aiding implantation of cardiac devices under the guidance of imaging, in accordance with some applications.
Figure 62A:
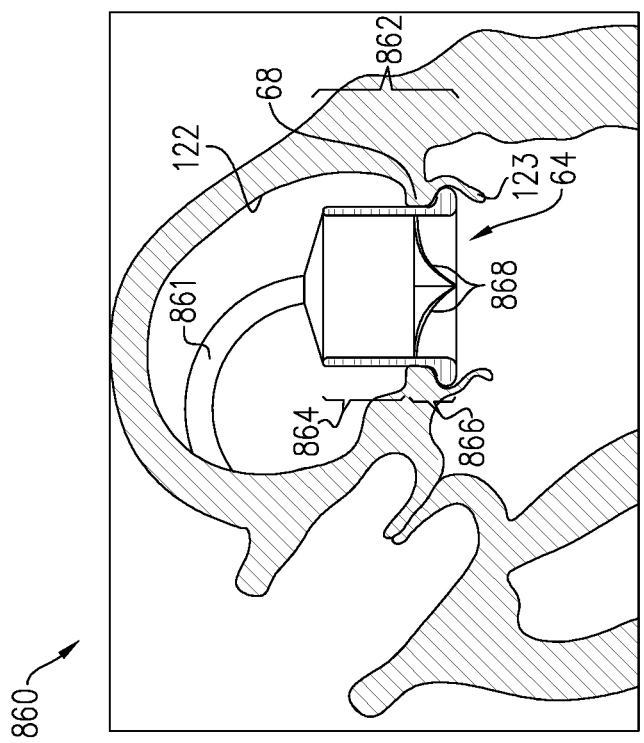

Reference is now made to FIGS. 62A-B, which are schematic illustrations of a system 860 comprising an annulus-marking device 862 that is positioned in the orifice of valve 64 in advance of an implant, e.g., an annuloplasty structure 812, in accordance with some applications. A delivery tool 861 is used to deliver annulus-marking device 862. For some applications, annulus-marking device 862 comprises or is coupled to a flexible, radiopaque material. Device 862 comprises an inflatable temporary valve that is inflatable from a collapsed state to an inflated state. In the expanded state, the inflatable temporary valve defines (1) a proximal non-compliant cylindrical balloon 864 configured for positioning within the native heart valve 64 and partially within the atrium, and (2) a distal compliant balloon 866, e.g., a toroidal balloon, configured for positioning in a subannular space of native heart valve 64. Device 862 comprises two or more leaflets 868 which regulate blood flow while device 862 is positioned in valve 64.

Device 862 is inflated until compliant balloon 866 cannot expand further due to resistance by the subannular tissue surrounding balloon 866. When device 862 is pulled proximally, distal compliant balloon 866 engages with subannular tissue thereby temporarily anchoring device 862 to valve 64.

For some applications, annulus-marking device 862 is placed in advance of the implant such that device 862 guides implantation of the implant. That is, the implant slides along the proximal non-compliant balloon 864.

Annulus-marking device 862 can be removed by deflating balloons 864 and 866 and then pulling and constraining device 862 within tool 861 in order to be retrieved and removed from the body of the subject.

It is to be noted that annulus-marking device 862 can be coupled to a plurality of radiopaque elements or filaments 99 and can be shaped in any suitable shape.

It is to be noted that although system 860 is shown on mitral valve 64, system 860 can be used on any cardiac valve, e.g., a tricuspid valve, or any other tissue of the subject.

Figure 63A:
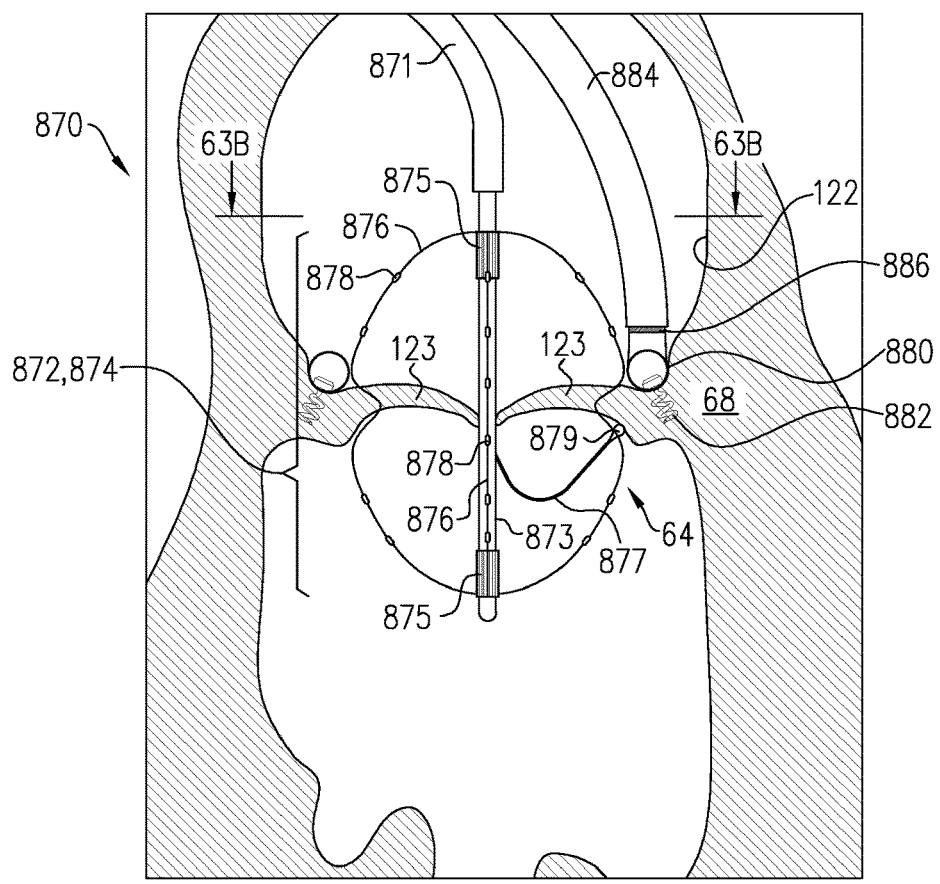
FIGS. 63A-B are schematic illustrations of an annulus-marking device comprising a scaffolding and a magnet for aiding implantation of cardiac devices under the guidance of imaging, in accordance with some applications.
Figure 63B:
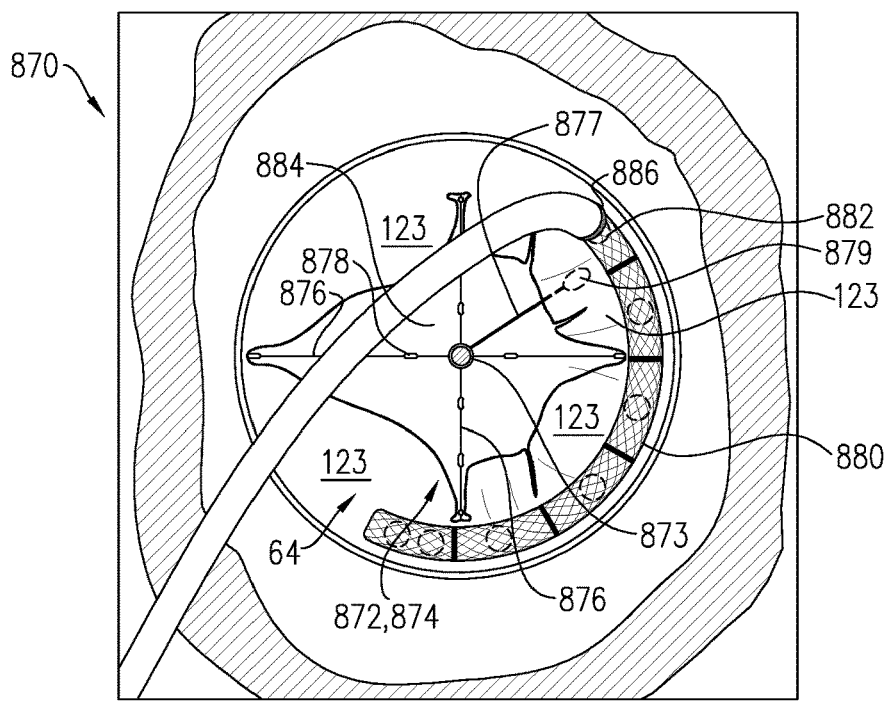

Reference is now made to FIGS. 63A-B, which are schematic illustrations of a system 870 comprising an annulus-marking device 872 for aiding implantation of cardiac devices under the guidance of imaging, in accordance with some applications. Device 872 comprises a scaffolding 874 that is collapsible and expandable. Scaffolding 874, is configured, when expanded, to laterally push against tissue of valve 64 (e.g., leaflet 123, annulus 68, or a commissure). Scaffolding 874 is radiopaque and comprises a plurality of radiopaque elements 878 which are flexible and shaped as bulbs by way of illustration and not limitation. For some applications of the present invention, radiopaque elements 878 can comprise radiopaque elements or filaments 99 described hereinabove.

Scaffolding 874 comprises a central rod 873, a first loop element 876 configured to expand laterally away from central rod 873 and a second loop element 876 configured to expand laterally away from central rod 873. At least one curved, flexible wire 877 is coupled to and extends from central rod 873 at least within a space defined by first and second loop elements 876. A first magnetic element 879 is coupled to an end of flexible wire 877 and is moveable by a second magnetic element that is not coupled to scaffolding 874. That is, for some applications, the second magnetic element comprises a magnetic element 886 that is coupled to a distal end of a portion of a delivery tool 884 used to deliver a cardiac implant, e.g., annuloplasty structure 880.

For some applications, wire 877 has shape-memory and curves toward the subannular groove. Wire 877 may be protractible and extendable from within rod 873. For some applications, magnetic elements 879 and 886 comprise electromagnets. For some applications, magnetic elements 879 and 886 comprise ferromagnets. For some applications, magnetic element 879 comprises an electromagnet and magnetic element 886 comprises a ferromagnet. For some applications, magnetic element 879 comprises a ferromagnet and magnetic element 886 comprises an electromagnet. Wire 877 and magnetic element 879 are guided around the subannular groove responsively to movement of the portion of a delivery tool 884 and magnetic element 886 coupled thereto. As shown in FIG. 63B, wire 877 and magnetic element 879 are guided toward a location along annulus 68 for implanting tissue anchor 882. Once tissue anchor 882 is implanted, delivery tool 884 is moved to a different location along an atrial surface of annulus 68, and wire 877 and magnetic element 879 are guided to a corresponding location in the subannular space of valve 64. In such a manner, wire 877 and magnetic element 879 provide increased fluoroscopic visualization of the implantation procedure, because wire 877 and magnetic element 879 comprise radiopaque material.

First and second loop elements 876 are configured to expand laterally away from central rod 873. For some applications, first and second loop elements 876 are configured to move longitudinally with respect to central rod 873. When scaffolding 874 is expanded, a first half of each of first and second loop elements 876 is configured to be disposed in the atrium of the heart and a second half of each of first and second loop elements 876 is configured to be disposed in the ventricle of the heart. When scaffolding 874 is expanded, loop elements 876 are configured to push against the tissue of valve 64 as is described hereinbelow. It is to be noted that scaffolding 874 comprises two loop elements 876 by way of illustration and not limitation. For some applications, scaffolding 874 can comprise any number of loop elements 876. Loop elements 876 comprise a flexible, radiopaque material, e.g., nitinol. The operating physician is able to discern whether loop elements 876 come in contact with tissue of the heart (e.g., leaflet, commissure, or annulus) by observing deformation of loop elements 876 responsively to the presence of tissue and the force applied to loop elements 876 by the tissue.

Scaffolding 874 helps stabilize device 872 in valve 64.

For some applications, scaffolding 874 comprises two loop elements 876 to help center device 872 and/or its delivery tool 871 as each wire loop element 876 pushes against the tissue. It is to be noted that device 872 can comprise any suitable number of loop elements 876.

A radius of expansion of scaffolding 874 is controlled by movement of structural elements 875 toward or away from each other along a central rod 873. When elements 875 are distanced from each other, scaffolding 874 assumes a narrower configuration. The closer elements 875 are toward each other, the more expanded and wider scaffolding 87 is. For some applications, scaffolding 874 is manually expanded. For some applications, scaffolding 874 is configured to self-expand.

For some applications, loop elements 876 push against tissue of valve 64 at the commissures. For some applications, loop elements 876 push against tissue of leaflet 123 of valve 64. For some applications, as each loop element 876 pushes against tissue of leaflet 123, loop element 876 creates a bicuspidization of the leaflet in a manner in which leaflet 123 assumes two subcusps.

Annulus-marking device 872 is configured help visualize the placement of an implant (e.g., an annuloplasty structure 880, as shown) configured for placement along annulus 68 of valve 64 of the subject.

Annulus-marking device 872 is coupled to a delivery tool 871 and is collapsible within a lumen of tool 871 during delivery of device 872 within valve 64. Annulus-marking device 872 is retrievable upon removal of delivery tool 871 from the subject.

Scaffolding 874 comprises radiopaque material (e.g., nitinol or stainless steel) and is flexible. A plurality of radiopaque elements or radiopaque filaments 99 (not shown) can be coupled to scaffolding 874 at any suitable portion thereof. The plurality of radiopaque elements or radiopaque filaments 99 function as additional annulus-marking devices. Annulus-marking device 872 is configured for aiding implantation of cardiac devices under the guidance of imaging, in accordance with some applications. The steering procedure is performed with the aid of imaging, such as fluoroscopy, transesophageal echo, and/or echocardiography.

Device 872 may be delivered percutaneously, thoracoscopically through the chest, or using open heart surgical techniques. If delivered percutaneously, device 872 may be made from a superelastic material (e.g., nitinol or stainless steel) enabling it to be folded and collapsed such that it can be delivered in a catheter and subsequently self-expand into the desired shape and tension when released from the catheter. For example, percutaneous vascular access can be achieved by conventional methods into the femoral or jugular vein under image guidance (e.g., fluoroscopic, ultrasonic, magnetic element resonance, computed tomography, or combinations thereof). For some applications, device 872 comprises a wire.

Device 872 enables mapping of the anatomy of the atrium, atrial wall, heart valve, annulus, and ventricle. Additionally, device 872 is made from radiopaque material to facilitate fluoroscopic visualization. For some applications, tissue of valve annulus 68 and tissue coupled thereto is viewed using device 872. Additionally, the tissue of the native heart valve annulus 68 and tissue coupled thereto is viewed by imaging annulus-marking device 872 with respect to the tissue of the native heart valve annulus and the tissue coupled thereto by viewing device 872 placed against the tissue. For some applications, the tissue of the native heart valve annulus 68 and tissue coupled thereto is viewed by imaging annulus-marking device 872 with respect to the tissue of the native heart valve annulus and the tissue coupled thereto by viewing movement of device 872 responsively to movement of the tissue.

Subsequently to implanting of annuloplasty structure 880, annulus-marking device 872 is retrieved. Since device 872 is flexible and compressible, device 872 is constrained within the tool during the retrieval of device 872 and subsequent removal of device 872 from the body of the subject. That is, device 872 does not function as an implant for such embodiments and is used only to guide implantation of implant 684; rather, device 872 acts as a guide for implantation while placed temporarily within the body of the patient to be subsequently removed therefrom following the implantation of structure 880.

It is to be noted that although system 870 is shown on mitral valve 64, system 870 can be used on any cardiac valve, e.g., a tricuspid valve, or any other tissue of the subject.

Figure 64:
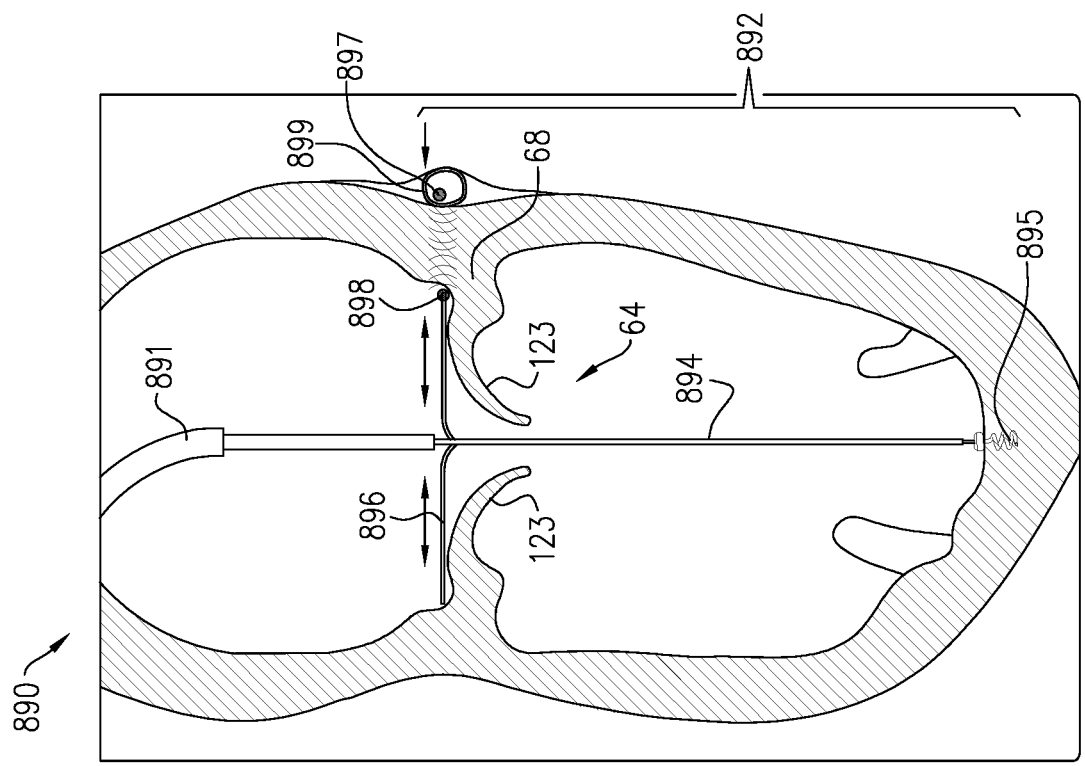

Reference is now made to FIG. 64, which is a schematic illustration of a system 890 comprising an annulus-marking device 892 comprising at least one magnetic element, e.g., first and second magnetic elements 898 and 899, configured to be positioned at respective cardiac tissue of or in a vicinity of valve 64 of the subject, in accordance with some applications. For some applications, first magnetic element 898 is coupled to a cross-beam 896 which extends from a central rod 894. Cross-beam 896 is expandable within an atrium of the heart of the subject. For some applications, cross-beam 896 extends in both directions, laterally from central rod 894. For some applications, cross-beam 896 extends in a single direction, laterally from central rod 894. Central rod 894 is coupled at a distal end thereof to a tissue anchor 895 which is reversibly coupled to tissue of the heart (e.g., to tissue at the apex, as shown by way of illustration and not limitation). In such a manner, central rod 894 functions to stabilize device 892 during the imaging and implantation of the implant. For some applications, second magnetic element 897 is configured to be disposed in vasculature 899 surrounding valve 64 (e.g., in a right circumflex artery). For some applications, second magnetic element 897 comprises a wire that is partially ring-shaped, e.g., C-shaped.

For some applications, first and second magnetic elements 898 and 897 comprise electromagnets. For some applications, first and second magnetic elements 898 and 897 comprise ferromagnets.

For some applications, first magnetic element 898 comprises a ferromagnet while second magnetic element 897 comprises an electromagnet. For some applications, first magnetic element 898 comprises an electromagnet while second magnetic element 897 comprises a ferromagnet.

Device 892 is delivered to valve 64 using a delivery tool 891, e.g., during transvascular approach or during a minimally-invasive procedure.

Positioning of first and second magnetic elements 898 and 897 generates a magnetic field. The magnetic field helps ensure proper positioning of device 892 with respect to tissue of valve 64. The magnetic field helps prevent movement of device 892 with respect to tissue of valve 64.

Once device 892 is positioned at valve 64, under imaging guidance, e.g., under fluoroscopy, an implant, e.g., an annuloplasty structure, is implanted at annulus 68 of valve 64 using annulus-marking device 892 as a guide. The annuloplasty structure can be positioned between an external surface of magnetic element 898 and the atrial wall.

For some applications, tissue of native heart valve annulus 68 and tissue coupled thereto is viewed using device 892, i.e., using magnetic elements 898 and 897. The tissue is viewed by imaging annulus-marking device 892 with respect to the tissue of native heart valve annulus 68 and the tissue coupled thereto by viewing elements 898 and 897 against the tissue. Annulus-marking device 892 is imaged with respect to the tissue of native heart valve annulus 68, tissue of at least one leaflet 123, and tissue of the atrial wall.

Once the annuloplasty structure is implanted along annulus 68, annulus-marking device 892 is retrieved. For some applications, device 892 is constrained within tool 891 and extracted from the body of the subject.

It is to be noted that although system 890 is shown on mitral valve 64, system 890 can be used on any cardiac valve, e.g., a tricuspid valve, or any other tissue of the subject.

Figure 65:
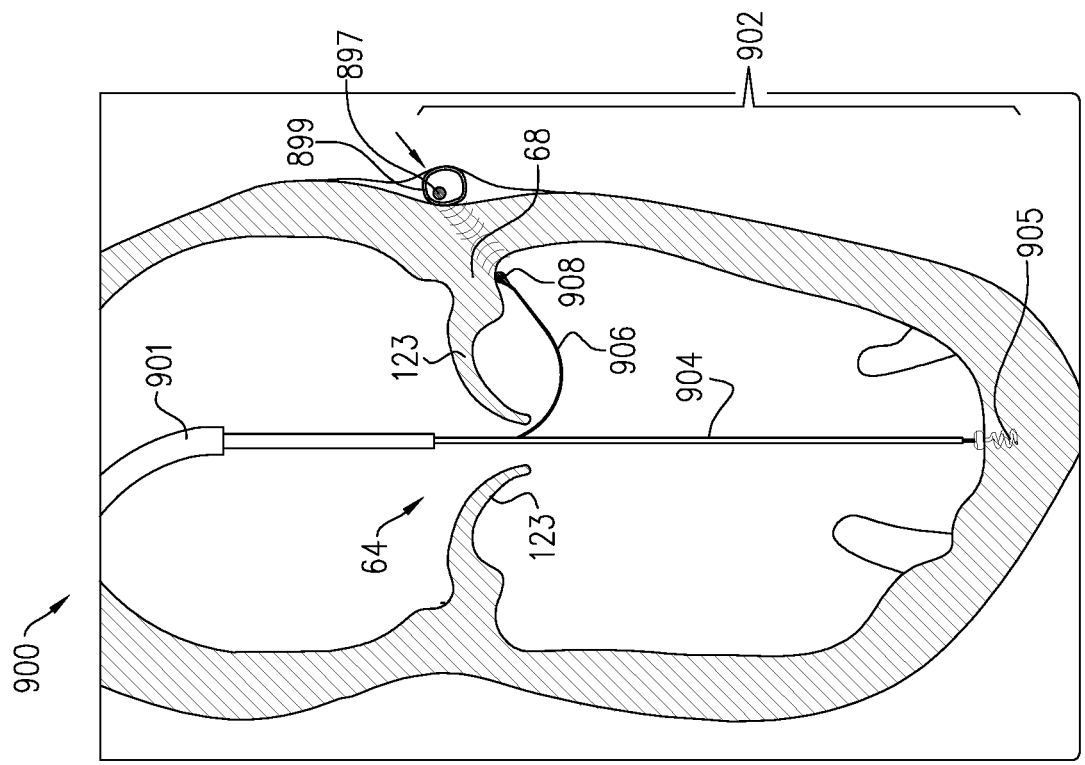
FIGS. 64-65 are schematic illustrations of an annulus-marking device comprises magnetic elements for aiding implantation of cardiac devices under the guidance of imaging, in accordance with respective applications.

Reference is now made to FIG. 65, which is a schematic illustration of a system 900 comprising an annulus-marking device 902 comprising at least one magnetic element, e.g., first and second magnetic elements 908 and 899, configured to be positioned at respective cardiac tissue of or in a vicinity of valve 64 of the subject, in accordance with some applications. For some applications, first magnetic element 908 is coupled to at least one curved, flexible wire 906 that is coupled to and extends from central tube or rod 904. For some applications, wire 906 has shape-memory and curves toward the subannular groove. Wire 906 may be protractible and extendable from within rod 904. In some applications, wire 906 extends and retracts from a side opening in rod or tube 904

In some embodiments, central rod 904 is coupled at a distal end thereof to a tissue anchor 905 which is reversibly coupled to tissue of the heart (e.g., to tissue at the apex, as shown by way of illustration and not limitation). In such a manner, central rod 904 functions to stabilize device 902 during the imaging and implantation of the implant. However, it is not required for central tube or rod 904 to extend so deep into the ventricle or to be anchored at all. For some applications, second magnetic element 897 is configured to be disposed in vasculature 899 surrounding valve 64 (e.g., in a right circumflex artery). For some applications, second magnetic element 897 comprises a wire that is partially ring-shaped, e.g., C-shaped.

For some applications, first and second magnetic elements 908 and 897 comprise electromagnets. For some applications, first and second magnetic elements 908 and 897 comprise ferromagnets.

For some applications, first magnetic element 908 comprises a ferromagnet while second magnetic element 897 comprises an electromagnet. For some applications, first magnetic element 908 comprises an electromagnet while second magnetic element 897 comprises a ferromagnet.

Device 902 is delivered to valve 64 using a delivery tool 901, e.g., during transvascular approach or during a minimally-invasive procedure.

Positioning of first and second magnetic elements 908 and 897 generates a magnetic field. The magnetic field helps ensure proper positioning of device 902, in particular wire 906, with respect to tissue of valve 64. The magnetic field helps prevent movement of device 902 with respect to tissue of valve 64.

Once device 902 is positioned at valve 64, under imaging guidance, e.g., under fluoroscopy, an implant, e.g., an annuloplasty structure, is implanted at annulus 68 of valve 64 using annulus-marking device 902 as a guide. The annuloplasty structure can be positioned between an external surface of magnetic element 908 and the atrial wall.

For some applications, tissue of native heart valve annulus 68 and tissue coupled thereto is viewed using device 902, i.e., using magnetic elements 908 and 897. The tissue is viewed by imaging annulus-marking device 902 with respect to the tissue of native heart valve annulus 68 and the tissue coupled thereto by viewing elements 908 and 897 placed against the tissue. Annulus-marking device 902 is imaged with respect to the tissue of native heart valve annulus 68, tissue of at least one leaflet 123, and tissue of the atrial wall.

Once the annuloplasty structure is implanted along annulus 68, annulus-marking device 902 is retrieved. For some applications, device 902 is constrained within tool 901 and extracted from the body of the subject.

It is to be noted that although system 900 is shown on mitral valve 64, system 900 can be used on any cardiac valve, e.g., a tricuspid valve, or any other tissue of the subject. Further, the system 900 can include features, components, elements, etc. from other systems and embodiments herein. For example, the system 900 can include and/or be used with a scaffolding 713 and/or basket 714 (e.g., as shown in FIG. 51A-C), and the scaffolding and/or basket 714 can include any of the features described above, e.g., radiopaque elements, filaments, etc. As another example, the system 900 can include and/or be used with one or more radiopaque markers or loops 734 (e.g., as shown in FIG. 52A-B), and the markers or loops 734 can include any of the features described above, e.g., radiopaque elements, filaments, etc. spaced there around. Other combinations are also possible.

It is to be noted that, whereas some techniques known in the art comprise selecting an annuloplasty structure based on a target (e.g., desired, calculated, and/or physiological) circumference of the posterior portion of the annulus, applications of the present invention comprise selecting an annuloplasty structure based on an existing (e.g., pathological) circumference of the annulus or a portion thereof (e.g., a posterior portion of the annulus).

Reference is made to FIGS. 1-65. Following implantation of the annuloplasty structures described herein, the dimensions of the annuloplasty structures can be adjusted remotely and while the patient is not on a cardio-pulmonary bypass pump (i.e., with a beating heart), under fluoroscopy and/or echo guidance.

Systems 20, 30, 40, 60, 90, 100, 120, 140, 160, 170, 180, 190, 200, 220, 230, 250, 270, 280, 300, 320, 330, 340, 350, 360, 370, 380, 390, 400, 410, 420, 430, 440, 450, 460, 470, 480, 490, 500, 510, 520, 530, 540, 560, 570, 580, 590, 600, 610, 620, 630, 640, 650, 670, 680, 700, 710, 730, 740, 760, 780, 790, 800, 820, 830, 840, 850, 860, 870, 890, and 900 can be advanced using (1) a trans-septal procedure in which the system is advanced through vasculature of the patient at any suitable access location (e.g., femoral vein), (2) a minimally-invasive transapical approach (as shown in FIG. 28), (3) a minimally-invasive transatrial approach (e.g., an intercostal approach), and/or (4) a surgical, open-heart approach. Furthermore, for some applications, the systems described herein are not steerable and can comprise straight elements (e.g., in a surgical, open-heart procedure).

Systems 20, 30, 40, 60, 90, 100, 120, 140, 160, 170, 180, 190, 200, 220, 230, 250, 270, 280, 300, 320, 330, 340, 350, 360, 370, 380, 390, 400, 410, 420, 430, 440, 450, 460, 470, 480, 490, 500, 510, 520, 530, 540, 560, 570, 580, 590, 600, 610, 620, 630, 640, 650, 670, 680, 700, 710, 730, 740, 760, 780, 790, 800, 820, 830, 840, 850, 860, 870, 890, and 900 for imaging and repairing a dilated annulus of the patient can be used to treat any cardiac valve of the patient, e.g., the aortic valve, the pulmonary valve, the mitral valve, and the tricuspid valve. Systems described herein for treatment of valves can be used to treat other annular muscles within the body of the patient. For example, the systems described herein can be used in order to treat a sphincter muscle within a stomach of the patient.

The scope of the present invention includes the use systems 20, 30, 40, 60, 90, 100, 120, 140, 160, 170, 180, 190, 200, 220, 230, 250, 270, 280, 300, 320, 330, 340, 350, 360, 370, 380, 390, 400, 410, 420, 430, 440, 450, 460, 470, 480, 490, 500, 510, 520, 530, 540, 560, 570, 580, 590, 600, 610, 620, 630, 640, 650, 670, 680, 700, 710, 730, 740, 760, 780, 790, 800, 820, 830, 840, 850, 860, 870, 890, and 900 (or subcomponents thereof) and methods described hereinabove on any suitable tissue of the patient (e.g., stomach tissue, urinary tract, and prostate tissue).

Reference is now made to FIGS. 1-37 and 39-65. Systems 20, 30, 40, 60, 90, 100, 120, 140, 160, 170, 180, 190, 200, 220, 230, 250, 270, 280, 300, 320, 330, 340, 350, 360, 370, 380, 390, 400, 410, 420, 430, 440, 450, 460, 470, 480, 490, 500, 510, 520, 530, 540, 570, 580, 590, 600, 610, 620, 630, 640, 650, 670, 680, 700, 710, 730, 740, 760, 780, 790, 800, 820, 830, 840, 850, 860, 870, 890, and 900 are designed in order to enhance fluoroscopic imaging of cardiac procedures while reducing the need to utilize other types of imaging such as echocardiographic, ultrasound, etc. However, the radiopaque features and/or other features of these systems can also be configured to be more visible under echocardiography, ultrasound, etc., such as by adding an echogenic coating and/or modifying the features in other ways to be more visible. For some applications, the radiopaque features can be replaced and or modified to adapt those features and/or the associated structures for viewing under echocardiography, ultrasound, etc.

Reference is again made to FIGS. 1-65. The annuloplasty structures described herein and the methods of delivery therefor include annuloplasty structures and methods of delivery therefor as described in PCT Patent Application PCT/IL2013/050860 to Sheps et al., entitled, "Controlled steering functionality for implant-delivery tool," filed on Oct. 23, 2013, which published as WO/2014/064694 and which is incorporated herein by reference. For some applications, the systems described herein can be used to guide implantation of annuloplasty structure combining a flat band, e.g., a braided fabric or metal band, as described hereinabove with reference to FIG. 6B. That is, for such applications, the annuloplasty structure can be sleeveless, e.g., not tubular, etc.

Additionally, the scope of the present invention includes applications described in one or more of the following:

U.S. patent application Ser. No. 12/435,291 to Maisano et al., entitled, "Adjustable repair chords and spool mechanism therefor," filed on May 4, 2009, which published as US Patent Application Publication 2010/0161041;

U.S. patent application Ser. No. 12/437,103 to Zipory et al., entitled, "Annuloplasty ring with intra-ring anchoring," filed on May 7, 2009, which published as US Patent Application Publication 2010/0286767;

U.S. patent application Ser. No. 12/548,991 to Maisano et al., entitled, "Implantation of repair chords in the heart," filed on Aug. 27, 2009, which published as US Patent Application Publication 2010/0161042;

PCT Patent Application PCT/IL2009/001209 to Cabiri et al., entitled, "Adjustable annuloplasty devices and mechanisms therefor," filed on Dec. 22, 2009, which published as PCT Publication WO 10/073246;

PCT Patent Application PCT/IL2010/000357 to Maisano et al., entitled, "Implantation of repair chords in the heart," filed on May 4, 2010, which published as WO 10/128502;

PCT Patent Application PCT/IL2010/000358 to Zipory et al., entitled, "Deployment techniques for annuloplasty ring and over-wire rotation tool," filed on May 4, 2010, which published as WO 10/128503;

PCT Patent Application PCT/IL2012/050451 to Sheps et al., entitled, "Controlled steering functionality for implant-delivery tool," filed on Nov. 8, 2012, which published as WO/2013/069019; and/or PCT Patent Application PCT/IL2013/050860 to Sheps et al., entitled, "Controlled steering functionality for implant-delivery tool," filed on Oct. 23, 2013, which published as WO/2014/064694.

All of these applications are incorporated herein by reference. Techniques described herein can be practiced in combination with techniques described in one or more of these applications. Further, each of the techniques, methods, operations, steps, etc. described herein can be performed on a living animal or on a non-living simulation, such as on a cadaver, cadaver heart, simulator (e.g. with the body parts, tissue, etc. being simulated), etc.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use at a valve disposed between an atrium and a ventricle of a heart of a subject, the valve having an annulus, and the method comprising:

transluminally advancing a radiopaque frame to the atrium;

expanding the frame within the valve such that part of the frame remains disposed in the atrium;

while the frame remains expanded within the valve with the part of the frame disposed in the atrium, progressively positioning and anchoring progressive portions of an annuloplasty structure around the annulus using multiple anchors by, for each of the multiple anchors sequentially:

while fluoroscopically imaging the frame and a distal end of a delivery tool, and facilitated by mechanical guidance from the frame, positioning the distal end of the delivery tool between the frame and a wall of the atrium; and while the distal end of the delivery tool remains disposed between the frame and the wall of the atrium, driving the anchor into the annulus laterally from the frame; and subsequently, contracting the frame and withdrawing the frame from the subject while leaving the annuloplasty structure anchored around the annulus.

2. The method according to claim 1, wherein expanding the frame comprises expanding the frame such that a rail of the frame extends along the annulus.

3. The method according to claim 2, wherein positioning the distal end of the delivery tool between the frame and the wall of the atrium facilitated by mechanical guidance from the frame comprises positioning the distal end of the delivery tool between the frame and the wall of the atrium facilitated by mechanical guidance from the rail.

4. The method according to claim 1, wherein:
the frame includes a mesh, and
expanding the frame comprises expanding the frame such that the mesh defines a bulging ledge portion disposed against the valve, and a sloped upstream portion, tapering away from the bulging ledge portion into the atrium.

5. The method according to claim 4, wherein positioning the distal end of the delivery tool between the frame and the wall of the atrium facilitated by mechanical guidance from the frame comprises sliding the distal end of the delivery tool along the sloped upstream portion.

6. The method according to claim 4, wherein expanding the frame comprises expanding the frame such that the mesh further defines a trumpet portion within the ventricle.

7. The method according to claim 1, wherein expanding the frame comprises expanding the frame into a bulbous shape.

8. The method according to claim 1, wherein expanding the frame comprises expanding the frame into a generally umbrella shape.

9. The method according to claim 1, wherein expanding the frame comprises expanding the frame into a generally spherical shape.

10. The method according to claim 1, wherein expanding the frame comprises expanding the frame into a generally partially spherical shape.

11. The method according to claim 1, wherein expanding the frame comprises expanding the frame into a generally ovoid shape.

12. The method according to claim 1, wherein expanding the frame comprises expanding the frame into a generally teardrop shape.

13. The method according to claim 1, wherein expanding the frame comprises expanding the frame into a generally conical shape.

14. The method according to claim 1, wherein expanding the frame comprises expanding the frame into a pear shape.

15. The method according to claim 1, wherein the frame includes a braided mesh, and wherein expanding the frame comprises expanding the braided mesh.

16. The method according to claim 1, wherein the frame defines a conical stent, and wherein expanding the frame comprises expanding the conical stent.

17. The method according to claim 1, wherein expanding the frame comprises expanding the frame by inflating a balloon disposed within the frame.

18. The method according to claim 1, wherein positioning the distal end of the delivery tool comprises positioning the distal end of the delivery tool facilitated by fluoroscopic identification of bending of the frame caused by pressing of the frame against tissue of the heart.

19. The method according to claim 1, wherein the frame has leaflets connected thereto, and wherein progressively positioning and anchoring progressive portions of the annuloplasty structure around the annulus while the frame remains expanded within the valve with the part of the frame disposed in the atrium comprises progressively positioning and anchoring progressive portions of the annuloplasty structure around the annulus while the frame remains expanded within the valve with the part of the frame disposed in the atrium and the leaflets regulate blood flow through the valve.

20. The method according to claim 1, wherein the valve is a mitral valve of the heart, and wherein expanding the frame comprises expanding the frame such that an asymmetrical portion of the frame, in which the frame is shorter, is oriented toward an aortic valve of the heart.

21. The method according to claim 1, wherein positioning the distal end of the delivery tool between the frame and the wall of the atrium facilitated by mechanical guidance from the frame comprises positioning the distal end of the delivery tool between the frame and the wall of the atrium facilitated by tactile feedback from contact between the delivery tool and the frame.

* * * * *